US006906104B2

United States Patent
Schostarez et al.

(10) Patent No.: US 6,906,104 B2
(45) Date of Patent: Jun. 14, 2005

(54) AMINEDIOLS FOR THE TREATMENT OF ALZHEIMER'S DISEASE

(75) Inventors: Heinrich Josef Schostarez, Portage, MI (US); Robert Alan Chrusciel, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/171,343

(22) Filed: Jun. 13, 2002

(65) Prior Publication Data

US 2003/0092747 A1 May 15, 2003

Related U.S. Application Data

(60) Provisional application No. 60/297,827, filed on Jun. 13, 2000, and provisional application No. 60/333,084, filed on Nov. 19, 2001.

(51) Int. Cl.[7] .................... A61K 31/164; A61K 31/166; A61K 31/133; C07D 235/26; C07D 235/70
(52) U.S. Cl. ...................... 514/649; 564/297; 564/300; 564/306; 514/615; 514/645
(58) Field of Search ............................. 564/297, 300, 564/306; 514/615, 645, 649

(56) References Cited

U.S. PATENT DOCUMENTS

| | | | |
|---|---|---|---|
| 4,522,811 A | 6/1985 | Eppstein et al. ................ 514/2 |
| 5,145,684 A | 9/1992 | Liversidge et al. .......... 424/489 |
| 5,387,742 A | 2/1995 | Cordell ........................... 800/2 |
| 5,441,870 A | 8/1995 | Seubert et al. ................ 435/7.1 |
| 5,593,846 A | 1/1997 | Schenk et al. ................ 435/7.9 |
| 5,604,102 A | 2/1997 | McConlogue et al. ....... 435/7.1 |
| 5,612,486 A | 3/1997 | McConlogue et al. ......... 800/2 |
| 5,720,936 A | 2/1998 | Wadsworth et al. .......... 424/9.1 |
| 5,721,130 A | 2/1998 | Seubert et al. ........... 425/240.7 |
| 5,721,131 A | 2/1998 | Rudolph et al. ............. 435/240 |
| 5,744,346 A | 4/1998 | Chrysler et al. ............. 435/226 |
| 5,811,633 A | 9/1998 | Wadsworth et al. ........... 800/2 |
| 5,850,003 A | 12/1998 | McLonlogue et al. ......... 800/2 |
| 5,877,015 A | 3/1999 | Hardy et al. ................. 435/325 |
| 5,877,399 A | 3/1999 | Hsiao et al. .................... 800/2 |
| 5,912,410 A | 6/1999 | Cordell ........................... 800/2 |
| 5,942,400 A | 8/1999 | Anderson et al. ............ 435/7.1 |
| 6,045,829 A | 4/2000 | Liversidge et al. ......... 424/489 |
| 6,191,166 B1 | 2/2001 | Audia et al. ................. 514/534 |
| 2002/0192543 A1 * | 7/2002 | Schostarez et al. | |
| 2002/0192625 A1 * | 7/2002 | Schostarez et al. | |

FOREIGN PATENT DOCUMENTS

| | | |
|---|---|---|
| WO | WO 98/22597 | 5/1998 |
| WO | WO 99/64001 | 12/1999 |
| WO | WO 00/03819 | 1/2000 |
| WO | WO 00/17369 | 3/2000 |
| WO | WO 00/47618 | 8/2000 |
| WO | WO 01/10387 | 2/2001 |
| WO | WO 01/23533 | 4/2001 |

OTHER PUBLICATIONS

Lunney, Elizabeth et al. "Analyses of Ligand Binding in Five Endothiapepsin Crystal Complexes and Their Use in the Design and Evaluation of Novel Renin Inhibitors" Journal Medicinal Chemistry (1993), vol. 36, No. 24, pp. 3809–3820.*
CAPLUS listing of Lunney et al, Accession No. 1993:662007, with RN structures.*
U.S. Appl. No. 60/297,827, Schostarez, filed Jun. 13, 2001.
U.S. Appl. No. 60/333,084, Schostarez et al., filed Nov. 19, 2001.
Selkoe DJ., "The molecular pathology of Alzheimer's disease," Neuron, Apr. 1991, 487–498.
Seubert et al., "Isolation and quantification of soluble Alzheimer's beta–peptide from biological fluids," Sep. 1992, 325–327.
Luo et al., "Mice deficient in BACE1, the Alzheimer's beta–secretase, have normal phenotype and abolished beta–amyloid generation," Nature Neuroscience, Mar. 2001, 231–232.
Hyafil et al., "In vitro and in vivo reversal of multidrug resistance by GF 120918, an acridonecarboxamide derivative," Cancer Research, Oct. 1993, 4595–4602.
Dantzing, et al., "Reversal of P–glycoprotein–mediated multidrug resistance by a potent cyclopropyldibenzosuberane modulator, LY335979," Cancer Research, Sep. 1996, 4171–4179.
Hardy, John, "Framing beta–amyloid," Nature Genetics, Jul. 1992, 233–234.
Vassar et al., Beta–secretase cleavage of Alzheimer's amyloid precursor protein by the transmembrane aspartic protease BACE, Science, Oct. 1999, 735–741.
Yan et al., Membrane–anchored aspartyl protease with Alzheimer's disease beta–secretase activity, Nature Dec. 1999, 533–537.
Sihna et al., Purification and cloning of amyloid precursor protein beta–secretase from human brain, Nature, Dec. 1999, 537–540.

(Continued)

*Primary Examiner*—Ceila Chang
*Assistant Examiner*—Janet L. Coppins
(74) *Attorney, Agent, or Firm*—McDonnell Boehnen; Hulbert & Berghoff LLP

(57) ABSTRACT

The present invention relates to compounds of formula (I):

$$\underset{R_N}{\overset{R_2}{\underset{|}{N}}}\!\!-\!\!\underset{R_1}{\overset{OH}{\underset{|}{C}}}\!\!-\!\!\underset{OH}{\overset{}{C}}\!\!-\!\!R_C \quad (I)$$

useful in treating Alzheimer's disease and other similar diseases. These compounds include inhibitors of the beta-secretase enzyme that are useful in the treatment of Alzheimer's disease and other diseases characterized by deposition of A beta peptide in a mammal. The compounds of the invention are useful in pharmaceutical compositions and methods of treatment to reduce A beta peptide formation.

9 Claims, No Drawings

OTHER PUBLICATIONS

Lin et al., Human aspartic protease memapsin 2 cleaves the beta–secretase site of beta–amyloid precursor protein, PNAS—Proceedings of the National Academy of Sciences, Feb. 2000, 1456–1460.

Kang et al., "The precursor of Alzheimer's disease amyloid !4 protein resembles a cell–surface receptor," Nature, Feb. 1987, 733–736.

Citron et al., "Mutation of the beta–amyloid precursor protein in familial Alzheimer's disease increases beta–protein production," Nature, Dec. 1992, 672–674.

Games et al., "Alzheimer's–type neuropathology in transgenic mice overexpressig V717F beta–amyloid precursor protein, " Nature, Feb. 1995, 523–527.

Hussain et al., Identification of a novel aspartic protease (Asp2) as beta–secretase, Molecular and Cellular Neurosciences, 1999, 419–427.

Pirttila et al., "Longitudinal study of cerebrospinal fluid amyloid proteins and apolipoprotein E in patients with probably Alzheimer's disease," Neuroscience Letters, 1998, 21–24.

* cited by examiner

AMINEDIOLS FOR THE TREATMENT OF ALZHEIMER'S DISEASE

CROSS REFERENCE TO RELATED APPLICATIONS

This application claims priority from U.S. Provisional Application Ser. No. 60/297,827, filed Jun. 13, 2001, and U.S. Provisional Application Ser. No. 60/333,084, filed Nov. 19, 2001.

BACKGROUND OF THE INVENTION

1. Field of the Invention

The invention relates to aminediols and to such compounds that are useful in the treatment of Alzheimer's disease and related diseases. More specifically, it relates to such compounds that are capable of inhibiting beta-secretase, an enzyme that cleaves amyloid precursor protein to produce amyloid beta peptide (A beta), a major component of the amyloid plaques found in the brains of Alzheimer's sufferers.

2. Background of the Invention

Alzheimer's disease (AD) is a progressive degenerative disease of the brain primarily associated with aging. Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid (or neuritic) plaques, comprised predominantly of an aggregate of a peptide fragment know as A beta. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHWA-D), and other neurodegenerative disorders. Beta-amyloid is a defining feature of AD, now believed to be a causative precursor or factor in the development of disease. Deposition of A beta in areas of the brain responsible for cognitive activities is a major factor in the development of AD. Beta-amyloid plaques are predominantly composed of amyloid beta peptide (A beta, also sometimes designated betaA4). A beta peptide is derived by proteolysis of the amyloid precursor protein (APP) and is comprised of 39–42 amino acids. Several proteases called secretases are involved in the processing of APP.

Cleavage of APP at the N-terminus of the A beta peptide by beta-secretase and at the C-terminus by one or more gamma-secretases constitutes the beta-amyloidogenic pathway, i.e. the pathway by which A beta is formed. Cleavage of APP by alpha-secretase produces alpha-sAPP, a secreted form of APP that does not result in beta-amyloid plaque formation. This alternate pathway precludes the formation of A beta peptide. A description of the proteolytic processing fragments of APP is found, for example, in U.S. Pat. Nos. 5,441,870; 5,721,130; and 5,942,400.

An aspartyl protease has been identified as the enzyme responsible for processing of APP at the beta-secretase cleavage site. The beta-secretase enzyme has been disclosed using varied nomenclature, including BACE, Asp, and Memapsin. See, for example, Sinha et al., 1999, *Nature* 402:537–554 (p501) and published PCT application WO00/17369.

Several lines of evidence indicate that progressive cerebral deposition of beta-amyloid peptide (A beta) plays a seminal role in the pathogenesis of AD and can precede cognitive symptoms by years or decades. See, for example, Selkoe, 1991, *Neuron* 6:487. Release of A beta from neuronal cells grown in culture and the presence of A beta in cerebrospinal fluid (CSF) of both normal individuals and AD patients has been demonstrated. See, for example, Seubert et al., 1992, *Nature* 359:325–327.

It has been proposed that A beta peptide accumulates as a result of APP processing by beta-secretase, thus inhibition of this enzyme's activity is desirable for the treatment of AD. In vivo processing of APP at the beta-secretase cleavage site is thought to be a rate-limiting step in A beta production, and is thus a therapeutic target for the treatment of AD. See for example, Sabbagh, M., et al., 1997, *Alz. Dis. Rev.* 3, 1–19.

BACE1 knockout mice fail to produce A beta, and present a normal phenotype. When crossed with transgenic mice that over express APP, the progeny show reduced amounts of A beta in brain extracts as compared with control animals (Luo et al., 2001 *Nature Neuroscience* 4:231–232). This evidence further supports the proposal that inhibition of beta-secretase activity and reduction of A beta in the brain provides a therapeutic method for the treatment of AD and other beta amyloid disorders.

At present there are no effective treatments for halting, preventing, or reversing the progression of Alzheimer's disease. Therefore, there is an urgent need for pharmaceutical agents capable of slowing the progression of Alzheimer's disease and/or preventing it in the first place.

Compounds that are effective inhibitors of beta-secretase, that inhibit beta-secretase-mediated cleavage of APP, that are effective inhibitors of A beta production, and/or are effective to reduce amyloid beta deposits or plaques, are needed for the treatment and prevention of disease characterized by amyloid beta deposits or plaques, such as AD.

SUMMARY OF THE INVENTION

The invention encompasses the compounds of formula (I) shown below, pharmaceutical compositions containing the compounds and methods employing such compounds or compositions in the treatment of Alzheimer's disease and more specifically compounds that are capable of inhibiting beta-secretase, an enzyme that cleaves amyloid precursor protein to produce A-beta peptide, a major component of the amyloid plaques found in the brains of Alzheimer's sufferers.

In one aspect, the invention provides compounds of the formula I:

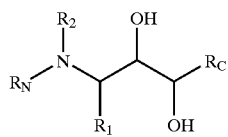

(I)

and pharmaceutically acceptable salts thereof, wherein $R_1$ is
  $C_1$–$C_{10}$ alkyl optionally substituted with 1, 2, or 3 groups independently selected from halogen, —OH, =O, —SH, —C≡N, —CF$_3$, —C$_1$–C$_3$ alkoxy, amino, mono- or dialkylamino, —N(R)C(O)R'—, —OC(=O)— amino and —OC(=O)-mono- or dialkylamino, or
  $C_2$–$C_6$ alkenyl or $C_2$–$C_6$ alkynyl, each of which is optionally substituted with 1, 2, or 3 groups independently selected from halogen, —OH, —SH, —C≡N, —CF$_3$, $C_1$–$C_3$ alkoxy, amino, and mono- or dialkylamino, or
  aryl, heteroaryl, heterocyclyl, aryl($C_1$–$C_6$)alkyl-, heteroaryl($C_1$–$C_6$)alkyl-, or heterocyclyl($C_1$–$C_6$)alkyl-, where the ring portions of each are optionally substituted with 1, 2, 3, or 4 groups independently selected from halogen, —OH, —SH, —C≡N, —NO$_2$, —NR$_{105}$R'$_{105}$, —CO$_2$R, —N(R)COR', —N(R)SO$_2$R', —C(=O)—($C_1$–$C_4$) alkyl, —SO$_2$-amino, —SO$_2$-monoalkylamino, —SO$_2$-dialkylamino, —C(=O)-amino, —C(=O)-monoalkylamino, —C(=O)-dialkylamino, —SO$_2$—($C_1$–$C_4$) alkyl,
    $C_1$–$C_6$ alkoxy optionally substituted with 1, 2, or 3 groups which are independently selected from halogen,
    $C_3$–$C_7$ cycloalkyl optionally substituted with 1, 2, or 3 groups independently selected from halogen, —OH, —SH, —C≡N, —CF$_3$, $C_1$–$C_3$ alkoxy, amino, —$C_1$–$C_6$ alkyl and mono- or dialkylamino,
    $C_1$–$C_{10}$ alkyl optionally substituted with 1, 2, or 3 groups independently selected from halogen, —OH, —SH, —C≡N, —CF$_3$, —$C_1$–$C_3$ alkoxy, amino, mono- or dialkylamino and —$C_1$–$C_3$ alkyl, and
    $C_2$–$C_{10}$ alkenyl or $C_2$–$C_{10}$ alkynyl each of which is optionally substituted with 1, 2, or 3 groups independently selected from halogen, —OH, —SH, —C≡N, —CF$_3$, $C_1$–$C_3$ alkoxy, amino, $C_1$–$C_6$ alkyl and mono- or dialkylamino; and the heterocyclyl group is optionally further substituted with oxo;
R and R' independently are hydrogen, $C_1$–$C_{10}$ alkyl, $C_1$–$C_{10}$ alkylaryl or $C_1$–$C_{10}$ alkylheteroaryl;
$R_2$ is H or is —CO—O—(CH$_2$)$_{n8}$—R$_{25}$ where $n_8$ is 0, 1, or 2 and $R_{25}$ is $C_1$–$C_6$ alkyl or phenyl;
$R_C$ is hydrogen, —(CR$_{245}$R$_{250}$)$_{0-4}$-aryl, —(CR$_{245}$R$_{250}$)$_{0-4}$-heteroaryl, —(CR$_{245}$R$_{250}$)$_{0-4}$-heterocyclyl, —(CR$_{245}$R$_{250}$)$_{0-4}$-aryl-heteroaryl, —(CR$_{245}$R$_{250}$)$_{0-4}$-aryl-heterocyclyl, —(CR$_{245}$R$_{250}$)$_{0-4}$-aryl-aryl, —(CR$_{245}$R$_{250}$)$_{0-4}$-heteroaryl-aryl, —(CR$_{245}$R$_{250}$)$_{0-4}$-heteroaryl-heterocyclyl, —(CR$_{245}$R$_{250}$)$_{0-4}$-heteroaryl-heteroaryl, —(CR$_{245}$R$_{250}$)$_{0-4}$-heterocyclyl-heteroaryl, —(CR$_{245}$R$_{250}$)$_{0-4}$-heterocyclyl-heterocyclyl, —(CR$_{245}$R$_{250}$)$_{0-4}$-heterocyclyl-aryl, —CH(aryl)$_2$, —CH(heteroaryl)$_2$, —CH(heterocyclyl)$_2$, —CH (aryl)(heteroaryl), —(CH$_2$)$_{0-1}$—CH((CH$_2$)$_{0-6}$—OH)—(CH$_2$)$_{0-1}$-aryl, —(CH$_2$)$_{0-1}$—CH((CH$_2$)$_{0-6}$—OH)—(CH$_2$)$_{0-1}$-heteroaryl, —CH(-aryl or -heteroaryl)—CO—O($C_1$–$C_4$ alkyl), —($C_1$–$C_6$ alkyl)-O—($C_1$–$C_6$ alkyl)-OH; —CH$_2$—NH—CH$_2$—CH(—O—CH$_2$—CH$_3$)$_2$,
  —(CH$_2$)$_{0-6}$—C(=NR$_{235}$)(NR$_{235}$R$_{240}$), $C_1$–$C_{10}$ alkyl optionally substituted with 1, 2, or 3 groups independently selected from the group consisting of $R_{110}$, $R_{120}$ and $R_{130}$,
  $C_2$–$C_{10}$ alkyl optionally substituted with 1, 2, or 3 groups independently selected from the group consisting of $R_{205}$, $R_{110}$, $R_{120}$, $R_{130}$, —OC=ONR$_{235}$R$_{240}$, —S(=O)$_{0-2}$($C_1$–$C_6$ alkyl), —SH, and —S(=O)$_2$NR$_{235}$R$_{240}$,
  —(CH$_2$)$_{0-3}$—($C_3$–$C_8$) cycloalkyl wherein the cycloalkyl is optionally substituted with 1, 2, or 3 groups independently selected from the group consisting of $R_{205}$, —CO$_2$H, and —CO$_2$—($C_1$–$C_4$ alkyl), or
  cyclopentyl, cyclohexyl, or cycloheptyl ring fused to aryl, heteroaryl, or heterocyclyl wherein one, two or three carbons of the cyclopentyl, cyclohexyl, or cycloheptyl is optionally replaced with a heteroatom independently selected from NH, NR$_{215}$, O, and S(=O)$_{0-2}$, and wherein the cyclopentyl, cyclohexyl, or cycloheptyl group is optionally substituted with one or two groups that are independently $R_{205}$, =O, —CO—NR$_{235}$R$_{240}$, or —SO$_2$—($C_1$–$C_4$ alkyl), or
  $C_2$–$C_{10}$ alkenyl or $C_2$–$C_{10}$ alkynyl, each of which is optionally substituted with 1, 2, or 3 independently selected $R_{205}$ groups, wherein
  each aryl and heteroaryl is optionally substituted with 1, 2, or 3 $R_{200}$, and wherein each heterocyclyl is optionally substituted with 1, 2, 3, or 4 independently selected $R_{210}$;
$R_{200}$ at each occurrence is independently selected from —OH, —NO$_2$, halogen, —CO$_2$H, C≡N, —(CH$_2$)$_{0-4}$—CO—NR$_{220}$R$_{225}$, —(CH$_2$)$_{0-4}$—CO—($C_1$–$C_{12}$ alkyl), —(CH$_2$)$_{0-4}$—CO—($C_2$–$C_{12}$ alkenyl), —(CH$_2$)$_{0-4}$—CO—($C_2$–$C_{12}$ alkynyl), —(CH$_2$)$_{0-4}$—CO—($C_3$–$C_7$ cycloalkyl), —(CH$_2$)$_{0-4}$—CO-aryl, —(CH$_2$)$_{0-4}$—CO-heteroaryl, —(CH$_2$)$_{0-4}$—CO-heterocyclyl, —(CH$_2$)$_{0-4}$—CO—O—R$_{215}$, —(CH$_2$)$_{0-4}$—SO$_2$—NR$_{220}$R$_{225}$, —(CH$_2$)$_{0-4}$—SO—($C_1$–$C_8$ alkyl), —(CH$_2$)$_{0-4}$—SO$_2$—($C_1$–$C_{12}$ alkyl), —(CH$_2$)$_{0-4}$—SO$_2$—($C_3$–$C_7$ cycloalkyl), —(CH$_2$)$_{0-4}$—N(H or R$_{215}$)—CO—O—R$_{215}$, —(CH$_2$)$_{0-4}$—N(H or R$_{215}$)—CO—N(R$_{215}$)$_2$, —(CH$_2$)$_{0-4}$—N—CS—N(R$_{215}$)$_2$, —(CH$_2$)$_{0-4}$—N(—H or R$_{215}$)—CO—R$_{220}$, —(CH$_2$)$_{0-4}$—NR$_{220}$R$_{225}$, —(CH$_2$)$_{0-4}$—O—CO—($C_1$–$C_6$ alkyl), —(CH$_2$)$_{0-4}$—O—P(O)—(OR$_{240}$)$_2$, —(CH$_2$)$_{0-4}$—O—CO—N(R$_{215}$)$_2$, —(CH$_2$)$_{0-4}$—O—CS—N(R$_{215}$)$_2$, —(CH$_2$)$_{0-4}$—O—(R$_{215}$), —(CH$_2$)$_{0-4}$—O—(R$_{215}$)—COOH, —(CH$_2$)$_{0-4}$—S—(R$_{215}$), —(CH$_2$)$_{0-4}$—O—($C_1$–$C_6$ alkyl optionally substituted with 1, 2, 3, or 5 —F), $C_3$–$C_7$ cycloalkyl, —(CH$_2$)$_{0-4}$—N(H or R$_{215}$)—SO$_2$—R$_{220}$, —(CH$_2$)$_{0-4}$—$C_3$–$C_7$ cycloalkyl,
  $C_1$–$C_{10}$ alkyl optionally substituted with 1, 2, or 3 independently selected $R_{205}$ groups,
  $C_2$–$C_{10}$ alkenyl and $C_2$–$C_{10}$ alkynyl, each of which is optionally substituted with 1 or 2 independently selected $R_{205}$ groups, wherein
  the aryl and heteroaryl groups at each occurrence are optionally substituted with 1, 2, or 3 groups that are independently $R_{205}$, $R_{210}$, or
  $C_1$–$C_6$ alkyl substituted with 1, 2, or 3 groups that are independently $R_{205}$ or $R_{210}$, and wherein
  the heterocyclyl group at each occurrence is optionally substituted with 1, 2, or 3 groups that are independently $R_{210}$;
$R_{205}$ at each occurrence is independently selected from $C_1$–$C_6$ alkyl, halogen, —OH, —O—phenyl, —SH, —S—$C_1$–$C_6$ alkyl, —C≡N, —$CF_3$, $C_1$–$C_6$ alkoxy, $NH_2$, NH($C_1$–$C_6$ alkyl) or N—($C_1$–$C_6$ alkyl)($C_1$–$C_6$ alkyl)

$R_{210}$ at each occurrence is independently selected from halogen, $C_1$–$C_6$ alkoxy, $C_1$–$C_6$ haloalkoxy, —$NR_{220}R_{225}$, OH, C≡N, —CO—($C_1$–$C_4$ alkyl), —$SO_2$—$NR_{235}R_{240}$, —CO—$NR_{235}R_{240}$, —$SO_2$—($C_1$–$C_4$ alkyl), =O, or $C_1$–$C_6$ alkyl, $C_2$–$C_6$ alkenyl, $C_2$–$C_6$ alkynyl or $C_3$–$C_7$ cycloalkyl, each of which is optionally substituted with 1, 2, or 3 $R_{205}$ groups;

$R_{215}$ at each occurrence is independently selected from $C_1$–$C_6$ alkyl, —$(CH_2)_{0-2}$-(aryl), $C_2$–$C_6$ alkenyl, $C_2$–$C_6$ alkynyl, $C_3$–$C_7$ cycloalkyl, and —$(CH_2)_{0-2}$—(heteroaryl), —$(CH_2)_{0-2}$—(heterocyclyl), wherein
the aryl group at each occurrence is optionally substituted with 1, 2, or 3 groups that are independently $R_{205}$ or $R_{210}$, and wherein
the heterocyclyl and heteroaryl groups at each occurrence are optionally substituted with 1, 2, or 3 independently selected $R_{210}$;

$R_{220}$ and $R_{225}$ at each occurrence are independently selected from —H, —$C_3$–$C_7$ cycloalkyl, —($C_1$–$C_2$ alkyl)-($C_3$–$C_7$ cycloalkyl), —($C_1$–$C_6$ alkyl)-O—($C_1$–$C_3$ alkyl), —$C_2$–$C_6$ alkenyl, —$C_2$–$C_6$ alkynyl, —$C_1$–$C_6$ alkyl chain with one double bond and one triple bond, -aryl, -heteroaryl, and -heterocyclyl, and
—$C_1$–$C_{10}$ alkyl optionally substituted with —OH, —$NH_2$ or halogen, wherein
the aryl, heterocyclyl and heteroaryl groups at each occurrence are optionally substituted with 1, 2, or 3 independently selected $R_{270}$ groups $R_{235}$ and $R_{240}$ at each occurrence are independently H, or $C_1$–$C_6$ alkyl;

$R_{245}$ and $R_{250}$ at each occurrence are independently selected from —H, $C_1$–$C_4$ alkyl, $C_1$–$C_4$ alkylaryl, $C_1$–$C_4$ alkylheteroaryl, $C_1$–$C_4$ hydroxyalkyl, $C_1$–$C_4$ alkoxy, $C_1$–$C_4$ haloalkoxy, —$(CH_2)_{0-4}$—$C_3$–$C_7$ cycloalkyl, $C_2$–$C_6$ alkenyl, $C_2$–$C_6$ alkynyl, and phenyl; or $R_{245}$ and $R_{250}$ are taken together with the carbon to which they are attached to form a carbocycle of 3, 4, 5, 6, or 7 carbon atoms, where one carbon atom is optionally replaced by a heteroatom selected from —O—, —S—, —$SO_2$—, and —$NR_{220}$—;

$R_{255}$ and $R_{260}$ at each occurrence are independently selected from —H, —$(CH_2)_{1-2}$—S (O)$_{0-2}$—($C_1$–$C_6$ alkyl), —($C_1$–$C_4$ alkyl)-aryl, —($C_1$–$C_4$ alkyl)-heteroaryl, —($C_1$–$C_4$ alkyl)-heterocyclyl, -aryl, -heteroaryl, -heterocyclyl, —$(CH_2)_{1-4}$—$R_{265}$—$(CH_2)_{0-4}$-aryl, —$(CH_2)_{1-4}$—$R_{265}$—$(CH_2)_{0-4}$-heteroaryl, —$(CH_2)_{1-4}$—$R_{265}$—$(CH_2)_{0-4}$-heterocyclyl, and $C_1$–$C_6$ alkyl, $C_2$–$C_6$ alkenyl, $C_2$–$C_6$ alkynyl and —$(CH_2)_{0-4}$—$C_3$–$C_7$ cycloalkyl, each of which is optionally substituted with 1, 2, or 3 independently, selected $R_{205}$ groups, wherein
each aryl or phenyl is optionally substituted with 1, 2, or 3 groups that are independently $R_{205}$, $R_{210}$, or
$C_1$–$C_6$ alkyl substituted with 1, 2, or 3 groups that are independently $R_{205}$ or $R_{210}$, and wherein
each heterocyclyl is optionally substituted with 1, 2, 3, or 4 $R_{210}$;

$R_{265}$ at each occurrence is independently —O—, —S— or —N($C_1$–$C_6$ alkyl)-;

$R_{270}$ at each occurrence is independently $R_{205}$, halogen $C_1$–$C_6$ alkoxy, $C_1$–$C_6$ haloalkoxy, $NR_{235}R_{240}$, —OH, —C≡N, —CO—($C_1$–$C_4$ alkyl), —$SO_2$—$NR_{235}R_{240}$, —CO—$NR_{235}R_{240}$, —$SO_2$—($C_1$–$C_4$ alkyl), =O, or $C_1$–$C_6$ alkyl, $C_2$–$C_6$ alkenyl, $C_2$–$C_6$ alkynyl or —$(CH_2)_{0-4}$—$C_3$–$C_7$ cycloalkyl, each of which is optionally substituted with 1, 2, or 3 $R_{205}$ groups;

$R_N$ is $R'_{100}$, —$SO_2R'_{100}$, —$(CRR')_{1-6}R'_{100}$, —C(=O)—$(CRR')_{0-6}R_{100}$, —C(=O)—$(CRR')_{1-6}$—O—$R'_{100}$, —C(=O)—$(CRR')_{1-6}$—S—$R'_{100}$, —C(=O)—$(CRR')_{1-6}$—C(=O)—$(CRR')_{1-6}$ —C(=O)—$R_{100}$, —C(=O)—$(CRR')_{1-6}$—$SO_2$—$R_{100}$ or —C(=O)—$(CRR')_{1-6}$—$NR_{100}$—$R'_{100}$;

$R_{100}$ and $R'_{100}$ independently represent aryl, heteroaryl, heterocyclyl, -aryl-W-aryl, -aryl-W-heteroaryl, -aryl-W-heterocyclyl, -heteroaryl-W-aryl, -heteroaryl-W-heteroaryl, -heteroaryl-W-heterocyclyl, -heterocyclyl-W-aryl, -heterocyclyl-W-heteroaryl, -heterocyclyl-W-heterocyclyl, —CH[$(CH_2)_{0-2}$—O—$R_{150}$]—$(CH_2)_{0-2}$-aryl, —CH[$(CH_2)_{0-2}$—O—$R_{150}$]—$(CH_2)_{0-2}$-heterocyclyl or —CH[$(CH_2)_{0-2}$—O—$R_{150}$]—$(CH_2)_{0-2}$-heteroaryl, where the ring portions of each are optionally substituted with 1, 2, or 3 groups independently selected from
—OR, —$NO_2$, $C_1$–$C_6$ alkyl, halogen, —C≡N, —$OCF_3$, —$CF_3$, —$(CH_2)_{0-4}$—O—P(=O)(OR)(OR'), —$(CH_2)_{0-4}$—CO—$NR_{105}R'_{105}$, —$(CH_2)_{0-4}$—O—$(CH_2)_{0-4}$—$CONR_{102}R_{102}'$, —$(CH_2)_{0-4}$—CO—($C_1$–$C_{12}$ alkyl), —$(CH_2)_{0-4}$—CO—($C_2$–$C_{12}$ alkenyl), —$(CH_2)_{0-4}$—CO—($C_2$–$C_{12}$ alkynyl), —$(CH_2)_{0-4}$—CO—$(CH_2)_{0-4}$ ($C_3$–$C_7$ cycloalkyl), —$(CH_2)_{0-4}$—$R_{110}$, —$(CH_2)_{0-4}$—$R_{120}$, —$(CH_2)_{0-4}$—$R_{130}$, —$(CH_2)_{0-4}$—CO—$R_{110}$, —$(CH_2)_{0-4}$—CO—$R_{120}$, —$(CH_2)_{0-4}$—CO—$R_{130}$, —$(CH_2)_{0-4}$—CO—$R_{140}$, —$(CH_2)_{0-4}$—CO—O—$R_{150}$, —$(CH_2)_{0-4}$—$SO_2$—$NR_{105}R'_{105}$, —$(CH_2)_{0-4}$—SO—($C_1$–$C_8$ alkyl), —$(CH_2)_{0-4}$—$SO_2$—($C_1$–$C_{12}$ alkyl), —$(CH_2)_{0-4}$—$SO_2$—$(CH_2)_{0-4}$—($C_3$–$C_7$ cycloalkyl), —$(CH_2)_{0-4}$—N($R_{150}$)—CO—O—$R_{150}$, —$(CH_2)_{0-4}$—N($R_{150}$)—CO—N($R_{150}$)$_2$, —$(CH_2)_{0-4}$—N($R_{150}$)—CS—N($R_{150}$)$_2$, —$(CH_2)_{0-4}$—N($R_{150}$)—CO—$R_{105}$, —$(CH_2)_{0-4}$—$NR_{105}R'_{105}$, —$(CH_2)_{0-4}$—$R_{140}$, —$(CH_2)_{0-4}$—O—CO—($C_1$–$C_6$ alkyl), —$(CH_2)_{0-4}$—O—P(O)—(O—$R_{110}$)$_2$, —$(CH_2)_{0-4}$—O—CO—N($R_{150}$)$_2$, —$(CH_2)_{0-4}$—O—CS—N($R_{150}$)$_2$, —$(CH_2)_{0-4}$—O—($R_{150}$), —$(CH_2)_{0-4}$—O—$R_{150}'$—COOH, —$(CH_2)_{0-4}$—S—($R_{150}$), —$(CH_2)_{0-4}$—N($R_{150}$)—$SO_2$—$R_{105}$, —$(CH_2)_{0-4}$—$C_3$–$C_7$ cycloalkyl, ($C_2$–$C_{10}$)alkenyl, and ($C_2$–$C_{10}$)alkynyl, or $R_{100}$ is $C_1$–$C_{10}$ alkyl optionally substituted with 1, 2, or 3 $R_{115}$ groups, or $R_{100}$ is —($C_1$–$C_6$ alkyl)-O—$C_1$–$C_6$ alkyl) or —($C_1$–$C_6$ alkyl)-S—($C_1$–$C_6$ alkyl), each of which is optionally substituted with 1, 2, or 3 $R_{115}$ groups, or $R_{100}$ is $C_3$–$C_8$ cycloalkyl optionally substituted with 1, 2, or 3 $R_{115}$ groups;

W is —$(CH_2)_{0-4}$—, —O—, —S(O)$_{0-2}$—, —N($R_{135}$)—, —CR (OH)— or —C(O)—;

$R_{102}$ and $R_{102}'$ independently are hydrogen, or
$C_1$–$C_{10}$ alkyl optionally substituted with 1, 2, or 3 groups that are independently halogen, aryl or —$R_{110}$;

R105 and $R'_{105}$ independently represent —H, —$R_{110}$, —$R_{120}$, $C_3$–$C_7$ cycloalkyl, —($C_1$–$C_2$ alkyl)-($C_3$–$C_7$ cycloalkyl), —($C_1$–$C_6$ alkyl)-O—($C_1$–$C_3$ alkyl), $C_2$–$C_6$ alkenyl, $C_2$–$C_6$ alkynyl, or $C_1$–$C_6$ alkyl chain with one double bond and one triple bond, or
$C_1$–$C_6$ alkyl optionally substituted with —OH or —$NH_2$; or,
$C_1$–$C_6$ alkyl optionally substituted with 1, 2, or 3 groups independently selected from halogen, or $R_{105}$ and $R'_{105}$ together with the atom to which they are attached form a 3 to 7 membered carbocyclic ring, where one member is optionally a heteroatom selected from —O—, —S (O)$_{0-2}$—, —N($R_{135}$)—, the ring being optionally substituted with 1, 2 or 3 independently selected $R_{140}$ groups;

$R_{115}$ at each occurrence is independently halogen, —OH, —$CO_2R_{102}$, —$C_1$–$C_6$ thioalkoxy, —$CO_2$-phenyl, —$NR_{105}R'_{135}$, —$SO_2$—($C_1$–$C_8$ alkyl), —C(=O)$R_{180}$, $R_{180}$, —$CONR_{105}R'_{105}$, —$SO_2NR_{105}R'_{105}$, —NH—CO—($C_1$–$C_6$ alkyl), —NH—C(=O)—OH, —NH—C(=O)—OR, —NH—C(=O)—O-phenyl, —O—C(=O)—($C_1$–$C_6$ alkyl), —O—C(=O)-amino, —O—C(=O)-mono- or dialkylamino, —O—C(=O)-phenyl, —O—($C_1$–$C_6$ alkyl)-$CO_2$H, —NH—$SO_2$—($C_1$–$C_6$ alkyl), $C_1$–$C_6$ alkoxy or $C_1$–$C_6$ haloalkoxy;

$R_{135}$ is $C_1$–$C_6$ alkyl, $C_2$–$C_6$ alkenyl, $C_2$–$C_6$ alkynyl, $C_3$–$C_7$ cycloalkyl, —$(CH_2)_{0-2}$-(aryl), —$(CH_2)_{0-2}$-(heteroaryl), or —$(CH_2)_{0-2}$-(heterocyclyl);

$R_{140}$ is heterocyclyl optionally substituted with 1, 2, 3, or 4 groups independently selected from $C_1$–$C_6$ alkyl, $C_1$–$C_6$ alkoxy, halogen, hydroxy, cyano, nitro, amino, mono ($C_1$–$C_6$)alkylamino, di($C_1$–$C_6$) alkylamino, $C_2$–$C_6$ alkenyl, $C_2$–$C_6$ alkynyl, $C_1$–$C_6$ haloalkyl, $C_1$–$C_6$ haloalkoxy, amino($C_1$–$C_6$)alkyl, mono($C_1$–$C_6$) alkylamino ($C_1$–$C_6$)alkyl, di($C_1$–$C_6$)alkylamino($C_1$–$C_6$) alkyl, and =O;

$R_{145}$ is $C_1$–$C_6$ alkyl or $CF_3$;

$R_{150}$ is hydrogen, $C_3$–$C_7$ cycloalkyl, —($C_1$–$C_2$ alkyl)-($C_3$–$C_7$ cycloalkyl), $C_2$–$C_6$ alkenyl, $C_2$–$C_6$ alkynyl, $C_1$–$C_6$ alkyl with one double bond and one triple bond, —$R_{110}$, —$R_{120}$, or $C_1$–$C_6$ alkyl optionally substituted with 1, 2, 3, or 4 groups independently selected from —OH, —$NH_2$, $C_1$–$C_3$ alkoxy, $R_{110}$, and halogen;

$R_{150}'$ is $C_3$–$C_7$ cycloalkyl, —($C_1$–$C_3$ alkyl)-($C_3$–$C_7$ cycloalkyl), $C_2$–$C_6$ alkenyl, $C_2$–$C_6$ alkynyl, $C_1$–$C_6$ alkyl with one double bond and one triple bond, —$R_{110}$, —$R_{120}$, or $C_1$–$C_6$ alkyl optionally substituted with 1, 2, 3, or 4 groups independently selected from —OH, —$NH_2$, $C_1$–$C_3$ alkoxy, $R_{110}$, and halogen;

$R_{155}$ is $C_3$–$C_7$ cycloalkyl, —($C_1$–$C_2$ alkyl)-($C_3$–$C_7$ cycloalkyl) $C_2$–$C_6$ alkenyl, $C_2$–$C_6$ alkynyl, $C_1$–$C_6$ alkyl with one double bond and one triple bond, —$R_{110}$, —$R_{120}$, or $C_1$–$C_6$ alkyl optionally substituted with 1, 2, 3, or 4 groups independently selected from —OH, —$NH_2$, $C_1$–$C_3$ alkoxy, and halogen;

$R_{180}$ is selected from morpholinyl, thiomorpholinyl, piperazinyl, piperidinyl, homomorpholinyl, homothiomorpholinyl, homothiomorpholinyl S-oxide, homothiomorpholinyl S, S-dioxide, pyrrolinyl and pyrrolidinyl, each of which is optionally substituted with 1, 2, 3, or 4 groups independently selected from $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$ alkenyl, $C_2$–$C_6$ alkynyl, $C_1$–$C_6$ haloalkyl, $C_1$–$C_6$ haloalkoxy, amino($C_1$–$C_6$)alkyl, mono ($C_1$–$C_6$) alkylamino ($C_1$–$C_6$)alkyl, di($C_1$–$C_6$)alkylamino ($C_1$–$C_6$) alkyl, and =O;

$R_{110}$ is aryl optionally substituted with 1 or 2 $R_{125}$ groups;

$R_{125}$ at each occurrence is independently halogen, amino, mono- or dialkylamino, —OH, —C≡N, —$SO_2$—$NH_2$, —$SO_2$—NH—$C_1$–$C_6$ alkyl, —$SO_2$—N($C_1$–$C_6$ alkyl)$_2$, —$SO_2$—($C_1$–$C_4$ alkyl) —CO—$NH_2$, —CO—NH—$C_1$–$C_6$ alkyl, or —CO—N($C_1$–$C_6$ alkyl)$_2$, or $C_1$–$C_6$ alkyl, $C_2$–$C_6$ alkenyl or $C_2$–$C_6$ alkynyl, each of which is optionally substituted with 1, 2, or 3 groups that are independently selected from $C_1$–$C_3$ alkyl, halogen, —OH, —SH, —C≡N, —$CF_3$, $C_1$–$C_3$ alkoxy, amino, and mono- and dialkylamino, or $C_1$–$C_6$ alkoxy optionally substituted with one, two or three of halogen;

$R_{120}$ is heteroaryl, which is optionally substituted with 1 or 2 $R_{125}$ groups; and $R_{130}$ is heterocyclyl optionally substituted with 1 or 2 $R_{125}$ groups.

The invention also provides methods for the treatment or prevention of Alzheimer's disease, mild cognitive impairment Down's syndrome, Hereditary Cerebral Hemorrhage with Amyloidosis of the Dutch-Type, cerebral amyloid angiopathy, other degenerative dementias, dementias of mixed vascular and degenerative origin, dementia associated with Parkinson's disease, dementia associated with progressive supranuclear palsy, dementia associated with cortical basal degeneration, diffuse Lewy body type of Alzheimer's disease comprising administration of a therapeutically effective amount of a compound or salt of formula I, to a patient in need thereof.

Preferably, the patient is a human.

More preferably, the disease is Alzheimer's disease.

More preferably, the disease is dementia.

The invention also provides pharmaceutical compositions comprising a compound or salt of formula I and at least one pharmaceutically acceptable carrier, solvent, adjuvant or diluent.

The invention also provides the use of a compound or salt according to formula I for the manufacture of a medicament.

The invention also provides the use of a compound or salt of formula I for the treatment or prevention of Alzheimer's disease, mild cognitive impairment Down's syndrome, Hereditary Cerebral Hemorrhage with Amyloidosis of the Dutch-Type, cerebral amyloid angiopathy, other degenerative dementias, dementias of mixed vascular and degenerative origin, dementia associated with Parkinson's disease, dementia associated with progressive supranuclear palsy, dementia associated with cortical basal degeneration, or diffuse Lewy body type of Alzheimer's disease.

The invention also provides compounds, pharmaceutical compositions, kits, and methods for inhibiting beta-secretase-mediated cleavage of amyloid precursor protein (APP). More particularly, the compounds, compositions, and methods of the invention are effective to inhibit the production of A-beta peptide and to treat or prevent any human or veterinary disease or condition associated with a pathological form of A-beta peptide.

The compounds, compositions, and methods of the invention are useful for treating humans who have Alzheimer's Disease (AD), for helping prevent or delay the onset of AD, for treating patients with mild cognitive impairment (MCI), and preventing or delaying the onset of AD in those patients who would otherwise be expected to progress from MCI to AD, for treating Down's syndrome, for treating Hereditary Cerebral Hemorrhage with Amyloidosis of the Dutch Type, for treating cerebral beta-amyloid angiopathy and preventing its potential consequences such as single and recurrent lobar hemorrhages, for treating other degenerative dementias, including dementias of mixed vascular and degenerative origin, for treating dementia associated with Parkinson's disease, dementia associated with progressive supranuclear palsy, dementia associated with cortical basal degeneration, and diffuse Lewy body type AD, and for treating frontotemporal dementias with parkinsonism (FTDP).

The compounds of the invention possess beta-secretase inhibitory activity. The inhibitory activities of the compounds of the invention is readily demonstrated, for example, using one or more of the assays described herein or known in the art.

Unless the substituents for a particular formula are expressly defined for that formula, they are understood to carry the definitions set forth in connection with the preceeding formula to which the particular formula makes reference.

The invention also provides methods of preparing the compounds of the invention and the intermediates used in those methods.

DETAILED DESCRIPTION OF THE INVENTION

As noted above, the invention provides compounds of formula I.

Preferred compounds of formula I include those of formula I-1, i.e., compounds of formula I wherein $R_2$ is H.

Preferred compounds of formula I and formula I-1 include those of formula I-2, i.e., compounds of the formula I or I-1 wherein $R_1$ is aryl, heteroaryl, heterocyclyl, —$C_1$–$C_6$ alkyl-aryl, —$C_1$–$C_6$ alkyl-heteroaryl, or —$C_1$–$C_6$ alkyl-heterocyclyl, where the ring portions of each are optionally substituted with 1, 2, 3, or 4 groups independently selected from halogen, —OH, —SH, —C≡N, —$NO_2$, —$NR_{105}R'_{105}$, —$CO_2R$, —N(R)COR', or —N(R)$SO_2$R', —C(=O)—($C_1$–$C_4$)alkyl, —$SO_2$-amino, —$SO_2$-mono or dialkylamino, —C(=O)—amino, —C(=O)-mono or dialkylamino, —$SO_2$—($C_1$–$C_4$) alkyl, or $C_1$–$C_6$ alkoxy optionally substituted with 1, 2, or 3 groups which are independently selected from halogen, or $C_3$–$C_7$ cycloalkyl optionally substituted with 1, 2, or 3 groups independently selected from halogen, —OH, —SH, —C≡N, —$CF_3$, $C_1$–$C_3$ alkoxy, amino, —$C_1$–$C_6$ alkyl and mono- or dialkylamino, or $C_1$–$C_{10}$ alkyl optionally substituted with 1, 2, or 3 groups independently selected from halogen, —OH, —SH, —C≡N, —$CF_3$, —$C_1$–$C_3$ alkoxy, amino, mono- or dialkylamino and —$C_1$–$C_3$ alkyl, or $C_2$–$C_{10}$ alkenyl or $C_2$–$C_{10}$ alkynyl each of which is optionally substituted with 1, 2, or 3 groups independently selected from halogen, —OH, —SH, —C≡N, —$CF_3$, $C_1$–$C_3$ alkoxy, amino, $C_1$–$C_6$ alkyl and mono- or dialkylamino; and the heterocyclyl group is optionally further substituted with oxo.

More preferred compounds of formula I-2 include those wherein $R_1$ is —$C_1$–$C_6$ alkyl-aryl, —$C_1$–$C_6$ alkyl-heteroaryl, or —$C_1$–$C_6$ alkyl-heterocyclyl, where the ring portions of each are optionally substituted with 1, 2, 3, or 4 groups independently selected from halogen, —OH, —SH, —C≡N, —$NO_2$, —$NR_{105}R'_{105}$, —$CO_2R$, —N(R)COR', or —N(R)$SO_2$R', —C(=O)—($C_1$–$C_4$) alkyl, —$SO_2$-amino, —$SO_2$-mono or dialkylamino, —C(=O)-amino, —C(=O)-mono or dialkylamino, —$SO_2$—($C_1$–$C_4$) alkyl, or $C_1$–$C_6$ alkoxy optionally substituted with 1, 2, or 3 groups which are independently selected from halogen, or $C_3$–$C_7$ cycloalkyl optionally substituted with 1, 2, or 3 groups independently selected from halogen, —OH, —SH, —C≡N, —$CF_3$, $C_1$–$C_3$ alkoxy, amino, —$C_1$–$C_6$ alkyl and mono- or dialkylamino, or $C_1$–$C_{10}$ alkyl optionally substituted with 1, 2, or 3 groups independently selected from halogen, —OH, —SH, —C≡N, —$CF_3$, —$C_1$–$C_3$ alkoxy, amino, mono- or dialkylamino and —$C_1$–$C_3$ alkyl, or $C_2$–$C_{10}$ alkenyl or $C_2$–$C_{10}$ alkynyl each of which is optionally substituted with 1, 2, or 3 groups independently selected from halogen, —OH, —SH, —C≡N, —$CF_3$, $C_1$–$C_3$ alkoxy, amino, $C_1$–$C_6$ alkyl and mono- or dialkylamino; and the heterocyclyl group is optionally further substituted with oxo.

Still more preferred compounds of formula I-2 include those wherein $R_1$ is —($CH_2$)-aryl, —($CH_2$)-heteroaryl, or —($CH_2$)-heterocyclyl, where the ring portions of each are optionally substituted with 1, 2, 3, or 4 groups independently selected from halogen, —OH, —SH, —C≡N, —$NO_2$, —$NR_{105}R'_{105}$, —$CO_2R$, —N(R)COR', or —N(R)$SO_2$R', —C(=O)—($C_1$–$C_4$) alkyl, —$SO_2$-amino, —$SO_2$-mono or dialkylamino, —C(=O)-amino, —C(=O)-mono or dialkylamino, —$SO_2$—($C_1$–$C_4$) alkyl, or $C_1$–$C_6$ alkoxy optionally substituted with 1, 2, or 3 groups which are independently selected from halogen, or $C_3$–$C_7$ cycloalkyl optionally substituted with 1, 2, or 3 groups independently selected from halogen, —OH, —SH, —C≡N, —$CF_3$, $C_1$–$C_3$ alkoxy, amino, —$C_1$–$C_6$ alkyl and mono- or dialkylamino, or $C_1$–$C_{10}$ alkyl optionally substituted with 1, 2, or 3 groups independently selected from halogen, —OH, —SH, —C≡N, —$CF_3$, —$C_1$–$C_3$ alkoxy, amino, mono- or dialkylamino and —$C_1$–$C_3$ alkyl, or $C_2$–$C_{10}$ alkenyl or $C_2$–$C_{10}$ alkynyl each of which is optionally substituted with 1, 2, or 3 groups independently selected from halogen, —OH, —SH, —C≡N, —$CF_3$, $C_1$–$C_3$ alkoxy, amino, $C_1$–$C_6$ alkyl and mono- or dialkylamino; and the heterocyclyl group is optionally further substituted with oxo.

Yet more preferred compounds of formula I-2 include those wherein $R_1$ is —$CH_2$-phenyl or —$CH_2$-pyridinyl where the ring portions of each are optionally substituted with 1, 2, 3, or 4 groups independently selected from halogen, $C_1$–$C_4$ alkoxy, hydroxy, —$NO_2$, and $C_1$–$C_4$ alkyl optionally substituted with 1, 2, or 3 substituents independently selected from halogen, OH, SH, $NH_2$, NH($C_1$–$C_6$ alkyl), N—($C_1$–$C_6$ alkyl)($C_1$–$C_6$ alkyl), C≡N, $CF_3$.

Still more preferred compounds of formula I-2 include those wherein $R_1$ is —$CH_2$-phenyl or —$CH_2$-pyridinyl where the phenyl or pyridinyl rings are each optionally substituted with 1 or 2 groups independently selected from halogen, $C_1$–$C_2$ alkyl, $C_1$–$C_2$ alkoxy, hydroxy, —$CF_3$, and —$NO_2$.

Preferred compounds of formula I-2 include those wherein $R_1$ is —$CH_2$-phenyl or —$CH_2$-pyridinyl where the phenyl or pyridinyl rings are each optionally substituted with 2 groups independently selected from halogen, $C_1$–$C_2$ alkyl, $C_1$–$C_2$ alkoxy, hydroxy, and —$NO_2$.

Still yet more preferred compounds of formula I-2 include those wherein $R_1$ is —$CH_2$-pyridinyl, benzyl, 3,5-difluorobenzyl, or 5-hydroxybenzyl.

Preferred compounds of the formula I-2 also include:

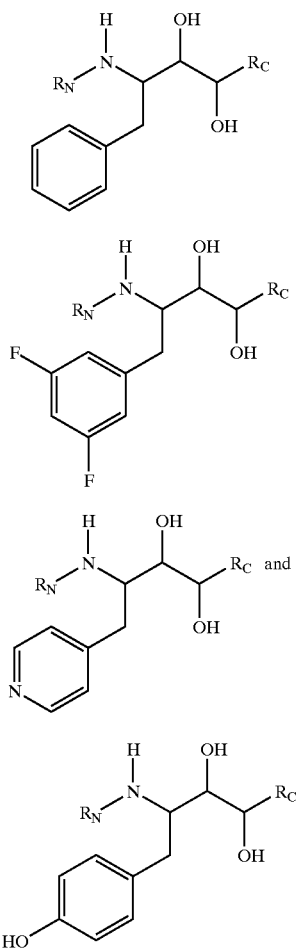

Preferred compounds of formula I-1 and formula I-2 include those of formula I-3, i.e., compounds of formula I-1 or formula I-2 wherein $R_C$ is hydrogen, —$(CR_{245}R_{250})_{0-4}$-aryl, —$(CR_{245}R_{250})_{0-4}$-heteroaryl, —$(CR_{245}R_{250})_{0-4}$-heterocyclyl, or
  $C_1$–$C_{10}$ alkyl optionally substituted with 1, 2, or 3 groups independently selected from the group consisting of $R_{110}$, $R_{120}$ and $R_{130}$, or
  $C_2$–$C_{10}$ alkyl optionally substituted with 1, 2, or 3 groups independently selected from the group consisting of $R_{205}$, $R_{110}$, $R_{120}$, $R_{130}$, —OC=ONR$_{235}$R$_{240}$, —S(=O)$_{0-2}$($C_1$–$C_6$ alkyl), —SH, and —S(=O)$_2$NR$_{235}$R$_{240}$, or
  $C_2$–$C_{10}$ alkenyl or $C_2$–$C_{10}$ alkynyl, each of which is optionally substituted with 1, 2, or 3 $R_{205}$ groups.

More preferred compounds of formula I-3 includes those wherein $R_C$ is $C_1$–$C_{10}$ alkyl optionally substituted with 1, 2, or 3 groups independently selected from the group consisting of $R_{110}$, $R_{120}$ and $R_{130}$, or
  $C_2$–$C_{10}$ alkyl optionally substituted with 1, 2, or 3 groups independently selected from the group consisting of $R_{205}$, $R_{110}$, $R_{120}$, $R_{130}$, —OC=ONR$_{235}$R$_{240}$, —S(=O)$_{0-2}$($C_1$–$C_6$ alkyl), —SH, and —S(=O)$_2$NR$_{235}$R$_{240}$, or
  $C_2$–$C_{10}$ alkenyl or $C_2$–$C_{10}$ alkynyl, each of which is optionally substituted with 1, 2, or 3 independently selected $R_{205}$ groups.

Still more preferred compounds of formula I-3 include those wherein $R_c$ is $C_2$–$C_{10}$ alkyl, $C_2$–$C_{10}$ alkenyl or $C_2$–$C_{10}$ alkynyl, each of which is optionally substituted with with 1, 2, or 3 groups independently selected from the group consisting of halogen, —OH, phenyl, —O—phenyl, —SH, —S—$C_1$–$C_6$ alkyl, —C≡N, —CF$_3$, $C_1$–$C_6$ alkoxy, NH$_2$, NH($C_1$–$C_6$ alkyl) and N—($C_1$–$C_6$ alkyl)($C_1$–$C_6$ alkyl)

Yet more preferred compounds of formula I-3 include those wherein $R_c$ is $C_2$–$C_6$ alkyl or $C_2$–$C_6$ alkynyl, each of which is optionally substituted with 1 or 2 groups independently selected from the group consisting of phenyl, —O-phenyl, —SH, —S—$C_1$–$C_6$ alkyl, —C≡N, $C_1$–$C_3$ alkoxy, and NH$_2$.

Still more preferred compounds of formula I-3 include those wherein $R_c$ is $C_2$–$C_6$ alkyl or $C_2$–$C_6$ alkynyl, each of which is optionally substituted with —S—$C_1$–$C_6$ alkyl, —C≡N, or $C_1$–$C_3$ alkoxy.

Still yet more preferred compounds of formula I-3 include those wherein Rc is —(CH$_2$)$_3$CH$_3$, —(CH$_2$)$_4$CH$_3$, —CH$_2$OCH$_3$, —(CH$_2$)$_2$OCH$_3$, —(CH$_2$)$_2$SCH$_3$, —(CH$_2$)$_3$SCH$_3$, —(CH$_2$)$_3$CCH, —CH$_2$CN, —(CH$_2$)$_2$CN, or —(CH$_2$)$_3$CN.

Preferred compounds of the formula I-3 also include:

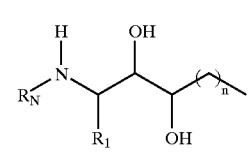

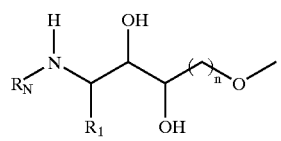

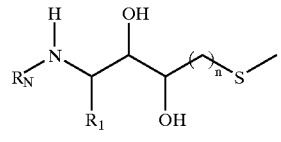

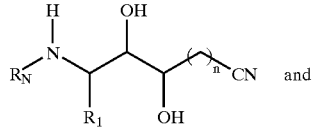

I-3-e

[Structure: $R_N$—NH—CH($R_1$)—CH(OH)—(CH$_2$)$_n$—CH(OH)—C≡CH]

wherein n is 0, 1, 2, 3, 4, or 5.

Other preferred compounds of formula I-1, I-2 and I-3 include compounds of formula I-4, i.e., those of formula I-1, I-2, or I-3 wherein $R_N$ is —C(=O)—(CRR')$_{0-6}$R$_{100}$;

$R_{100}$ represents aryl, heteroaryl, heterocyclyl, -aryl-W-aryl, -aryl-W-heteroaryl, -aryl-W-heterocyclyl, -heteroaryl-W-aryl, -heteroaryl-W-heteroaryl, -heteroaryl-W-heterocyclyl, -heterocyclyl-W-aryl, -heterocyclyl-W-heteroaryl, -heterocyclyl-W-heterocyclyl, —CH[(CH$_2$)$_{0-2}$—O—R$_{150}$]—(CH$_2$)$_{0-2}$-aryl, —CH[(CH$_2$)$_{0-2}$—O—R$_{150}$]—(CH$_2$)$_{0-2}$-heterocyclyl or —CH[(CH$_2$)$_{0-2}$—O—R$_{150}$]—(CH$_2$)$_{0-2}$-heteroaryl, where the ring portions of each are optionally substituted with 1, 2, or 3 groups independently selected from —OR, —NO$_2$, C$_1$–C$_6$ alkyl, halogen, —C≡N, —OCF$_3$, —CF$_3$, —(CH$_2$)$_{0-4}$—O—P(=O) (OR) (OR'), —(CH$_2$)$_{0-4}$—CO—NR$_{105}$R'$_{105}$, —(CH$_2$)$_{0-4}$—O—(CH$_2$)$_{0-4}$—CONR$_{102}$R$_{102}$', —(CH$_2$)$_{0-4}$—CO—(C$_1$–C$_{12}$ alkyl), —(CH$_2$)$_{0-4}$—CO—(C$_2$–C$_{12}$ alkenyl), —(CH$_2$)$_{0-4}$—CO—(C$_2$–C$_{12}$ alkynyl), —(CH$_2$)$_{0-4}$—CO—(CH$_2$)$_{0-4}$ (C$_3$–C$_7$ cycloalkyl), —(CH$_2$)$_{0-4}$—R$_{110}$, —(CH$_2$)$_{0-4}$—R$_{120}$, —(CH$_2$)$_{0-4}$—R$_{130}$, —(CH$_2$)$_{0-4}$—CO—R$_{110}$, —(CH$_2$)$_{0-4}$—CO—R$_{120}$, —(CH$_2$)$_{0-4}$—CO—R$_{130}$, —(CH$_2$)$_{0-4}$—CO—R$_{140}$, —(CH$_2$)$_{0-4}$—CO—O—R$_{150}$, —(CH$_2$)$_{0-4}$—SO$_2$—NR$_{105}$R'$_{105}$, —(CH$_2$)$_{0-4}$—SO—(C$_1$–C$_8$ alkyl), —(CH$_2$)$_{0-4}$—SO$_2$(C$_1$–C$_{12}$ alkyl), —(CH$_2$)$_{0-4}$—SO$_2$—(CH$_2$)$_{0-4}$—(C$_3$–C$_7$ cycloalkyl), —(CH$_2$)$_{0-4}$—N(R$_{150}$)—CO—O—R$_{150}$, —(CH$_2$)$_{0-4}$—N(R$_{150}$)—CO—N(R$_{15}$O)$_2$, —(CH$_2$)$_{0-4}$—N(R$_{150}$)—CS—N(R$_{150}$)$_2$, —(CH$_2$)$_{0-4}$—N(R$_{150}$)—CO—R$_{105}$, —(CH$_2$)$_{0-4}$—NR$_{105}$R'$_{105}$, —(CH$_2$)$_{0-4}$—R$_{140}$, —(CH$_2$)$_{0-4}$—O—(C$_1$–C$_6$ alkyl), —(CH$_2$)$_{0-4}$—O—P(O)—(O—R$_{110}$)$_2$, —(CH$_2$)$_{0-4}$—O—CO—N(R$_{150}$)$_2$, —(CH$_2$)$_{0-4}$—O—CS—N(R$_{15}$O)$_2$, —(CH$_2$)$_{0-4}$—O—(R$_{150}$), —(CH$_2$)$_{0-4}$—O—R$_{150}$'—COOH, —(CH$_2$)$_{0-4}$—S—(R$_{150}$), —(CH$_2$)$_{0-4}$—N(R$_{150}$)—SO$_2$—R$_{105}$, —(CH$_2$)$_{0-4}$—C$_3$–C$_7$ cycloalkyl, (C$_2$–C$_{10}$) alkenyl, or (C$_2$–C$_{10}$)alkynyl, or $R_{100}$ is C$_1$–C$_{10}$ alkyl optionally substituted with 1, 2, or 3 R$_{115}$ groups, or $R_{100}$ is —(C$_1$–C$_6$ alkyl)-O—C$_1$–C$_6$ alkyl) or —(C$_1$–C$_6$ alkyl)-S—(C$_1$–C$_6$ alkyl), each of which is optionally substituted with 1, 2, or 3 R$_{115}$ groups, or $R_{100}$ is C$_3$–C$_8$ cycloalkyl optionally substituted with 1, 2, or 3 R$_{115}$ groups.

Preferred compounds of formula I-4 include compounds wherein $R_N$ is —C(=O)—(CRR')$_{0-6}$R$_{100}$; and $R_{100}$ represents aryl, heteroaryl, or heterocyclyl, where the ring portions of each are optionally substituted with 1, 2, or 3 groups independently selected from —OR, —NO$_2$, C$_1$–C$_6$ alkyl, halogen, —C≡N, —OCF$_3$, —CF$_3$, —(CH$_2$)$_{0-4}$—O—P(=O) (OR) (OR'), —(CH$_2$)$_{0-4}$—CO—NR$_{105}$R'$_{105}$, —(CH$_2$)$_{0-4}$—O—(CH$_2$)$_{0-4}$—CONR$_{102}$R$_{102}$', —(CH$_2$)$_{0-4}$—CO—(C$_1$–C$_{12}$-alkyl), —(CH$_2$)$_{0-4}$—CO—(C$_2$–C$_{12}$ alkenyl), —(CH$_2$)$_{0-4}$—CO—(C$_2$–C$_{12}$ alkynyl), —(CH$_2$)$_{0-4}$—CO—(CH$_2$)$_{0-4}$ (C$_3$–C$_7$ cycloalkyl), —(CH$_2$)$_{0-4}$—R$_{110}$, —(CH$_2$)$_{0-4}$—R$_{120}$, —(CH$_2$)$_{0-4}$—R$_{130}$, —(CH$_2$)$_{0-4}$—CO—R$_{110}$, —(CH$_2$)$_{0-4}$—CO—R$_{120}$, —(CH$_2$)$_{0-4}$—CO—R$_{130}$, —(CH$_2$)$_{0-4}$—CO—R$_{140}$, —(CH$_2$)$_{0-4}$—CO—O—R$_{150}$, —(CH$_2$)$_{0-4}$—SO$_2$—NR$_{105}$R'$_{105}$, —(CH$_2$)$_{0-4}$—SO—(C$_1$–C$_8$ alkyl), —(CH$_2$)$_{0-4}$—SO$_2$(C$_1$–C$_{12}$ alkyl), —(CH$_2$)$_{0-4}$—SO$_2$—(CH$_2$)$_{0-4}$—(C$_3$–C$_7$ cycloalkyl), —(CH$_2$)$_{0-4}$—N(R$_{150}$)—CO—O—R$_{150}$, —(CH$_2$)$_{0-4}$—N(R$_{150}$)—CO—N(R$_{150}$)$_2$, —(CH$_2$)$_{0-4}$—N(R$_{150}$)—CS—N(R$_{150}$)$_2$, —(CH$_2$)$_{0-4}$—N(R$_{150}$)—CO—R$_{105}$, —(CH$_2$)$_{0-4}$—NR$_{105}$R'$_{105}$, —(CH$_2$)$_{0-4}$—R$_{140}$, —(CH$_2$)$_{0-4}$—O—CO—(C$_1$–C$_6$ alkyl), —(CH$_2$)$_{0-4}$—O—P(O)—(O—R$_{110}$)$_2$, —(CH$_2$)$_{0-4}$—O—CO—N(R$_{150}$)$_2$, —(CH$_2$)$_{0-4}$—O—CS—N(R$_{150}$)$_2$, —(CH$_2$)$_{0-4}$—O—(R$_{150}$), —(CH$_2$)$_{0-4}$—O—R$_{150}$'—COOH, —(CH$_2$)$_{0-4}$—S—(R$_{150}$), —(CH$_2$)$_{0-4}$—N(R$_{150}$)—SO$_2$—R$_{105}$, —(CH$_2$)$_{0-4}$—C$_3$–C$_7$ cycloalkyl, (C$_2$–C$_{10}$)alkenyl, or (C$_2$–C$_{10}$)alkynyl.

Still more preferred compounds of formula I-4 include compounds wherein $R_N$ is —C(=O)—R$_{100}$; and $R_{100}$ represents aryl, or heteroaryl, where the ring portions of each are optionally substituted with 1, 2, or 3 groups independently selected from —OR, —NO$_2$, C$_1$–C$_6$ alkyl, halogen, —C≡N, —OCF$_3$, —CF$_3$, —(CH$_2$)$_{0-4}$—O—P(=O) (OR) (OR'), —(CH$_2$)$_{0-4}$—CO—NR$_{105}$R'$_{105}$, —(CH$_2$)$_{0-4}$—O—(CH$_2$)$_{0-4}$—CONR$_{102}$R$_{102}$', —(CH$_2$)$_{0-4}$—CO—(C$_1$–C$_{12}$ alkyl), —(CH$_2$)$_{0-4}$—CO—(C$_2$–C$_{12}$ alkenyl), —(CH$_2$)$_{0-4}$—CO—(C$_2$–C$_{12}$ alkynyl), —(CH$_2$)$_{0-4}$—CO—(CH$_2$)$_{0-4}$ (C$_3$–C$_7$ cycloalkyl), —(CH$_2$)$_{0-4}$—R$_{110}$, —(CH$_2$)$_{0-4}$—R$_{120}$, —(CH$_2$)$_{0-4}$—R$_{130}$, —(CH$_2$)$_{0-4}$—CO—R$_{110}$, —(CH$_2$)$_{0-4}$—CO—R$_{120}$, —(CH$_2$)$_{0-4}$—CO—R$_{130}$, —(CH$_2$)$_{0-4}$—CO—R$_{140}$, —(CH$_2$)$_{0-4}$—CO—O—R$_{150}$, —(CH$_2$)$_{0-4}$—SO$_2$—NR$_{105}$R'$_{105}$, —(CH$_2$)$_{0-4}$—SO—(C$_1$–C$_8$ alkyl), —(CH$_2$)$_{0-4}$—SO$_2$—(C$_1$–C$_{12}$ alkyl), —(CH$_2$)$_{0-4}$—SO$_2$—(CH$_2$)$_{0-4}$ (C$_3$–C$_7$ cycloalkyl), —(CH$_2$)$_{0-4}$—N(R$_{150}$)—CO—O—R$_{150}$, —(CH$_2$)$_{0-4}$—N(R$_{150}$)—CO—N(R$_{150}$)$_2$, —(CH$_2$)$_{0-4}$—N(R$_{150}$)—CS—N(R$_{150}$)$_2$, —(CH$_2$)$_{0-4}$—N(R$_{150}$)—CO—R$_{105}$, —(CH$_2$)$_{0-4}$—NR$_{105}$R'$_{105}$, —(CH$_2$)$_{0-4}$—R$_{140}$, —(CH$_2$)$_{0-4}$—O—CO—(C$_1$–C$_6$ alkyl), —(CH$_2$)$_{0-4}$—O—P(O)—(O—R$_{110}$)$_2$, —(CH$_2$)$_{0-4}$—O—CO—N(R$_{150}$)$_2$, —(CH$_2$)$_{0-4}$—O—CS—N(R$_{150}$)$_2$, —(CH$_2$)$_{0-4}$—O—(R$_{150}$), —(CH$_2$)$_{0-4}$—O—R$_{150}$'—COOH, —(CH$_2$)$_{0-4}$—S—(R$_{150}$) —(CH$_2$)$_{0-4}$—N(R$_{150}$)—SO$_2$—R$_{105}$, —(CH$_2$)$_{0-4}$—C$_3$–C$_7$ cycloalkyl, (C$_2$–C$_{10}$)alkenyl, or (C$_2$–C$_{10}$)alkynyl.

More preferred compounds of formula I-4 include compounds wherein $R_N$ is —C(=O)-aryl or —C(=O)-heteroaryl where the ring portions of each are optionally substituted with 1, 2, or 3 groups independently selected from —OR, —NO$_2$, C$_1$–C$_6$ alkyl, halogen, —C≡N, —OCF$_3$, —CF$_3$, —(CH$_2$)$_{0-4}$—CO—NR$_{105}$R'$_{105}$, —(CH$_2$)$_{0-4}$—O—(CH$_2$)$_{0-4}$—CONR$_{102}$R$_{102}$', —(CH$_2$)$_{0-4}$—CO—(C$_1$–C$_{12}$ alkyl), —(CH$_2$)$_{0-4}$—CO—(C$_2$–C$_{12}$ alkenyl), —(CH$_2$)$_{0-4}$—CO—(C$_2$–C$_{12}$ alkynyl), —(CH$_2$)$_{0-4}$—R$_{110}$, —(CH$_2$)$_{0-4}$—R$_{120}$, —(CH$_2$)$_{0-4}$—R$_{130}$, —(CH$_2$)$_{0-4}$—CO—R$_{110}$, —(CH$_2$)$_{0-4}$—CO—R$_{120}$, —(CH$_2$)$_{0-4}$—CO—R$_{130}$, —(CH$_2$)$_{0-4}$—CO—R$_{140}$, —(CH$_2$)$_{0-4}$—

CO—O—R$_{150}$, —(CH$_2$)$_{0-4}$—SO$_2$—NR$_{105}$R'$_{105}$, —(CH$_2$)$_{0-4}$—SO—(C$_1$-C$_8$ alkyl), —(CH$_2$)$_{0-4}$—SO$_2$ (C$_1$-C$_{12}$ alkyl), —(CH$_2$)$_{0-4}$—N(R$_{150}$)—CO—O—R$_{150}$, —(CH$_2$)$_{0-4}$—N(R$_{150}$)—CO—N(R$_{150}$)$_2$, —(CH$_2$)$_{0-4}$
ba —N(R$_{150}$)—CO—R$_{105}$, —(CH$_2$)$_{0-4}$—NR$_{105}$R'$_{105}$, —(CH$_2$)$_{0-4}$—R$_{140}$, —(CH$_2$)$_{0-4}$—O—CO—(C$_1$-C$_6$ alkyl), —(CH$_2$)$_{0-4}$—O—CO—N(R$_{150}$)$_2$, —(CH$_2$)$_{0-4}$—O—(R$_{150}$), —(CH$_2$)$_{0-4}$—N(R$_{150}$) SO$_2$—R$_{105}$, —(CH$_2$)$_{0-4}$—C$_3$-C$_7$ cycloalkyl, (C$_2$-C$_{10}$)alkenyl, or (C$_2$-C$_{10}$)alkynyl.

Still more preferred compounds of formula I-4 include compounds wherein

R$_N$ is —C(=O)-aryl or —C(=O)-heteroaryl where the ring portions of each are optionally substituted with 1 or 2 groups independently selected from
C$_1$-C$_6$ alkyl, halogen, —(CH$_2$)$_{0-4}$—CO—NR$_{105}$R'$_{105}$, —(CH$_2$)$_{0-4}$—O—CO—N(R$_{150}$)$_2$, —(CH$_2$)$_{0-4}$—N (R$_{150}$)-SO$_2$—R$_{105}$.

More preferred compounds of formula I-4 include compounds wherein

R$_N$ is —C(=O)-phenyl, —C(=O)-oxazolyl, or —C(=O)-thiazolyl, where the ring portion of each is optionally substituted with 1 Or 2 groups independently selected from
C$_1$-C$_6$ alkyl, halogen, —(CH$_2$)$_{0-4}$—CO—NR$_{105}$R'$_{105}$, —(CH$_2$)$_{0-4}$—O—CO—N(R$_{150}$)$_2$, —(CH$_2$)$_{0-4}$—N (R$_{150}$)—SO$_2$—R$_{105}$.

Still more preferred compounds of formula I-4 include compounds wherein

R$_N$ is —C(=O)-phenyl, —C(=O)-oxazolyl, or —C(=O)-thiazolyl, where the ring portion of each is optionally substituted with 1 or 2 groups independently selected from
C$_1$-C$_3$ alkyl, halogen, —CO—NR$_{105}$R'$_{105}$, and —N(R$_{150}$)—SO$_2$—R$_{105}$, wherein R$_{105}$ and R'105 R$_{150}$ are independently H or C$_1$-C$_6$ alkyl.

Preferred compounds of the formula I-4 also include:

I-4-a
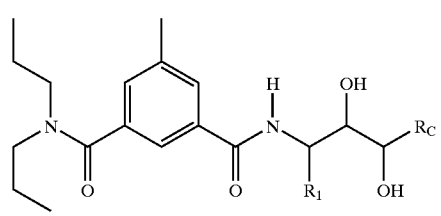

I-4-b
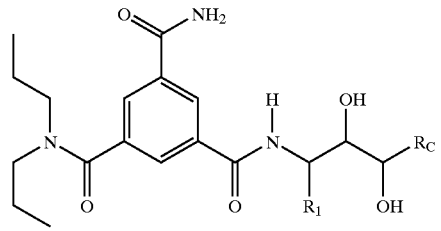

I-4-c
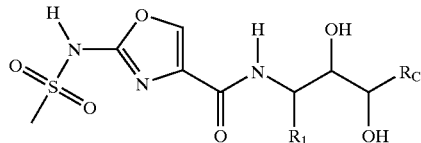

I-4-d
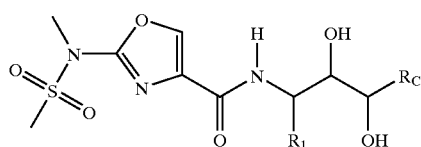

I-4-e
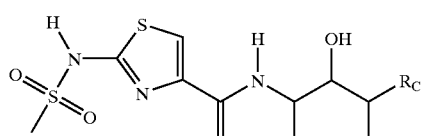

I-4-f
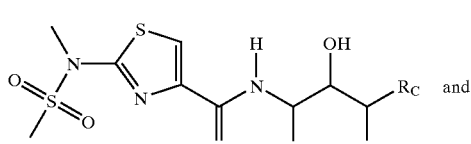 and

I-4-g
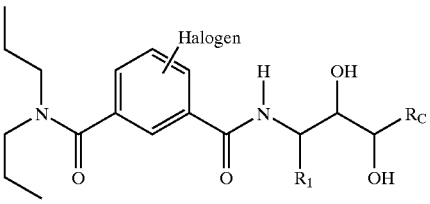

Other preferred compounds of formula I-4 include those of formula I-5, i.e., compounds of I-4 wherein R$_1$ is —(CH$_2$)-aryl, —(CH$_2$)-heteroaryl, or —(CH$_2$)-heterocyclyl, where the ring portions of each are optionally substituted with 1, 2, 3, or 4 groups independently selected from halogen, —OH, —SH, —C≡N, —NO$_2$, —NR$_{105}$R'$_{105}$, —CO$_2$R, —N(R)COR', or —N(R)SO$_2$R', —C(=O)—(C$_1$-C$_4$) alkyl, —SO$_2$-amino, —SO$_2$-mono or dialkylamino, —C(=O)—amino, —C(=O)-mono or dialkylamino, —SO$_2$—(C$_1$-C$_4$) alkyl, or
C$_1$-C$_6$ alkoxy optionally substituted with 1, 2, or 3 groups which are independently selected from halogen, or
C$_3$-C$_7$ cycloalkyl optionally substituted with 1, 2, or 3 groups independently selected from halogen, —OH, —SH, —C≡N, —CF$_3$, C$_1$-C$_3$ alkoxy, amino, —C$_1$-C$_6$ alkyl and mono- or dialkylamino, or
C$_1$-C$_{10}$ alkyl optionally substituted with 1, 2, or 3 groups independently selected from halogen, —OH, —SH, —C≡N —CF$_3$, —C$_1$-C$_3$ alkoxy, amino, mono- or dialkylamino and —C$_1$-C$_3$ alkyl, or
C$_2$-C$_{10}$ alkenyl or C$_2$-C$_{10}$ alkynyl each of which is optionally substituted with 1, 2, or 3 groups independently selected from halogen, —OH, —SH, —C≡N, —CF$_3$, C$_1$-C$_3$ alkoxy, amino, C$_1$-C$_6$ alkyl and mono- or dialkylamino; and the heterocyclyl group is optionally further substituted with oxo;

R$_2$ is H;

R$_C$ C$_1$-C$_{10}$ alkyl optionally substituted with 1, 2, or 3 groups independently selected from the group consisting of R$_{110}$, R$_{120}$ and R$_{130}$, or $C_2$–$C_{10}$ alkyl optionally substituted with 1, 2, or 3 groups independently selected from the group consisting of $R_{205}$, $R_{110}$, $R_{120}$, $R_{130}$, —OC=ON$R_{235}R_{240}$, —S(=O)$_{0-2}$($C_1$–$C_6$ alkyl), —SH, and —S(=O)$_2$ N$R_{235}R_{240}$, or $C_2$–$C_{10}$ alkenyl or $C_2$–$C_{10}$alkynyl, each of which is optionally substituted with 1, 2, or 3 $R_{205}$ groups;

$R_N$ is —C(=O)—(CRR')$_{0-6}R_{100}$; and $R_{100}$ represents aryl, heteroaryl, or heterocyclyl, where the ring portions of each are optionally substituted with 1, 2, or 3 groups independently selected from —OR, —NO$_2$, $C_1$–$C_6$ alkyl, halogen, —C≡N, —OCF$_3$, —CF$_3$, —(CH$_2$)$_{0-4}$—O—P(=O) (OR) (OR'), —(CH$_2$)$_{0-4}$—CO—N$R_{105}R'_{105}$, —(CH$_2$)$_{0-4}$—O—(CH$_2$)$_{0-4}$—CON$R_{102}R_{102}$', —(CH$_2$)$_{0-4}$—CO—($C_1$–$C_{12}$alkyl), —(CH$_2$)$_{0-4}$—CO—($C_2$–$C_{12}$ alkenyl), —(CH$_2$)$_{0-4}$—CO—($C_2$–$C_{12}$ alkynyl), —(CH$_2$)$_{0-4}$—CO—(CH$_2$)$_{0-4}$ ($C_3$–$C_7$ cycloalkyl), —(CH$_2$)$_{0-4}$—$R_{110}$, —(CH$_2$)$_{0-4}$—$R_{120}$, —(CH$_2$)$_{0-4}$—$R_{130}$, —(CH$_2$)$_{0-4}$—CO—$R_{110}$, —(CH$_2$)$_{0-4}$—CO—$R_{120}$, —(CH$_2$)$_{0-4}$—CO—$R_{130}$, —(CH$_2$)$_{0-4}$—CO—$R_{140}$, —(CH$_2$)$_{0-4}$—CO—O—$R_{150}$, —(CH$_2$)$_{0-4}$—SO$_2$—N$R_{105}R'_{105}$, —(CH$_2$)$_{0-4}$—SO—($C_1$–$C_8$ alkyl), —(CH$_2$)$_{0-4}$—SO$_2$ ($C_1$–$C_{12}$ alkyl), —(CH$_2$)$_{04}$—SO$_2$—(CH$_2$)$_{0-4}$—($C_3$–$C_7$ cycloalkyl), —(CH$_2$)$_{0-4}$—N($R_{150}$)—CO—O—$R_{150}$, —(CH$_2$)$_{0-4}$—N($R_{150}$)—CO—N($R_{150}$)$_2$, —(CH$_2$)$_{0-4}$—N($R_{150}$)—CS—N($R_{150}$)$_2$, —(CH$_2$)$_{0-4}$—N($R_{150}$)—CO—$R_{105}$, —(CH$_2$)$_{0-4}$—N$R_{105}R'_{105}$, —(CH$_2$)$_{0-4}$—$R_{140}$, —(CH$_2$)$_{0-4}$—O—CO—($C_1$–$C_6$ alkyl), —(CH$_2$)$_{0-4}$—O—P(O)—(O—$R_{110}$)$_2$, —(CH$_2$)$_{0-4}$—O—CO—N($R_{150}$)$_2$, —(CH$_2$)$_{0-4}$—O—CS—N($R_{150}$)$_2$, —(CH$_2$)$_{0-4}$—O—($R_{150}$), —(CH$_2$)$_{0-4}$—O—$R_{150}$'—COOH, —(CH$_2$)$_{0-4}$—S—($R_{150}$), —(CH$_2$)$_{0-4}$—N ($R_{150}$)—SO$_2$—$R_{105}$, —(CH$_2$)$_{0-4}$—$C_3$–$C_7$ cycloalkyl, ($C_2$–$C_{10}$) alkenyl, or ($C_2$–$C_{10}$)alkynyl.

Preferred compounds of formula I-5 include those of formula I-6, i.e., compounds of formula I-5 wherein $R_1$ is —CH$_2$-phenyl or —CH$_2$-pyridinyl where the ring portions of each are optionally substituted with 1, 2, 3, or 4 groups independently selected from halogen, $C_1$–$C_4$ alkoxy, hydroxy, —NO$_2$, and $C_1$–$C_4$ alkyl optionally substituted with 1, 2, or 3 substituents halogen, OH, SH, NH$_2$, NH($C_1$–$C_6$ alkyl), N—($C_1$–$C_6$ alkyl) ($C_1$–$C_6$ alkyl), C≡N, CF$_3$;

$R_2$ is H;

$R_C$ is $C_1$–$C_{10}$ alkyl optionally substituted with 1, 2, or 3 groups independently selected from the group consisting of $R_{110}$, $R_{120}$ and $R_{130}$, or $C_2$–$C_{10}$alkyl optionally substituted with 1, 2, or 3 groups independently selected from the group consisting of $R_{205}$, $R_{110}$, $R_{120}$, $R_{130}$, —OC=ON$R_{235}R_{240}$, —S(=O)$_{0-2}$($C_1$–$C_6$ alkyl), —SH, and —S(=O)$_2$ N$R_{235}R_{240}$, or $C_2$–$C_{10}$alkenyl or $C_2$–$C_{10}$alkynyl, each of which is optionally substituted with 1, 2, or 3 $R_{205}$ groups;

$R_N$ is —C(=O)—$R_{100}$; and $R_{100}$ represents aryl, or heteroaryl, where the ring portions of each are optionally substituted with 1, 2, or 3 groups independently selected from —OR, —NO$_2$, $C_1$–$C_6$ alkyl, halogen, —C≡N, —OCF$_3$, —CF$_3$, —(CH$_2$)$_{0-4}$—O—P(=O) (OR) (OR'), —(CH$_2$)$_{0-4}$—CO—N$R_{105}R'_{105}$, —(CH$_2$)$_{0-4}$—O—(CH$_2$)$_{0-4}$—CON$R_{102}R_{102}$', —(CH$_2$)$_{0-4}$—CO—($C_1$– alkyl), —(CH$_2$)$_{0-4}$—CO—($C_2$–$C_{12}$ alkenyl), —(CH$_2$)$_{0-4}$—CO—($C_2$–$C_{12}$ alkynyl), —(CH$_2$)$_{0-4}$—CO—(CH$_2$)$_{0-4}$ ($C_3$–$C_7$ cycloalkyl), —(CH$_2$)$_{0-4}$—$R_{110}$, —(CH$_2$)$_{0-4}$—$R_{120}$, —(CH$_2$)$_{0-4}$—$R_{130}$, —(CH$_2$)$_{0-4}$—CO—$R_{110}$, —(CH$_2$)$_{0-4}$—CO—$R_{120}$, —(CH$_2$)$_{0-4}$—CO—$R_{130}$, —(CH$_2$)$_{0-4}$—CO—$R_{140}$, —(CH$_2$)$_{0-4}$—CO—O—$R_{150}$, —(CH$_2$)$_{0-4}$—SO$_2$—N$R_{105}R'_{105}$, -(CH$_2$)$_{0-4}$—SO—($C_1$–$C_8$ alkyl), —(CH$_2$)$_{0-4}$—SO$_2$ ($C_1$–$C_{12}$ alkyl), —(CH$_2$)$_{0-4}$-SO$_2$—(CH$_2$)$_{0-4}$—($C_3$–$C_7$ cycloalkyl), —(CH$_2$)$_{0-4}$—N($R_{150}$)—CO—O—$R_{150}$, —(CH$_2$)$_{0-4}$—N($R_{150}$)—CO—N($R_{150}$)$_2$, —(CH$_2$)$_{0-4}$—N($R_{150}$)—CS—N($R_{150}$)$_2$, —(CH$_2$)$_{0-4}$—N($R_{150}$)—CO—$R_{105}$, —(CH$_2$)$_{0-4}$—N$R_{105}R'_{105}$, —(CH$_2$)$_{0-4}$—$R_{140}$, —(CH$_2$)$_{0-4}$—O—CO—($C_1$–$C_6$ alkyl), —(CH$_2$)$_{0-4}$—O—P(O)—(O—$R_{110}$)$_2$, —(CH$_2$)$_{0-4}$—O—CO—N($R_{150}$)$_2$, —(CH$_2$)$_{0-4}$—O—CS—N($R_{150}$)$_2$, —(CH$_2$)$_{0-4}$—O—($R_{150}$), —(CH$_2$)$_{0-4}$—O—$R_{150}$—COOH, —(CH$_2$)$_{0-4}$—S—($R_{150}$), —(CH$_2$)$_{0-4}$—N ($R_{150}$)—SO$_2$—$R_{105}$, —(CH$_2$)$_{0-4}$—$C_3$–$C_7$ cycloalkyl, ($C_2$–$C_{10}$)alkenyl, or ($C_2$–$C_{10}$)alkynyl.

Preferred compounds of formula I-6 include compounds of formula I-7:

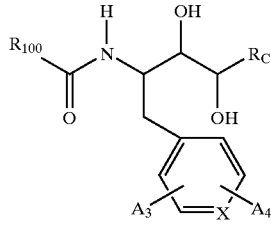

I-7 wherein X is CH or N;

$A_3$ and $A_4$ are independently hydrogen, halogen, $C_1$–$C_4$ alkoxy, hydroxy, and $C_1$–$C_4$ alkyl optionally substituted with 1, 2, or 3 substituents halogen, OH, SH, NH$_2$, NH ($C_1$–$C_6$ alkyl), N—($C_1$–$C_6$ alkyl) ($C_1$–$C_6$ alkyl), C≡N, CF$_3$;

$R_{100}$ represents aryl, or heteroaryl, where the ring portions of each are optionally substituted with 1, 2, or 3 groups independently selected from —OR, —NO$_2$, $C_1$–$C_6$ alkyl, halogen, —C≡N, —OCF$_3$, —CF$_3$, —(CH$_2$)$_{0-4}$—O—P(=O)(OR)(OR'), —(CH$_2$)$_{0-4}$—CO—N$R_{105}R'_{105}$, —(CH$_2$)$_{0-4}$—O—(CH$_2$)$_{0-4}$—CON$R_{102}R_{102}$', —(CH$_2$)$_{0-4}$—CO—($C_1$–$C_{12}$ alkyl), —(CH$_2$)$_{0-4}$—CO—($C_2$–$C_{12}$ alkenyl), —(CH$_2$)$_{0-4}$—CO—($C_2$–$C_{12}$ alkynyl), —(CH$_2$)$_{0-4}$—CO—(CH$_2$)$_{0-4}$ ($C_3$–$C_7$ cycloalkyl), —(CH$_2$)$_{0-4}$—$R_{110}$, —(CH$_2$)$_{0-4}$—$R_{120}$, —(CH$_2$)$_{0-4}$—$R_{130}$, —(CH$_2$)$_{0-4}$—CO—$R_{110}$, —(CH$_2$)$_{0-4}$—CO—$R_{120}$, —(CH$_2$)$_{0-4}$—CO—$R_{130}$, —(CH$_2$)$_{0-4}$—CO—$R_{140}$, —(CH$_2$)$_{0-4}$—CO—O—$R_{150}$, —(CH$_2$)$_{0-4}$—SO$_2$—N$R_{105}R'_{105}$, —(CH$_2$)$_{0-4}$—SO—($C_1$–$C_8$ alkyl), —(CH$_2$)$_{0-4}$—SO$_2$ ($C_1$–$C_{12}$ alkyl), —(CH$_2$)$_{0-4}$—SO$_2$—(CH$_2$)$_{0-4}$—($C_3$–$C_7$ cycloalkyl), —(CH$_2$)$_{0-4}$—N($R_{150}$)—CO—O—$R_{150}$, —(CH$_2$)$_{0-4}$—N($R_{150}$)—CO—N($R_{150}$)$_2$, —(CH$_2$)$_{0-4}$—N($R_{150}$)—CS—N($R_{150}$)$_2$, —(CH$_2$)$_{0-4}$—N($R_{150}$)—CO—$R_{105}$, —(CH$_2$)$_{0-4}$—N$R_{105}R'_{105}$, —(CH$_2$)$_{0-4}$—$R_{140}$, —(CH$_2$)$_{0-4}$—O—CO—($C_1$–$C_6$ alkyl), —(CH$_2$)$_{0-4}$—O—P(O)—(O—$R_{110}$)$_2$, —(CH$_2$)$_{0-4}$—O—CO—N(R,50)$_2$, —(CH$_2$)$_{0-4}$—O—CS—N($R_{150}$)$_2$, —(CH$_2$)$_{0-4}$—O—($R_{150}$), —(CH$_2$)$_{0-4}$—O—$R_{150}$'—COOH, —(CH$_2$)$_{04}$—S—($R_{150}$), —(CH$_2$)$_{0-4}$—N ($R_{150}$)—SO$_2$—$R_{105}$, —(CH$_2$)$_{0-4}$—$C_3$–$C_7$ cycloalkyl, ($C_2$–$C_{10}$)alkenyl, or ($C_2$–$C_{10}$)alkynyl;

$R_c$ is $C_1$–$C_{10}$ alkyl optionally substituted with 1, 2, or 3 groups independently selected from the group consisting of $R_{110}$, $R_{120}$ and $R_{130}$, or $C_2$–$C_{10}$ alkyl optionally substituted with 1, 2, or 3 groups independently selected from the group consisting of $R_{205}$, $R_{110}$, $R_{120}$, $R_{130}$, —OC=ON$R_{235}R_{240}$, —S(=O)$_{0-2}$($C_1$–$C_6$ alkyl), —SH, and —S(=O)$_2$N$R_{235}R_{240}$, or $C_2$–$C_{10}$ alkenyl or $C_2$–$C_{10}$ alkynyl, each of which is optionally substituted with 1, 2, or 3 $R_{205}$ groups; and $R_{102}$, $R_{102}'$, $R_{105}$, $R_{105}'$, $R_{110}$, $R_{120}$, $R_{130}$, $R_{140}$, $R_{150}$, $R_{150}'$, $R_{205}$, $R_{235}$ and $R_{240}$ are as defined above for formula I.

Preferred compounds of formula I-7 include those of formula I-7-a:

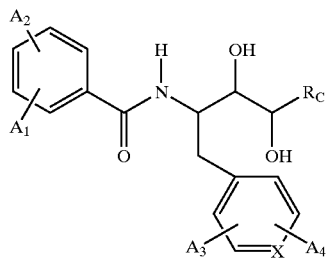

I-7-a wherein $A_1$ and $A_2$ are independently —OR, —NO$_2$, $C_1$–$C_6$ alkyl, halogen, —C≡N, —OCF$_3$, —CF$_3$, —(CH$_2$)$_{0-4}$—O—P(=O)(OR)(OR'), —(CH$_2$)$_{0-4}$—CO—N$R_{105}R'_{105}$, —(CH$_2$)$_{0-4}$—O—(CH$_2$)$_{0-4}$—CON$R_{102}R_{102}'$, —(CH$_2$)$_{0-4}$—CO—($C_1$–$C_{12}$ alkyl), —(CH$_2$)$_{0-4}$—CO—($C_2$–$C_{12}$ alkenyl), —(CH$_2$)$_{0-4}$—CO—($C_2$–$C_{12}$ alkynyl), —(CH$_2$)$_{0-4}$—CO—(CH$_2$)$_{0-4}$($C_3$–$C_7$ cycloalkyl), —(CH$_2$)$_{0-4}$—$R_{110}$, —(CH$_2$)$_{0-4}$—$R_{120}$, —(CH$_2$)$_{0-4}$—$R_{130}$, -(CH$_2$)$_{0-4}$—CO—$R_{110}$, —(CH$_2$)$_{0-4}$—O—$R_{120}$, —(CH$_2$)$_{0-4}$—CO—$R_{130}$, —(CH$_2$)$_{0-4}$—CO—$R_{140}$, —(CH$_2$)$_{0-4}$—CO—O—$R_{150}$, —(CH$_2$)$_{0-4}$-SO$_2$—N$R_{105}R'_{105}$, —(CH$_2$)$_{0-4}$—SO—($C_1$–$C_8$ alkyl), —(CH$_2$)$_{0-4}$—SO$_2$ ($C_1$–$C_{12}$ alkyl), —(CH$_2$)$_{0-4}$—SO$_2$—(CH$_2$)$_{0-4}$—($C_3$–$C_7$ cycloalkyl), —(CH$_2$)$_{0-4}$—N($R_{150}$)—CO—O—$R_{150}$, —(CH$_2$)$_{0-4}$—N($R_{150}$)—CO—N($R_{150}$)$_2$, —(CH$_2$)$_{0-4}$—N($R_{150}$)—CS—N($R_{150}$)$_2$, —(CH$_2$)$_{0-4}$—N($R_{150}$)—CO—$R_{105}$, —(CH$_2$)$_{0-4}$—N$R_{105}R'$—(CH$_2$)$_{0-4}$—$R_{140}$, —(CH$_2$)$_{0-4}$—O—CO-($C_1$–$C_6$ alkyl), —(CH$_2$)$_{0-4}$—O—P(O)—(O—$R_{110}$)$_2$, —(CH$_2$)$_{0-4}$—O—CO—N($R_{150}$)$_2$, —(CH$_2$)$_{0-4}$—N($R_{150}$)$_2$, —(CH$_2$)$_{0-4}$—O—($R_{150}$), —(CH$_2$)$_{0-4}$—O—$R_{150}'$—COOH, —(CH$_2$)$_{0-4}$—S—($R_{150}$), —(CH$_2$)$_{0-4}$—N(RI$_{50}$)—SO$_2$—$R_{105}$, —(CH$_2$)$_{0-4}$—$C_3$–$C_7$ cycloalkyl, ($C_2$–$C_{10}$) alkenyl, or ($C_2$–$C_{10}$)alkynyl;

$A_3$ and $A_4$ are independently F, Cl, Br, I, OH, methyl, methoxy, or H; and $R_c$ is $C_2$–$C_{10}$ alkyl, $C_2$–$C_{10}$ alkenyl or $C_2$–$C_{10}$ alkynyl, each of which is optionally substituted with with 1, 2, or 3 groups independently selected from the group consisting of halogen, —OH, phenyl, —O-phenyl, —SH, —S—$C_1$–$C_6$ alkyl, —C≡N, —CF$_3$, $C_1$–$C_6$ alkoxy, NH$_2$, NH($C_1$–$C_6$ alkyl) or N—($C_1$–$C_6$ alkyl)($C_1$–$C_6$ alkyl).

Also preferred compounds of formula I-7 include those of formula I-7-b:

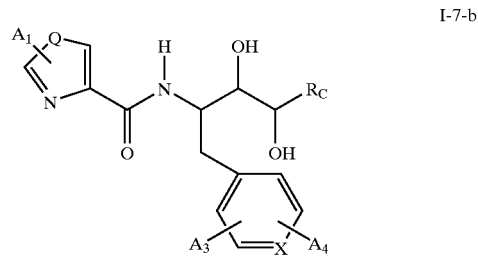

I-7-b wherein

Q is O or S;

$A_1$ is —OR, —NO$_2$, $C_1$–$C_6$ alkyl, halogen, —C≡N, —OCF$_3$, —CF$_3$, —(CH$_2$)$_{0-4}$—O—P(=O)(OR)(OR'), —(CH$_2$)$_{0-4}$—CO—N$R_{105}R'105$, —(CH$_2$)$_{0-4}$—O—(CH$_2$)$_{0-4}$—CONR$_{102}R_{102}'$, —(CH$_2$)$_{0-4}$—CO—($C_1$–$C_{12}$ alkyl), —(CH$_2$)$_{0-4}$—CO—($C_2$–$C_{12}$ alkenyl), —(CH$_2$)$_{0-4}$—CO—($C_2$–$C_{12}$ alkynyl), —(CH$_2$)$_{0-4}$—CO—(CH$_2$)$_{0-4}$ ($C_3$–$C_7$ cycloalkyl), —(CH$_2$)$_{0-4}$—$R_{110}$, —(CH$_2$)$_{0-4}$—$R_{120}$, —(CH$_2$)$_{0-4}$—$R_{130}$, —(CH$_2$)$_{0-4}$—CO—$R_{110}$, —(CH$_2$)$_{0-4}$—CO—$R_{120}$, —(CH$_2$)$_{0-4}$—CO—$R_{130}$, —CH$_2$)$_{0-4}$—CO—$R_{140}$, —(CH$_2$)$_{0-4}$—CO—O—$R_{150}$-(CH$_2$)$_{0-4}$—SO$_2$—N$R_{105}R'_{105}$, —(CH$_2$)$_{0-4}$—SO—($C_1$–$C_8$ alkyl), —(CH$_2$)$_{0-4}$—SO$_2$—($C_1$–$C_{12}$ alkyl), —(CH$_2$)$_{0-4}$—SO$_2$—(CH$_2$)$_{0-4}$—($C_3$–$C_7$ cycloalkyl), —(CH$_2$)$_{0-4}$—N($R_{150}$)—CO—O—$R_{150}$, —(CH$_2$)$_{0-4}$—N($R_{150}$)—CO—N($R_{150}$)$_2$, —(CH$_2$)$_{0-4}$—N($R_{150}$)—CS—N($R_{150}$)$_2$, —(CH$_2$)$_{0-4}$—N($R_{150}$)—CO—$R_{05}$, —(CH$_2$)$_{0-4}$—N$R_{105}R'_{105}$, —(CH$_2$)$_{0-4}$—$R_{140}$, —(CH$_2$)$_{0-4}$—O—CO—($C_1$–$C_6$ alkyl), —(CH$_2$)$_{0-4}$—O—P(O)—(O—$R_{110}$)$_2$, —(CH$_2$)$_{0-4}$—O—CO—N($R_{150}$)$_2$, —(CH$_2$)$_{0-4}$—O—CS—N($R_{150}$)$_2$, —(CH$_2$)$_{0-4}$—O—($R_{150}$), —(CH$_2$)$_{0-4}$—$R_{150}'$—COOH, —(CH$_2$)$_{0-4}$—S—($R_{150}$), —(CH$_2$)$_{0-4}$—N($R_{150}$)—SO$_2$—$R_{105}$, —(CH$_2$)$_{0-4}$—$C_3$–$C_7$ cycloalkyl, ($C_2$–$C_{10}$)alkenyl, or ($C_2$–$C_{10}$)alkynyl;

$A_3$ and $A_4$ are independently F, Cl, Br, I, OH, methyl, methoxy, or H; and $R_c$ is $C_2$–$C_{10}$ alkyl, $C_2$–$C_{10}$ alkenyl or $C_2$–$C_{10}$ alkynyl, each of which is optionally substituted with with 1, 2, or 3 groups independently selected from the group consisting of halogen, —OH, phenyl, —O—phenyl, —SH, —S—$C_1$–$C_6$ alkyl, —C≡N, —CF$_3$, $C_1$–$C_6$ alkoxy, NH$_2$, NH($C_1$–$C_6$ alkyl) or N—($C_1$–$C_6$ alkyl)($C_1$–$C_6$ alkyl).

Also preferred compounds of formula I-7 include those of formula I-7-c:

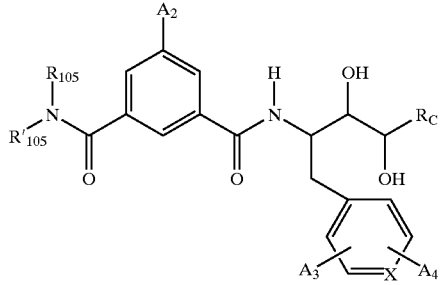

I-7-c wherein $A_2$ is $C_1$–$C_6$ alkyl, halogen, —C≡N, or —CO—$NR_{105}R'_{105}$;

$A_3$ and $A_4$ are independently F, Cl, Br, I, OH, methyl, methoxy, or H;

$R_c$ is $C_2$–$C_{10}$ alkyl, $C_2$–$C_{10}$ alkenyl or $C_2$–$C_{10}$ alkynyl, each of which is optionally substituted with with 1, 2, or 3 groups independently selected from the group consisting of halogen, —OH, phenyl, —O-phenyl, —SH, —S—$C_1$–$C_6$ alkyl, —C≡N, —$CF_3$, $C_1$–$C_6$ alkoxy, $NH_2$, NH($C_1$–$C_6$ alkyl) or N—($C_1$–$C_6$ alkyl)($C_1$–$C_6$ alkyl); and $R_{105}$ and $R'_{105}$ are independently selected from H and $C_1$–$C_6$ alkyl.

Other compounds of the formula I-7 include those of formula I-7-d:

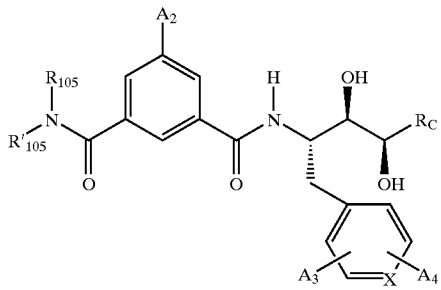

I-7-d wherein $A_2$, $A_3$, $A_4$, $R_c$, $R_{105}$ and $R'_{105}$ are as defined for formula I-7-c.

Other compounds of the formula I-7 include those of formula I-7-e:

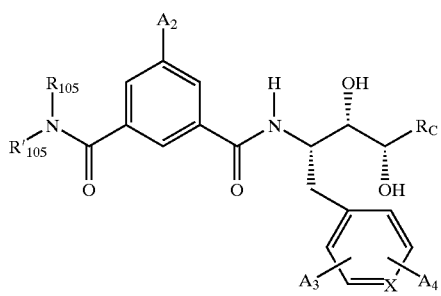

I-7-e wherein $A_2$, $A_3$, $A_4$, $R_c$, $R_{105}$ and $R'_{105}$ are as defined for formula I-7-c.

Other compounds of the I-7 include those of formula I-7-f:

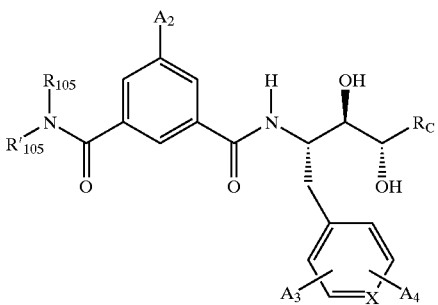

I-7-f wherein $A_2$, $A_3$, $A_4$, $R_c$, $R_{105}$ and $R_{105}$ are as defined for formula I-7-c.

Representative compounds of the formula I include the compounds described in chemistry examples 1–253, below.

In another aspect, the invention provides intermediates of the formula X:

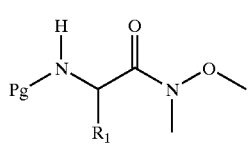

X wherein Pg is —CO—O—$(CH_2)_{n8}$—$R_{25}$ where $n_8$ is 0, 1, or 2 and $R_{25}$ is $C_1$–$C_6$ alkyl or aryl; and $R_1$ is as defined above.

The invention further provides intermediates of the formula XI:

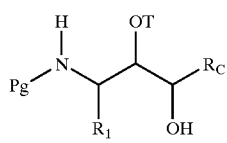

XI wherein Pg is —CO—O—$(CH_2)_{n8}$—$R_{25}$ where $n_8$ is 0, 1, or 2 and $R_{25}$ is $C_1$–$C_6$ alkyl or aryl;

$R_1$ and $R_c$ are as defined above; and

T is H— or $CH_3C(O)$—.

The invention also provides intermediates of the formula XII:

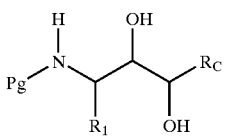

XII wherein Pg is —CO—O—$(CH_2)_{n8}$—$R_{25}$ where $n_8$ is 0, 1, or 2 and $R_{25}$ is $C_1$–$C_6$ alkyl or aryl; and $R_1$ and $R_c$ are as defined above.

The invention further provides intermediates of the formula XIII:

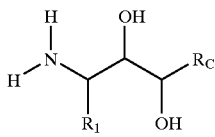

XIII wherein $R_1$ and $R_c$ are as defined above.

The invention also provides intermediates of the formula XIV:

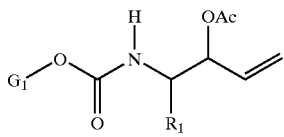

XIV wherein $G_1$ is —$(CH_2)_{n8}$—$R_{25}$ where $n_8$ is 0, 1, or 2 and $R_{25}$ is $C_1$–$C_6$ alkyl, $C_1$–$C_6$ alkenyl, or aryl; and
$R_1$ is as defined above.

The invention further provides intermediates of the formula XV:

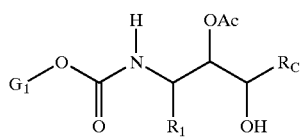

XV wherein $G_1$ is —$(CH_2)_{n8}$—$R_{25}$ where $n_8$ is 0, 1, or 2 and $R_{25}$ is $C_1$–$C_6$ alkyl, $C_1$–$C_6$ alkenyl, or aryl; and
$R_1$ and $R_c$ are as defined above.

The invention also provides intermediates of the formula XVI:

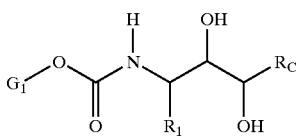

XVI wherein $G_1$ is —$(CH_2)_{n8}$—$R_{25}$ where $n_8$ is 0, 1, or 2 and $R_{25}$ is $C_1$–$C_6$ alkyl, $C_1$–$C_6$ alkenyl, or aryl; and
$R_1$ and $R_c$ are as defined above.

The invention also provides methods for treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, or diffuse Lewy body type of Alzheimer's disease and who is in need of such treatment which includes administration of a therapeutically effective amount of a compound of formula (I) or a pharmaceutically acceptable salts thereof.

In an embodiment, this method of treatment can be used where the disease is Alzheimer's disease.

In an embodiment, this method of treatment can help prevent or delay the onset of Alzheimer's disease.

In an embodiment, this method of treatment can be used where the disease is mild cognitive impairment.

In an embodiment, this method of treatment can be used where the disease is Down's syndrome.

In an embodiment, this method of treatment can be used where the disease is Hereditary Cerebral Hemorrhage with Amyloidosis of the Dutch-Type.

In an embodiment, this method of treatment can be used where the disease is cerebral amyloid angiopathy.

In an embodiment, this method of treatment can be used where the disease is degenerative dementias.

In an embodiment, this method of treatment can be used where the disease is diffuse Lewy body type of Alzheimer's disease.

In an embodiment, this method of treatment can treat an existing disease.

In an embodiment, this method of treatment can prevent a disease from developing.

In an embodiment, this method of treatment can employ therapeutically effective amounts: for oral administration from about 0.1 mg/day to about 1,000 mg/day; for parenteral, sublingual, intranasal, intrathecal administration from about 0.5 to about 100 mg/day; for depo administration and implants from about 0.5 mg/day to about 50 mg/day; for topical administration from about 0.5 mg/day to about 200 mg/day; for rectal administration from about 0.5 mg to about 500 mg.

In an embodiment, this method of treatment can employ therapeutically effective amounts: for oral administration from about 1 mg/day to about 100 mg/day; and for parenteral administration from about 5 to about 50 mg daily.

In an embodiment, this method of treatment can employ therapeutically effective amounts for oral administration from about 5 mg/day to about 50 mg/day.

The invention also includes pharmaceutical compositions which include a compound of formula (I) or a pharmaceutically acceptable salts thereof.

The invention also includes the use of a compound of formula (I) or pharmaceutically acceptable salts thereof for the manufacture of a medicament for use in treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease and who is in need of such treatment.

In an embodiment, this use of a compound of formula (I) can be employed where the disease is Alzheimer's disease.

In an embodiment, this use of a compound of formula (I) can help prevent or delay the onset of Alzheimer's disease.

In an embodiment, this use of a compound of formula (I) can be employed where the disease is mild cognitive impairment.

In an embodiment, this use of a compound of formula (I) can be employed where the disease is Down's syndrome.

In an embodiment, this use of a compound of formula (I) can be employed where the disease is Hereditary Cerebral Hemorrhage with Amyloidosis of the Dutch-Type.

In an embodiment, this use of a compound of formula (I) can be employed where the disease is cerebral amyloid angiopathy.

In an embodiment, this use of a compound of formula (I) can be employed where the disease is degenerative dementias.

In an embodiment, this use of a compound of formula (I) can be employed where the disease is diffuse Lewy body type of Alzheimer's disease.

In an embodiment, this use of a compound employs a pharmaceutically acceptable salt selected from the group consisting of salts of the following acids hydrochloric, hydrobromic, hydroiodic, nitric, sulfuric, phosphoric, citric, methanesulfonic, $CH_3$—$(CH_2)_n$—COOH where n is 0 thru 4, HOOC—$(CH_2)_n$—COOH where n is as defined above, HOOC—CH=CH—COOH, and phenyl-COOH.

The invention also includes methods for inhibiting beta-secretase activity, for inhibiting cleavage of amyloid precursor protein (APP), in a reaction mixture, at a site between Met596 and Asp597, numbered for the APP-695 amino acid isotype, or at a corresponding site of an isotype or mutant thereof; for inhibiting production of amyloid beta peptide (A beta) in a cell; for inhibiting the production of beta-amyloid plaque in an animal; and for treating or preventing a disease characterized by beta-amyloid deposits in the brain. These methods each include administration of a therapeutically effective amount of a compound of formula (I) or a pharmaceutically acceptable salts thereof.

The invention also includes a method for inhibiting beta-secretase activity, including exposing said beta-secretase to an effective inhibitory amount of a compound of formula (I), or a pharmaceutically acceptable salt thereof.

In an embodiment, this method employs a compound that inhibits 50% of the enzyme's activity at a concentration of less than 50 micromolar.

In an embodiment, this method employs a compound that inhibits 50% of the enzyme's activity at a concentration of 10 micromolar or less.

In an embodiment, this method employs a compound that inhibits 50% of the enzyme's activity at a concentration of 1 micromolar or less.

In an embodiment, this method employs a compound that inhibits 50% of the enzyme's activity at a concentration of 10 nanomolar or less.

In an embodiment, this method includes exposing said beta-secretase to said compound in vitro.

In an embodiment, this method includes exposing said beta-secretase to said compound in a cell.

In an embodiment, this method includes exposing said beta-secretase to said compound in a cell in an animal.

In an embodiment, this method includes exposing said beta-secretase to said compound in a human.

The invention also includes a method for inhibiting cleavage of amyloid precursor protein (APP), in a reaction mixture, at a site between Met596 and Asp597, numbered for the APP-695 amino acid isotype; or at a corresponding site of an isotype or mutant thereof, including exposing said reaction mixture to an effective inhibitory amount of a compound of formula (I), or a pharmaceutically acceptable salt thereof.

In an embodiment, this method employs a cleavage site: between Met652 and Asp653, numbered for the APP-751 isotype; between Met 671 and Asp 672, numbered for the APP-770 isotype; between Leu596 and Asp597 of the APP-695 Swedish Mutation; between Leu652 and Asp653 of the APP-751 Swedish Mutation; or between Leu671 and Asp672 of the APP-770 Swedish Mutation.

In an embodiment, this method exposes said reaction mixture in vitro.

In an embodiment, this method exposes said reaction mixture in a cell.

In an embodiment, this method exposes said reaction mixture in an animal cell.

In an embodiment, this method exposes said reaction mixture in a human cell.

The invention also includes a method for inhibiting production of amyloid beta peptide (A beta) in a cell, including administering to said cell an effective inhibitory amount of a compound of formula (I), or a pharmaceutically acceptable salt thereof.

In an embodiment, this method includes administering to an animal.

In an embodiment, this method includes administering to a human.

The invention also includes a method for inhibiting the production of beta-amyloid plaque in an animal, including administering to said animal an effective inhibitory amount of a compound of formula (I), or a pharmaceutically acceptable salt thereof.

In an embodiment, this method includes administering to a human.

The invention also includes a method for treating or preventing a disease characterized by beta-amyloid deposits in the brain including administering to a patient an effective therapeutic amount of a compound of formula (I), or a pharmaceutically acceptable salt thereof.

In an embodiment, this method employs a compound that inhibits 50% of the enzyme's activity at a concentration of less than 50 micromolar.

In an embodiment, this method employs a compound that inhibits 50% of the enzyme's activity at a concentration of 10 micromolar or less.

In an embodiment, this method employs a compound that inhibits 50% of the enzyme's activity at a concentration of 1 micromolar or less.

In an embodiment, this method employs a compound that inhibits 50% of the enzyme's activity at a concentration of 10 nanomolar or less.

In an embodiment, this method employs a compound at a therapeutic amount in the range of from about 0.1 to about 1000 mg/day.

In an embodiment, this method employs a compound at a therapeutic amount in the range of from about 15 to about 1500 mg/day.

In an embodiment, this method employs a compound at a therapeutic amount in the range of from about 1 to about 100 mg/day.

In an embodiment, this method employs a compound at a therapeutic amount in the range of from about 5 to about 50 mg/day.

In an embodiment, this method can be used where said disease is Alzheimer's disease.

In an embodiment, this method can be used where said disease is Mild Cognitive Impairment, Down's Syndrome, or Hereditary Cerebral Hemorrhage with Amyloidosis of the Dutch Type.

The invention also includes a composition including beta-secretase complexed with a compound of formula (I), or a pharmaceutically acceptable salt thereof.

The invention also includes a method for producing a beta-secretase complex including exposing beta-secretase to a compound of formula (I), or a pharmaceutically acceptable salt thereof, in a reaction mixture under conditions suitable for the production of said complex.

In an embodiment, this method employs exposing in vitro.

In an embodiment, this method employs a reaction mixture that is a cell.

The invention also includes a component kit including component parts capable of being assembled, in which at least one component part includes a compound of formula I enclosed in a container.

In an embodiment, this component kit includes lyophilized compound, and at least one further component part includes a diluent.

The invention also includes a container kit including a plurality of containers, each container including one or more unit dose of a compound of formula (I):, or a pharmaceutically acceptable salt thereof.

In an embodiment, this container kit includes each container adapted for oral delivery and includes a tablet, gel, or capsule.

In an embodiment, this container kit includes each container adapted for parenteral delivery and includes a depot product, syringe, ampoule, or vial.

In an embodiment, this container kit includes each container adapted for topical delivery and includes a patch, medipad, ointment, or cream.

The invention also includes an agent kit including a compound of formula (I), or a pharmaceutically acceptable salt thereof; and one or more therapeutic agent selected from the group consisting of an antioxidant, an anti-inflammatory, a gamma secretase inhibitor, a neurotrophic agent, an acetyl cholinesterase inhibitor, a statin, an A beta peptide, and an anti-A beta antibody.

The invention also includes a composition including a compound of formula (I), or a pharmaceutically acceptable salt thereof; and an inert diluent or edible carrier.

In an embodiment, this composition includes a carrier that is an oil.

The invention also includes a composition including: a compound of formula (I), or a pharmaceutically acceptable salt thereof; and a binder, excipient, disintegrating agent, lubricant, or gildant.

The invention also includes a composition including a compound of formula (I), or a pharmaceutically acceptable salt thereof; disposed in a cream, ointment, or patch.

The invention provides compounds of formula (I) that are useful in treating and preventing Alzheimer's disease. The compounds of the invention can be prepared by one skilled in the art based only on knowledge of the compound's chemical structure. The chemistry for the preparation of the compounds of this invention is known to those skilled in the art. In fact, there is more than one process to prepare the compounds of the invention. Examples of various processes that can be used to prepare the compounds of the invention are set forth in CHART I.

Chart I

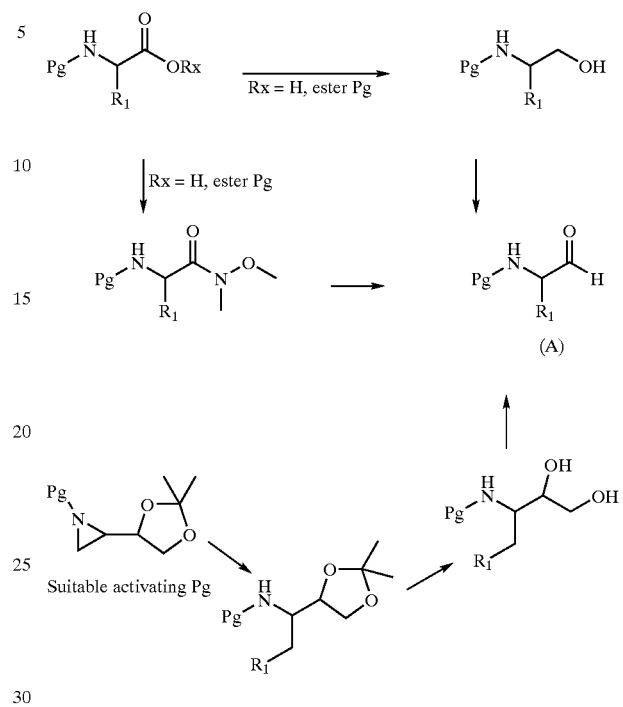

Pg=protecting group see Greene & Wuts in *Protective Groups in Organic Synthesis*, $1^{st}$–$3^{rd}$ Ed.

Process 1: An N-protected α-amino aldehyde (intermediate A) is synthesized from known a-amino acids or their derivatives through methods known in the art (for a review see: *Chem. Rev.* 1989, 89, 149)

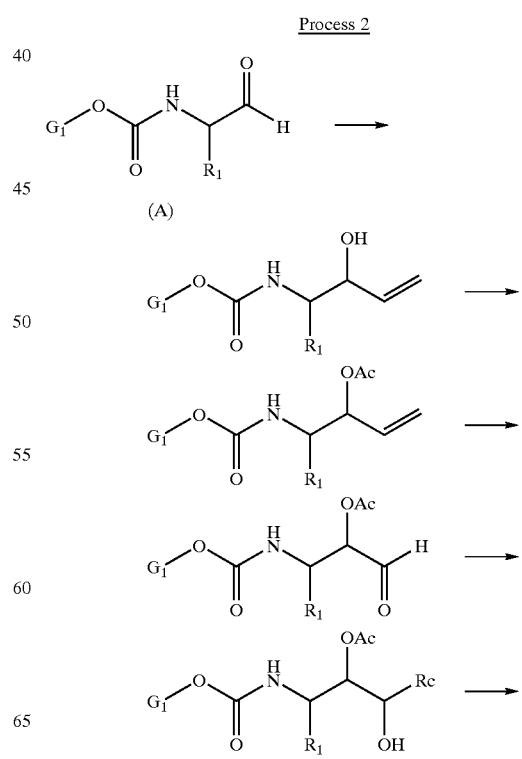

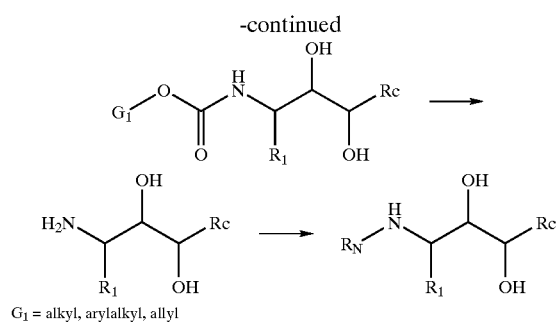

$G_1$ = alkyl, arylalkyl, allyl

Process 2: Intermediate A is reacted, at low temperature with vinyl magnesium bromide or chloride to afford a diastereomeric mixture of allylic alcohols, which are separable by chromatography (*J. Org. Chem.* 1985, 50, 5399). The hydroxyl group is protected as an acetate or another appropriate protecting group such as a silyl group and the resulting compound converted to the corresponding aldehyde by a standard method (e.g., ozonolysis followed by reductive work up or $OsO_4$ followed by $NaIO_4$). Once obtained, the aldehyde is treated at low temperature with an organometallic reagent such as a Grignard reagent to produce, after removal of the hydroxyl protecting group by standard methods, a mixture of diols which are separable by chromatography. For a specific example, the synthesis of tert-butyl (1S,2R,3S)-1-benzyl-2,3-dihydroxy-5-methylhexylcarbamate ($G_1$=t-Bu, $R_1$=benzyl and $R_c$=isobutyl) is described in U.S. Pat. No. 4,977,141. Deprotection by known methods provides the amine that is condensed with carboxylic acid to give the final compounds.

PROCESS 3

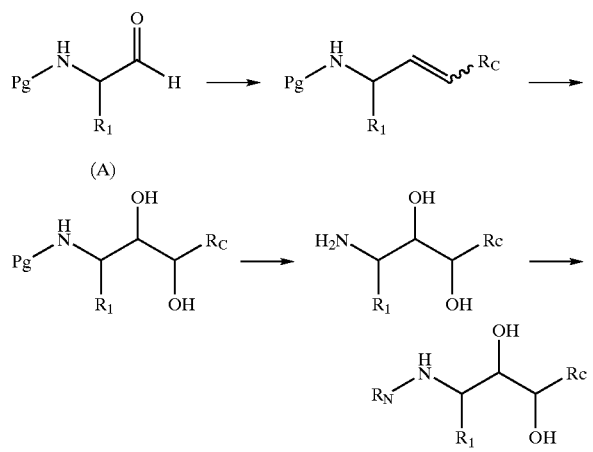

Process 3: Intermediate A is reacted with a Wittig or Horner-Emmons reagent to give the olefin. The product may be a single olefin regioisomer or a mixture of the Z and E forms. The olefin is dihydroxylated using osmium tetroxide as has been reported in *J. Med. Chem.* 31, 2264–2276 (1988). Deprotection by known methods provides the aminodiol that is condensed with carboxylic acid to give the final compounds.

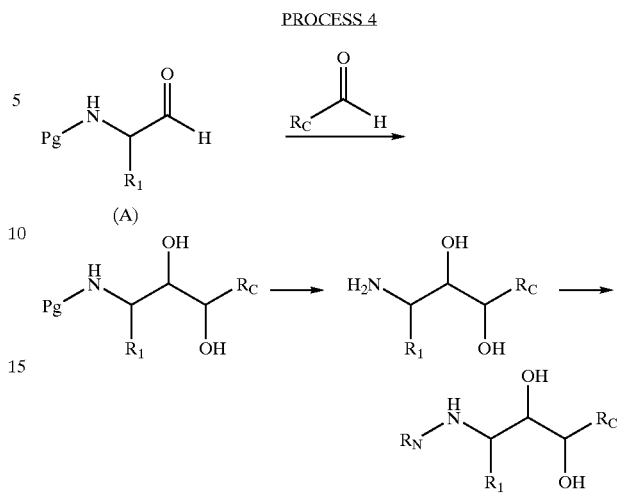

Process 4: Intermediate A is reacted with an aldehyde in a Pinacol reaction to give the diol. This reaction is catalyzed by vanadium salts as is known in the art (see *J. Am. Chem. Soc.* 111, 8014–8016 (1989) and *J. Org. Chem.* 55, 4506–4508 (1990)). Deprotection by known methods provides the amine that is condensed with carboxylic acid to give the final compounds.

In addition, the compounds of the invention can be prepared by one skilled in the art using one or more of the processes disclosed in *J. Med. Chem.* 38, 2893–2905 1995), *J. Med. Chem.* 31, 2277–2288 (1988), *J. Med. Chem.* 32, 1371–1378 (1989),*J. Med. Chem.* 34, 2692–2701 (1991), *J. Org. Chem.* 58, 3277–3284 (1993), *Bioorg. Med. Chem. Lett.* 5, 2623–2626 (1995), *Tetrahedron Lett.* 33, 3567–3570 (1992).

The protection of amines is conducted, where appropriate, by methods known to those skilled in the art. Amino protecting groups are known to those skilled in the art. See for example, "Protecting Groups in Organic Synthesis", John Wiley and sons, New York, N.Y., 1981, Chapter 7; "Protecting Groups in Organic Chemistry", Plenum Press, New York, N.Y., 1973, Chapter 2. When the amino protecting group is no longer needed, it is removed by methods known to those skilled in the art. By definition the amino protecting group must be readily removable. A variety of suitable methodologies are known ro those skilled in the art; see also T. W. Green and P. G. M. Wuts in "Protective Groups in Organic Chemistry, John Wiley and Sons, 1991. Suitable amino protecting groups include t-butoxycarbonyl, benzyloxycarbonyl, formyl, trityl, phthalimido, trichloroacetyl, chloroacetyl, bromoacetyl, iodoacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycabonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy) benzyloxycarbonyl, isobrornyloxycarbonyl, 1-piperidyloxycarbonyl, 9-fluoroenylmethyl carbonate, —CH—) CH=CH$_2$ and phenyl-C(=N—)—H.

It is preferred that the protecting group be t-butoxycarbonyl (BOC) and/or benzyloxycarbonyl (CBZ), it is more preferred that the protecting group be t-butoxycarbonyl. One skilled in the art will recognize suitable methods of introducing a t-butoxycarbonyl or benzyloxycarbonyl protecting group and may additionally consult T. W. Green and P. G. M. Wuts in "Protective Groups in Organic Chemistry, John Wiley and Sons, 1991 for guidance.

The compounds of the invention may contain geometric or optical isomers as as tautomers. Thus, the invention includes all tautomers and pure geometric isomers, such as the E and Z geometric isomers, as as mixtures thereof. Further, the invention includes pure enantiomers and diastereomers as as mixtures thereof, including racemic mixtures. The individual geometric isomers, enantiomers or diastereomers may be prepared or isolated by methods known to those skilled in the art, including but not limited to chiral chromatography; preparing diastereomers, separating the diastereomers and converting the diastereomers into enantiomers through the use of a chiral resolving agent.

Compounds of the invention with designated stereochemistry can be included in mixtures, including racemic mixtures, with other enantiomers, diastereomers, geometric isomers or tautomers. In a preferred aspect, compounds of the invention with (S, R, R), (S, S, S), or (S, R, S) stereochemistry are typically present in these mixtures in excess of 50 percent. Preferably, compounds of the invention with designated stereochemistry are present in these mixtures in excess of 80 percent. More preferably, compounds of the invention with designated stereochemistry are present in these mixtures in excess of 90 percent. Even more preferably, compounds of the invention with designated stereochemistry are present in these mixtures in excess of 99 percent.

Several of the compounds of formula (I) are amines, and as such form salts when reacted with acids. Pharmaceutically acceptable salts are preferred over the corresponding amines of formula (I) since they produce compounds which are more water soluble, stable and/or more crystalline. Pharmaceutically acceptable salts are any salt which retains the activity of the parent compound and does not impart any deleterious or undesirable effect on the subject to whom it is administered and in the context in which it is administered. Pharmaceutically acceptable salts include salts of both inorganic and organic acids. The preferred pharmaceutically acceptable salts include salts of the following acids acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, succinic, sulfamic, sulfanilic, sulfonic, sulfuric, tannic, tartaric, teoclic and toluenesulfonic. For other acceptable salts, see *Int. J. Pharm.*, 33, 201–217 (1986) and *J. Pharm. Sci.*, 66(1), 1, (1977).

The invention provides compounds, compositions, kits, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

Methods of the Invention

The compounds of the invention, and pharmaceutically acceptable salts thereof, are useful for treating humans or animals suffering from a condition characterized by a pathological form of beta-amyloid peptide, such as beta-amyloid plaques, and for helping to prevent or delay the onset of such a condition. For example, the compounds are useful for treating Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease. The compounds and compositions of the invention are particularly useful for treating or preventing Alzheimer's disease. When treating or preventing these diseases, the compounds of the invention can either be used individually or in combination, as is best for the patient.

As used herein, the term "treating" means that the compounds of the invention can be used in humans with at least a tentative diagnosis of disease. The compounds of the invention will delay or slow the progression of the disease thereby giving the individual a more useful life span.

The term "preventing" means that the compounds of the invention are useful when administered to a patient who has not been diagnosed as possibly having the disease at the time of administration, but who would normally be expected to develop the disease or be at increased risk for the disease. The compounds of the invention will slow the development of disease symptoms, delay the onset of the disease, or prevent the individual from developing the disease at all. Preventing also includes administration of the compounds of the invention to those individuals thought to be predisposed to the disease due to age, familial history, genetic or chromosomal abnormalities, and/or due to the presence of one or more biological markers for the disease, such as a known genetic mutation of APP or APP cleavage products in brain tissues or fluids.

In treating or preventing the above diseases, the compounds of the invention are administered in a therapeutically effective amount. The therapeutically effective amount will vary depending on the particular compound used and the route of administration, as is known to those skilled in the art.

In treating a patient displaying any of the diagnosed above conditions a physician may administer a compound of the invention immediately and continue administration indefinitely, as needed. In treating patients who are not diagnosed as having Alzheimer's disease, but who are believed to be at substantial risk for Alzheimer's disease, the physician should preferably start treatment when the patient first experiences early pre-Alzheimer's symptoms such as, memory or cognitive problems associated with aging. In addition, there are some patients who may be determined to be at risk for developing Alzheimer's through the detection of a genetic marker such as APOE4 or other biological indicators that are predictive for Alzheimer's disease. In these situations, even though the patient does not have symptoms of the disease, administration of the compounds of the invention may be started before symptoms appear, and treatment may be continued indefinitely to prevent or delay the onset of the disease.

Dosage Forms and Amounts

The compounds of the invention can be administered orally, parenterally, (IV, IM, depo-IM, SQ, and depo SQ), sublingually, intranasally (inhalation), intrathecally, topically, or rectally. Dosage forms known to those of skill in the art are suitable for delivery of the compounds of the invention.

Compositions are provided that contain therapeutically effective amounts of the compounds of the invention. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

About 1 to 500 mg of a compound or mixture of compounds of the invention or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 2 to about 100 mg, more preferably about 10 to about 30 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more compounds of the invention are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The compounds of the invention may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need or the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered orally, parenterally (IV, IM, depo-IM, SQ, and depo-SQ), sublingually, intranasally (inhalation), intrathecally, topically, or rectally. Dosage forms known to those skilled in the art are suitable for delivery of the compounds of the invention.

Compounds of the invention may be administered enterally or parenterally. When administered orally, compounds of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The oral dosage forms are administered to the patient 1, 2, 3, or 4 times daily. It is preferred that the compounds of the invention be administered either three or fewer times, more preferably once or twice daily. Hence, it is preferred that the compounds of the invention be administered in oral dosage form. It is preferred that whatever oral dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art.

When administered orally, an administered amount therapeutically effective to inhibit beta-secretase activity, to inhibit A beta production, to inhibit A beta deposition, or to treat or prevent AD is from about 0.1 mg/day to about 1,000 mg/day. It is preferred that the oral dosage is from about 1 mg/day to about 100 mg/day. It is more,preferred that the oral dosage is from about 5 mg/day to about 50 mg/day. It is understood that while a patient may be started at one dose, that dose may be varied over time as the patient's condition changes.

Compounds of the invention may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

The compounds of the invention can be administered parenterally, for example, by IV, IM, depo-IM, SC, or depo-SC. When administered parenterally, a therapeutically effective amount of about 0.5 to about 100 mg/day, preferably from about 5 to about 50 mg daily should be delivered. When a depot formulation is used for injection once a month or once every two weeks, the dose should be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

The compounds of the invention can be administered sublingually. When given sublingually, the compounds of the invention should be given one to four times daily in the amounts described above for IM administration.

The compounds of the invention can be administered intranasally. When given by this route, the appropriate dosage forms are a nasal spray or dry powder, as is known to those skilled in the art. The dosage of the compounds of the invention for intranasal administration is the amount described above for IM administration.

The compounds of the invention can be administered intrathecally. When given by this route the appropriate dosage form can be a parenteral dosage form as is known to those skilled in the art. The dosage of the compounds of the invention for intrathecal administration is the amount described above for IM administration.

The compounds of the invention can be administered topically. When given by this route, the appropriate dosage form is a cream, ointment, or patch. Because of the amount of the compounds of the invention to be administered, the patch is preferred. When administered topically, the dosage is from about 0.5 mg/day to about 200 mg/day. Because the amount that can be delivered by a patch is limited, two or more patches may be used. The number and size of the patch is not important, what is important is that a therapeutically effective amount of the compounds of the invention be delivered as is known to those skilled in the art. The compounds of the invention can be administered rectally by suppository as is known to those skilled in the art. When administered by suppository, the therapeutically effective amount is from about 0.5 mg to about 500 mg.

The compounds of the invention can be administered by implants as is known to those skilled in the art. When administering a compound of the invention by implant, the therapeutically effective amount is the amount described above for depot administration.

Given a particular compound of the invention and a desired dosage form, one skilled in the art would know how to prepare and administer the appropriate dosage form.

The compounds of the invention are used in the same manner, by the same routes of administration, using the same pharmaceutical dosage forms, and at the same dosing schedule as described above, for preventing disease or treating patients with MCI (mild cognitive impairment) and preventing or delaying the onset of Alzheimer's disease in those who would progress from MCI to AD, for treating or preventing Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type of Alzheimer's disease.

The compounds of the invention can be used in combination, with each other or with other therapeutic agents or approaches used to treat or prevent the conditions listed above. Such agents or approaches include: acetylcholine esterase inhibitors such as tacrine (tetrahydroaminoacridine, marketed as COGNEX®), donepezil hydrochloride, (marketed as Aricept® and rivastigmine (marketed as Exelon®); gamma-secretase inhibitors; anti-inflammatory agents such as cyclooxygenase II inhibitors; anti-oxidants such as Vitamin E and ginkolides; immunological approaches, such as, for example, immunization with A beta peptide or administration of anti-A beta peptide antibodies; statins; and direct or indirect neurotropic agents such as Cerebrolysin®, AIT-082 (Emilieu, 2000, Arch. Neurol. 57:454), and other neurotropic agents of the future.

In addition, the compounds of formula (I) can also be used with inhibitors of P-glycoprotein (P-gp). P-gp inhibitors and the use of such compounds are known to those skilled in the art. See for example, Cancer Research, 53, 4595–4602 (1993), Clin. Cancer Res., 2, 7–12 (1996), Cancer Research, 56, 4171–4179 (1996), International Publications WO99/64001 and WO01/10387. The important thing is that the blood level of the P-gp inhibitor be such that it exerts its effect in inhibiting P-gp from decreasing brain blood levels of the compounds of formula (A). To that end the P-gp inhibitor and the compounds of formula (A) can be administered at the same time, by the same or different route of administration, or at different times. The important thing is not the time of administration but having an effective blood level of the P-gp inhibitor.

Suitable P-gp inhibitors include cyclosporin A, verapamil, tamoxifen, quinidine, Vitamin E-TGPS, ritonavir, megestrol acetate, progesterone, rapamycin, 10,11-methanodibenzosuberane, phenothiazines, acridine derivatives such as GF120918, FK506, VX-710, LY335979, PSC-833, GF-102,918 and other steroids. It is to be understood that additional agents will be found that have the same function and therefore achieve the same outcome; such compounds are also considered to be useful.

The P-gp inhibitors can be administered orally, parenterally, (IV, IM, IM-depo, SQ, SQ-depo), topically, sublingually, rectally, intranasally, intrathecally and by implant.

The therapeutically effective amount of the P-gp inhibitors is from about 0.1 to about 300 mg/kg/day, preferably about 0.1 to about 150 mg/kg daily. It is understood that while a patient may be started on one dose, that dose may have to be varied over time as the patient's condition changes.

When administered orally, the P-gp inhibitors can be administered in usual dosage forms for oral administration as is known to those skilled in the art. These dosage forms include the usual solid unit dosage forms of tablets and capsules as well as liquid dosage forms such as solutions, suspensions and elixirs. When the solid dosage forms are used, it is preferred that they be of the sustained release type so that the P-gp inhibitors need to be administered only once or twice daily. The oral dosage forms are administered to the patient one thru four times daily. It is preferred that the P-gp inhibitors be administered either three or fewer times a day, more preferably once or twice daily. Hence, it is preferred that the P-gp inhibitors be administered in solid dosage form and further it is preferred that the solid dosage form be a sustained release form which permits once or twice daily dosing. It is preferred that what ever dosage form is used, that it be designed so as to protect the P-gp inhibitors from the acidic environment of the stomach. Enteric coated tablets are well known to those skilled in the art. In addition, capsules filled with small spheres each coated to protect from the acidic stomach, are also well known to those skilled in the art.

In addition, the P-gp inhibitors can be administered parenterally. When administered parenterally they can be administered IV, IM, depo-IM, SQ or depo-SQ.

The P-gp inhibitors can be given sublingually. When given sublingually, the P-gp inhibitors should be given one thru four times daily in the same amount as for IM administration.

The P-gp inhibitors can be given intranasally. When given by this route of administration, the appropriate dosage forms are a nasal spray or dry powder as is known to those skilled in the art. The dosage of the P-gp inhibitors for intranasal administration is the same as for IM administration.

The P-gp inhibitors can be given intrathecally. When given by this route of administration the appropriate dosage form can be a parenteral dosage form as is known to those skilled in the art.

The P-gp inhibitors can be given topically. When given by this route of administration, the appropriate dosage form is a cream, ointment or patch. Because of the amount of the P-gp inhibitors needed to be administered the patch is preferred. However, the amount that can be delivered by a patch is limited. Therefore, two or more patches may be required. The number and size of the patch is not important, what is important is that a therapeutically effective amount of the P-gp inhibitors be delivered as is known to those skilled in the art.

The P-gp inhibitors can be administered rectally by suppository as is known to those skilled in the art.

The P-gp inhibitors can be administered by implants as is known to those skilled in the art.

There is nothing novel about the route of administration nor the dosage forms for administering the P-gp inhibitors. Given a particular P-gp inhibitor, and a desired dosage form, one skilled in the art would know how to prepare the appropriate dosage form for the P-gp inhibitor.

It should be apparent to one skilled in the art that the exact dosage and frequency of administration will depend on the particular compounds of the invention administered, the particular condition being treated, the severity of the condition being treated, the age, weight, general physical condition of the particular patient, and other medication the individual may be taking as is well known to administering physicians who are skilled in this art.

Inhibition of APP Cleavage

The compounds of the invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site"). While not wishing to be bound by a particular theory, inhibition of beta-secretase activity is thought to inhibit production of beta amyloid peptide (A beta). Inhibitory activity is demonstrated in one of a variety of inhibition assays, whereby cleavage of an APP substrate in the presence of a beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compound inhibitors of the invention are known. Representative assay systems are described, for example, in U.S. Pats. Nos. 5,942,400, 5,744, 346, as well as in the Examples below.

The enzymatic activity of beta-secretase and the production of A beta can be analyzed in vitro or in vivo, using natural, mutated, and/or synthetic APP substrates, natural, mutated, and/or synthetic enzyme, and the test compound. The analysis may involve primary or secondary cells expressing native, mutant, and/or synthetic APP and enzyme, animal models expressing native APP and enzyme, or may utilize transgenic animal models expressing the substrate and enzyme. Detection of enzymatic activity can be by analysis of one or more of the cleavage products, for example, by immunoassay, fluorometric or chromogenic assay, HPLC, or other means of detection. Inhibitory compounds are determined as those having the ability to decrease the amount of beta-secretase cleavage product produced in comparison to a control, where beta-secretase mediated cleavage in the reaction system is observed and measured in the absence of inhibitory compounds.

Beta-Secretase

Various forms of beta-secretase enzyme are known, and are available and useful for assay of enzyme activity and inhibition of enzyme activity. These include native, recombinant, and synthetic forms of the enzyme. Human beta-secretase is known as Beta Site APP Cleaving Enzyme (BACE), Asp2, and memapsin 2, and has been characterized, for example, in U.S. Pat. No. 5,744,346 and published PCT patent applications WO98/22597, WO00/03819, WO01/23533, and WO00/17369, as well as in literature publications (Hussain et al., 1999, *Mol. Cell. Neurosci.* 14:419–427; Vassar et al., 1999, *Science* 286:735–741; Yan et al., 1999, *Nature* 402:533–537; Sinha et al., 1999, *Nature* 40:537–540; and Lin et al., 2000, *PNAS USA* 97:1456–1460). Synthetic forms of the enzyme have also been described (WO98/22597 and WO00/17369). Beta-secretase can be extracted and purified from human brain tissue and can be produced in cells, for example mammalian cells expressing recombinant enzyme.

Preferred compounds are effective to inhibit 50% of beta-secretase enzymatic activity at a concentration of less than 50 micromolar, preferably at a concentration of 10 micromolar or less, more preferably 1 micromolar or less, and most preferably 10 nanomolar or less.

APP Substrate

Assays that demonstrate inhibition of beta-secretase-mediated cleavage of APP can utilize any of the known forms of APP, including the 695 amino acid "normal" isotype described by Kang et al., 1987, *Nature* 325:733–6, the 770 amino acid isotype described by Kitaguchi et. al., 1981, *Nature* 331:530–532, and variants such as the Swedish Mutation (KM670-1NL) (APP-SW), the London Mutation (V7176F), and others. See, for example, U.S. Pat. No. 5,766,846 and also Hardy, 1992, *Nature Genet.* 1:233–234, for a review of known variant mutations. Additional useful substrates include the dibasic amino acid modification, APP-KK disclosed, for example, in WO 00/17369, fragments of APP, and synthetic peptides containing the beta-secretase cleavage site, wild type (WT) or mutated form, e.g., SW, as described, for example, in U.S. Pat. No. 5,942,400 and WO00/03819.

The APP substrate contains the beta-secretase cleavage site of APP (KM-DA or NL-DA) for example, a complete APP peptide or variant, an APP fragment, a recombinant or synthetic APP, or a fusion peptide. Preferably, the fusion peptide includes the beta-secretase cleavage site fused to a peptide having a moiety useful for enzymatic assay, for example, having isolation and/or detection properties. A useful moiety may be an antigenic epitope for antibody binding, a label or other detection moiety, a binding substrate, and the like.

Antibodies

Products characteristic of APP cleavage can be measured by immunoassay using various antibodies, as described, for example, in Pirttila et al., 1999, *Neuro. Lett.* 249:21–4, and in U.S. Pat. No. 5,612,486. Useful antibodies to detect A beta include, for example, the monoclonal antibody 6E10 (Senetek, St. Louis, Mo.) that specifically recognizes an epitope on amino acids 1–16 of the A beta peptide; antibodies 162 and 164 (New York State Institute for Basic Research, Staten Island, N.Y.) that are specific for human A beta 1–40 and 1–42, respectively; and antibodies that recognize the junction region of beta-amyloid peptide, the site between residues 16 and 17, as described in U.S. Pat. No. 5,593,846. Antibodies raised against a synthetic peptide of residues 591 to 596 of APP and SW192 antibody raised against 590–596 of the Swedish mutation are also useful in immunoassay of APP and its cleavage products, as described in U.S. Pat. Nos. 5,604,102 and 5,721,130.

Assay Systems

Assays for determining APP cleavage at the beta-secretase cleavage site are well known in the art. Exemplary assays, are described, for example, in U.S. Pat. Nos. 5,744,346 and 5,942,400, and described in the Examples below.

Cell Free Assays

Exemplary assays that can be used to demonstrate the inhibitory activity of the compounds of the invention are described, for example, in WO00/17369, WO 00/03819, and U.S. Pat. Nos. 5,942,400 and 5,744,346. Such assays can be performed in cell-free incubations or in cellular incubations using cells expressing a beta-secretase and an APP substrate having a beta-secretase cleavage site.

An APP substrate containing the beta-secretase cleavage site of APP, for example, a complete APP or variant, an APP fragment, or a recombinant or synthetic APP substrate containing the amino acid sequence: KM-DA or NL-DA, is incubated in the presence of beta-secretase enzyme, a fragment thereof, or a synthetic or recombinant polypeptide variant having beta-secretase activity and effective to cleave the beta-secretase cleavage site of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nanomolar to 10 micromolar substrate, approximately 10 to 200 picomolar enzyme, and approximately 0.1 nanomolar to 10 micromolar inhibitor compound, in aqueous solution, at an approximate pH of 4–7, at approximately 37 degrees C., for a time period of approximately 10 minutes to 3 hours. These incubation conditions are exemplary only, and can be varied as required for the particular assay components and/or desired measurement system. Optimization of the incubation conditions for the particular assay components should account for the specific beta-secretase enzyme used and its pH optimum, any additional enzymes and/or markers that might be used in the assay, and the like. Such optimization is routine and will not require undue experimentation.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assay

Numerous cell-based assays can be used to analyze beta-secretase activity and/or processing of APP to release A beta. Contact of an APP substrate with a beta-secretase enzyme within the cell and in the presence or absence of a compound inhibitor of the invention can be used to demonstrate beta-secretase inhibitory activity of the compound. Preferably, assay in the presence of a useful inhibitory compound provides at least about 30%, most preferably at least about 50% inhibition of the enzymatic activity, as compared with a non-inhibited control.

In one embodiment, cells that naturally express beta-secretase are used. Alternatively, cells are modified to express a recombinant beta-secretase or synthetic variant enzyme as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Human cell lines that normally process A beta from APP provide a useful means to assay inhibitory activities of the compounds of the invention. Production and release of A beta and/or other cleavage products into the culture medium can be measured, for example by immunoassay, such as Western blot or enzyme-linked immunoassay (EIA) such as by ELISA.

Cells expressing an APP substrate and an active beta-secretase can be incubated in the presence of a compound inhibitor to demonstrate inhibition of enzymatic activity as compared with a control. Activity of beta-secretase can be measured by analysis of one or more cleavage products of the APP substrate. For example, inhibition of beta-secretase activity against the substrate APP would be expected to decrease release of specific beta-secretase induced APP cleavage products such as A beta.

Although both neural and non-neural cells process and release A beta, levels of endogenous beta-secretase activity are low and often difficult to detect by EIA. The use of cell types known to have enhanced beta-secretase activity, enhanced processing of APP to A beta, and/or enhanced production of A beta are therefore preferred. For example, transfection of cells with the Swedish Mutant form of APP (APP-SW); with APP-KK; or with APP-SW-KK provides cells having enhanced beta-secretase activity and producing amounts of A beta that can be readily measured.

In such assays, for example, the cells expressing APP and beta-secretase are incubated in a culture medium under conditions suitable for beta-secretase enzymatic activity at its cleavage site on the APP substrate. On exposure of the cells to the compound inhibitor, the amount of A beta released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells where the transgene is APP, and other cells such as those of a stable 293 cell line expressing APP, for example, APP-SW.

In vivo Assays: Animal Models

Various animal models can be used to analyze beta-secretase activity and/or processing of APP to release A beta, as described above. For example, transgenic animals expressing APP substrate and beta-secretase enzyme can be used to demonstrate inhibitory activity of the compounds of the invention. Certain transgenic animal models have been described, for example, in U.S. Pat. Nos. 5,877,399; 5,612,486; 5,387,742; 5,720,936; 5,850,003; 5,877,015, and 5,811,633, and in Ganes et al., 1995, *Nature* 373:523. Preferred are animals that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

Inhibition of beta-secretase mediated cleavage of APP at the beta-secretase cleavage site and of A beta release can be analyzed in these animals by measure of cleavage fragments in the animal's body fluids such as cerebral fluid or tissues. Analysis of brain tissues for A beta deposits or plaques is preferred.

On contacting an APP substrate with a beta-secretase enzyme in the presence of an inhibitory compound of the invention and under conditions sufficient to permit enzymatic mediated cleavage of APP and/or release of A beta from the substrate, the compounds of the invention are effective to reduce beta-secretase-mediated cleavage of APP at the beta-secretase cleavage site and/or effective to reduce released amounts of A beta. Where such contacting is the administration of the inhibitory compounds of the invention to an animal model, for example, as described above, the compounds are effective to reduce A beta deposition in brain tissues of the animal, and to reduce the number and/or size of beta amyloid plaques. Where such administration is to a human subject, the compounds are effective to inhibit or slow the progression of disease characterized by enhanced amounts of A beta, to slow the progression of AD in the, and/or to prevent onset or development of AD in a patient at risk for the disease.

Unless defined otherwise, all scientific and technical terms used herein have the same meaning as commonly understood by one of skill in the art to which this invention belongs. All patents and publications referred to herein are hereby incorporated by reference for all purposes.

Definitions

The definitions and explanations below are for the terms as used throughout this entire document including both the specification and the claims.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The symbol "—" in general represents a bond between two atoms in the chain. Thus $CH_3$—O—$CH_2$—$CH(R_i)$—$CH_3$ represents a 2-substituted-1-methoxypropane compound. In addition, the symbol "-" represents the point of attachment of the substituent to a compound. Thus for example aryl($C_1$–$C_6$)alkyl- indicates an alkylaryl group, such as benzyl, attached to the compound at the alkyl moiety.

Where multiple substituents are indicated as being attached to a structure, it is to be understood that the substituents can be the same or different. Thus for example "$R_m$ optionally substituted with 1, 2 or 3 $R_q$ groups" indicates that $R_m$ is substituted with 1, 2, or 3 $R_q$ groups where the $R_q$ groups can be the same or different.

APP, amyloid precursor protein, is defined as any APP polypeptide, including APP variants, mutations, and isoforms, for example, as disclosed in U.S. Pat. No. 5,766,846.

A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Beta-secretase (BACE1, Asp2, Memapsin 2) is an aspartyl protease that mediates cleavage of APP at the amino-terminal edge of A beta. Human beta-secretase is described, for example, in WO00/17369.

Pharmaceutically acceptable refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

A therapeutically effective amount is defined as an amount effective to reduce or lessen at least one symptom of the disease being treated or to reduce or delay onset of one or more clinical markers or symptoms of the disease.

By "alkyl" and "$C_1$–$C_6$ alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$–$C_{10}$" indicates a maximum of 10 carbons.

By "alkoxy" and "$C_1$–$C_6$ alkoxy" in the present invention is meant straight or branched chain alkyl groups having 1–6 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy.

By the term "halogen" in the present invention is meant fluorine, bromine, chlorine, and iodine.

"Alkenyl" and "$C_2$–$C_6$ alkenyl" means straight and branched hydrocarbon radicals having from 2 to 6 carbon atoms and from one to three double bonds and includes, for example, ethenyl, propenyl, 1-but-3-enyl, 1-pent-3-enyl, 1-hex-5-enyl and the like.

"Alkynyl" and "$C_2$–$C_6$ alkynyl" means straight and branched hydrocarbon radicals having from 2 to 6 carbon atoms and one or two triple bonds and includes ethynyl, propynyl, butynyl, pentyn-2-yl and the like.

As used herein, the term "cycloalkyl" refers to saturated carbocyclic radicals having three to twelve carbon atoms. The cycloalkyl can be monocyclic, or a polycyclic fused system. Examples of such radicals include cyclopropyl, cyclobutyl, cyclopentyl, cyclohexyl and cycloheptyl. The cycloalkyl groups herein are unsubstituted or, as specified, substituted in one or more substitutable positions with various groups. For example, such cycloalkyl groups may be optionally substituted with $C_1$–$C_6$ alkyl, $C_1$–$C_6$ alkoxy, halogen, hydroxy, cyano, nitro, amino, mono($C_1$–$C_6$) alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino ($C_1$–$C_6$)alkyl, mono($C_1$–$C_6$)alkylamino($C_1$–$C_6$)alkyl or di($C_1$–$C_6$)alkylamino($C_1$–$C_6$)alkyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted. Preferred aryl groups of the present invention are phenyl, 1-naphthyl, 2-naphthyl, indanyl, indenyl, dihydronaphthyl, tetralinyl or 6,7,8,9-tetrahydro-5H-benzo[a]cycloheptenyl. The aryl groups herein are unsubstituted or, as specified, substituted in one or more substitutable positions with various groups. For example, such aryl groups may be optionally substituted with, for example, $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono ($C_1$–$C_6$)alkylamino($C_1$–$C_6$)alkyl, di($C_1$–$C_6$)alkylamino ($C_1$–$C_6$)alkyl, —COOH, —C(=O)O($C_1$–$C_6$ alkyl), —C(=O)NH$_2$, —C(=O)N(mono- or di-$C_1$–$C_6$ alkyl), —S($C_1$–$C_6$ alkyl), —SO$_2$($C_1$–$C_6$ alkyl), —O—C(=O) ($C_1$–$C_6$ alkyl), —NH—C(=O)—($C_1$–$C_6$ alkyl), —N($C_1$–$C_6$ alkyl)-C(=O)—($C_1$–$C_6$ alkyl), —NH—SO$_2$—($C_1$–$C_6$ alkyl), —N($C_1$–$C_6$ alkyl)-SO$_2$—($C_1$–$C_6$ alkyl), —NH—C(=O)NH$_2$, —NH—C(=O)N(mono- or di-$C_1$–$C_6$ alkyl), —NH($C_1$–$C_6$ alkyl)-C(=O)—NH$_2$ or —NH($C_1$–$C_6$ alkyl)-C(=O)—N—(mono- or di-$C_1$–$C_6$ alkyl).

By "heteroaryl" is meant one or more aromatic ring systems of 5-, 6-, or 7-membered rings which includes fused ring systems of 9–11 atoms containing at least one and up to four heteroatoms selected from nitrogen, oxygen, or sulfur. Preferred heteroaryl groups of the present invention include pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. The heteroaryl groups herein are unsubstituted or, as specified, substituted in one or more substitutable positions with various groups. For example, such heteroaryl groups may be optionally substituted with $C_1$–$C_6$ alkyl, $C_1$–$C_6$ alkoxy, halogen, hydroxy, cyano, nitro, amino, mono ($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino ($C_1$–$C_6$)alkyl, mono($C_1$–$C_6$)alkylamino($C_1$–$C_6$)alkyl or di($C_1$–$C_6$)alkylamino($C_1$–$C_6$)alkyl, —COOH, —C(=O)O ($C_1$–$C_6$ alkyl), —C(=O) NH$_2$, —C(=O)N(mono- or di-$C_1$–$C_6$ alkyl), —S($C_1$–$C_6$ alkyl), —SO$_2$($C_1$–$C_6$ alkyl), —O—C(=O) ($C_1$–$C_6$ alkyl), —NH—C(=O)—($C_1$–$C_6$ alkyl), —N($C_1$–$C_6$ alkyl)-C(=O)—($C_1$–$C_6$ alkyl), —NH—SO$_2$—($C_1$–$C_6$ alkyl), —N($C_1$–$C_6$ alkyl)-SO$_2$—($C_1$–$C_6$ alkyl), —NH—C(=O) NH$_2$, —NH—C(=O)N(mono- or di-$C_1$–$C_6$ alkyl), —NH($C_1$–$C_6$ alkyl)-C(=O)—NH$_2$ or —NH($C_1$–$C_6$ alkyl)-C(=O)—N—(mono- or di-$C_1$–$C_6$ alkyl).

By "heterocycle", "heterocycloalkyl" or "heterocyclyl" is meant one or more carbocyclic ring systems of 3-, 4-, 5-, 6-, or 7-membered rings which includes fused ring systems of 9-11 atoms containing at least one and up to four heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, azepanyl, diazepanyl, tetrahydrothienyl S-oxide, tetrahydrothienyl S,S-dioxide and homothiomorpholinyl S-oxide. The heterocycle groups herein maybe unsubstituted or, as specified, substituted in one or more substitutable positions with various groups. For example, such heterocycle groups may be optionally substituted with $C_1$–$C_6$ alkyl, $C_1$–$C_6$ alkoxy, halogen, hydroxy, cyano, nitro, amino, mono ($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino ($C_1$–$C_6$)alkyl, mono($C_1$–$C_6$)alkylamino($C_1$–$C_6$)alkyl, di($C_1$–$C_6$)alkylamino($C_1$–$C_6$)alkyl or =O.

All patents and publications referred to herein are hereby incorporated by reference for all purposes.

Structures were named using Name Pro IUPAC Naming Software, version 5.09, available from Advanced Chemical Development, Inc., 90 Adelaide Street West, Toronto, Ontario, M5H 3V9, Canada.

The present invention may be better understood with reference to the following examples. These examples are intended to be representative of specific embodiments of the invention, and are not intended as limiting the scope of the invention.

Chemistry Examples

The following abbreviations are used in the Examples:

EDC (1-(3-dimethylaminopropyl)-3-ethylcarbodiimide or the hydrochloride salt);

DIEA (diisopropylethylamine);

PyBOP (benzotriazol-1-yloxy) tripyrrolidinophosphonium hexafluorophosphate);

HATU (O-(7-azabenzotriazol-1-yl)-1,1,3,3-tetramethyluronium hexafluorophosphate);

DCM (dichloromethane).

Example 1

Synthesis of 5-Bromo-N-[(1S,2R,3R)-1-(3,5-difluoro-benzyl)-2,3-dihydroxy-heptyl]-N',N'-dipropyl-isophthalamide

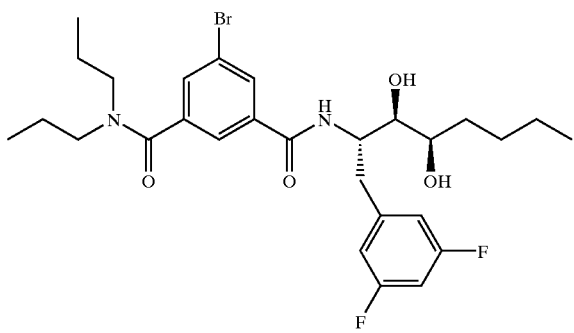

Preparation of N-(tert-butoxycarbonyl)-3,5-difluoro-N-methoxy-N-methyl-L-phenylalaninamide

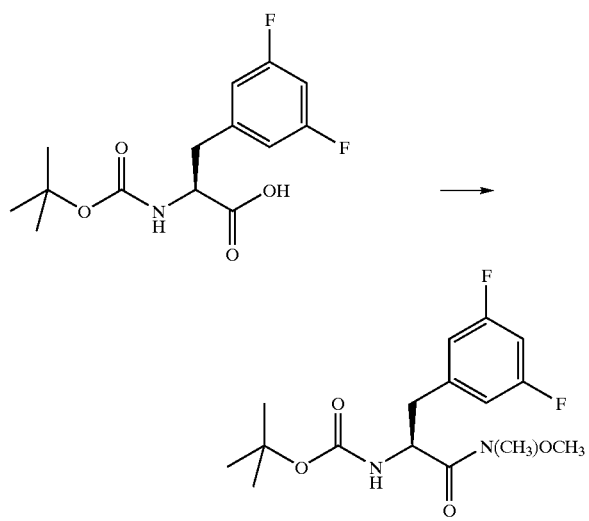

To a cooled (0–5° C.) solution of N-(tert-butoxycarbonyl)-3,5-difluoro-L-phenylalanine (15.00 g, 49.83 mmol), 1-hydroxybenzotriazole (8.39 g, 54.82 mmol), N,O-dimethylhydroxylamine hydrochloride (6.32 g, 64.78 mmol), and 4-dimethylaminopyridine (0.06 g, 0.50 mmol) in CH$_2$Cl$_2$ (200 mL) was added EDC (10.52 g, 54.82 mmol) followed by DIEA (11.28 mL, 64.78 mmol). After 20 min., the ice bath was removed and the mixture stirred overnight at ambient temperature. Volatiles were removed in vacuo and the residue partitioned between EtOAc and saturated NaHCO$_3$. The organic layer was extracted with saturated NaHCO$_3$, brine, 0.1 N HCl, and brine, dried (MgSO$_4$), filtered and evaporated in vacuo to afford the title compound as an oil which was used without further purification. MS (ESI+) for C$_{16}$H$_{22}$F$_2$N$_2$O$_4$ m/z 345 (M+H)$^+$.

Preparation of tert-butyl (1S,2R,3R)-1-(3,5-difluorobenzyl)-2,3-dihydroxyheptylcarbamate

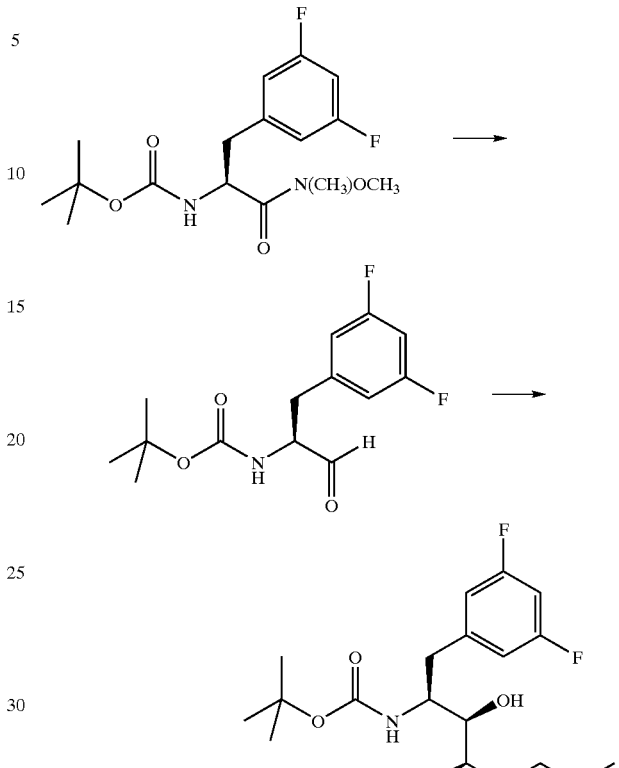

LiAlH$_4$ (23.6 mL of a 1 M solution in THF) was diluted with THF (50 mL) and cooled to (−78° C.). A solution of N-(tert-butoxycarbonyl)-3,5-difluoro-N-methoxy-N-methyl-L-phenylalaninamide (5.20 g, 15.75 mmol) was dissolved in THF (30 mL) and added to the cold LiAlH$_4$ solution via cannula over 10 mins. The mixture was stirred for 90 mins at −78° C. and the dry-ice/acetone bath was replaced with a dry ice/CCl$_4$ bath. Once the mixture had warmed to approx. −45° C., it was quenched by the careful addition of 0.5 N KHSO$_4$. The mixture was diluted with EtOAc and the organic layer washed with 0.1 N HCl, saturated NaHCO$_3$, and brine, dried (MgSO$_4$), filtered and evaporated in vacuo to afford tert-butyl (1S)-1-(3,5-difluorobenzyl)-2-oxoethylcarbamate as an oil which was used without further purification. In a flame dried, three-necked flask, a mixture of VCl$_3$(THF)$_3$ (11.70 g, 31.50 mmol) and zinc dust (1.29 g, 19.68 mmol) in anhydrous CH$_2$Cl$_2$ (150 mL) was stirred vigorously for 0.5 h to give a green solution. To this mixture, a solution of valeraldehyde (1.84 mL, 1.73 mmol) in anhydrous CH$_2$Cl$_2$ (10 mL) was added over 1 min. A solution of tert-butyl (1S)-1-(3,5-difluorobenzyl)-2-oxoethylcarbamate (prepared above) in anhydrous CH$_2$Cl$_2$ (50 mL) was added over 45 min via a syringe pump. The solution was stirred for an additional 45 min, poured into 10% aqueous sodium tartrate (400 mL) and stirred vigorously overnight. The layers were separated and the aqueous phase was extracted with CH$_2$Cl$_2$ (2×). The combined organic layers were washed with saturated NaHCO$_3$, dried (MgSO$_4$), filtered and concentrated under reduced pressure. The residue was purified via flash chromatography on silica gel using 1:1:2 to 1:1:1 Et$_2$O/CH$_2$Cl$_2$/ hexanes to give 2.60 g of tert-butyl (1S,2R,3R)-1-(3,5-difluorobenzyl)-2,3-dihydroxyheptylcarbamate as a solid. MS (ESI+) for $C_{19}H_{29}F_2NO_4$ m/z 374 (M+H)+.

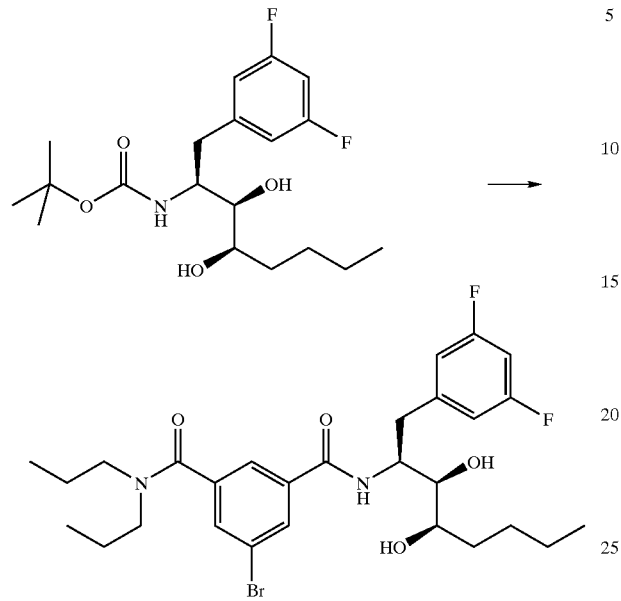

To a cooled (0–5° C.) solution of tert-butyl (1S,2R,3R)-1-(3,5-difluorobenzyl)-2,3-dihydroxyheptylcarbamate (100 mg, 0.27 mmol) in $CH_2Cl_2$ (5 mL) was added trifluoroacetic acid (5 mL). After 15 mins, the ice bath was removed and the solution stirred at ambient temp for 90 min. Volatiles were removed in vacuo and the residue dissolved in ethyl ether (20 mL). Volatiles were removed under reduced pressure and the ether dissolution/evaporation repeated. The oil was dissolved in DMF (5 mL) and cooled (0–5° C.). To this solution was added 3-bromo-5-[(dipropylamino)carbonyl] benzoic acid (96 mg, 0.29 mmol), 1-hydroxybenzotriazole (44 mg, 0.29 mmol), PyBOP (151 mg, 0.29 mmol) followed by DIEA (141 μL, 0.81 mmol). After 20 min., the ice bath was removed and the mixture stirred overnight at ambient temperature. Volatiles were removed in vacuo and the residue partitioned between EtOAc and saturated $NaHCO_3$. The organic layer was washed with saturated $NaHCO_3$, brine, 0.1 N HCl, and brine, dried ($MgSO_4$), filtered and concentrated under reduced pressure. The residue was purified via flash chromatography on silica gel using $CH_2Cl_2$ and a gradient of methanol 1–3%) as eluant to afford 5-bromo-N~1~-[(1S,2R,3R)-1-(3,5-difluorobenzyl)-2,3-dihydroxyheptyl]-N~3~-, N~3~--dipropylisophthalamide (145 mg) as a solid. MS (ESI+) for $C_{28}H_{37}BrF_2N_2O_4$ m/z 584 (M+H)+.

Example 2

General Method A (0.1 mmole Scale)

A mixture of the carboxylic acid (1.0 eq), HATU (1.2 eq.) and DIEA (2.4 eq.) in DMF (2 mL) was rocked at rt for 1 h. A solution of amine in DCM (1 mL) was added, and the reaction mixture rocked at rt overnight. The reaction was concentrated, redissolved in MeOH (2 mL for 3 mL) and Dowex 50WX2-400 (10 eq.) and MP-carbonate (10 eq.) added. The mixture was rocked for 2 h at rt, filtered and the resins washed resins with MeOH. The filtrate and washes were combined and concentrated. A 1000 mg C18 SPE cartridge was conditioned with 3 mL/6 mL MeCN, then 3 mL/6 mL 5% MeCN/0.1% TFA:water. The reaction residue was loaded onto the cartridge using (2×100 uL) DMF and eluted with 6 mL each of 5%, 10%, 15%, 25%, 50%, 100% MeCN/0.1% TFA:water. The fractions were analyzed by HPLC and the appropriate fractions were combined to give the desired product.

Example 3

Synthesis of N-[(1S,2R,3R)-1-(3,5-Difluoro-benzyl)-2,3-dihydroxy-heptyl]-5-methyl-N',N'-dipropyl-isophthalamide

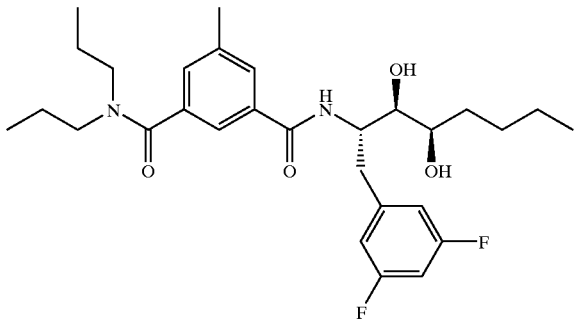

The trifluoroacetate salt of (1S,2R,3R)-1-(3,5-difluorobenzyl)-2,3-dihydroxyheptylamine (0.1 mmol) was reacted with 3-methyl-5-[(dipropylamino)carbonyl]benzoic acid as described in method A (addition of an extra equivalent of DIEA to neutralize the amine salt) to give $N^1$-[(1S,2R,3R)-1-(3,5-Difluorobenzyl)-2,3-dihydroxy-octyl]-5-methyl-$N^3$,$N^3$-dipropyl-isophthalamide. MS (ESI+) for $C_{29}H_{40}F_2N_2O_4$ m/z 519 (M+H)+.

Example 4

Synthesis of 5-Carboxamido-N-[(1S,2R,3R)-1-(3,5-difluoro-benzyl)-2,3-dihydroxy-heptyl]-N',N'-dipropyl-isophthalamide

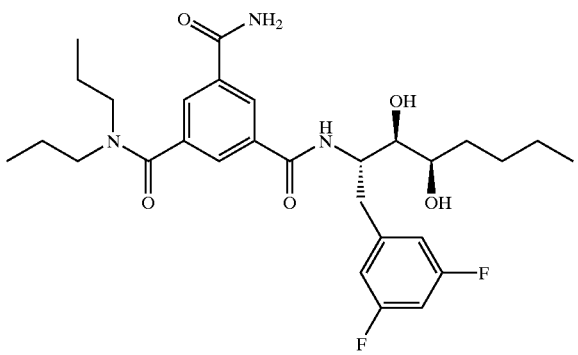

The trifluoroacetate salt of (1S,2R,3R)-1-(3,5-difluorobenzyl)-2,3-dihydroxyheptylamine (0.1 mmol) was reacted with 3-carboxamido-5-[(dipropylamino)carbonyl] benzoic acid as described in method A (addition of an extra equivalent of DIEA to neutralize the amine salt) to give $N^1$-[(1S,2R,3R)-1-(3,5-Difluoro-benzyl)-2,3-dihydroxy-octyl]-5-carboxamido-$N^3$,$N^3$-dipropyl-isophthalamide. MS (ESI+) for $C_{29}H_{39}F_2N_3O_5$ m/z 548 (M+H)+.

Example 5

Synthesis of N-[(1S,2R,3S)-1-benzyl-2,3-dihydroxy-heptyl]-5-methyl-N',N'-dipropyl-isophthalamide

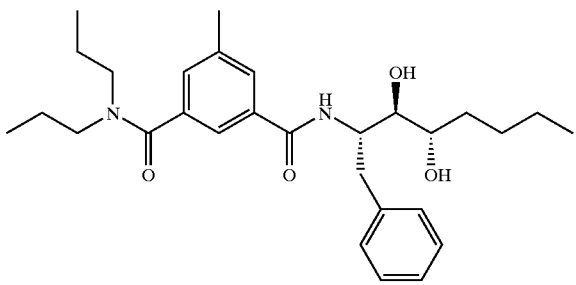

The trifluoroacetate salt of (1S,2R,3S)-1-benzyl-2,3-dihydroxyheptylamine (0.1 mmol) was reacted with 3-methyl-5-[(dipropylamino)carbonyl]benzoic acid as described in method A (addition of an extra equivalent of DIEA to neutralize the amine salt) to give $N^1$-[(1S,2R,3S)-1-benzyl-2,3-dihydroxy-octyl]-5-methyl-$N^3$,$N^3$-dipropyl-isophthalamide. MS (ESI+) for $C_{29}H_{42}N_2O_4$ m/z 483 (M+H)$^+$.

Example 6

Synthesis of (1S,2R,3S)-1-(3,5-difluorobenzyl)-2,3-dihydroxyheptylamine Hydrochloride Salt

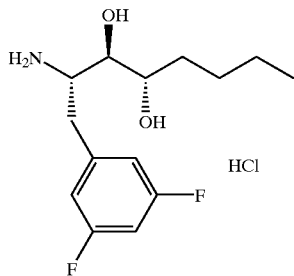

To a cooled (−55° C.) solution of (1S)-1-[(3,5-difluoro-benzyl)-2-oxo-ethyl]-carbamic acid tert-butyl ester (0.95 g, 3.32 mmol) in THF (10 mL) was slowly added vinyl magnesium bromide (1 M in THF, 8.5 mL, 8.5 mmol). The mixture was warmed to room temperature, stirred for 3 h and poured into saturated NH$_4$Cl. The mixture was diluted with ethyl acetate and the organic layer washed with 0.1 N HCl, brine, saturated NaHCO$_3$, brine, dried (MgSO$_4$), filtered, and concentrated under reduced pressure to afford a mixture of the (1S,2R)-1-(3,5-difluoro-benzyl)-2-hydroxy-but-3-enyl]-carbamic acid tert-butyl ester and (1S,2S)-1-(3,5-difluoro-benzyl)-2-hydroxy-but-3-enyl]-carbamic acid tert-butyl ester. The diastereomers were separated via flash chromatography on silica gel using hexanes/EtOAc (2–20%) containing 0.1% IPA as eluant to give (1S,2R)-1-(3,5-difluoro-benzyl)-2-hydroxy-but-3-enyl]-carbamic acid tert-butyl ester. MS (ESI+) for $C_{16}H_2F_{21}NO_3$ m/z 314.2 (M+H)$^+$.

To a cooled (0–5° C.) solution of (1S,2R)-1-(3,5-difluoro-benzyl)-2-hydroxy-but-3-enyl]-carbamic acid tert-butyl ester (6.60 g, 21.07 mmol) and DMAP (150 mg, 1.21 mmol) in pyridine (200 mL) was added acetic anhydride (20 mL, 212 mmol). After 2 h at 0° C. the volatiles were removed in vacuo and the residue was partitioned in EtOAc and 0.1 N HCl. The organic layer was washed with 0.1 N HCl, brine, saturated NaHCO$_3$, brine, dried (MgSO$_4$), filtered, and concentrated under reduced pressure to afford acetic acid (1R,1'S)-1-[1'-tert-butoxycarbonylamino-2'-(3,5-difluoro-phenyl)-ethyl]-allyl ester which was used without further purification. MS (ESI+) for $C_{18}H_{23}F_2NO_4$ m/z 356.1 (M+H)$^+$.

A cooled (−78° C.) solution of acetic acid (1R,1'S)-1-[1'-tert-butoxycarbonylamino-2'-(3,5-difluoro-phenyl)-ethyl]-allyl ester (4.55 g, 12.80 mmol) in MeOH (50 mL) was sparged with ozone until a blue color persisted. After 5 mins the solution was purged with oxygen until the blue color was absent. Dimethyl sulfide (5 mL, 68.08 mmol) was added and the solution warmed to room temperature and stirred overnight. The volatiles were removed in vacuo and the residue was partitioned in EtOAc and water. The organic layer was washed with water, brine, dried (MgSO$_4$), and concentrated under reduced pressure to afford acetic acid (1R,2S)-2-tert-butoxycarbonylamino-3-(3,5-difluoro-phenyl)-1-formyl-propyl ester, which was used without further purification. MS (ESI+) for $C_{17}H_{21}F_2NO_5$ m/z 358.1 (M+H)$^+$.

To a cooled (−78° C.) solution of acetic acid (1R,2S)-2-(tert-butoxycarbonylamino)-3-(3,5-difluoro-phenyl)-1-formyl-propyl ester (7.53 g, 21.07 mmol) in anhydrous THF (350 mL) was added slowly butyl magnesium chloride (2 M in THF, 44 mL, 88 mmol). The reaction mixture was warmed to room temperature, stirred for 3 h and poured into saturated NH$_4$Cl. The mixture was diluted with EtOAc and partitioned with 0.1 N HCl. The organic layer was separated and washed with 0.1 N HCl, brine, saturated NaHCO$_3$, brine, dried (MgSO$_4$), filtered, and concentrated under reduced pressure to yield acetic acid (1'S,1R,2S)-1-[1'-tert-butoxycarbonylamino-2'-(3,5-difluoro-phenyl)-ethyl]-2-hydroxy-hexyl ester and acetic acid (1'S,1R,2R)-1-[1'-tert-butoxycarbonylamino-2'-(3,5-difluoro-phenyl)-ethyl]-2-hydroxy-hexyl ester, which were used without purification. MS (ESI+) for $C_{21}H_{31}F_2NO_5$ m/z 416.1 (M+H)$^+$.

To a cooled (0–5° C.) solution of the mixture of (1'S,1R,2S)-1-[1'-tert-butoxycarbonylamino-2'-(3,5-difluoro-phenyl)-ethyl]-2-hydroxy-hexyl ester and acetic acid (1'S,1R,2R)-1-[1'-tert-butoxycarbonylamino-2'-(3,5-difluoro-phenyl)-ethyl]-2-hydroxy-hexyl ester (8.75 g, 21.07 mmol) in MeOH (300 mL) was added K$_2$CO$_3$ (5.7 g, 41.24 mmol). The suspension was stirred for 3 h then made acidic by the addition of 0.1 N HCl. The mixture was diluted with EtOAc and the organic layer was separated and washed with brine, saturated NaHCO$_3$, brine, dried (MgSO$_4$), filtered, and concentrated under reduced pressure to yield a mixture of (1S,2R,3S)-[1-(3,5-Difluoro-benzyl)-2,3-dihydroxy-heptyl]-carbamic acid tert-butyl ester and (1S,2R,3S)-[1-(3,5-Difluoro-benzyl)-2,3-dihydroxy-heptyl]-carbamic acid tert-butyl ester. The (1S,2R,3S) diastereomer was isolated via flash chromatography using 2% Acetone/CH$_2$Cl$_2$ containing 0.1% IPA followed by a second column using 10% EtOAc/hexane containing 0.1% IPA. MS (ESI+) for $C_{19}H_{29}F_2NO_4$ m/z 374.1 (M+H)$^+$.

To a cooled (0–5° C.) solution of (1S,2R,3S)-[1-(3,5-Difluoro-benzyl)-2,3-dihydroxy-heptyl]-carbamic acid tert-butyl ester (1.19 g, 3.2 mmol) in dioxane (20 mL) was added HCl (4 M in dioxane, 80 mL, 320 mmol) over 30 min. The reaction mixture was stirred at 0–5° C. for 30 min, then room temperature overnight. The volatiles were removed in vacuo and the residue was evaporated from ether to afford (1S,2R,3S)-1-(3,5-difluorobenzyl)-2,3-dihydroxyheptylamine as an HCl salt. MS (ESI+) for $C_{14}H_{21}F_2NO_2$ m/z 274.2 (M+H)+.

Example 7

Synthesis of (1S,2R,3S)-1-benzyl-2,3-dihydroxyheptylamine Trifluoroacetate Salt

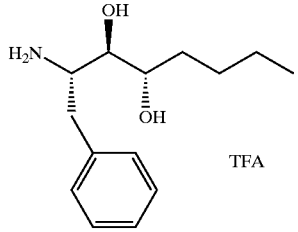

(1S,2R,3S)-1-benzyl-2,3-dihydroxyheptylamine trifluoroacetate Salt was prepared according to the procedure described in Example 6 from (1S)-(1-benzyl-2-oxo-ethyl)-carbamic acid tert-butyl ester. MS (ESI+) for $C_{14}H_{23}NO_2$ m/z 238 (M+H)+.

Example 8

Synthesis of N-[(1S,2R,3S)-1-(3,5-difluorobenzyl)-2,3-dihydroxy-heptyl]-5-methyl-N',N'-dipropyl-isophthalamide

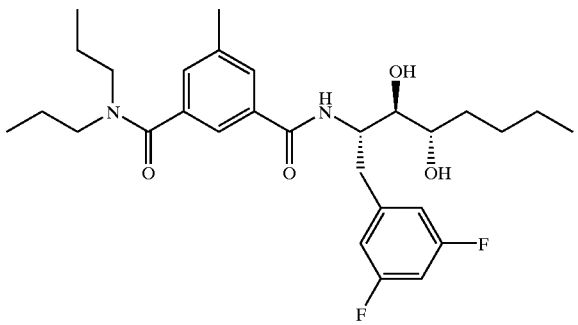

The hydrochloride salt of (1S,2R,3S)-1-(3,5-difluorobenzyl)-2,3-dihydroxyheptylamine (0.1 mmol) was reacted with 5-methyl-N,N-dipropyl-isophthalamic acid as described in method A (addition of an extra equivalent of DIEA to neutralize the amine salt) to give $N^1$-[(1S,2R,3S)-1-(3,5-difluorobenzyl)-2,3-dihydroxy-octyl]-5-methyl-$N^3$,$N^3$-dipropyl-isophthalamide. MS (ESI+) for $C_{29}H_{40}F_2N_2O_4$ m/z 540.9 (M+Na)+.

Example 9

Synthesis of 5-Carboxamido-N-[(1S,2R,3S)-1-(3,5-difluoro-benzyl)-2,3-dihydroxy-heptyl]-N',N'-dipropyl-isophthalamide

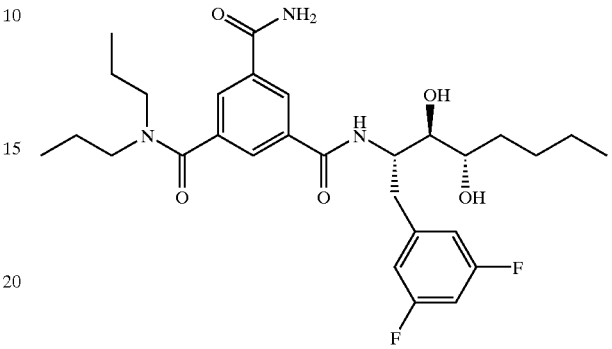

The hydrochloride salt of (1S,2R,3S)-1-(3,5-difluorobenzyl)-2,3-dihydroxyheptylamine (0.1 mmol) was reacted with 3-carbamoyl-5-dipropylcarbamoyl-benzoic acid as described in method A (addition of an extra equivalent of DIEA to neutralize the amine salt) to give $N^1$-[(1S,2R,3S)-1-(3,5-difluoro-benzyl)-2,3-dihydroxy-octyl]-5-carboxamido-$N^3$,$N^3$-dipropyl-isophthalamide. MS (ESI+) for $C_{29}H_{39}F_2N_3O_5$ m/z 569 (M+Na)+.

Example 10

Synthesis of (2S,3R,4R)-2-Amino-6-methylsulfanyl-1-phenyl-hexane-3,4-diol Trifluoroacetate Salt

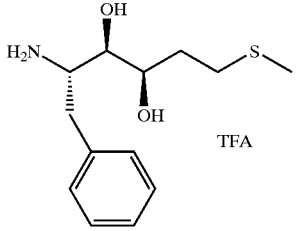

(2S,3R,4R)-2-Amino-6-methylsulfanyl-1-phenyl-hexane-3,4-diol trifluoroacetate salt was prepared according to the procedure described in Example 6 from (1S)-(1-benzyl-2-oxo-ethyl)-carbamic acid tert-butyl ester and 3-methylsulfanyl-propionaldehyde. MS (ESI+) for $C_{13}H_{21}NO_2S$ m/z 256 (M+H)+.

Example 11

Synthesis of 2-({3-bromo-5-[(dipropylamino)carbonyl]benzoyl}amino)-1,2,5-trideoxy-6-S-methyl-1-phenyl-6-thio-D-xylo-hexitol

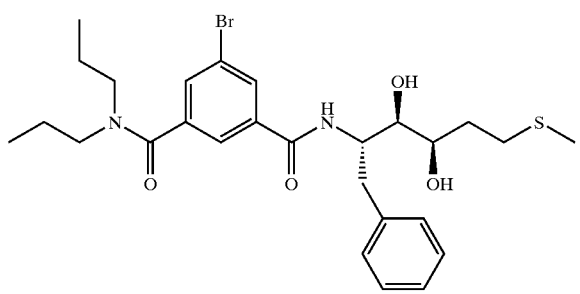

The trifluoroacetate salt of (2S,3R,4S)-2-Amino-6-methylsulfanyl-1-phenyl-hexane-3,4-diol (0.1 mmol) was reacted with 5-bromo-N,N-dipropyl-isophthalamic acid as described in method A (addition of an extra equivalent of DIEA to neutralize the amine salt) to give 2-({3-bromo-5-[(dipropylamino)carbonyl]benzoyl}amino)-1,2,5-trideoxy-6-S-methyl-1-phenyl-6-thio-D-xylo-hexitol. MS (ESI+) for $C_{27}H_{37}BrN_2O_4S$ m/z 567 (M+H)$^+$.

Example 12

Synthesis of (2S,3R,4R)-2-amino-1,7-diphenyl-heptane-3,4-diol Trifluoroacetate Salt

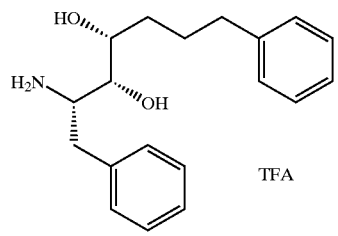

TFA (2S,3R,4R)-2-amino-1,7-diphenyl-heptane-3,4-diol trifluoroacetate salt was prepared according to the procedure described in Example 6 from (1S)-(1-benzyl-2-oxo-ethyl)-carbamic acid tert-butyl ester and 4-phenyl-butyraldehyde. MS (ESI+) for C19H25NO2 m/z 300 (M+H)$^+$.

Example 13

Synthesis of $N^1$-[(1S,2R,3R)-1-benzyl-2,3-dihydroxy-6-phenylhexyl]-$N^3$,$N^3$-dipropylbenzene-1,3,5-tricarboxamide

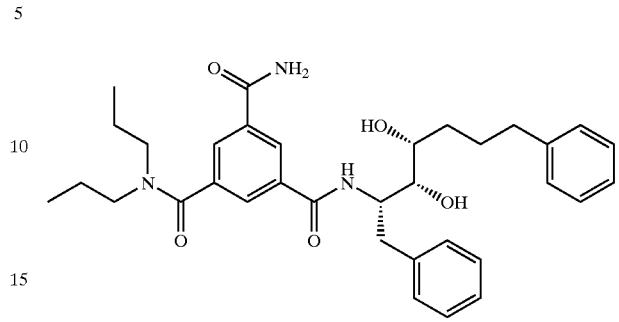

The trifluoroacetate salt of (2S,3R,4R)-2-amino-1,7-diphenyl-heptane-3,4-diol (0.1 mmol) was reacted with 3-carbamoyl-5-dipropylcarbamoyl-benzoic acid as described in method A (addition of an extra equivalent of DIEA to neutralize the amine salt) to give $N^1$-[(1S,2R,3R)-1-benzyl-2,3-dihydroxy-6-phenylhexyl]-$N^3$,$N^3$-dipropylbenzene-1,3,5-tricarboxamide. MS (ESI+) for $C_{34}H_{43}N_3O_5$ m/z 574 (M+H)$^+$.

Examples 14–253

The following compounds are prepared essentially according to the procedures described in the schemes, charts, examples and preparations set forth herein.

Example No.

14

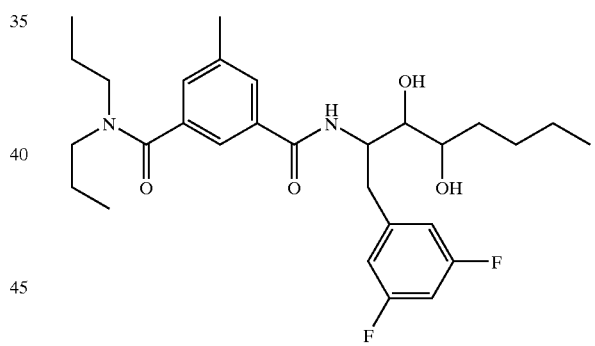

N'-[1-(3,5-difluorobenzyl)-2,3-dihydroxyheptyl]-5-methyl-N,N-dipropylisophthalamide

15

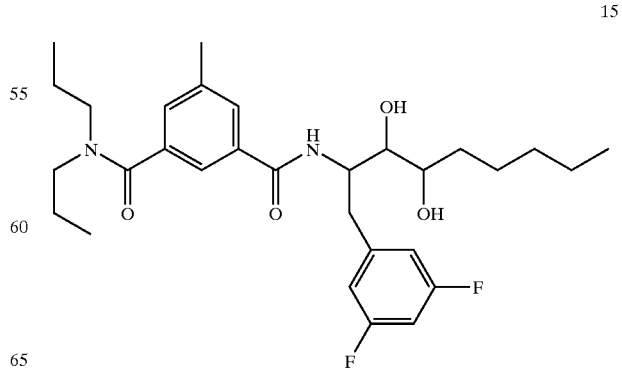

57
N'-[1-(3,5-difluorobenzyl)-2,3-dihydroxyoctyl]-5-methyl-N,N-dipropylisophthalamide

58
N'-[1-(3,5-difluorobenzyl)-2,3-dihydroxyoct-7-ynyl]-5-methyl-N,N-dipropylisophthalamide

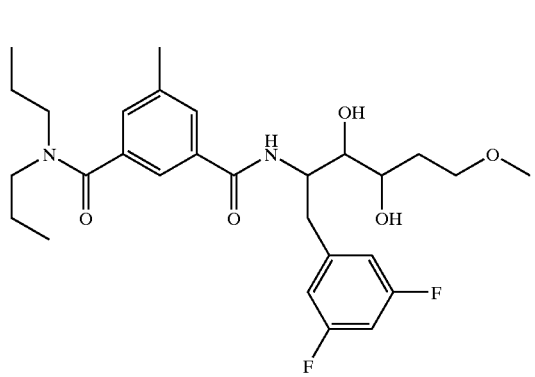

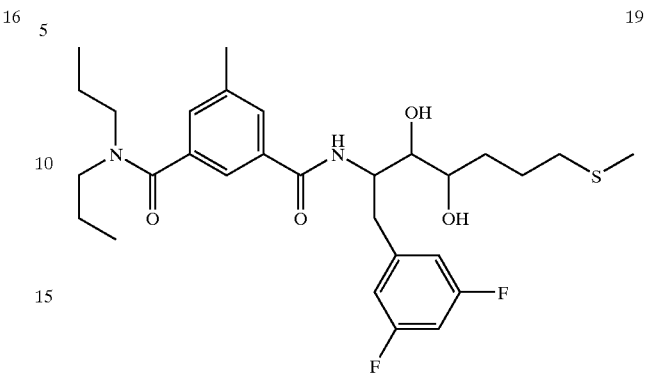

1,2,5-trideoxy-1-(3,5-difluorophenyl)-2-({3-[(dipropylamino)carbonyl]-5-methylbenzoyl}amino)-6-O-methylhexitol 1,2,5,6-tetradeoxy-1-(3,5-difluorophenyl)-2-({3-[(dipropylamino)carbonyl]-5-methylbenzoyl}amino)-7-S-methyl-7-thioheptitol

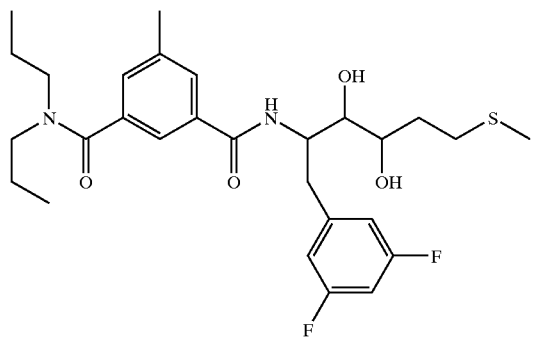

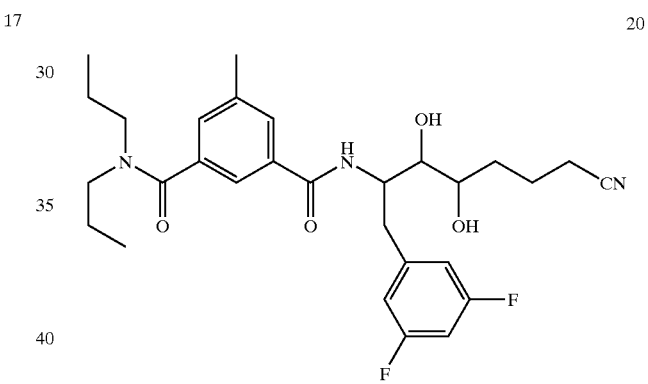

1,2,5-trideoxy-1-(3,5-difluorophenyl)-2-({3-[(dipropylamino)carbonyl]-5-methylbenzoyl}amino)-6-S-methyl-6-thiohexitol N'-[6-cyano-1-(3,5-difluorobenzyl)-2,3-dihydroxyhexyl]-5-methyl-N,N-dipropylisophthalamide

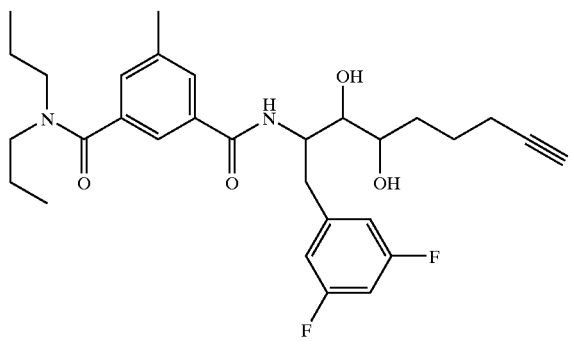

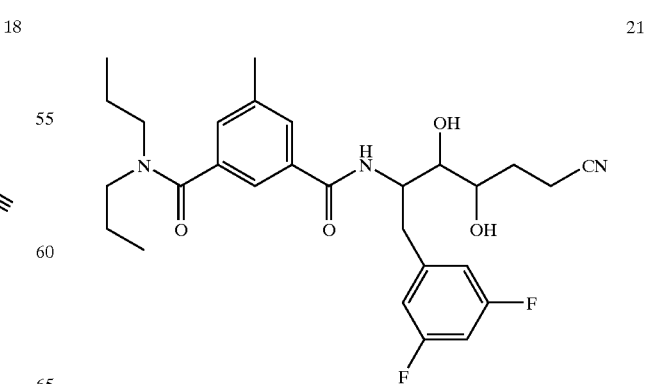

59

N'-[5-cyano-1-(3,5-difluorobenzyl)-2,3-dihydroxypentyl]-5-methyl-N,N-dipropylisophthalamide

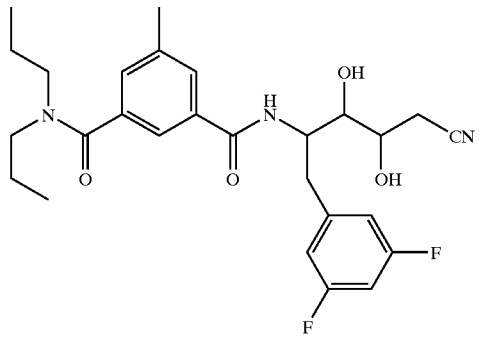

N'-[4-cyano-1-(3,5-difluorobenzyl)-2,3-dihydroxybutyl]-5-methyl-N,N-dipropylisophthalamide

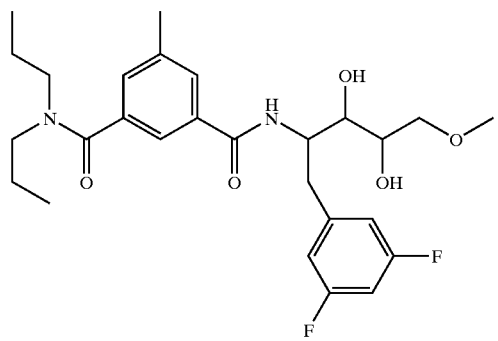

1,2-dideoxy-1-(3,5-difluorophenyl)-2-({3-[(dipropylamino)carbonyl]-5-methylbenzoyl}amino)-5-O-methylpentitol

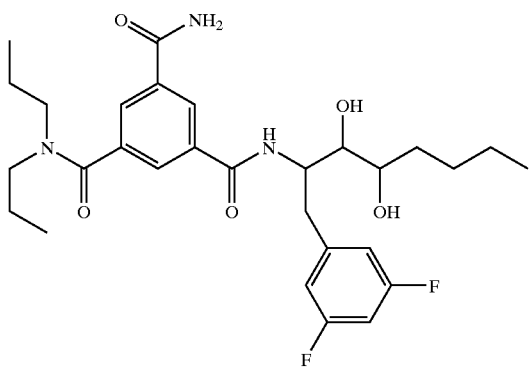

60

$N^3$-[1-(3,5-difluorobenzyl)-2,3-dihydroxyheptyl]-$N^1$,$N^1$-dipropylbenzene-1,3,5-tricarboxamide

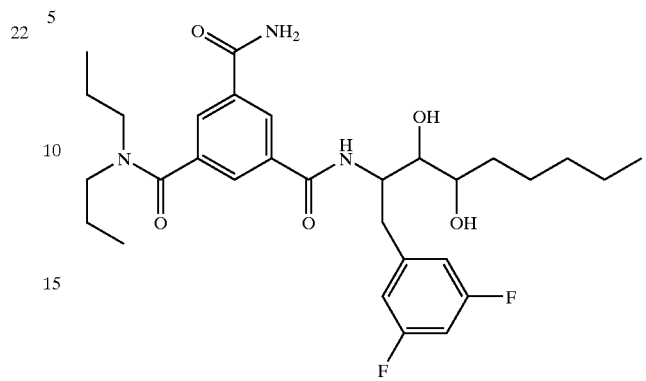

$N^3$-[1-(3,5-difluorobenzyl)-2,3-dihydroxyoctyl]-$N^1$,$N^1$-dipropylbenzene-1,3,5-tricarboxamide

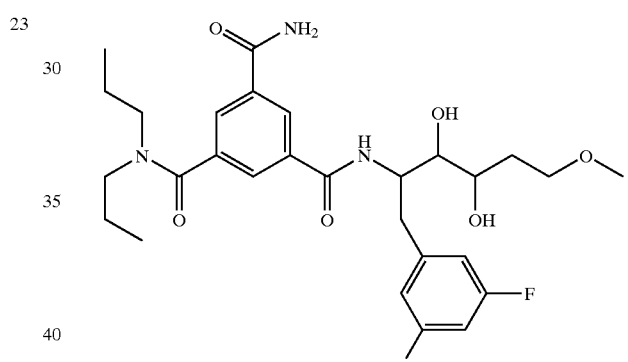

2-({3-(aminocarbonyl)-5-[(dipropylamino)carbonyl]benzoyl}amino)-1,2,5-trideoxy-1-(3,5-difluorophenyl)-6-O-methylhexitol

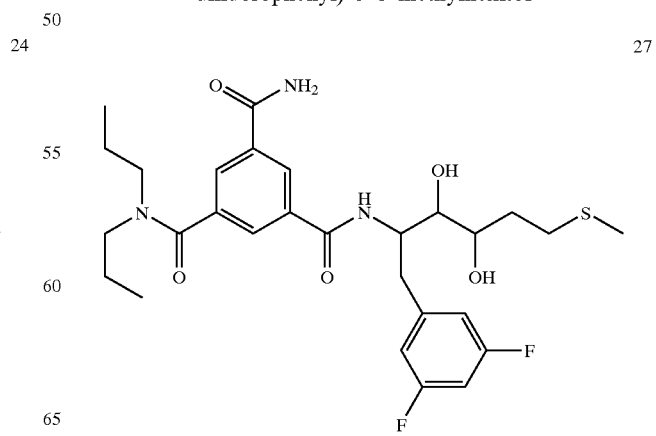

| 61 | 62 |
|---|---|
| 2-({3-(aminocarbonyl)-5-[(dipropylamino)carbonyl]benzoyl}amino)-1,2,5-trideoxy-1-(3,5-difluorophenyl)-6-S-methyl-6-thiohexitol | N³-[6-cyano-1-(3,5-difluorobenzyl)-2,3-dihydroxyhexyl]N¹,N¹-dipropylbenzene-1,3,5-tricarboxamide |

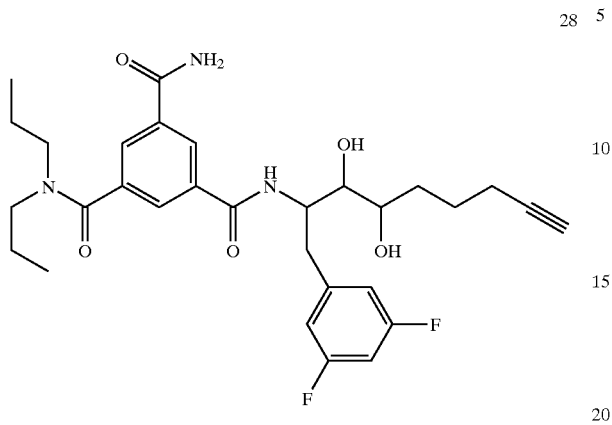

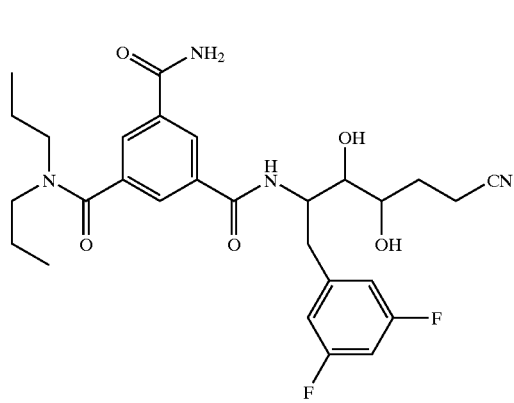

N³-[1-(3,5-difluorobenzyl)-2,3-dihydroxyoct-7-ynyl]-N¹,N¹-dipropylbenzene-1,3,5-tricarboxamide N³-[5-cyano-1-(3,5-difluorobenzyl)-2,3-dihydroxypentyl]-N¹,N¹-dipropylbenzene-1,3,5-tricarboxamide

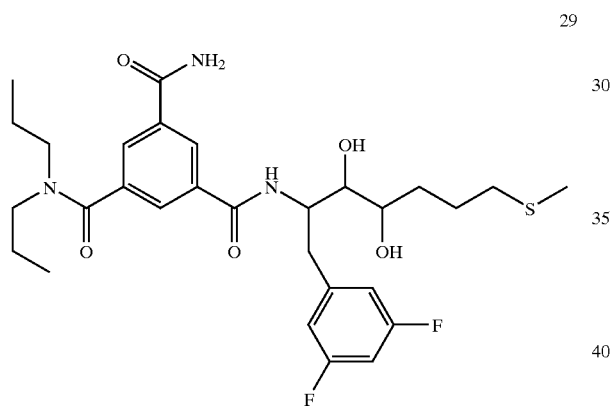

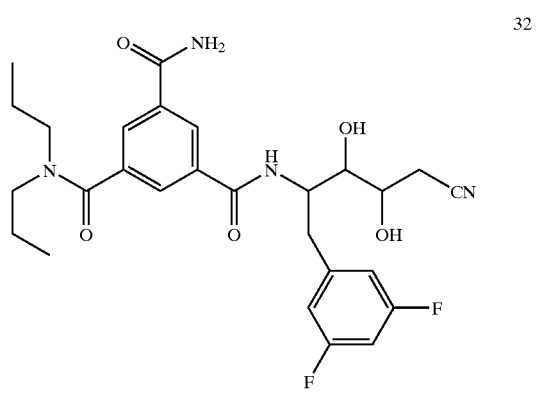

2-({3-(aminocarbonyl)-5-[(dipropylamino)carbonyl]benzoyl}amino)-1,2,5,6-tetradeoxy-1-(3,5-difluorophenyl)-7-S-methyl-7-thioheptitol N³-[4-cyano-1-(3,5-difluorobenzyl)-2,3-dihydroxybutyl]-N¹,N¹-dipropylbenzene-1,3,5-tricarboxamide

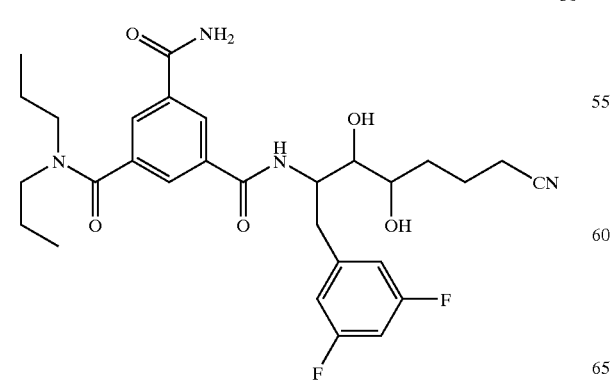

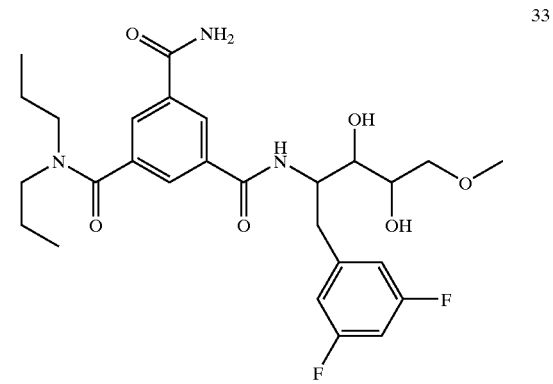

| 63 | 64 |
|---|---|
| 2-({3-(aminocarbonyl)-5-[(dipropylamino)carbonyl]benzoyl}amino)-1,2-dideoxy-1-(3,5-difluorophenyl)-5-O-methylpentitol | 1,2,5-trideoxy-1-(3,5-difluorophenyl)-6-O-methyl-2-[({2-[(methylsulfonyl)amino]-1,3-oxazol-4-yl}carbonyl)amino]hexitol |

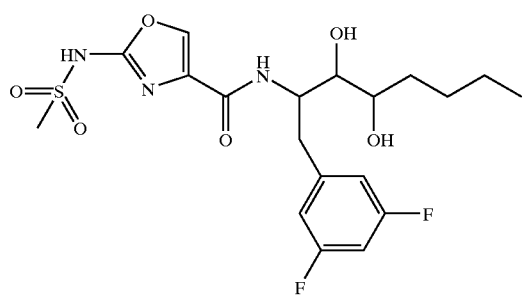

34

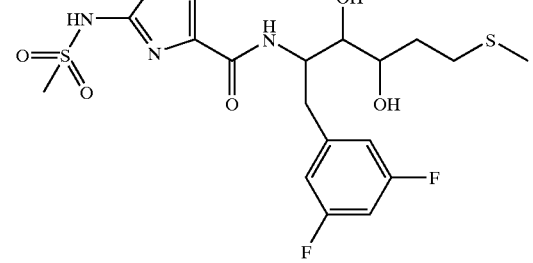

37

N-[1-(3,5-difluorobenzyl)-2,3-dihydroxyheptyl]-2-[(methylsulfonyl)amino]-1,3-oxazole-4-carboxamide 1,2,5-trideoxy-1-(3,5-difluorophenyl)-6-S-methyl-2-[({2-[(methylsulfonyl)amino]-1,3-oxazol-4-yl}carbonyl)amino]-6-thiohexitol

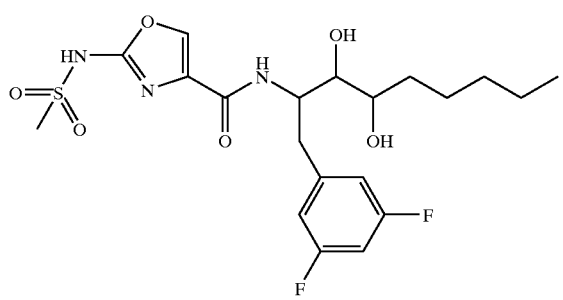

35

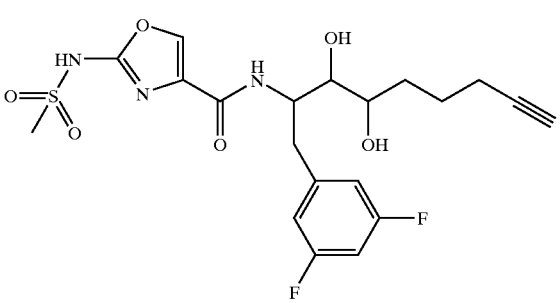

38

N-[1-(3,5-difluorobenzyl)-2,3-dihydroxyoctyl]-2-[(methylsulfonyl)amino]-1,3-oxazole-4-carboxamide N-[1-(3,5-difluorobenzyl)-2,3-dihydroxyoct-7-ynyl]-2-[(methylsulfonyl)amino]-1,3-oxazole-4-carboxamide

36

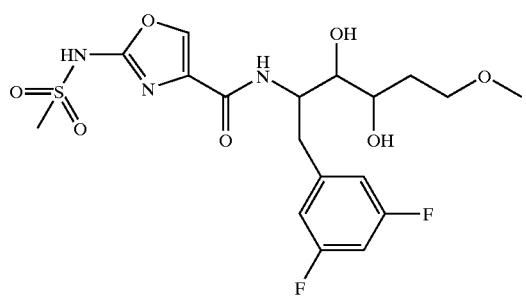

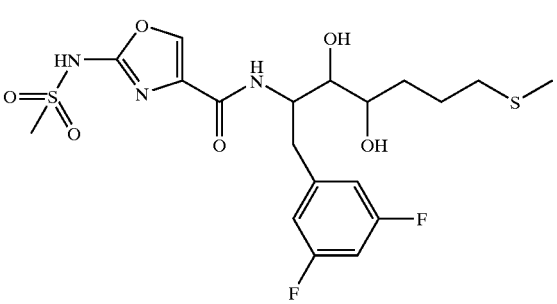

39

| 65 | 66 |
|---|---|
| 1,2,5,6-tetradeoxy-1-(3,5-difluorophenyl)-7-S-methyl-2-[({2-[(methylsulfonyl)amino]-1,3-oxazol-4-yl}carbonyl)amino]-7-thioheptitol | N-[4-cyano-1-(3,5-difluorobenzyl)-2,3-dihydroxybutyl]-2-[(methylsulfonyl)amino]-1,3-oxazole-4-carboxamide |

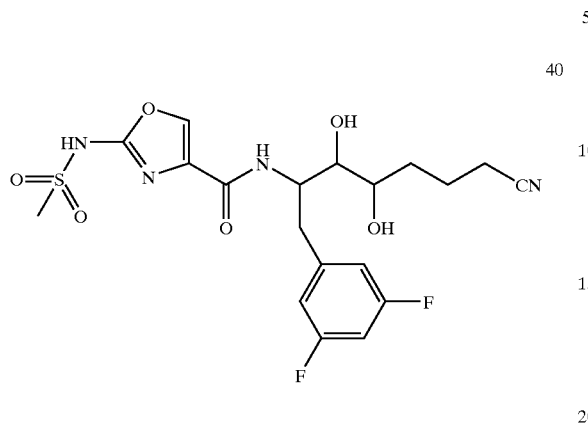

40

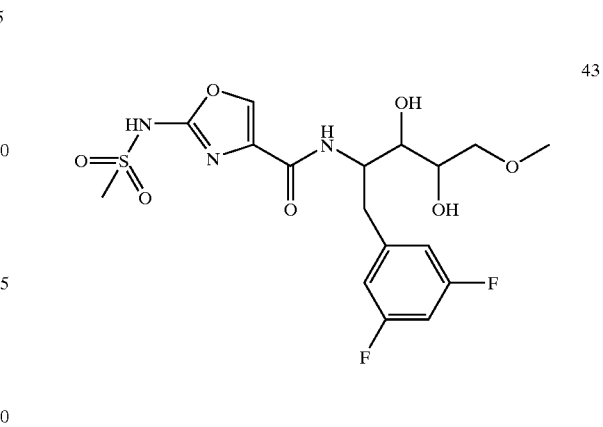

43

N-[6-cyano-1-(3,5-difluorobenzyl)-2,3-dihydroxyhexyl]-2-[(methylsulfonyl)amino]-1,3-oxazole-4-carboxamide 1,2-dideoxy-1-(3,5-difluorophenyl)-5-O-methyl-2-[({2-[(methylsulfonyl)amino]-1,3-oxazol-4-yl}carbonyl)amino]pentitol

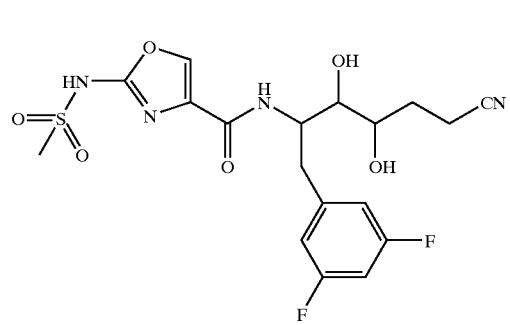

41

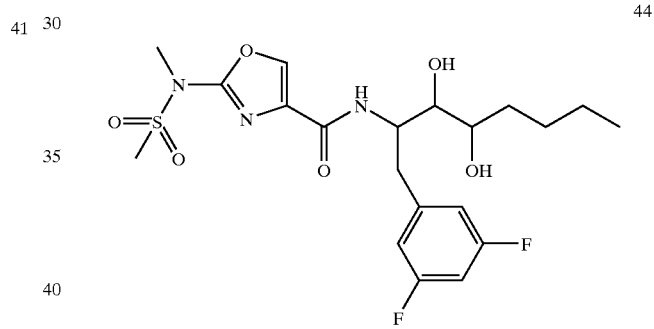

44

N-[5-cyano-1-(3,5-difluorobenzyl)-2,3-dihydroxypentyl]-2-[(methylsulfonyl)amino]-1,3-oxazole-4-carboxamide N-[1-(3,5-difluorobenzyl)-2,3-dihydroxyheptyl]-2-[methyl(methylsulfonyl)amino]-1,3-oxazole-4-carboxamide

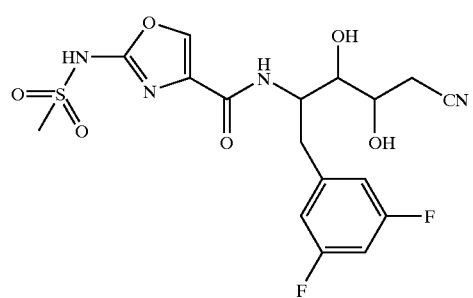

42

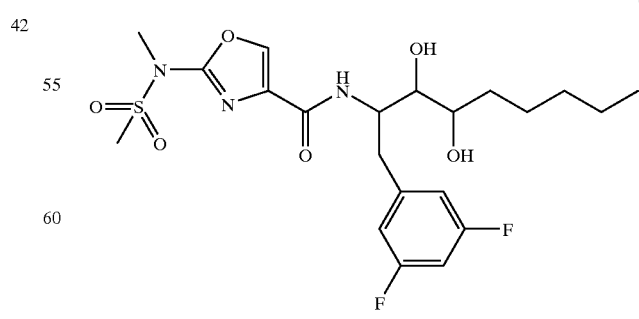

45

| 67 | 68 |
|---|---|
| N-[1-(3,5-difluorobenzyl)-2,3-dihydroxyoctyl]-2-[methyl(methylsulfonyl)amino]-1,3-oxazole-4-carboxamide | N-[1(3,5-difluorobenzyl)-2,3-dihydroxyoct-7-ynyl]-2-[methyl(methylsulfonyl)amino]-1,3-oxazole-4-carboxamide |

46

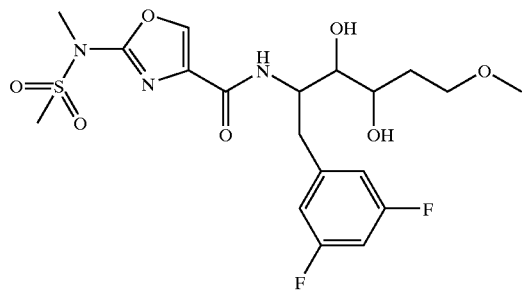

49

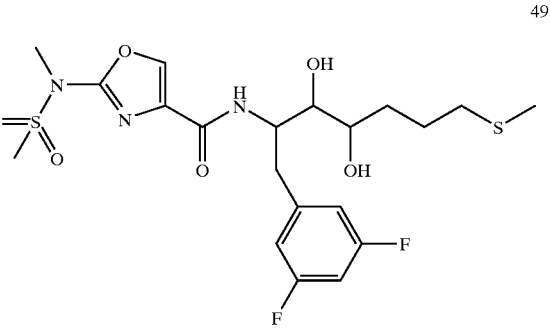

1,2,5-trideoxy-1-(3,5-difluorophenyl)-6-O-methyl-2-[({2-[methyl(methylsulfonyl)amino]-1,3-oxazol-4-yl}carbonyl)amino]hexitol 1,2,5,6-tetradeoxy-1-(3,5-difluorophenyl)-7-S-methyl-2-[({2-[methyl(methylsulfonyl)amino]-1,3-oxazol-4-yl}carbonyl)amino]-7-thioheptitol

47

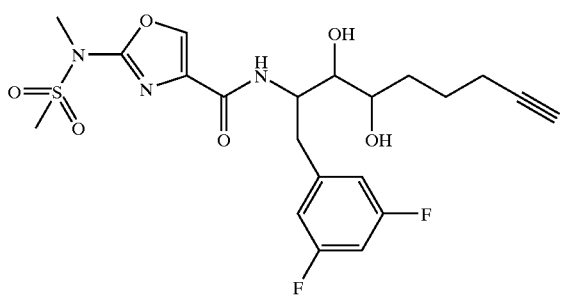

50

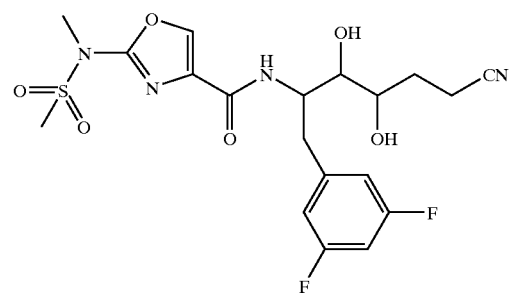

1,2,5-trideoxy-1-(3,5-difluorophenyl)-6-S-methyl-2-[({2-[methyl(methylsulfonyl)amino]-1,3-oxazol-4-yl}carbonyl)amino]-6-thiohexitol N-[6-cyano-1-(3,5-difluorobenzyl)-2,3-dihydroxyhexyl]-2-[methyl(methylsulfonyl)amino]-1,3-oxazole-4-carboxamide

48

51

69

N-[5-cyano-1-(3,5-difluorobenzyl)-2,3-dihydroxypentyl]-2-[methyl(methylsulfonyl)amino]-1,3-oxazole-4-carboxamide

70

N-[1-(3,5-difluorobenzyl)-2,3-dihydroxyheptyl]-2-[(methylsulfonyl)amino]-1,3-thiazole-4-carboxamide

51

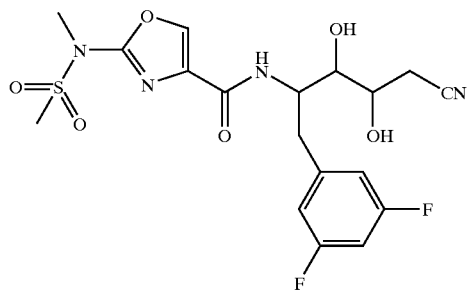

55

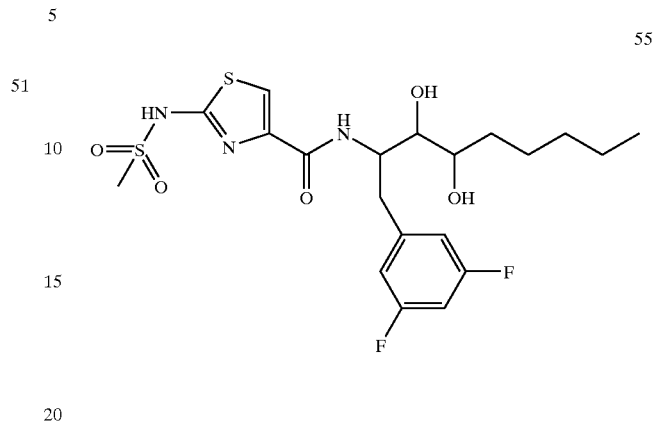

N-[4-cyano-1-(3,5-difluorobenzyl)-2,3-dihydroxybutyl]-2-[methyl(methylsulfonyl)amino]-1,3-oxazole-4-carboxamide N-[1-(3,5-difluorobenzyl)-2,3-dihydroxyoctyl]-2-[(methylsulfonyl)amino]-1,3-thiazole-4-carboxamide

53

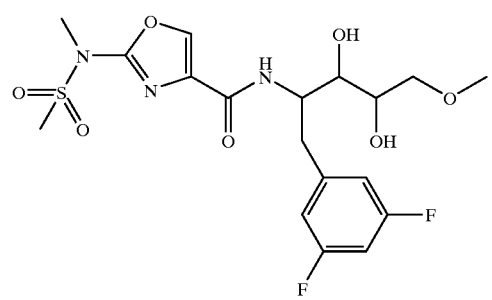

56

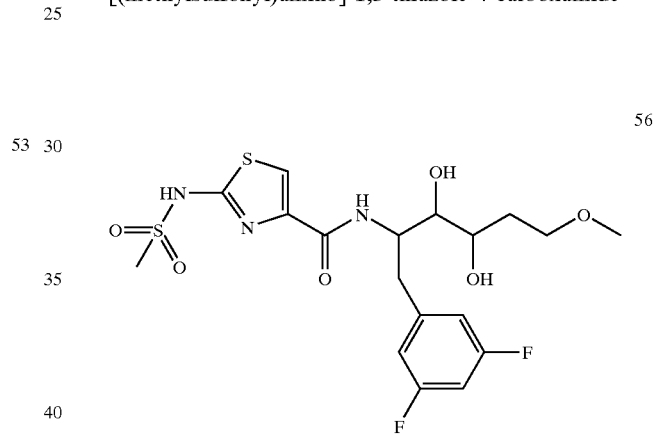

1,2-dideoxy-1-(3,5-difluorophenyl)-5-O-methyl-2-[({2-[methyl(methylsulfonyl)amino]-1,3-oxazol-4-yl}carbonyl)amino]pentitol 1,2,5-trideoxy-1-(3,5-difluorophenyl)-6-O-methyl-2-[({2-[(methylsulfonyl)amino]-1,3-thiazol-4-yl}carbonyl)amino]hexitol

54

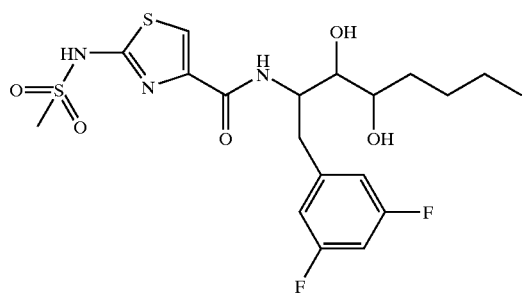

57

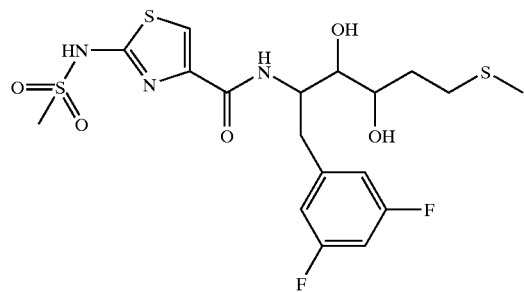

| 71 | 72 |
|---|---|
| 1,2,5-trideoxy-1-(3,5-difluorophenyl)-6-S-methyl-2-[({2-[(methylsulfonyl)amino]-1,3-thiazol-4-yl}carbonyl)amino]-6-thiohexitol | N-[6-cyano-1-(3,5-difluorobenzyl)-2,3-dihydroxyhexyl]-2-[(methylsulfonyl)amino]-1,3-thiazole-4-carboxamide |

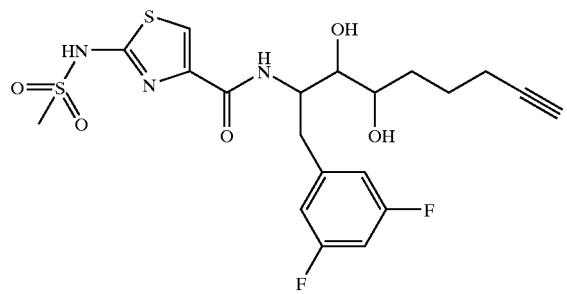      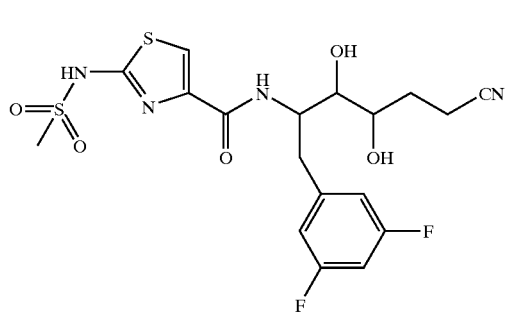

N-[1-(3,5-difluorobenzyl)-2,3-dihydroxyoct-7-ynyl]-2-[(methylsulfonyl)amino]-1,3-thiazole-4-carboxamide N-[5-cyano-1-(3,5-difluorobenzyl)-2,3-dihydroxypentyl]-2-[(methylsulfonyl)amino]-1,3-thiazole-4-carboxamide

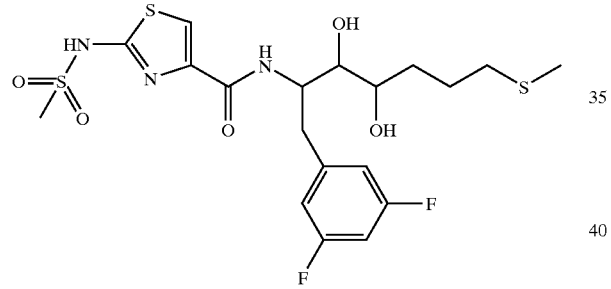      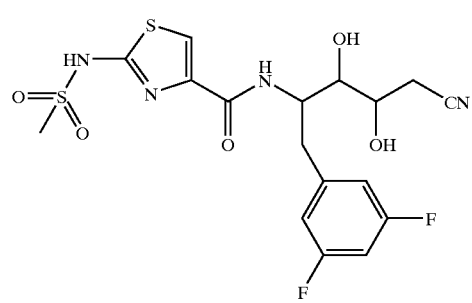

1,2,5,6-tetradeoxy-1-(3,5-difluorophenyl)-7-S-methyl-2-[({2-[(methylsulfonyl)amino]-1,3-thiazol-4-yl}carbonyl)amino]-7-thioheptitol N-[4-cyano-1-(3,5-difluorobenzyl)-2,3-dihydroxybutyl]-2-[(methylsulfonyl)amino]-1,3-thiazole-4-carboxamide

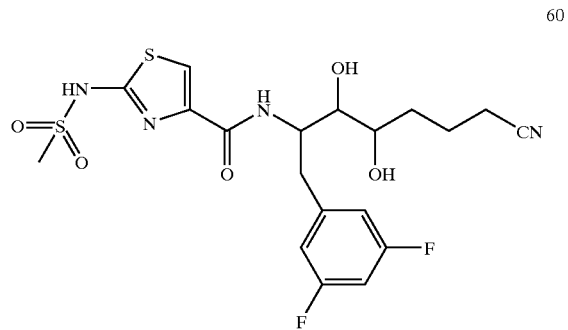      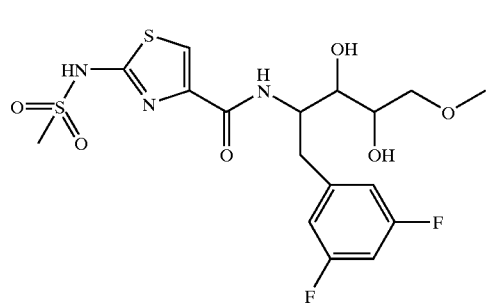

73
1,2-dideoxy-1-(3,5-difluorophenyl)-5-O-methyl-2-
[({2-[(methylsulfonyl)amino]-1,3-thiazol-4-
yl}carbonyl)amino]pentitol

74
1,2,5-trideoxy-1-(3,5-difluorophenyl)-6-O-methyl-2-
[({2-[methyl(methylsulfonyl)amino]-1,3-thiazol-4-
yl}carbonyl)amino]hexitol

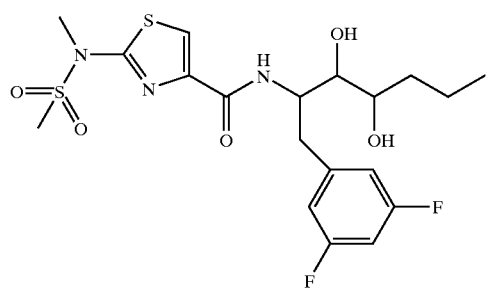

64

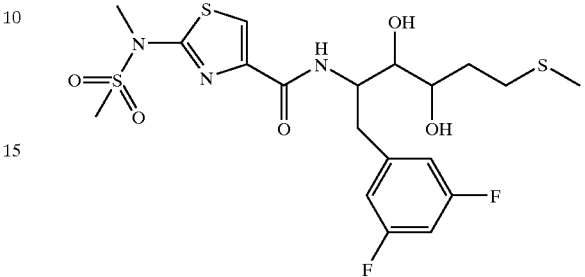

67

N-[1-(3,5-difluorobenzyl)-2,3-dihydroxyheptyl]-2-
[methyl(methylsulfonyl)amino]-1,3-thiazole-4-
carboxamide 1,2,5-trideoxy-1-(3,5-difluorophenyl)-6-S-methyl-2-
[({2-[methyl(methylsulfonyl)amino]-1,3-thiazol-4-
yl}carbonyl)amino]-6-thiohexitol

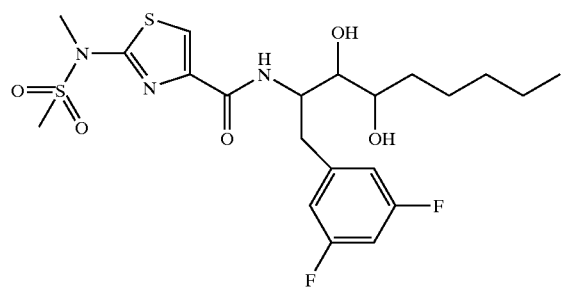

65

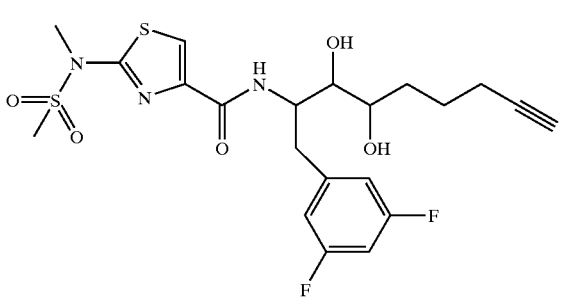

68

N-[1-(3,5-difluorobenzyl)-2,3-dihydroxyoctyl]-2-
[methyl(methylsulfonyl)amino]-1,3-thiazole-4-
carboxamide N-[1-(3,5-difluorobenzyl)-2,3-dihydroxyoct-7-ynyl]-
2-[methyl(methylsulfonyl)amino]-1,3-thiazole-4-
carboxamide

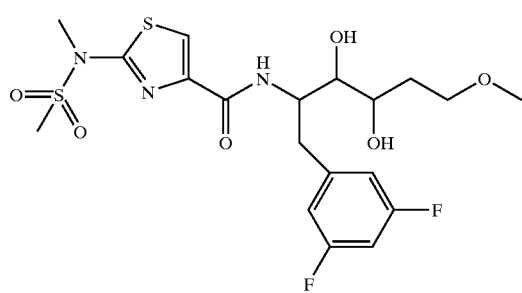

66

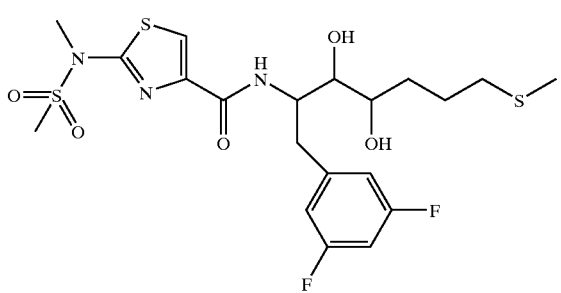

69

75

1,2,5,6-tetradeoxy-1-(3,5-difluorophenyl)-7-S-methyl-2-[({2-[methyl(methylsulfonyl)amino]-1,3-thiazol-4-yl}carbonyl)amino]-7-thioheptitol

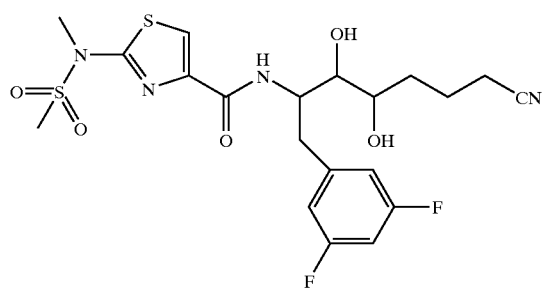

N-[6-cyano-1-(3,5-difluorobenzyl)-2,3-dihydroxyhexyl]-2-[methyl(methylsulfonyl)amino]-1,3-thiazole-4-carboxamide

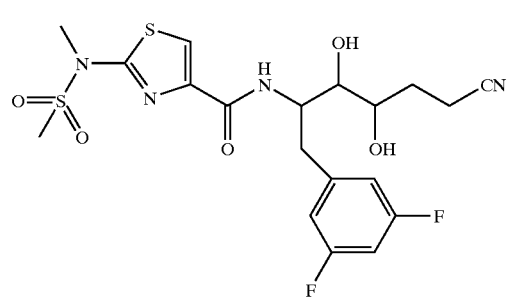

N-[5-cyano-1-(3,5-difluorobenzyl)-2,3-dihydroxypentyl]-2-[methyl(methylsulfonyl)amino]-1,3-thiazole-4-carboxamide

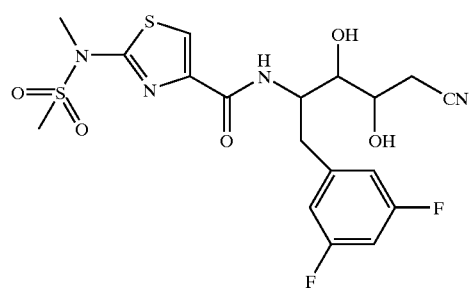

76

N-[4-cyano-1-(3,5-difluorobenzyl)-2,3-dihydroxybutyl]-2-[methyl(methylsulfonyl)amino]-1,3-thiazole-4-carboxamide

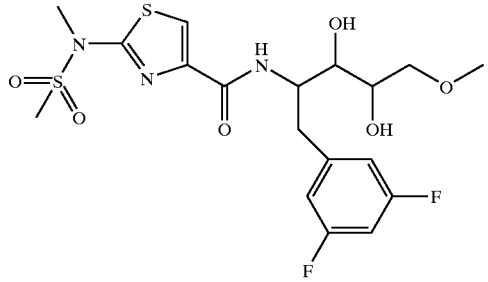

1,2-dideoxy-1-(3,5-difluorophenyl)-5-O-methyl-2-[({2-[methyl(methylsulfonyl)amino]-1,3-thiazol-4-yl}carbonyl)amino]pentitol

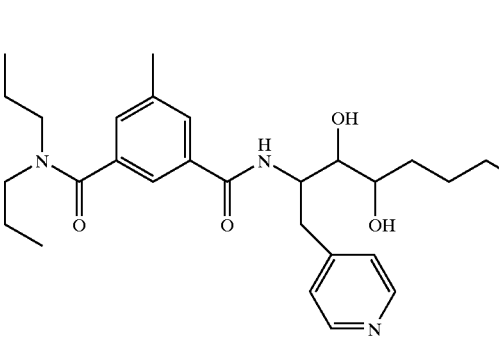

N'-[2,3-dihydroxy-1-(pyridin-4-ylmethyl)heptyl]-5-methyl-N,N-dipropylisophthalamide

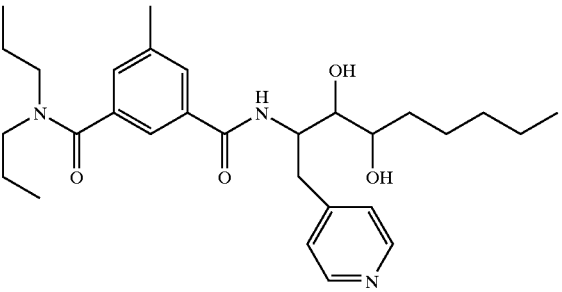

77
N'-[2,3-dihydroxy-1-(pyridin-4-ylmethyl)octyl]-5-methyl-N,N-dipropylisophthalamide

78
N'-[2,3-dihydroxy-1-(pyridin-4-ylmethyl)oct-7-ynyl]-5-methyl-N,N-dipropylisophthalamide

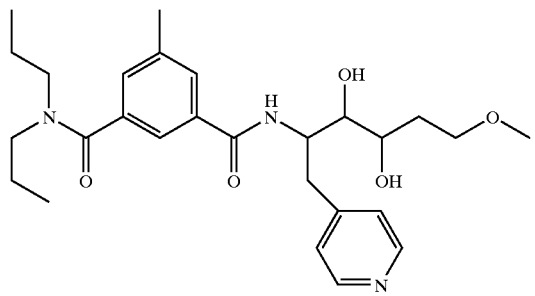

1,2,5-trideoxy-2-({3-[(dipropylamino)carbonyl]-5-methylbenzoyl}amino)-6-O-methyl-1-pyridin-4-ylhexitol

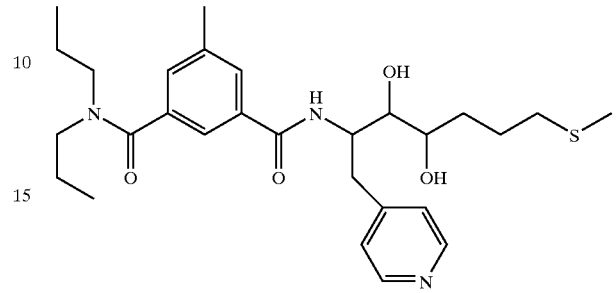

1,2,5,6-tetradeoxy-2-({3-[(dipropylamino)carbonyl]-5-methylbenzoyl}amino)-7-S-methyl-1-pyridin-4-yl-7-thioheptitol

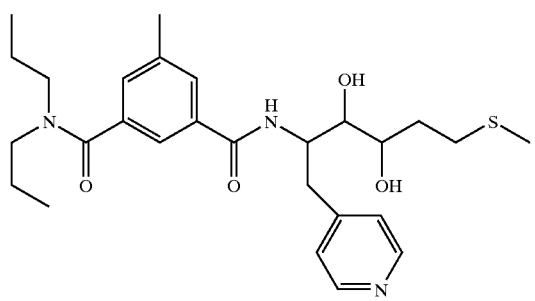

1,2,5-trideoxy-2-({3-[(dipropylamino)carbonyl]-5-methylbenzoyl}amino)-6-S-methyl-1-pyridin-4-yl-6-thiohexitol

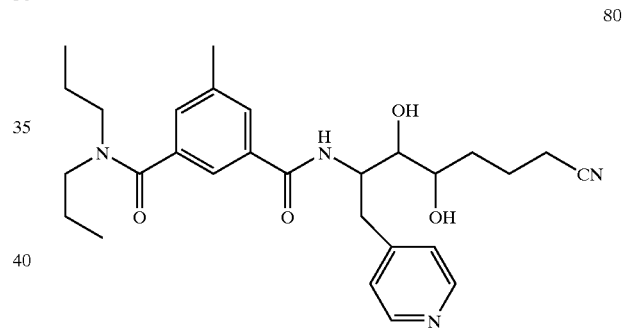

N'-[6-cyano-2,3-dihydroxy-1-(pyridin-4-ylmethyl)hexyl]-5-methyl-N,N-dipropylisophthalamide

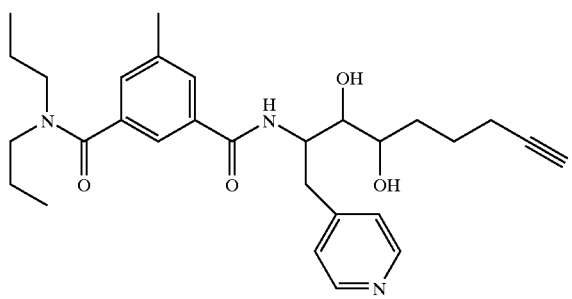

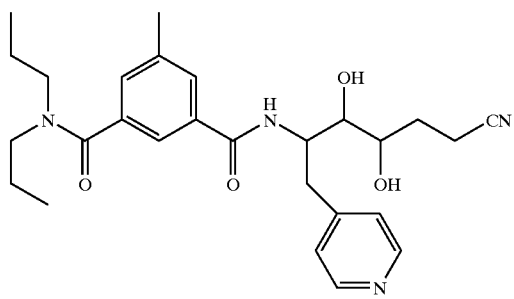

| 79 | 80 |
|---|---|
| N'-[5-cyano-2,3-dihydroxy-1-(pyridin-4-ylmethyl)pentyl]-5-methyl-N,N-dipropylisophthalamide | $N^3$-[2,3-dihydroxy-1-(pyridin-4-ylmethyl)heptyl]-$N^1,N^1$-dipropylbenzene-1,3,5-tricarboxamide |

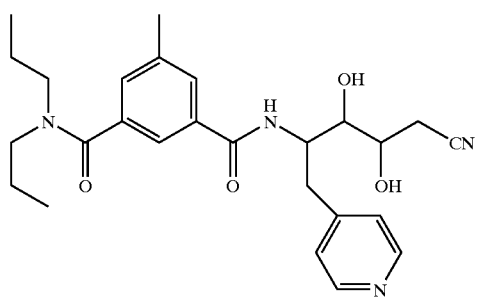

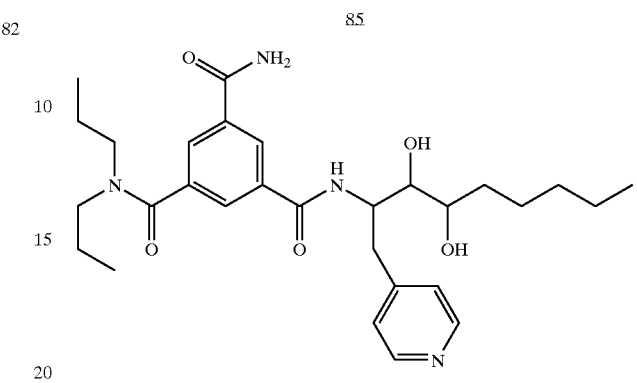

N'-[4-cyano-2,3-dihydroxy-1-(pyridin-4-ylmethyl)butyl]-5-methyl-N,N-dipropylisophthalamide $N^3$-[2,3-dihydroxy-1-(pyridin-4-ylmethyl)octyl]-$N^1,N^1$-dipropylbenzene-1,3,5-tricarboxamide

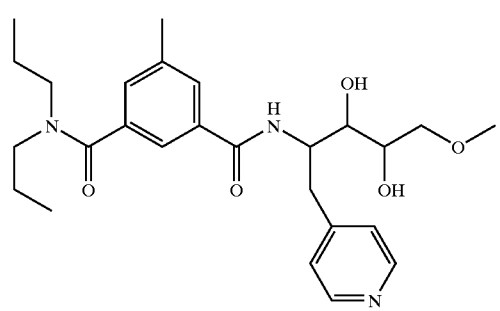

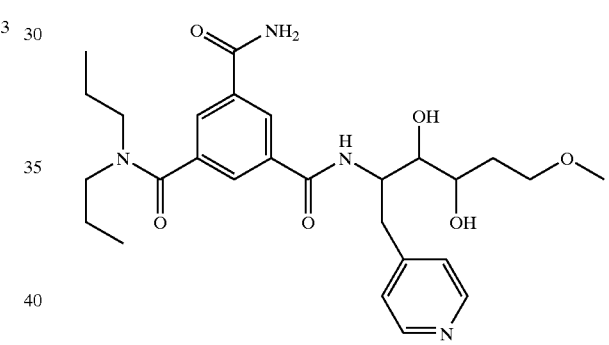

1,2-dideoxy-2-({3-[(dipropylamino)carbonyl]-5-methylbenzoyl}amino)-5-O-methyl-1-pyridin-4-ylpentitol 2-({3-(aminocarbonyl)-5-[(dipropylamino)carbonyl]benzoyl}amino)-1,2,5-trideoxy-6-O-methyl-1-pyridin-4-ylhexitol

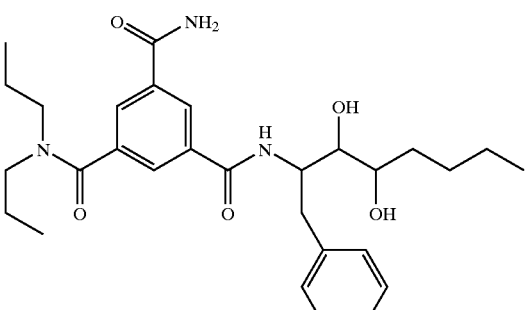

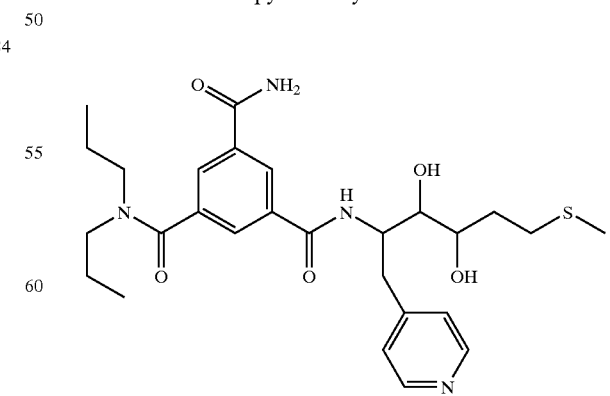

81

2-({3-(aminocarbonyl)-5-[(dipropylamino)carbonyl]
benzoyl}amino)-1,2,5-trideoxy-6-S-methyl-1-
pyridin-4-yl-6-thiohexitol

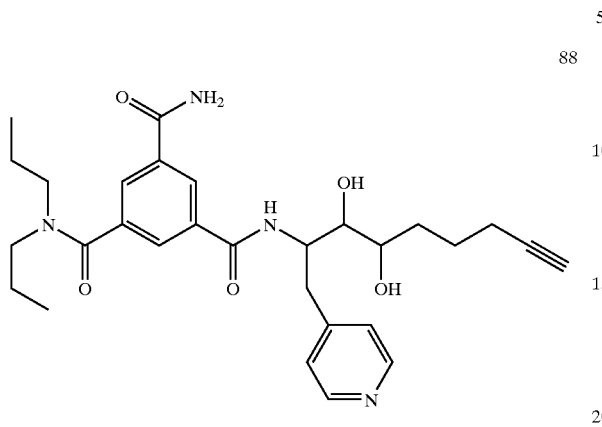

N³-[2,3-dihydroxy-1-(pyridin-4-ylmethyl)oct-7-
ynyl]-N¹,N¹-dipropylbenzene-1,3,5-tricarboxamide

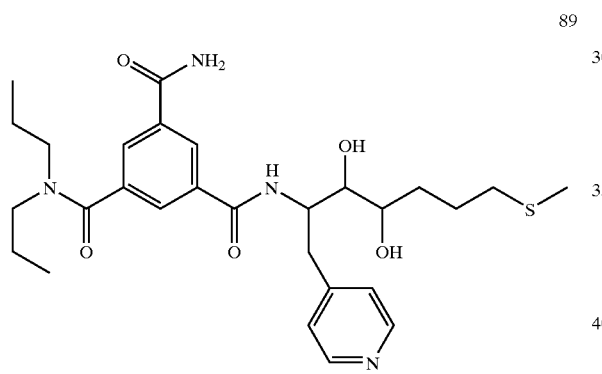

2-({3-(aminocarbonyl)-5-[(dipropylamino)carbonyl]
benzoyl}amino)-1,2,5,6-tetradeoxy-7-S-methyl-1-
pyridin-4-yl-7-thioheptitol

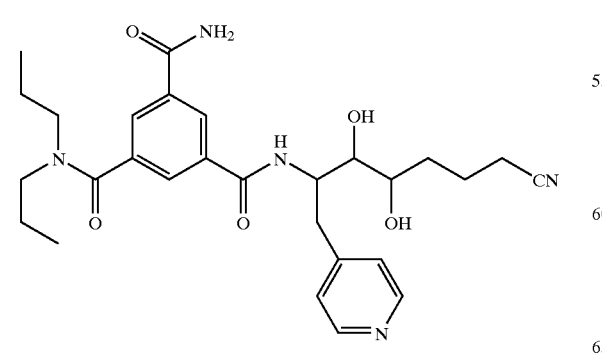

82

N³-[6-cyano-2,3-dihydroxy-1-(pyridin-4-ylmethyl)
hexyl]-N¹,N¹-dipropylbenzene-1,3,5-tricarboxamide

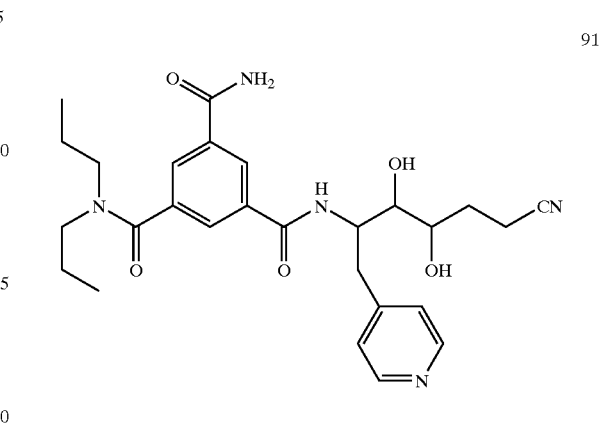

N³-[5-cyano-2,3-dihydroxy-1-(pyridin-4-ylmethyl)
pentyl]-N¹,N¹-dipropylbenzene-1,3,5-
tricarboxamide

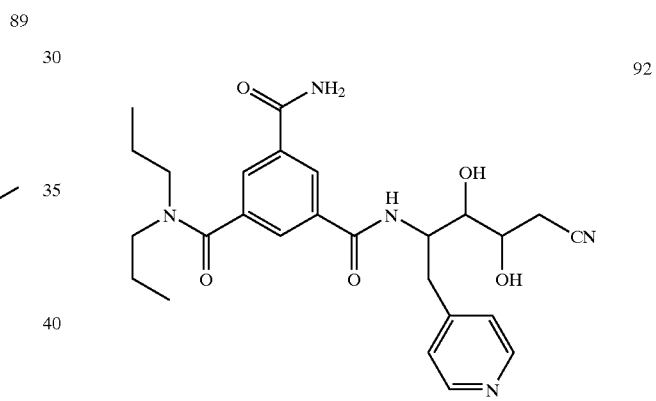

N³-[4-cyano-2,3-dihydroxy-1-(pyridin-4-ylmethyl)
butyl]-N¹,N¹-dipropylbenzene-1,3,5-tricarboxamide

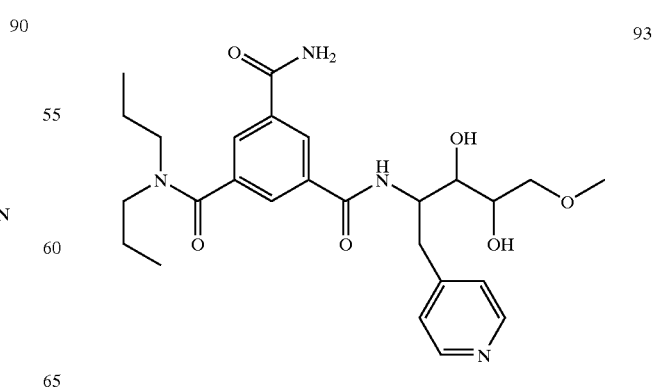

83

2-({3-(aminocarbonyl)-5-[(dipropylamino)carbonyl]benzoyl}amino)-1,2-dideoxy-5-O-methyl-1-pyridin-4-ylpentitol

84

1,2,5-trideoxy-6-O-methyl-2-[({2-[(methylsulfonyl)amino]-1,3-oxazol-4-yl}carbonyl)amino]-1-pyridin-4-ylhexitol

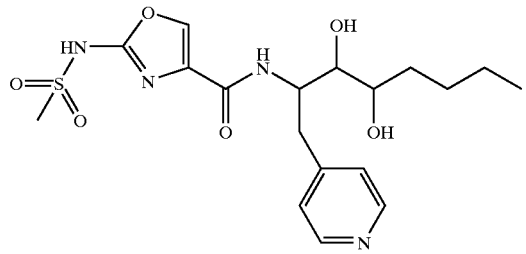

94

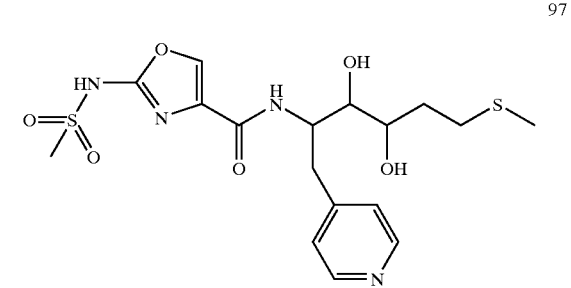

97

N-[2,3-dihydroxy-1-(pyridin-4-ylmethyl)heptyl]-2-[(methylsulfonyl)amino]-1,3-oxazole-4-carboxamide 1,2,5-trideoxy-6-S-methyl-2-[({2-[(methylsulfonyl)amino]-1,3-oxazol-4-yl}carbonyl)amino]-1-pyridin-4-yl-6-thiohexitol

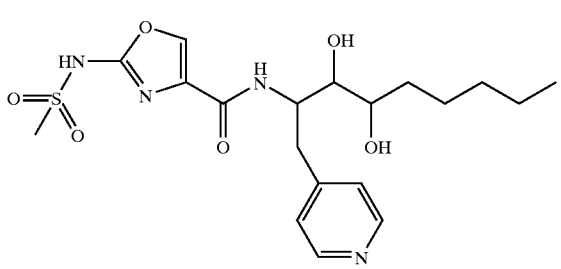

95

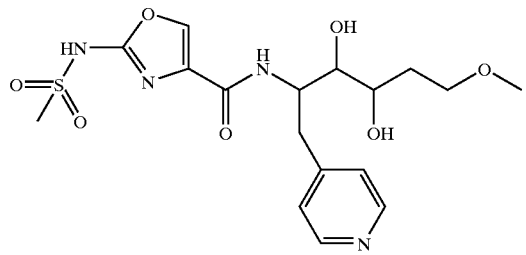

98

N-[2,3-dihydroxy-1-(pyridin-4-ylmethyl)octyl]-2-[(methylsulfonyl)amino]-1,3-oxazole-4-carboxamide N-[2,3-dihydroxy-1-(pyridin-4-ylmethyl)oct-7-ynyl]-2-[(methylsulfonyl)amino]-1,3-oxazole-4-carboxamide

96

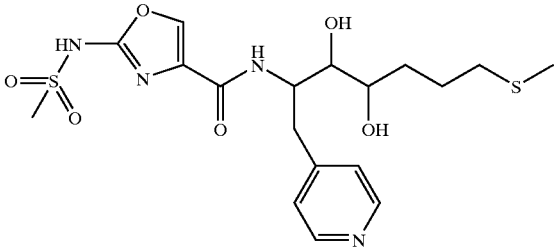

99

| 85 | 86 |
|---|---|
| 1,2,5,6-tetradeoxy-7-S-methyl-2-[({2-[(methylsulfonyl)amino]-1,3-oxazol-4-yl}carbonyl)amino]-1-pyridin-4-yl-7-thioheptitol | N-[4-cyano-2,3-dihydroxy-1-(pyridin-4-ylmethyl)butyl]-2-[(methylsulfonyl)amino]-1,3-oxazole-4-carboxamide |

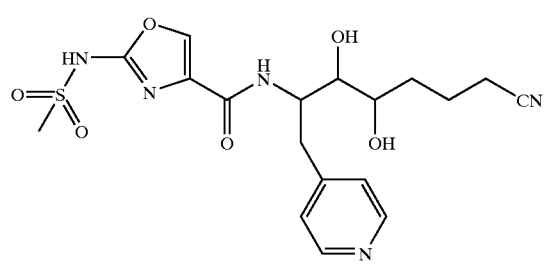

100

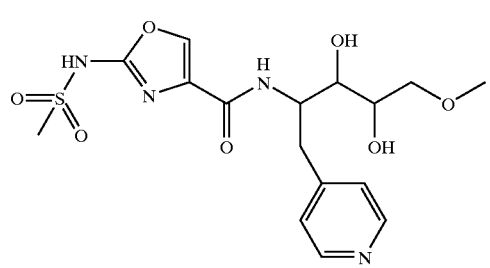

103

N-[6-cyano-2,3-dihydroxy-1-(pyridin-4-ylmethyl)hexyl]-2-[(methylsulfonyl)amino]-1,3-oxazole-4-carboxamide 1,2-dideoxy-5-O-methyl-2-[({2-[(methylsulfonyl)amino]-1,3-oxazol-4-yl}carbonyl)amino]-1-pyridin-4-ylpentitol

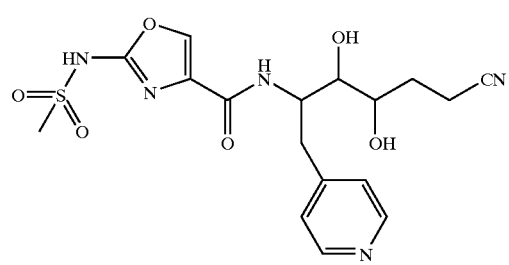

101

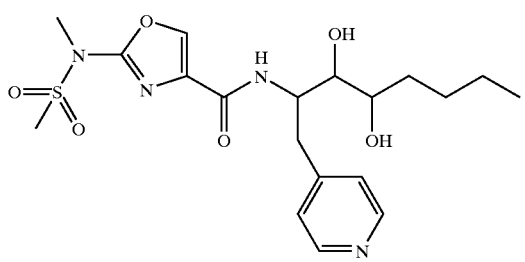

104

N-[5-cyano-2,3-dihydroxy-1-(pyridin-4-ylmethyl)pentyl]-2-[(methylsulfonyl)amino]-1,3-oxazole-4-carboxamide N-[2,3-dihydroxy-1-(pyridin-4-ylmethyl)heptyl]-2-[methyl(methylsulfonyl)amino]-1,3-oxazole-4-carboxamide

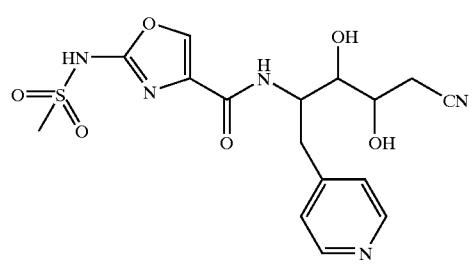

102

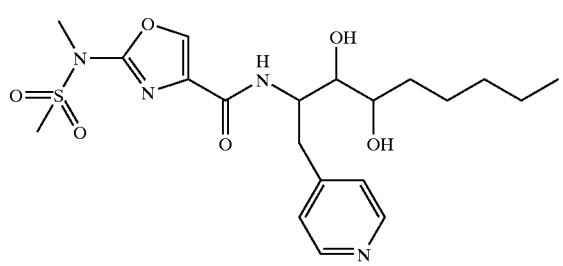

105

| 87 | 88 |
|---|---|
| N-[2,3-dihydroxy-1-(pyridin-4-ylmethyl)octyl]-2-[methyl(methylsulfonyl)amino]-1,3-oxazole-4-carboxamide | N-[2,3-dihydroxy-1-(pyridin-4-ylmethyl)oct-7-ynyl]-2-[methyl(methylsulfonyl)amino]-1,3-oxazole-4-carboxamide |

106

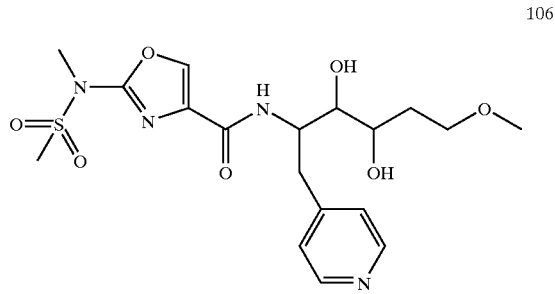

109

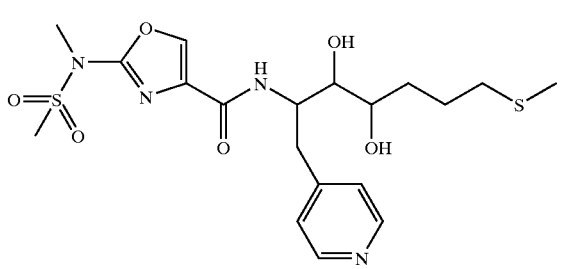

1,2,5-trideoxy-6-O-methyl-2-[({2-[methyl(methylsulfonyl)amino]-1,3-oxazol-4-yl}carbonyl)amino]-1-pyridin-4-ylhexitol 1,2,5,6-tetradeoxy-7-S-methyl-2-[({2-[methyl(methylsulfonyl)amino]-1,3-oxazol-4-yl}carbonyl)amino]-1-pyridin-4-yl-7-thioheptitol

107

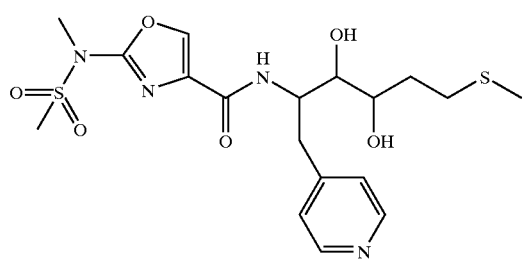

110

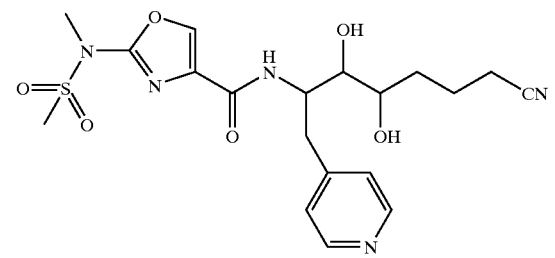

1,2,5-trideoxy-6-S-methyl-2-[({2-[methyl(methylsulfonyl)amino]-1,3-oxazol-4-yl}carbonyl)amino]-1-pyridin-4-yl-6-thiohexitol N-[6-cyano-2,3-dihydroxy-1-(pyridin-4-ylmethyl)hexyl]-2-[methyl(methylsulfonyl)amino]-1,3-oxazole-4-carboxamide

108

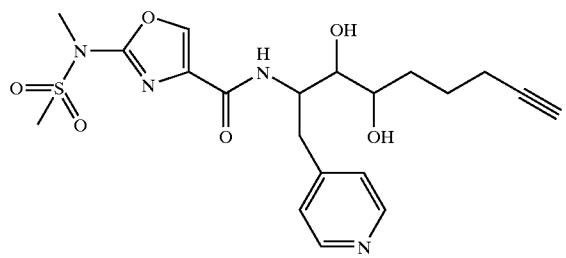

111

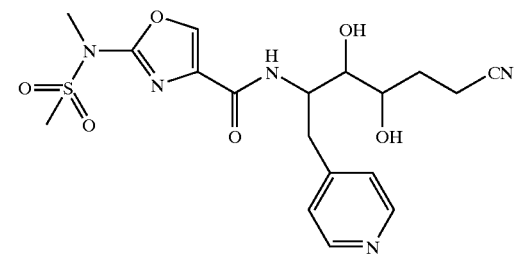

89

N-[5-cyano-2,3-dihydroxy-1-(pyridin-4-ylmethyl)
pentyl]-2-[methyl(methylsulfonyl)amino]-1,3-
oxazole-4-carboxamide

112

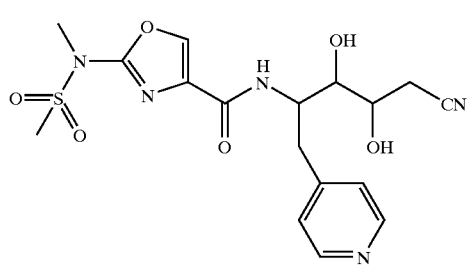

N-[4-cyano-2,3-dihydroxy-1-(pyridin-4-ylmethyl)
butyl]-2-[methyl(methylsulfonyl)amino]-1,3-
oxazole-4-carboxamide

113

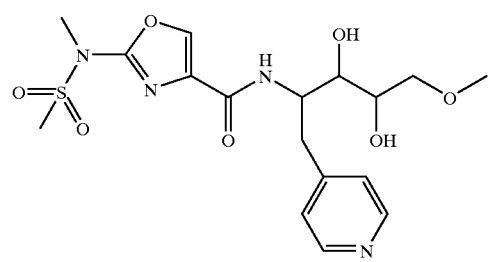

1,2-dideoxy-5-O-methyl-2-[({2-[methyl
(methylsulfonyl)amino]-1,3-oxazol-4-yl}carbonyl)
amino]-1-pyridin-4-ylpentitol

114

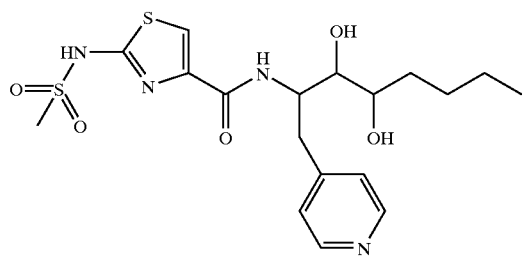

N-[2,3-dihydroxy-1-(pyridin-4-ylmethyl)heptyl]-2-
[(methylsulfonyl)amino]-1,3-thiazole-4-carboxamide

115

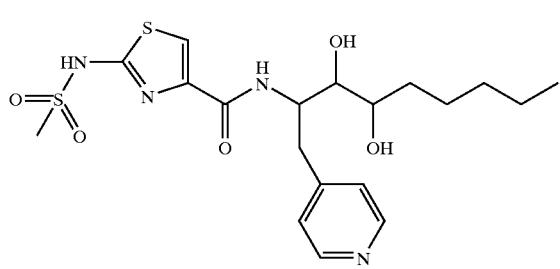

90

N-[2,3-dihydroxy-1-(pyridin-4-ylmethyl)octyl]-2-
[(methylsulfonyl)amino]-1,3-thiazole-4-carboxamide

116

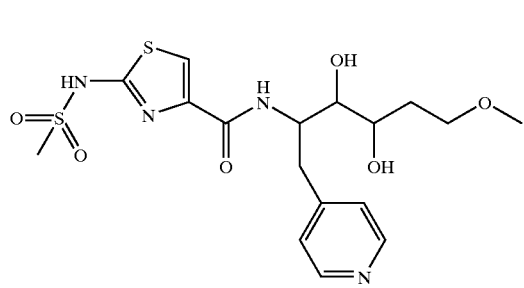

1,2,5-trideoxy-6-O-methyl-2-[({2-[(methylsulfonyl)
amino]-1,3-thiazol-4-yl}carbonyl)amino]-1-pyridin-
4-ylhexitol

117

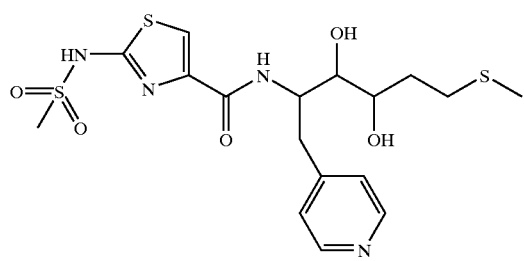

1,2,5-trideoxy-6-S-methyl-2-[({2-[(methylsulfonyl)
amino]-1,3-thiazol-4-yl}carbonyl)amino]-1-pyridin-
4-yl-6-thiohexitol

118

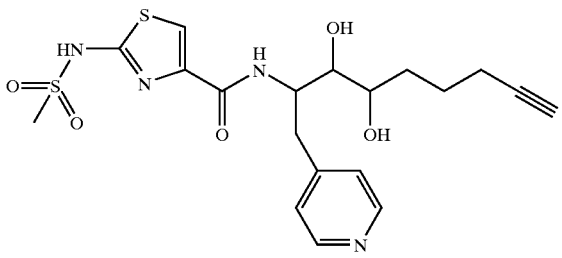

| 91 | 92 |
|---|---|
| N-[2,3-dihydroxy-1-(pyridin-4-ylmethyl)oct-7-ynyl]-2-[(methylsulfonyl)amino]-1,3-thiazole-4-carboxamide | N-[5-cyano-2,3-dihydroxy-1-(pyridin-4-ylmethyl)pentyl]-2-[(methylsulfonyl)amino]-1,3-thiazole-4-carboxamide |

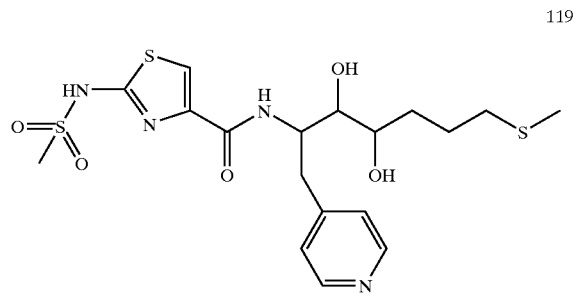

119

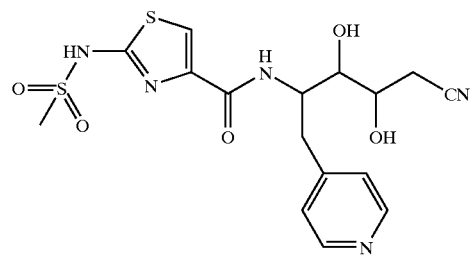

122

1,2,5,6-tetradeoxy-7-S-methyl-2-[({2-[(methylsulfonyl)amino]-1,3-thiazol-4-yl}carbonyl)amino]-1-pyridin-4-yl-7-thioheptitol N-[4-cyano-2,3-dihydroxy-1-(pyridin-4-ylmethyl)butyl]-2-[(methylsulfonyl)amino]-1,3-thiazole-4-carboxamide

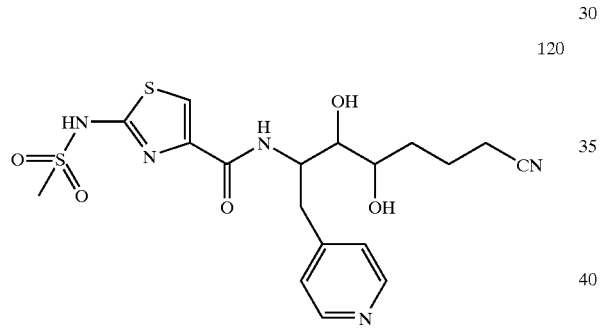

120

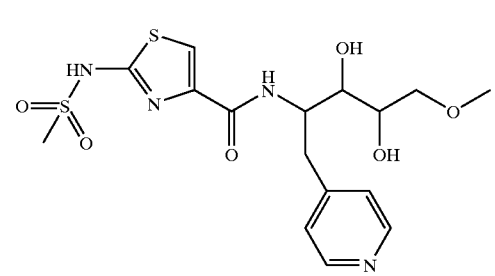

123

N-[6-cyano-2,3-dihydroxy-1-(pyridin-4-ylmethyl)hexyl]-2-[(methylsulfonyl)amino]-1,3-thiazole-4-carboxamide 1,2-dideoxy-5-O-methyl-2-[({2-[(methylsulfonyl)amino]-1,3-thiazol-4-yl}carbonyl)amino]-1-pyridin-4-ylpentitol

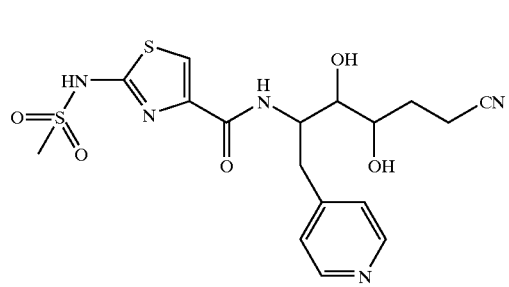

121

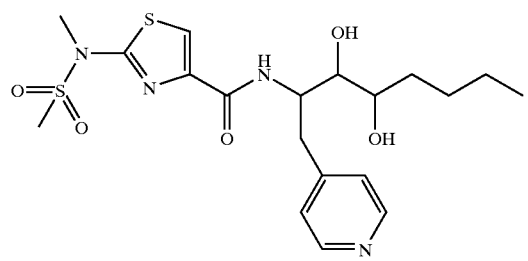

124

93

N-[2,3-dihydroxy-1-(pyridin-4-ylmethyl)heptyl]-2-[methyl(methylsulfonyl)amino]-1,3-thiazole-4-carboxamide

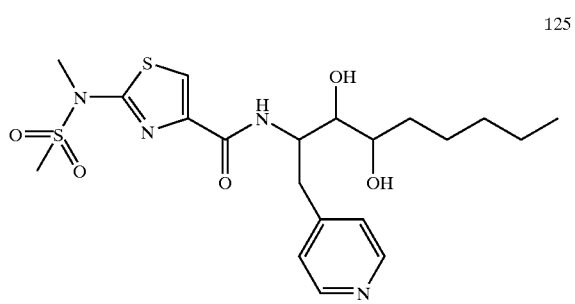

125

N-[2,3-dihydroxy-1-(pyridin-4-ylmethyl)octyl]-2-[methyl(methylsulfonyl)amino]-1,3-thiazole-4-carboxamide

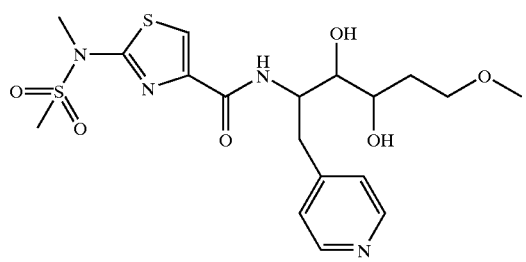

126

1,2,5-trideoxy-6-O-methyl-2-[({2-[methyl(methylsulfonyl)amino]-1,3-thiazol-4-yl}carbonyl)amino]-1-pyridin-4-ylhexitol

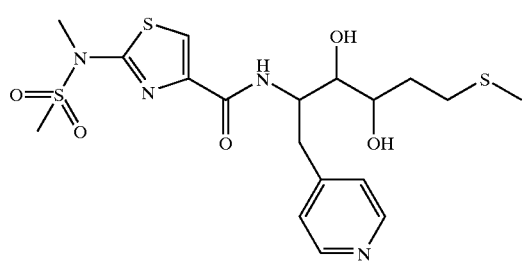

127

94

1,2,5-trideoxy-6-S-methyl-2-[({2-[methyl(methylsulfonyl)amino]-1,3-thiazol-4-yl}carbonyl)amino]-1-pyridin-4-yl-6-thiohexitol

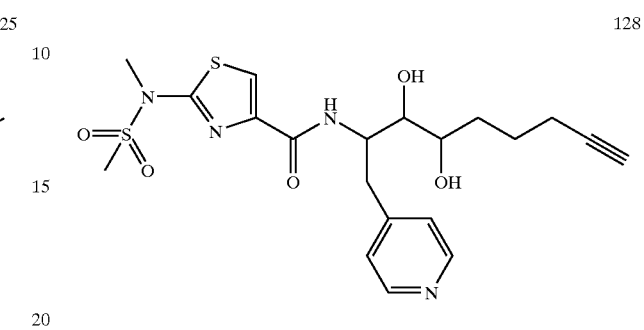

128

N-[2,3-dihydroxy-1-(pyridin-4-ylmethyl)oct-7-ynyl]-2-[methyl(methylsulfonyl)amino]-1,3-thiazole-4-carboxamide

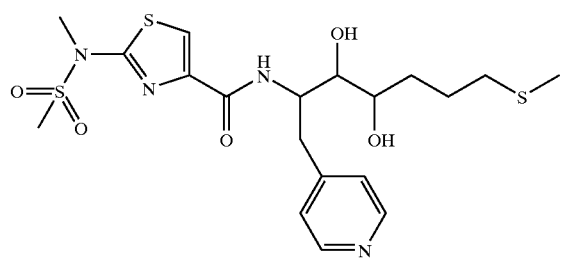

129

1,2,5,6-tetradeoxy-7-S-methyl-2-[({2-[methyl(methylsulfonyl)amino]-1,3-thiazol-4-yl}carbonyl)amino]-1-pyridin-4-yl-7-thioheptitol

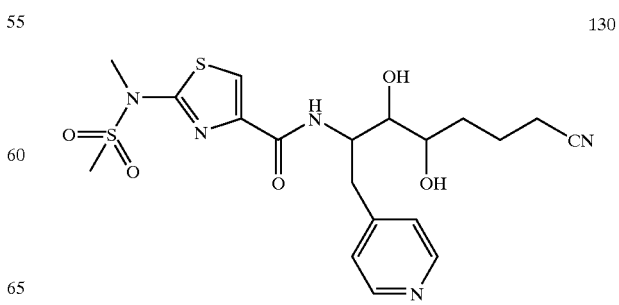

130

95

N-[6-cyano-2,3-dihydroxy-1-(pyridin-4-ylmethyl)hexyl]-2-[methyl(methylsulfonyl)amino]-1,3-thiazole-4-carboxamide

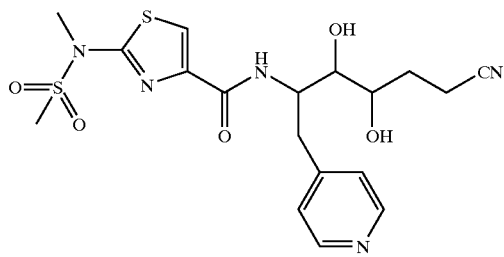

N-[5-cyano-2,3-dihydroxy-1-(pyridin-4-ylmethyl)pentyl]-2-[methyl(methylsulfonyl)amino]-1,3-thiazole-4-carboxamide

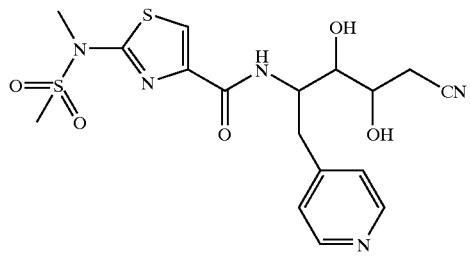

N-[4-cyano-2,3-dihydroxy-1-(pyridin-4-ylmethyl)butyl]-2-[methyl(methylsulfonyl)amino]-1,3-thiazole-4-carboxamide

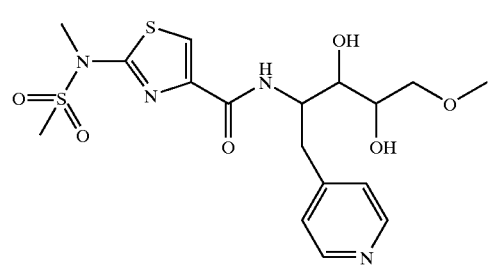

96

1,2-dideoxy-5-O-methyl-2-[({2-[methyl(methylsulfonyl)amino]-1,3-thiazol-4-yl}carbonyl)amino]-1-pyridin-4-ylpentitol

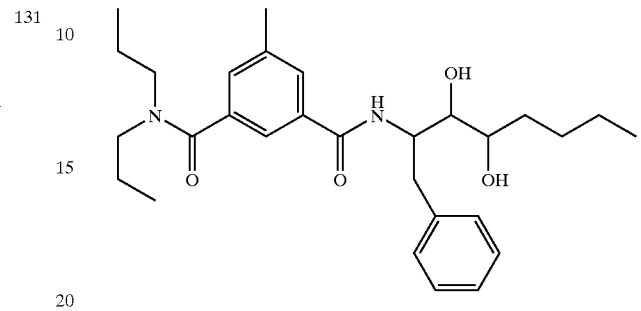

N'-(1-benzyl-2,3-dihydroxyheptyl)-5-methyl-N,N-dipropylisophthalamide

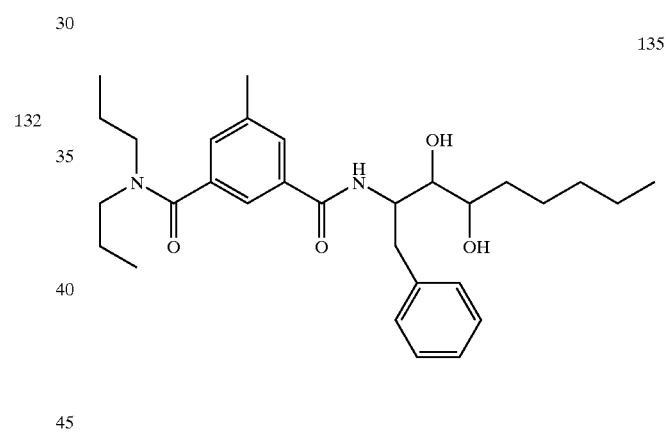

N'-(1-benzyl-2,3-dihydroxyoctyl)-5-methyl-N,N-dipropylisophthalamide

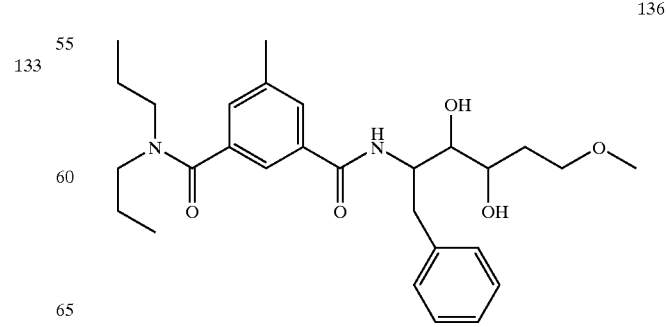

97

1,2,5-trideoxy-2-({3-[(dipropylamino)carbonyl]-5-methylbenzoyl}amino)-6-O-methyl-1-phenylhexitol

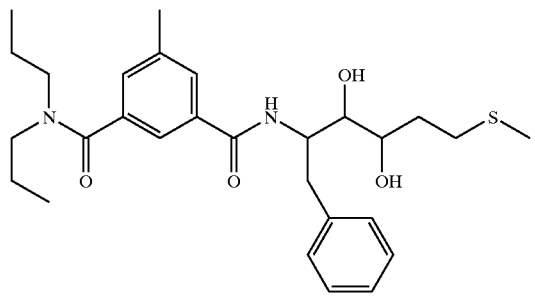

1,2,5-trideoxy-2-({3-[(dipropylamino)carbonyl]-5-methylbenzoyl}amino)-6-S-methyl-1-phenyl-6-thiohexitol

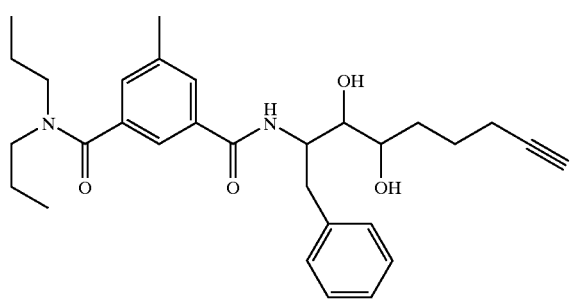

N'-(1-benzyl-2,3-dihydroxyoct-7-ynyl)-5-methyl-N,N-dipropylisophthalamide

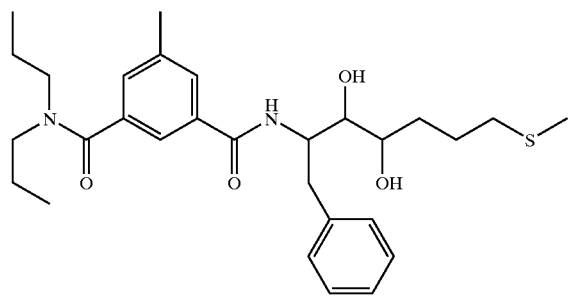

98

1,2,5,6-tetradeoxy-2-({3-[(dipropylamino)carbonyl]-5-methylbenzoyl}amino)-7-S-methyl-1-phenyl-7-thioheptitol

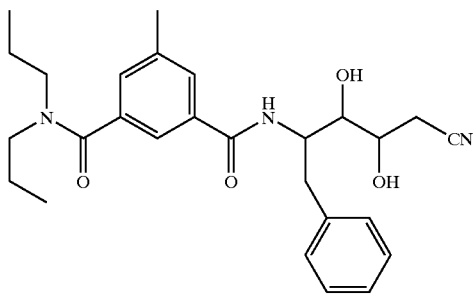

N'-(1-benzyl-6-cyano-2,3-dihydroxyhexyl)-5-methyl-N,N-dipropylisophthalamide

N'-(1-benzyl-5-cyano-2,3-dihydroxypentyl)-5-methyl-N,N-dipropylisophthalamide

99
N'-(1-benzyl-4-cyano-2,3-dihydroxybutyl)-5-methyl-N,N-dipropylisophthalamide

100
$N^3$-(1-benzyl-2,3-dihydroxyoctyl)-$N^1$, $N^1$-dipropylbenzene-1,3,5-tricarboxamide

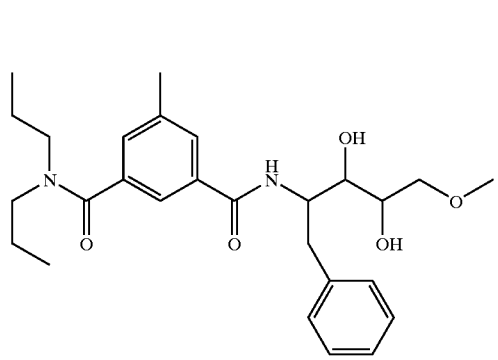

143

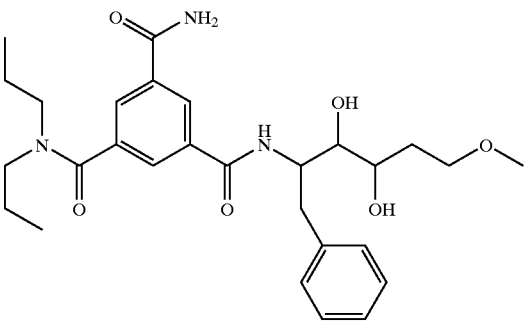

146

1,2-dideoxy-2-({3-[(dipropylamino)carbonyl]-5-methylbenzoyl}amino)-5-O-methyl-1-phenylpentitol 2-({3-(aminocarbonyl)-5-[(dipropylamino)carbonyl]benzoyl}amino)-1,2,5-trideoxy-6-O-methyl-1-phenylhexitol

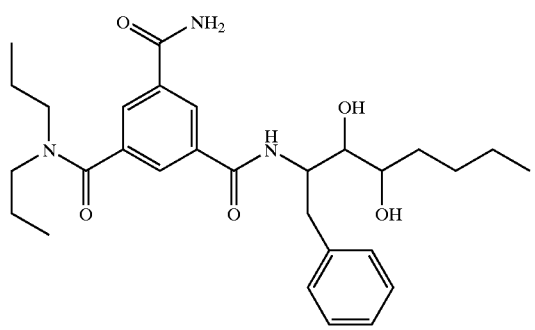

144

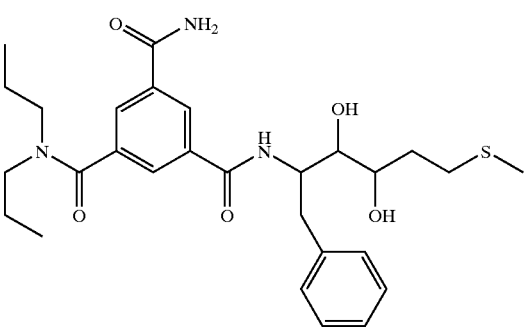

147

$N^3$-(1-benzyl-2,3-dihydroxyheptyl)-$N^1$, $N^1$-dipropylbenzene-1,3,5-tricarboxamide 2-({3-(aminocarbonyl)-5-[(dipropylamino)carbonyl]benzoyl}amino)-1,2,5-trideoxy-6-S-methyl-1-phenyl-6-thiohexitol

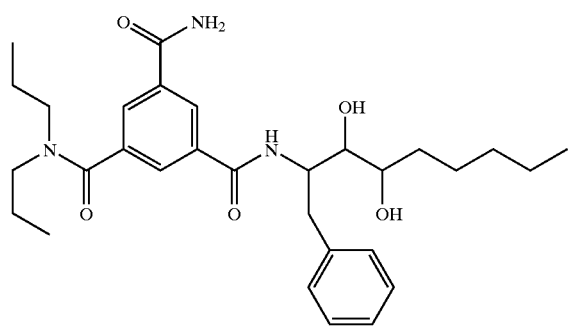

145

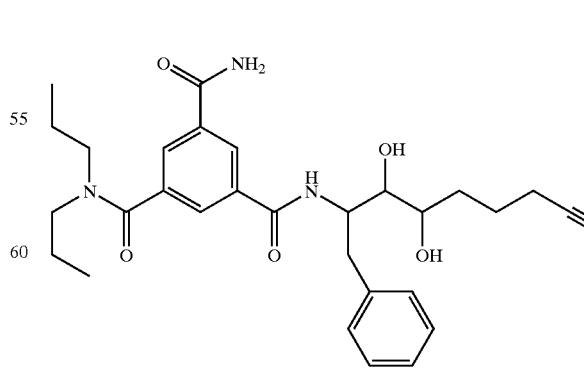

148

101
N³-(1-benzyl-2,3-dihydroxyoct-7-ynyl)-N¹, N¹-dipropylbenzene-1,3,5-tricarboxamide

102
N³-(1-benzyl-5-cyano-2,3-dihydroxypentyl)-N¹, N¹-dipropylbenzene-1,3,5-tricarboxamide

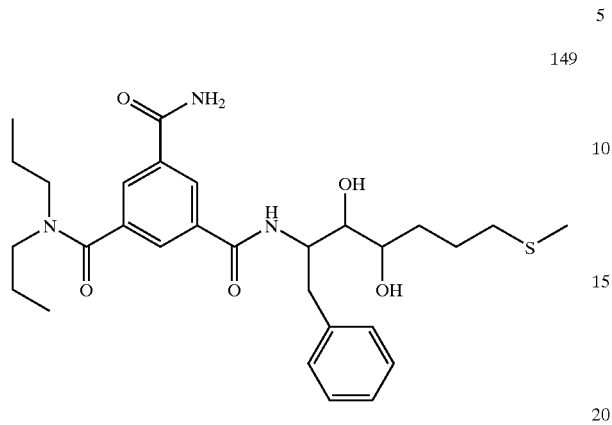

149

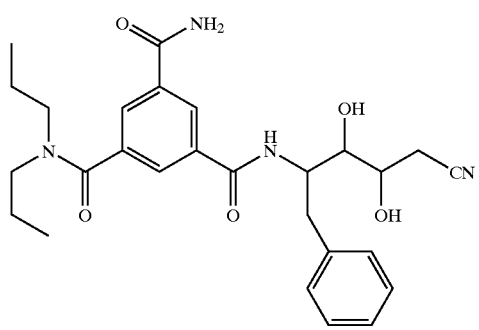

152

2-({3-(aminocarbonyl)-5-[(dipropylamino)carbonyl]benzoyl}amino)-1,2,5,6-tetradeoxy-7-S-methyl-1-phenyl-7-thioheptitol N³-(1-benzyl-4-cyano-2,3-dihydroxybutyl)-N¹, N¹-dipropylbenzene-1,3,5-tricarboxamide

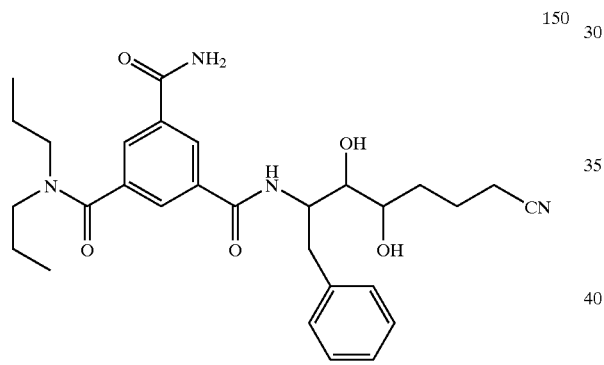

150

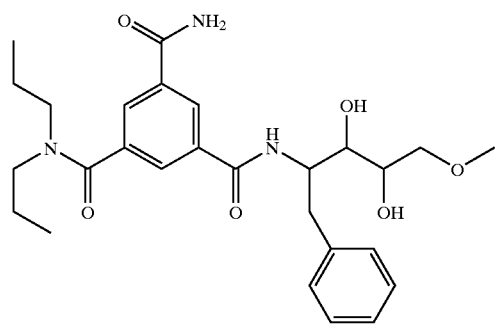

153

N³-(1-benzyl-6-cyano-2,3-dihydroxyhexyl)-N¹, N¹-dipropylbenzene-1,3,5-tricarboxamide 2-({3-(aminocarbonyl)-5-[(dipropylamino)carbonyl]benzoyl}amino)-1,2-dideoxy-5-O-methyl-1-phenylpentitol

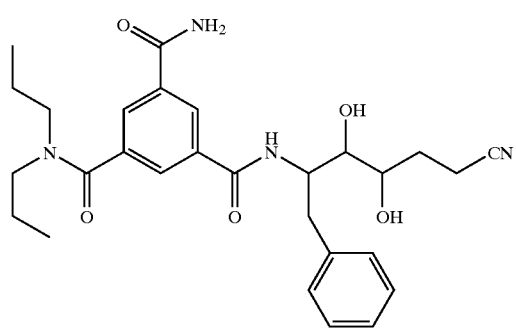

151

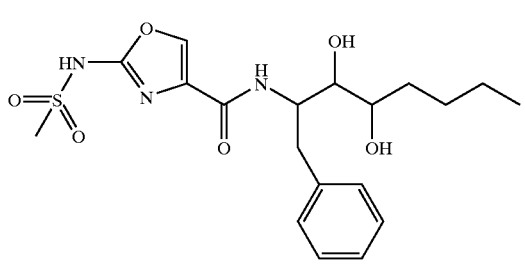

154

103

N-(1-benzyl-2,3-dihydroxyheptyl)-2-
[(methylsulfonyl)amino]-1,3-oxazole-4-carboxamide

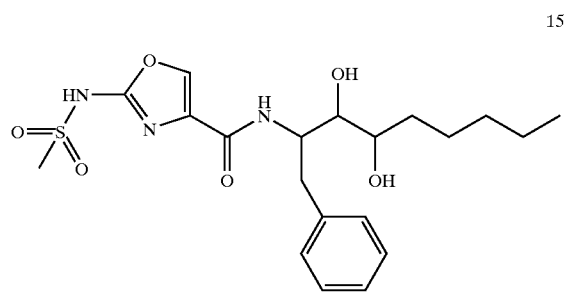

N-(1-benzyl-2,3-dihydroxyoctyl)-2-
[(methylsulfonyl)amino]-1,3-oxazole-4-carboxamide

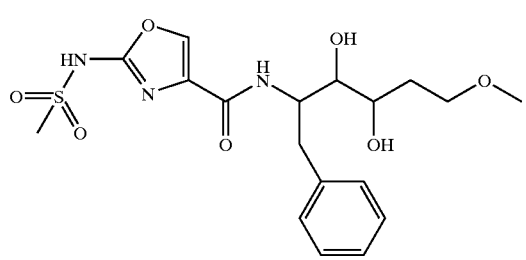

1,2,5-trideoxy-6-O-methyl-2-[({2-[(methylsulfonyl)
amino]-1,3-oxazol-4-yl}carbonyl)amino]-1-
phenylhexitol

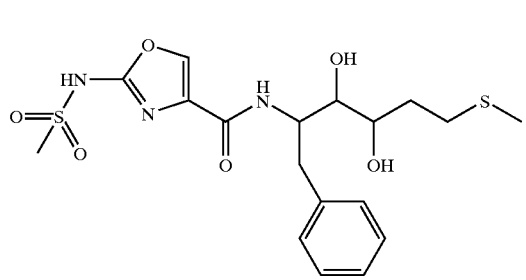

1,2,5-trideoxy-6-S-methyl-2-[({2-[(methylsulfonyl)
amino]-1,3-oxazol-4-yl}carbonyl)amino]-1-phenyl-
6-thiohexitol

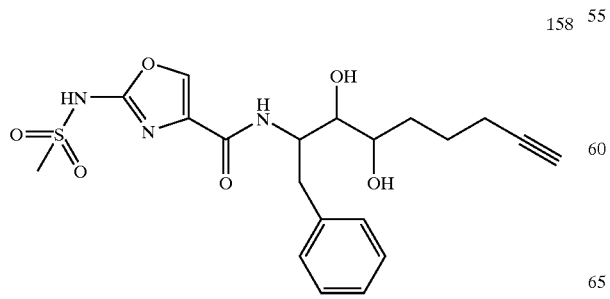

104

N-(1-benzyl-2,3-dihydroxyoct-7-ynyl)-2-
[(methylsulfonyl)amino]-1,3-oxazole-4-carboxamide

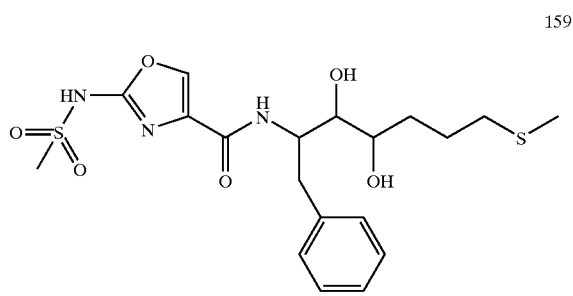

1,2,5,6-tetradeoxy-7-S-methyl-2-[({2-
[(methylsulfonyl)amino]-1,3-oxazol-4-yl}carbonyl)
amino]-1-phenyl-7-thioheptitol

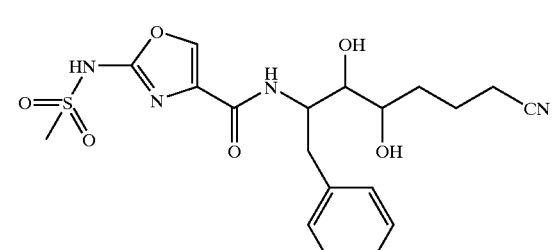

N-(1-benzyl-6-cyano-2,3-dihydroxyhexyl)-2-
[(methylsulfonyl)amino]-1,3-oxazole-4-carboxamide

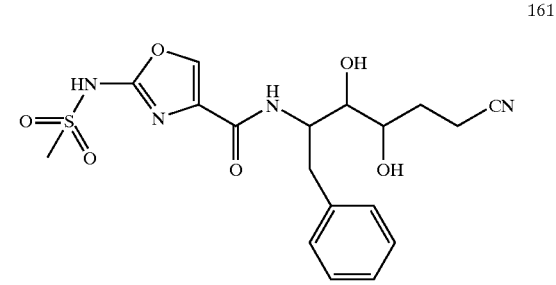

N-(1-benzyl-5-cyano-2,3-dihydroxypentyl)-2-
[(methylsulfonyl)amino]-1,3-oxazole-4-carboxamide

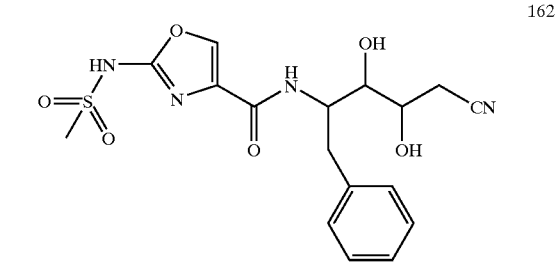

105

N-(1-benzyl-4-cyano-2,3-dihydroxybutyl)-2-[(methylsulfonyl)amino]-1,3-oxazole-4-carboxamide

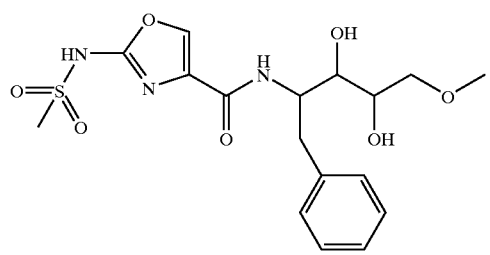

1,2-dideoxy-5-O-methyl-2-[({2-[(methylsulfonyl)amino]-1,3-oxazol-4-yl}carbonyl)amino]-1-phenylpentitol

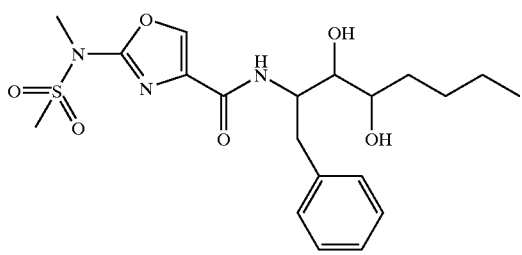

N-(1-benzyl-2,3-dihydroxyheptyl)-2-[methyl(methylsulfonyl)amino]-1,3-oxazole-4-carboxamide

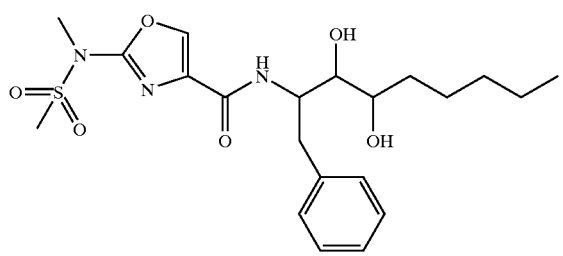

N-(1-benzyl-2,3-dihydroxyoctyl)-2-[methyl(methylsulfonyl)amino]-1,3-oxazole-4-carboxamide

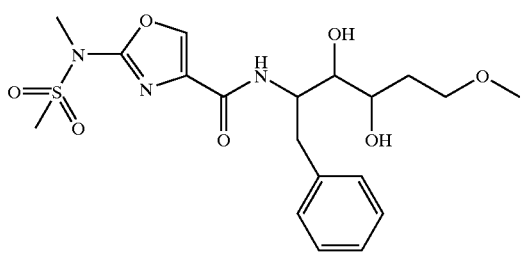

106

1,2,5-trideoxy-6-O-methyl-2-[({2-[methyl(methylsulfonyl)amino]-1,3-oxazol-4-yl}carbonyl)amino]-1-phenylhexitol

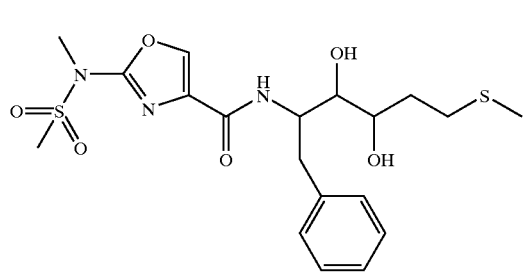

1,2,5-trideoxy-6-S-methyl-2-[({2-[methyl(methylsulfonyl)amino]-1,3-oxazol-4-yl}carbonyl)amino]-1-phenyl-6-thiohexitol

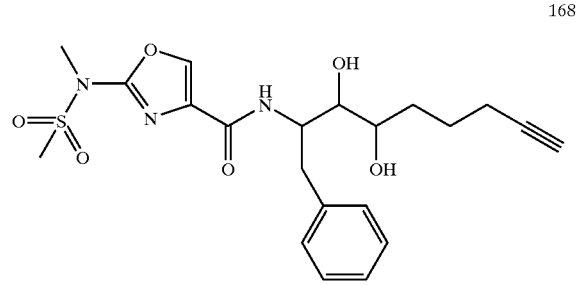

N-(1-benzyl-2,3-dihydroxyoct-7-ynyl)-2-[methyl(methylsulfonyl)amino]-1,3-oxazole-4-carboxamide

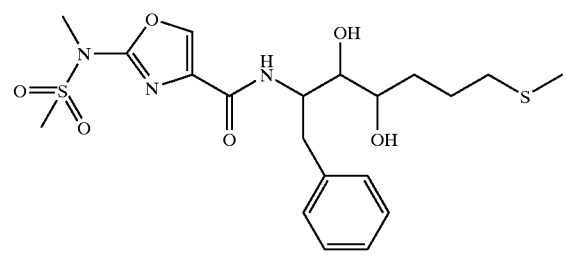

1,2,5,6-tetradeoxy-7-S-methyl-2-[({2-[methyl(methylsulfonyl)amino]-1,3-oxazol-4-yl}carbonyl)amino]-1-phenyl-7-thioheptitol

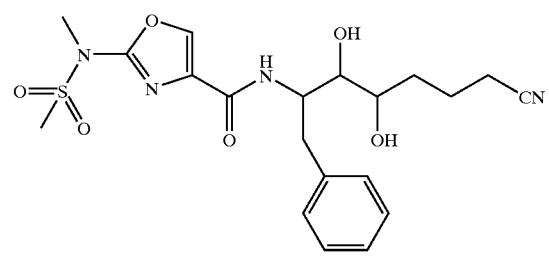

107

N-(1-benzyl-6-cyano-2,3-dihydroxyhexyl)-2-[methyl(methylsulfonyl)amino]-1,3-oxazole-4-carboxamide

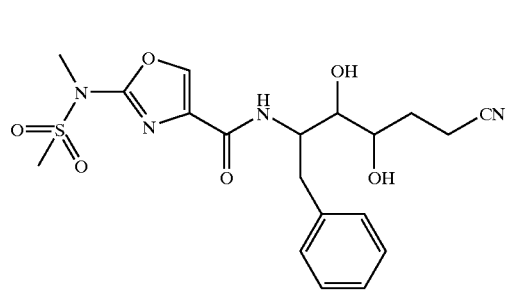

N-(1-benzyl-5-cyano-2,3-dihydroxypentyl)-2-[methyl(methylsulfonyl)amino]-1,3-oxazole-4-carboxamide

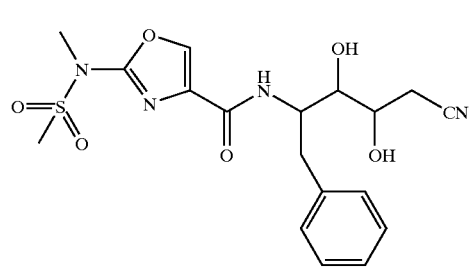

N-(1-benzyl-4-cyano-2,3-dihydroxybutyl)-2-[methyl(methylsulfonyl)amino]-1,3-oxazole-4-carboxamide

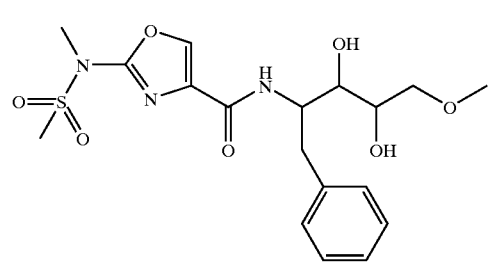

1,2-dideoxy-5-O-methyl-2-[({2-[methyl(methylsulfonyl)amino]-1,3-oxazol-4-yl}carbonyl)amino]-1-phenylpentitol

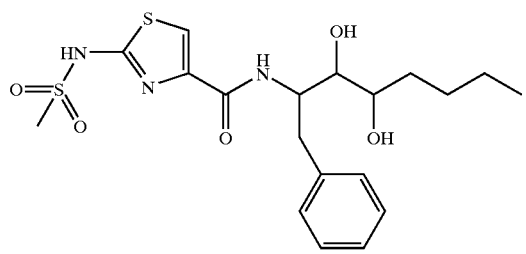

108

N-(1-benzyl-2,3-dihydroxyheptyl)-2-[(methylsulfonyl)amino]-1,3-thiazole-4-carboxamide

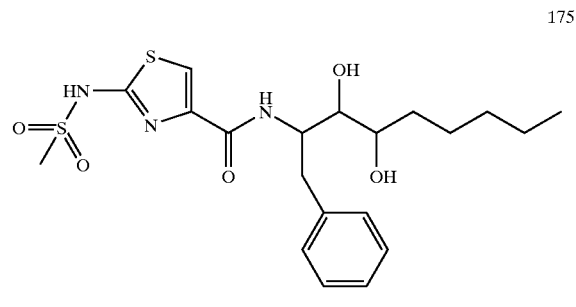

N-(1-benzyl-2,3-dihydroxyoctyl)-2-[(methylsulfonyl)amino]-1,3-thiazole-4-carboxamide

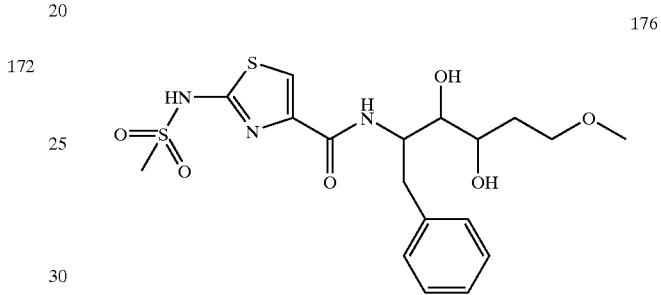

1,2,5-trideoxy-6-O-methyl-2-[({2-[(methylsulfonyl)amino]-1,3-thiazol-4-yl}carbonyl)amino]-1-phenylhexitol

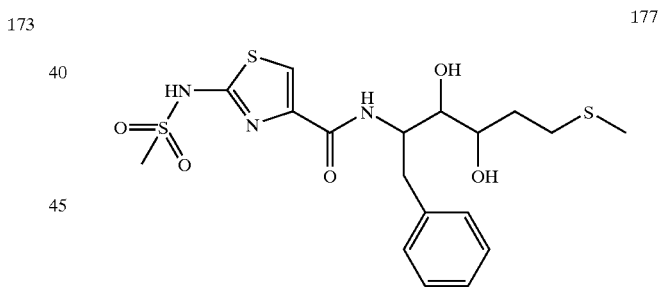

1,2,5-trideoxy-6-S-methyl-2-[({2-[(methylsulfonyl)amino]-1,3-thiazol-4-yl}carbonyl)amino]-1-phenyl-6-thiohexitol

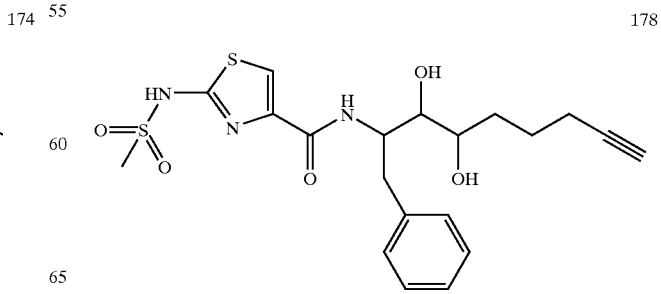

| 109 | 110 |
|---|---|
| N-(1-benzyl-2,3-dihydroxyoct-7-ynyl)-2-[(methylsulfonyl)amino]-1,3-thiazole-4-carboxamide | N-(1-benzyl-4-cyano-2,3-dihydroxybutyl)-2-[(methylsulfonyl)amino]-1,3-thiazole-4-carboxamide |

179

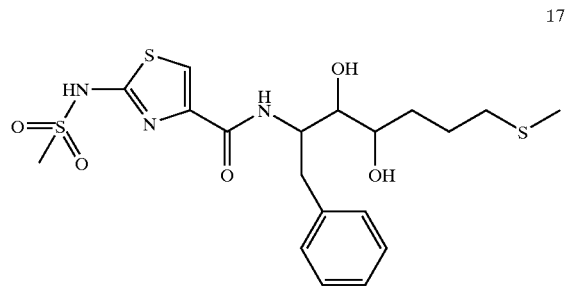

183

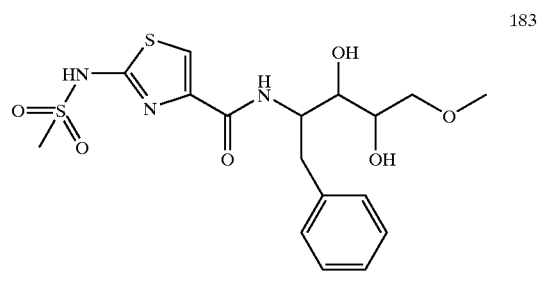

1,2,5,6-tetradeoxy-7-S-methyl-2-[({2-[(methylsulfonyl)amino]-1,3-thiazol-4-yl}carbonyl)amino]-1-phenyl-7-thioheptitol 1,2-dideoxy-5-O-methyl-2-[({2-[(methylsulfonyl)amino]-1,3-thiazol-4-yl}carbonyl)amino]-1-phenylpentitol

180

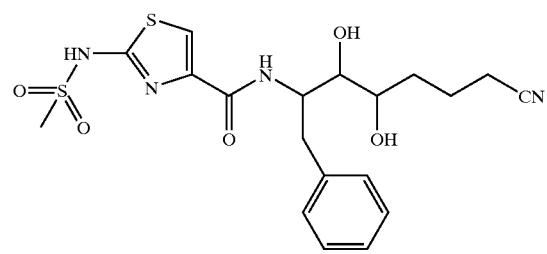

184

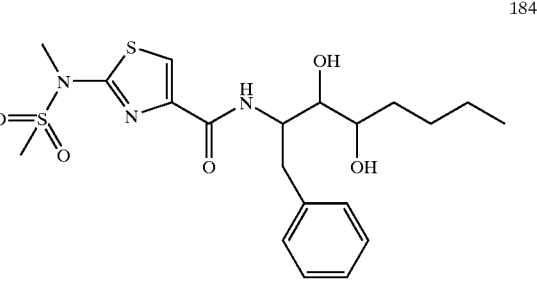

N-(1-benzyl-6-cyano-2,3-dihydroxyhexyl)-2-[(methylsulfonyl)amino]-1,3-thiazole-4-carboxamide N-(1-benzyl-2,3-dihydroxyheptyl)-2-[methyl(methylsulfonyl)amino]-1,3-thiazole-4-carboxamide

181

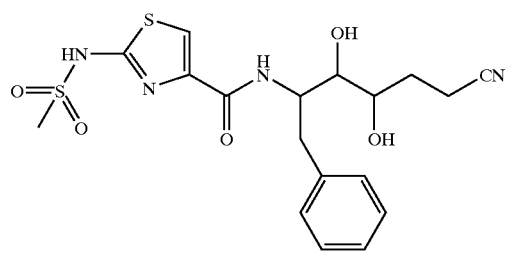

185

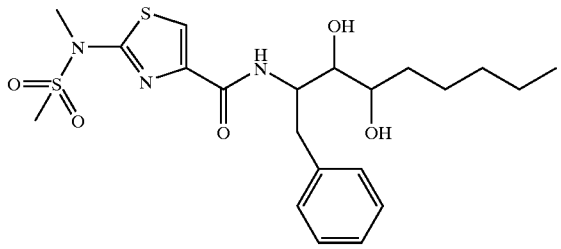

N-(1-benzyl-5-cyano-2,3-dihydroxypentyl)-2-[(methylsulfonyl)amino]-1,3-thiazole-4-carboxamide N-(1-benzyl-2,3-dihydroxyoctyl)-2-[methyl(methylsulfonyl)amino]-1,3-thiazole-4-carboxamide

182

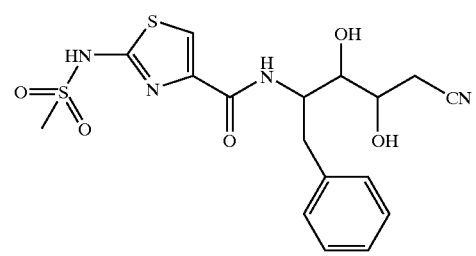

186

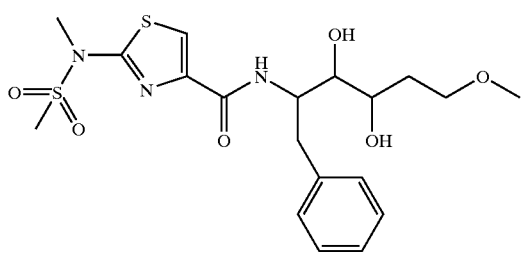

111

1,2,5-trideoxy-6-O-methyl-2-[({2-[methyl(methylsulfonyl)amino]-1,3-thiazol-4-yl}carbonyl)amino]-1-phenylhexitol

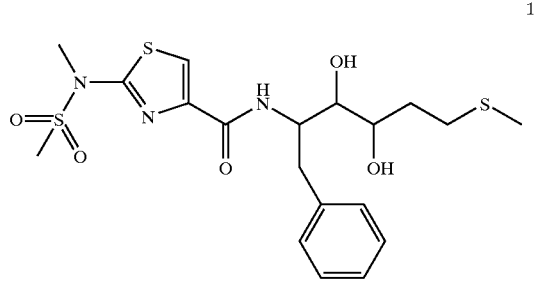

187

1,2,5-trideoxy-6-S-methyl-2-[({2-[methyl(methylsulfonyl)amino]-1,3-thiazol-4-yl}carbonyl)amino]-1-phenyl-6-thiohexitol

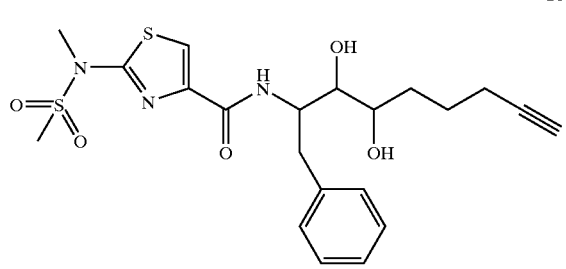

188

N-(1-benzyl-2,3-dihydroxyoct-7-ynyl)-2-[methyl(methylsulfonyl)amino]-1,3-thiazole-4-carboxamide

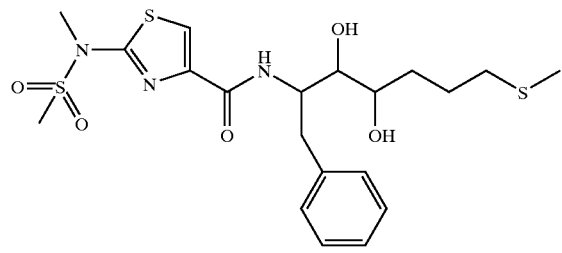

189

1,2,5,6-tetradeoxy-7-S-methyl-2-[({2-[methyl(methylsulfonyl)amino]-1,3-thiazol-4-yl}carbonyl)amino]-1-phenyl-7-thioheptitol

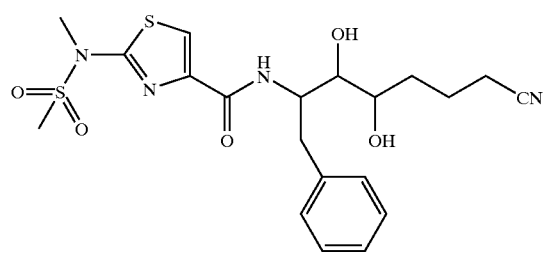

190

112

N-(1-benzyl-6-cyano-2,3-dihydroxyhexyl)-2-[methyl(methylsulfonyl)amino]-1,3-thiazole-4-carboxamide

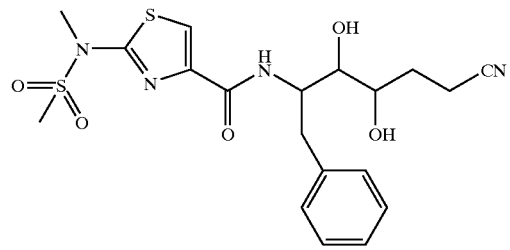

191

N-(1-benzyl-5-cyano-2,3-dihydroxypentyl)-2-[methyl(methylsulfonyl)amino]-1,3-thiazole-4-carboxamide

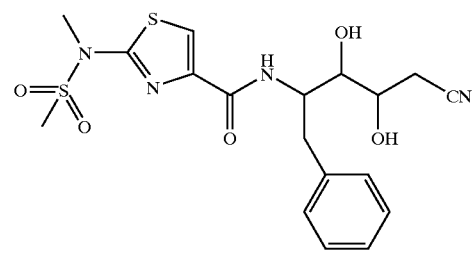

192

N-(1-benzyl-4-cyano-2,3-dihydroxybutyl)-2-[methyl(methylsulfonyl)amino]-1,3-thiazole-4-carboxamide

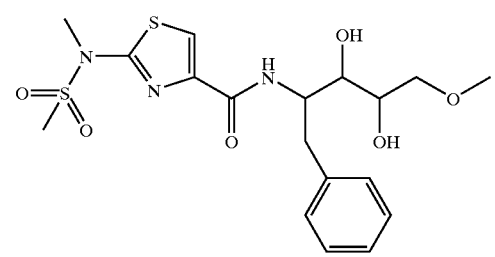

193

1,2-dideoxy-5-O-methyl-2-[({2-[methyl(methylsulfonyl)amino]-1,3-thiazol-4-yl}carbonyl)amino]-1-phenylpentitol

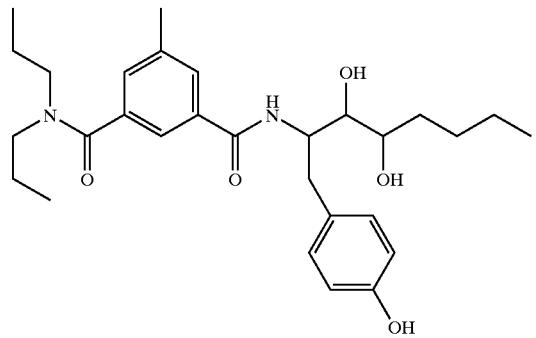

194

113

N'-[2,3-dihydroxy-1-(4-hydroxybenzyl)heptyl]-5-methyl-N,N-dipropylisophthalamide

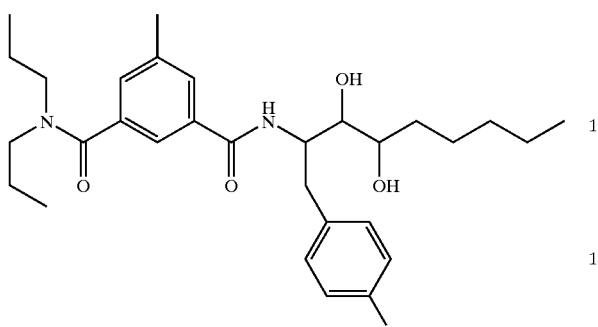

N'-[2,3-dihydroxy-1-(4-hydroxybenzyl)octyl]-5-methyl-N,N-dipropylisophthalamide

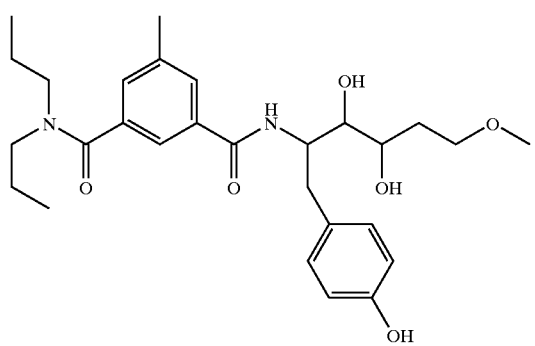

1,2,5-trideoxy-2-({3-[(dipropylamino)carbonyl]-5-methylbenzoyl}amino)-1-(4-hydroxyphenyl)-6-O-methylhexitol

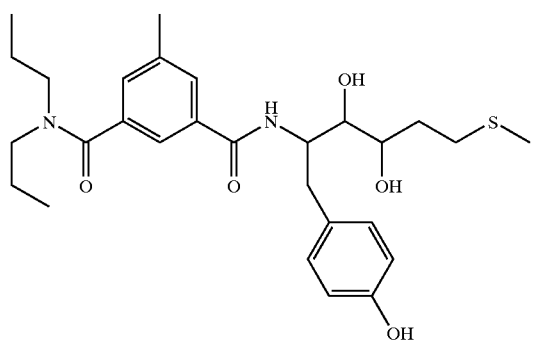

114

1,2,5-trideoxy-2-({3-[(dipropylamino)carbonyl]-5-methylbenzoyl}amino)-1-(4-hydroxyphenyl)-6-S-methyl-6-thiohexitol

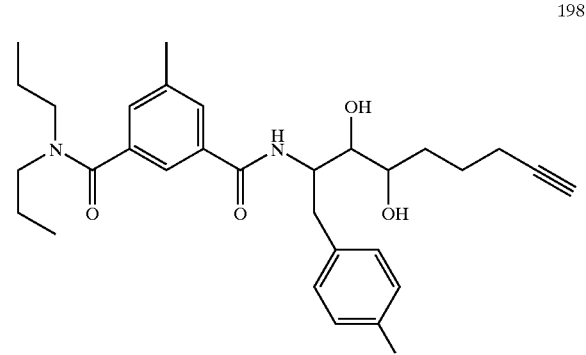

N'-[2,3-dihydroxy-1-(4-hydroxybenzyl)oct-7-ynyl]-5-methyl-N,N-dipropylisophthalamide

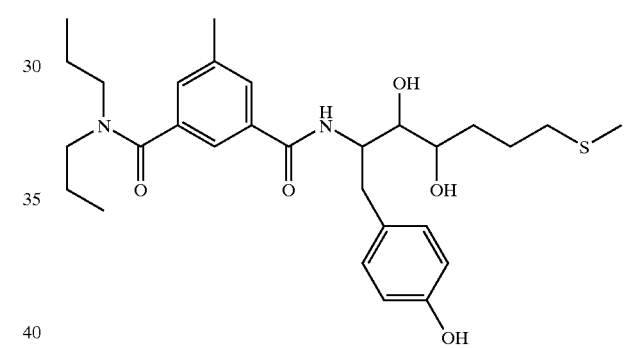

1,2,5,6-tetradeoxy-2-({3-[(dipropylamino)carbonyl]-5-methylbenzoyl}amino)-1-(4-hydroxyphenyl)-7-S-methyl-7-thioheptitol

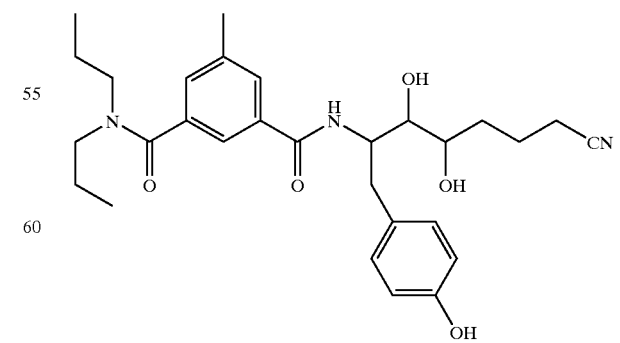

115
N'-[6-cyano-2,3-dihydroxy-1-(4-hydroxybenzyl)hexyl]-5-methyl-N,N-dipropylisophthalamide 116
1,2-dideoxy-2-({3-[(dipropylamino)carbonyl]-5-methylbenzoyl}amino)-1-(4-hydroxyphenyl)-5-O-methylpentitol

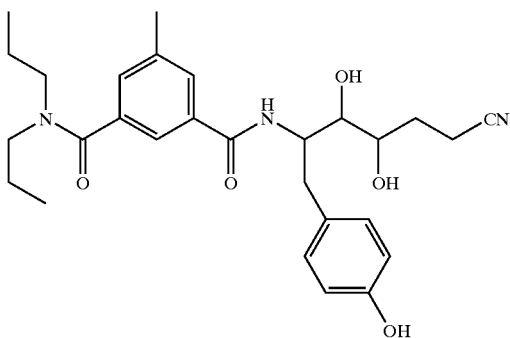

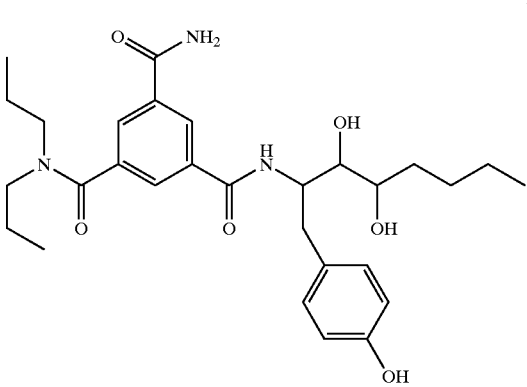

N'-[5-cyano-2,3-dihydroxy-1-(4-hydroxybenzyl)pentyl]-5-methyl-N,N-dipropylisophthalamide $N^3$-[2,3-dihydroxy-1-(4-hydroxybenzyl)heptyl]-$N^1$,N-dipropylbenzene-1,3,5-tricarboxamide

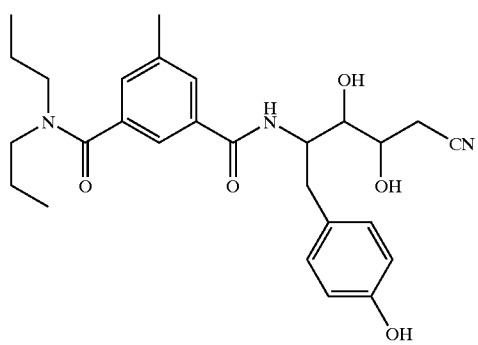

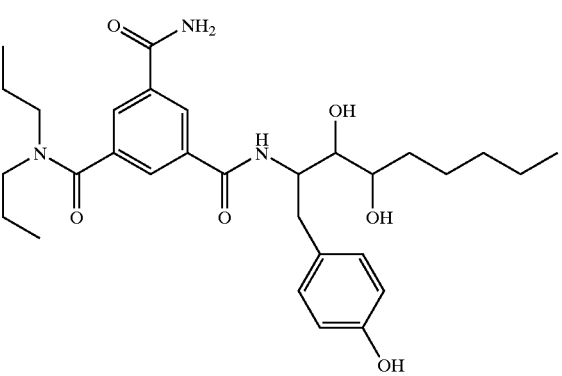

N'-[4-cyano-2,3-dihydroxy-1-(4-hydroxybenzyl)butyl]-5-methyl-N,N-dipropylisophthalamide $N^3$-[2,3-dihydroxy-1-(4-hydroxybenzyl)octyl]-$N^1$,N-dipropylbenzene-1,3,5-tricarboxamide

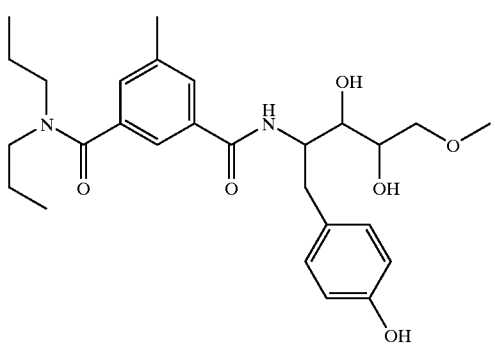

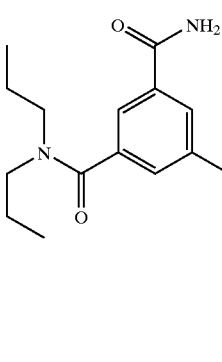

117

2-({3-(aminocarbonyl)-5-[(dipropylamino)carbonyl]benzoyl}amino)-1,2,5-trideoxy-1-(4-hydroxyphenyl)-6-O-methylhexitol

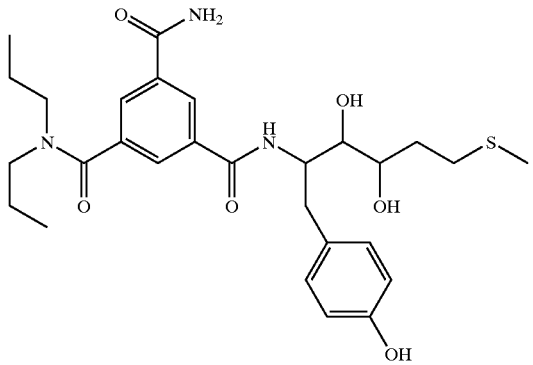

2-({3-(aminocarbonyl)-5-[(dipropylamino)carbonyl]benzoyl}amino)-1,2,5-trideoxy-1-(4-hydroxyphenyl)-6-S-methyl-6-thiohexitol

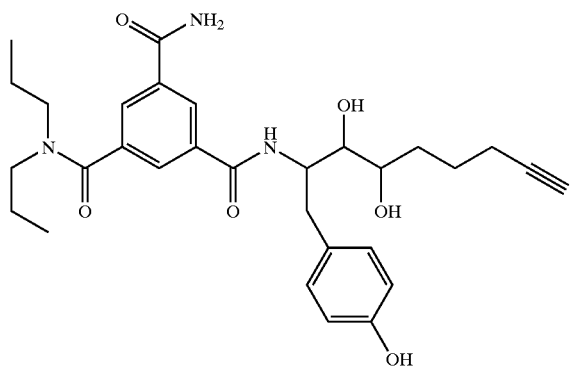

$N^3$-[2,3-dihydroxy-1-(4-hydroxybenzyl)oct-7-ynyl]-$N^1,N^1$-dipropylbenzene-1,3,5-tricarboxamide

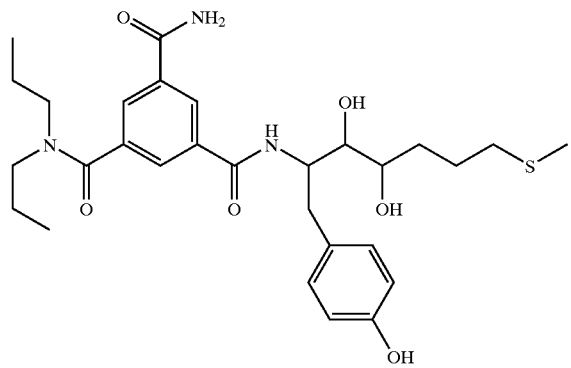

118

2-({3-(aminocarbonyl)-5-[(dipropylamino)carbonyl]benzoyl}amino)-1,2,5,6-tetradeoxy-1-(4-hydroxyphenyl)-7-S-methyl-7-thioheptitol

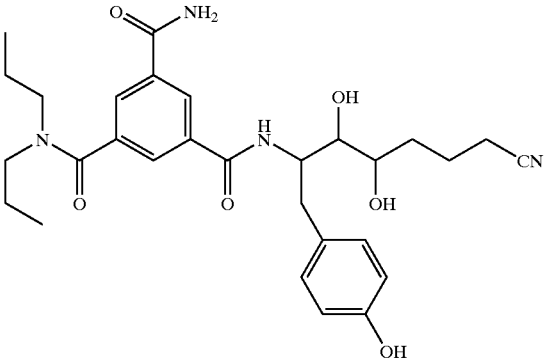

$N^3$-[6-cyano-2,3-dihydroxy-1-(4-hydroxybenzyl)hexyl]-$N^1,N^1$-dipropylbenzene-1,3,5-tricarboxamide

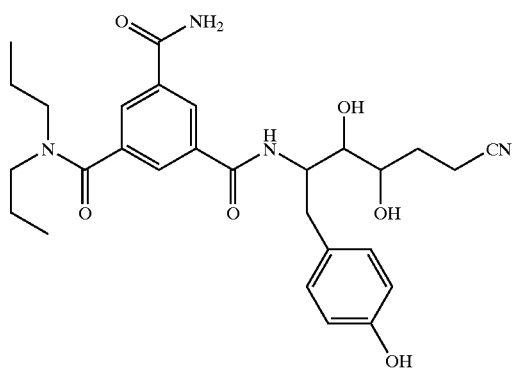

$N^3$-[5-cyano-2,3-dihydroxy-1-(4-hydroxybenzyl)pentyl]-$N^1,N^1$-dipropylbenzene-1,3,5-tricarboxamide

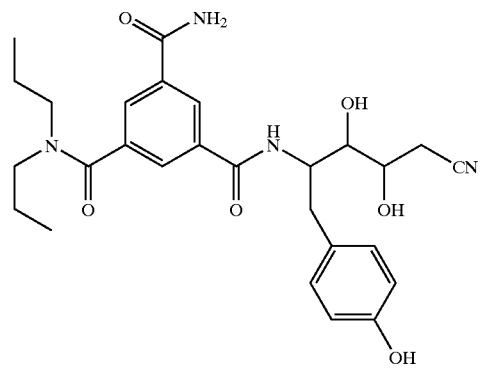

119

N³-[4-cyano-2,3-dihydroxy-1-(4-hydroxybenzyl)butyl]-N¹,N¹-dipropylbenzene-1,3,5-tricarboxamide

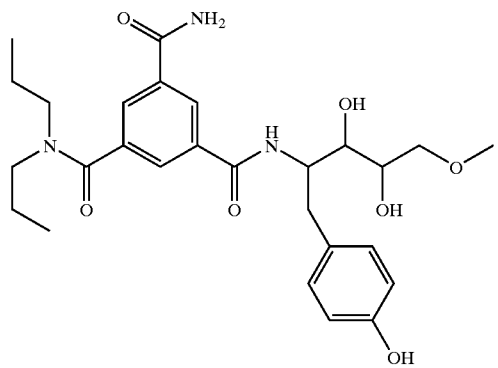

2-({3-(aminocarbonyl)-5-[(dipropylamino)carbonyl]benzoyl}amino)-1,2-dideoxy-1-(4-hydroxyphenyl)-5-O-methylpentitol

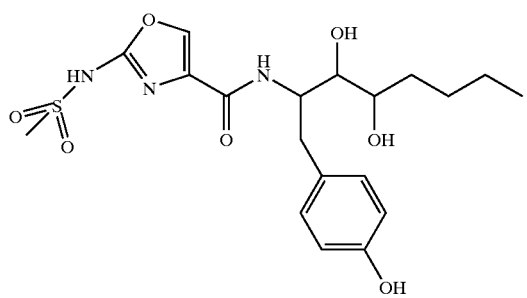

N-[2,3-dihydroxy-1-(4-hydroxybenzyl)heptyl]-2-[(methylsulfonyl)amino]-1,3-oxazole-4-carboxamide

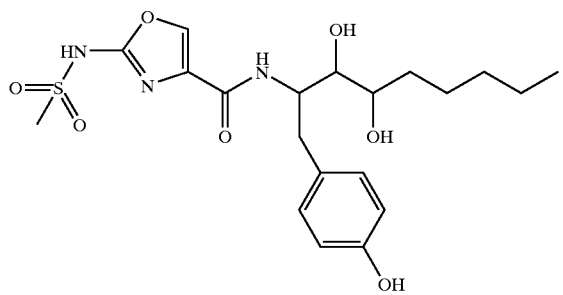

120

N-[2,3-dihydroxy-1-(4-hydroxybenzyl)octyl]-2-[(methylsulfonyl)amino]-1,3-oxazole-4-carboxamide

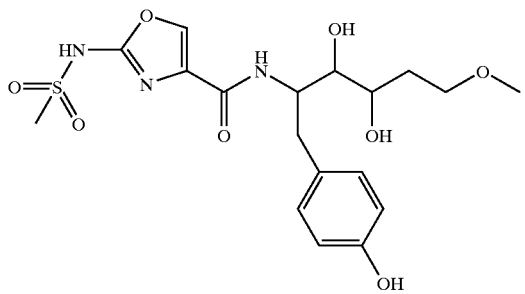

1,2,5-trideoxy-1-(4-hydroxyphenyl)-6-O-methyl-2-[({2-[(methylsulfonyl)amino]-1,3-oxazol-4-yl}carbonyl)amino]hexitol

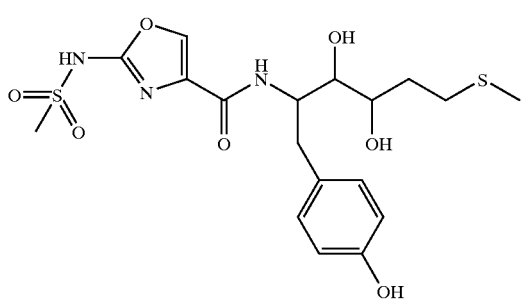

1,2,5-trideoxy-1-(4-hydroxyphenyl)-6-S-methyl-2-[({2-[(methylsulfonyl)amino]-1,3-oxazol-4-yl}carbonyl)amino]-6-thiohexitol

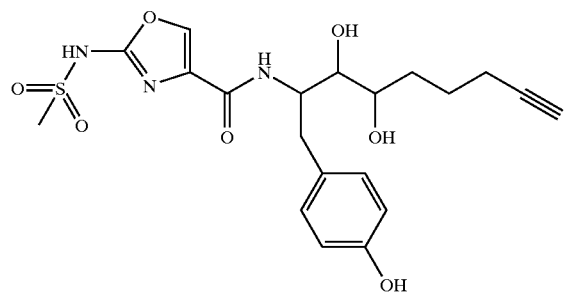

121
N-[2,3-dihydroxy-1-(4-hydroxybenzyl)oct-7-ynyl]-2-[(methylsulfonyl)amino]-1,3-oxazole-4-carboxamide

122
N-[5-cyano-2,3-dihydroxy-1-(4-hydroxybenzyl)pentyl]-2-[(methylsulfonyl)amino]-1,3-oxazole-4-carboxamide

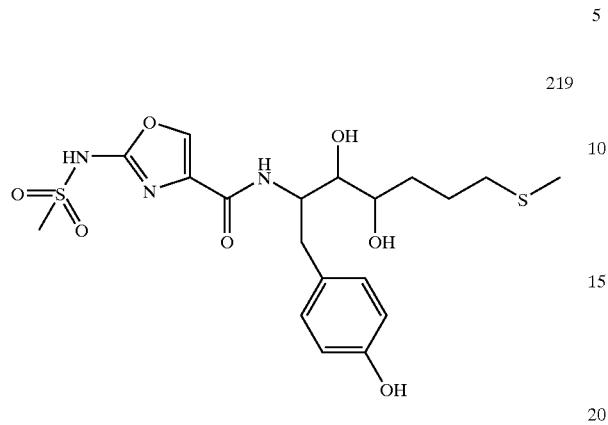

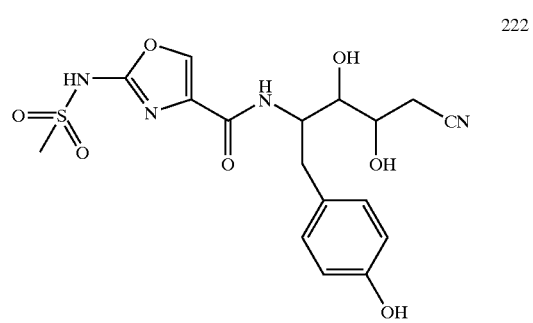

1,2,5,6-tetradeoxy-1-(4-hydroxyphenyl)-7-S-methyl-2-[({2-[(methylsulfonyl)amino]-1,3-oxazol-4-yl}carbonyl)amino]-7-thioheptitol N-[4-cyano-2,3-dihydroxy-1-(4-hydroxybenzyl)butyl]-2-[(methylsulfonyl)amino]-1,3-oxazole-4-carboxamide

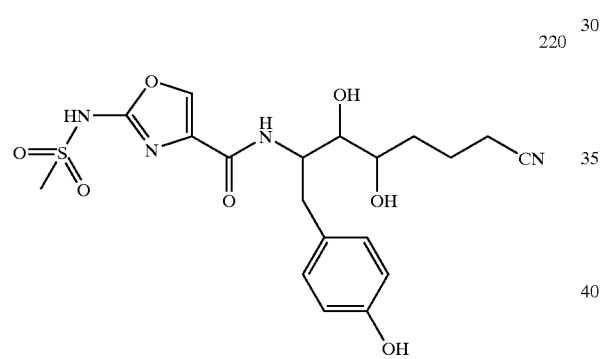

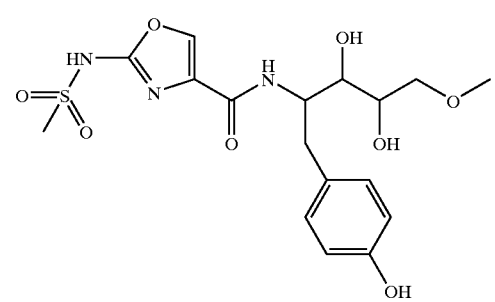

N-[6-cyano-2,3-dihydroxy-1-(4-hydroxybenzyl)hexyl]-2-[(methylsulfonyl)amino]-1,3-oxazole-4-carboxamide 1,2-dideoxy-1-(4-hydroxyphenyl)-5-O-methyl-2-[({2-[(methylsulfonyl)amino]-1,3-oxazol-4-yl}carbonyl)amino]pentitol

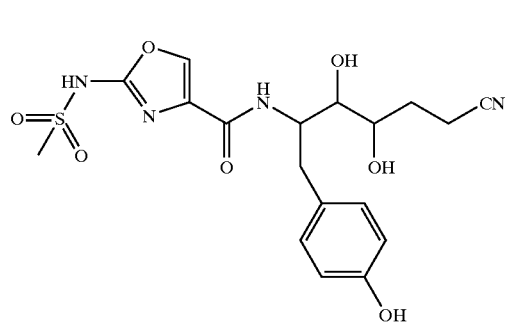

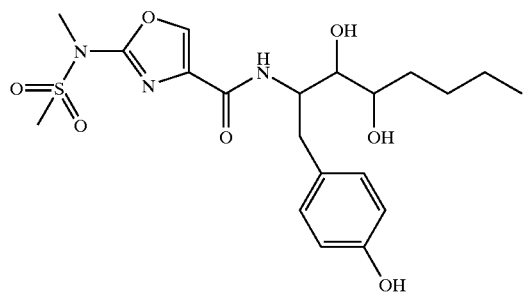

123

N-[2,3-dihydroxy-1-(4-hydroxybenzyl)heptyl]-2-[methyl(methylsulfonyl)amino]-1,3-oxazole-4-carboxamide

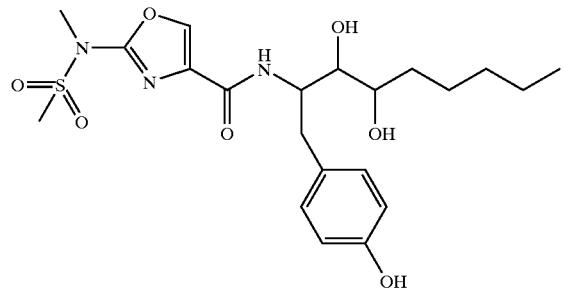

N-[2,3-dihydroxy-1-(4-hydroxybenzyl)octyl]-2-[methyl(methylsulfonyl)amino]-1,3-oxazole-4-carboxamide

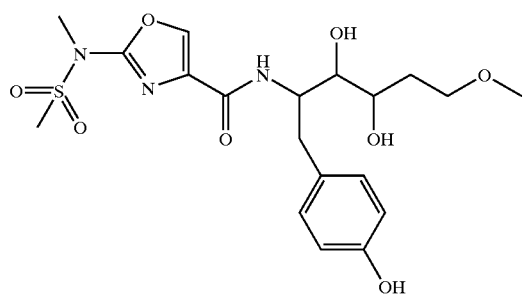

1,2,5-trideoxy-1-(4-hydroxyphenyl)-6-O-methyl-2-[({2-[methyl(methylsulfonyl)amino]-1,3-oxazol-4-yl}carbonyl)amino]hexitol

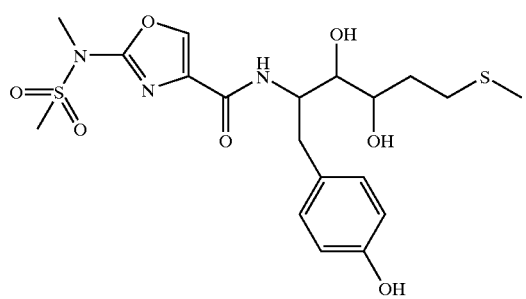

124

1,2,5-trideoxy-1-(4-hydroxyphenyl)-6-S-methyl-2-[({2-[methyl(methylsulfonyl)amino]-1,3-oxazol-4-yl}carbonyl)amino]-6-thiohexitol

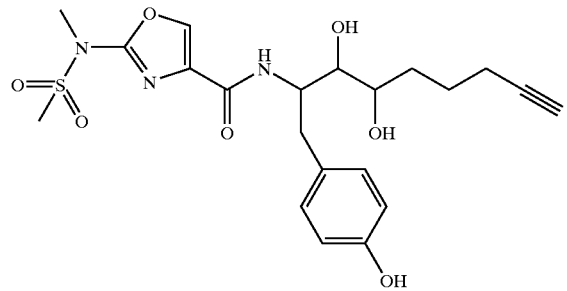

N-[2,3-dihydroxy-1-(4-hydroxybenzyl)oct-7-ynyl]-2-[methyl(methylsulfonyl)amino]-1,3-oxazole-4-carboxamide

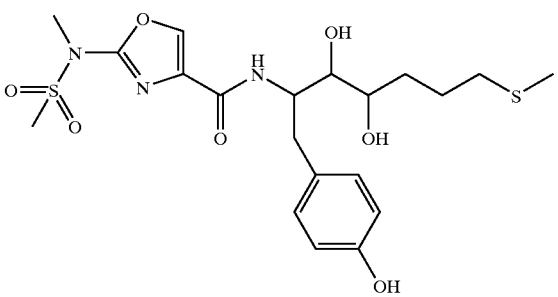

1,2,5,6-tetradeoxy-1-(4-hydroxyphenyl)-7-S-methyl-2-[({2-[methyl(methylsulfonyl)amino]-1,3-oxazol-4-yl}carbonyl)amino]-7-thioheptitol

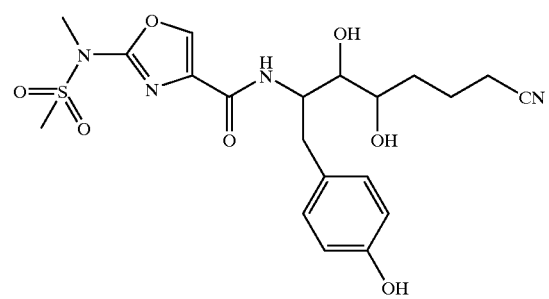

125

N-[6-cyano-2,3-dihydroxy-1-(4-hydroxybenzyl)hexyl]-2-[methyl(methylsulfonyl)amino]-1,3-oxazole-4-carboxamide

126

1,2-dideoxy-1-(4-hydroxyphenyl)-5-O-methyl-2-[({2-[methyl(methylsulfonyl)amino]-1,3-oxazol-4-yl}carbonyl)amino]pentitol

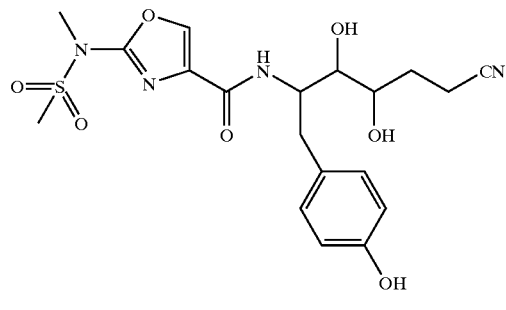

231

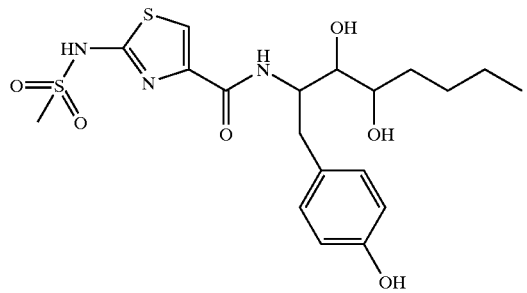

234

N-[5-cyano-2,3-dihydroxy-1-(4-hydroxybenzyl)pentyl]-2-[methyl(methylsulfonyl)amino]-1,3-oxazole-4-carboxamide N-[2,3-dihydroxy-1-(4-hydroxybenzyl)heptyl]-2-[(methylsulfonyl)amino]-1,3-thiazole-4-carboxamide

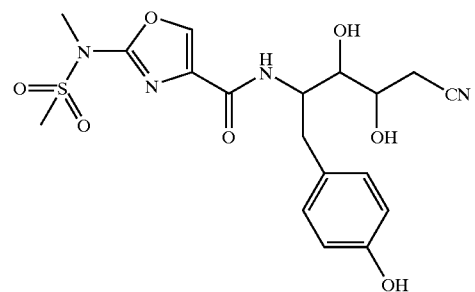

232

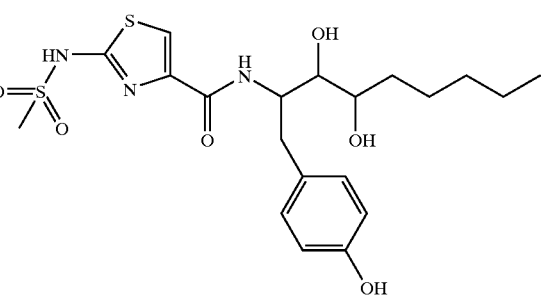

235

N-[4-cyano-2,3-dihydroxy-1-(4-hydroxybenzyl)butyl]-2-[methyl(methylsulfonyl)amino]-1,3-oxazole-4-carboxamide N-[2,3-dihydroxy-1-(4-hydroxybenzyl)octyl]-2-[(methylsulfonyl)amino]-1,3-thiazole-4-carboxamide

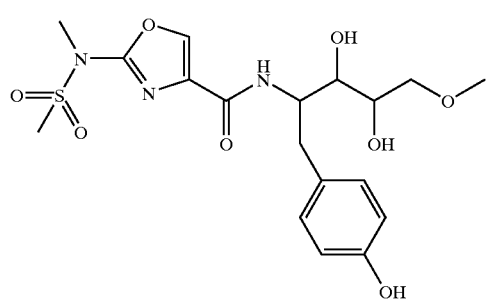

233

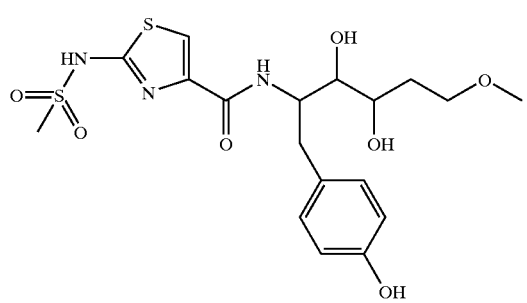

236

127

1,2,5-trideoxy-1-(4-hydroxyphenyl)-6-O-methyl-2-
[({2-[(methylsulfonyl)amino]-1,3-thiazol-4-
yl}carbonyl)amino]hexitol

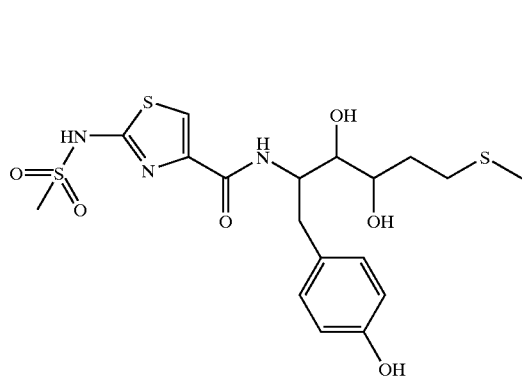

237

1,2,5-trideoxy-1-(4-hydroxyphenyl)-6-S-methyl-2-
[({2-[(methylsulfonyl)amino]-1,3-thiazol-4-
yl}carbonyl)amino]-6-thiohexitol

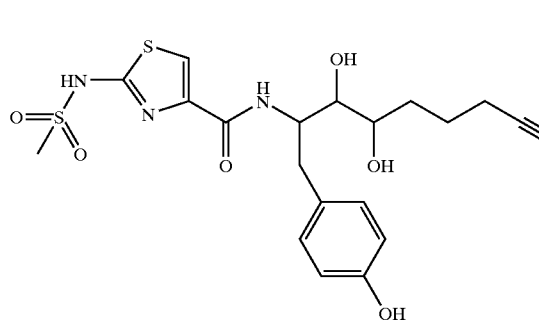

238

N-[2,3-dihydroxy-1-(4-hydroxybenzyl)oct-7-ynyl]-
2-[(methylsulfonyl)amino]-1,3-thiazole-4-
carboxamide

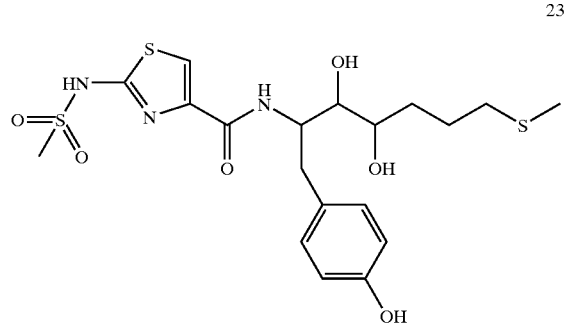

239

128

1,2,5,6-tetradeoxy-1-(4-hydroxyphenyl)-7-S-methyl-
2-[({2-[(methylsulfonyl)amino]-1,3-thiazol-4-
yl}carbonyl)amino]-7-thioheptitol

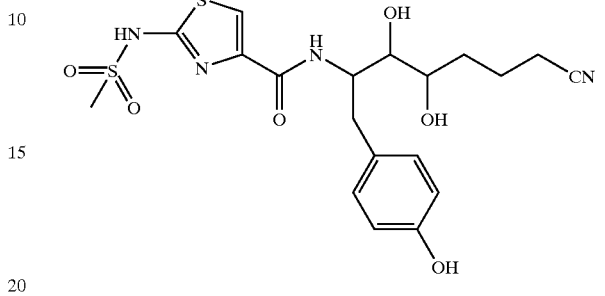

240

N-[6-cyano-2,3-dihydroxy-1-(4-hydroxybenzyl)
hexyl]-2-[(methylsulfonyl)amino]-1,3-thiazole-4-
carboxamide

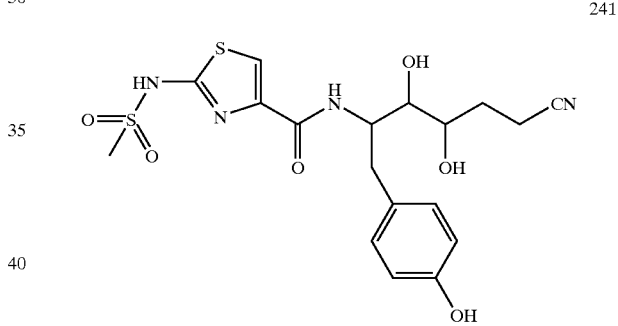

241

N-[5-cyano-2,3-dihydroxy-1-(4-hydroxybenzyl)
pentyl]-2-[(methylsulfonyl)amino]-1,3-thiazole-4-
carboxamide

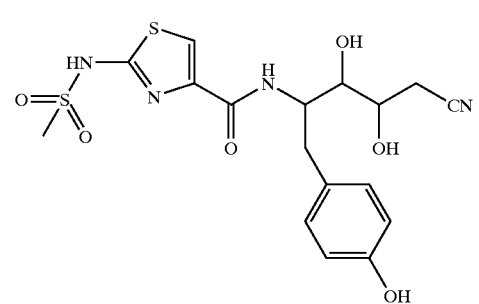

242

| 129 | 130 |
|---|---|
| N-[4-cyano-2,3-dihydroxy-1-(4-hydroxybenzyl)butyl]-2-[(methylsulfonyl)amino]-1,3-thiazole-4-carboxamide | N-[2,3-dihydroxy-1-(4-hydroxybenzyl)octyl]-2-[methyl(methylsulfonyl)amino]-1,3-thiazole-4-carboxamide |

243

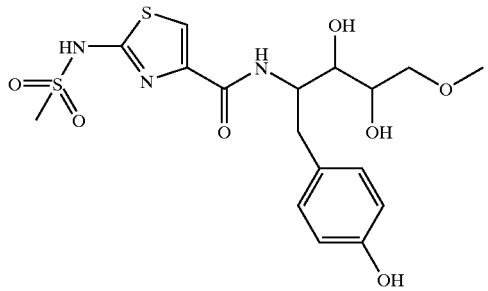

1,2-dideoxy-1-(4-hydroxyphenyl)-5-O-methyl-2-[({2-[(methylsulfonyl)amino]-1,3-thiazol-4-yl}carbonyl)amino]pentitol

244

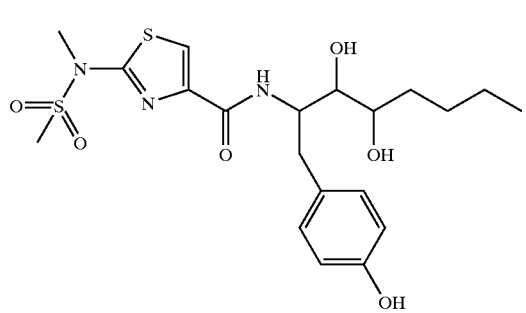

N-[2,3-dihydroxy-1-(4-hydroxybenzyl)heptyl]-2-[methyl(methylsulfonyl)amino]-1,3-thiazole-4-carboxamide

245

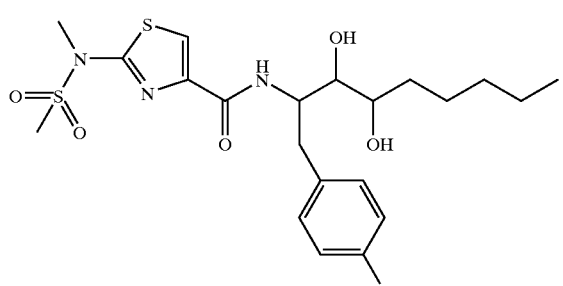

246

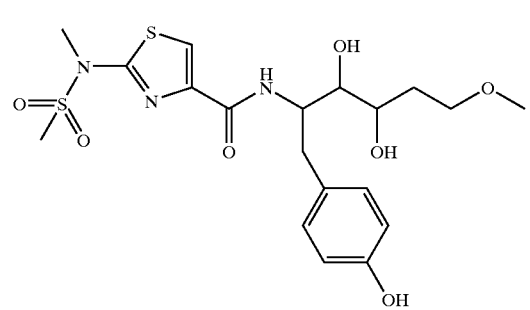

1,2,5-trideoxy-1-(4-hydroxyphenyl)-6-O-methyl-2-[({2-[methyl(methylsulfonyl)amino]-1,3-thiazol-4-yl}carbonyl)amino]hexitol

247

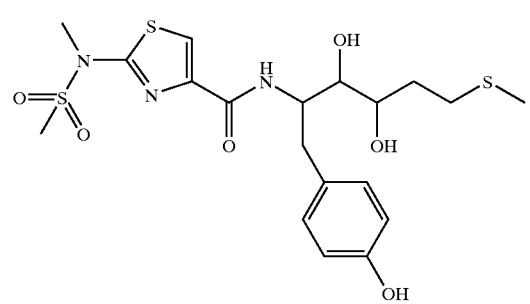

1,2,5-trideoxy-1-(4-hydroxyphenyl)-6-S-methyl-2-[({2-[methyl(methylsulfonyl)amino]-1,3-thiazol-4-yl}carbonyl)amino]-6-thiohexitol

248

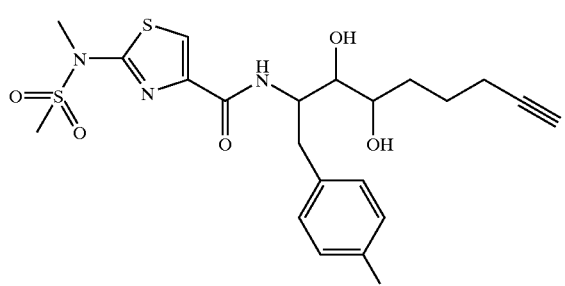

131
N-[2,3-dihydroxy-1-(4-hydroxybenzyl)oct-7-ynyl]-2-[methyl(methylsulfonyl)amino]-1,3-thiazole-4-carboxamide

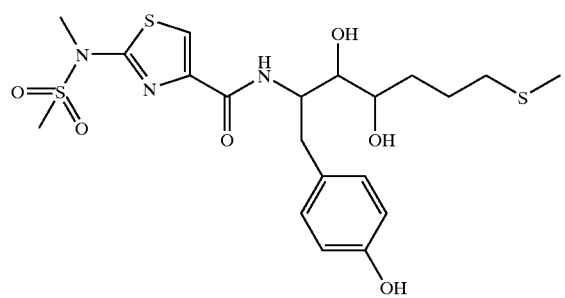
249

1,2,5,6-tetradeoxy-1-(4-hydroxyphenyl)-7-S-methyl-2-[({2-[methyl(methylsulfonyl)amino]-1,3-thiazol-4-yl}carbonyl)amino]-7-thioheptitol

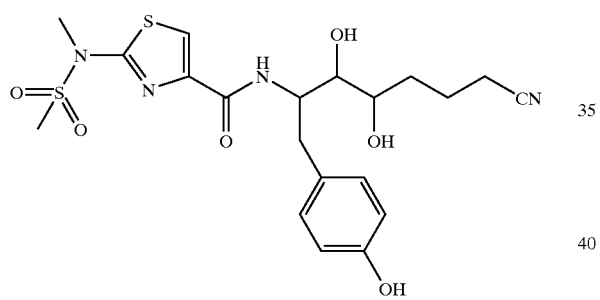
250

N-[6-cyano-2,3-dihydroxy-1-(4-hydroxybenzyl)hexyl]-2-[methyl(methylsulfonyl)amino]-1,3-thiazole-4-carboxamide

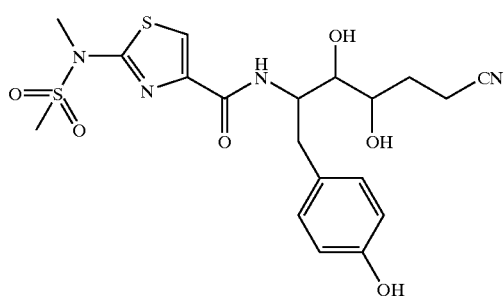
251

132
N-[5-cyano-2,3-dihydroxy-1-(4-hydroxybenzyl)pentyl]-2-[methyl(methylsulfonyl)amino]-1,3-thiazole-4-carboxamide

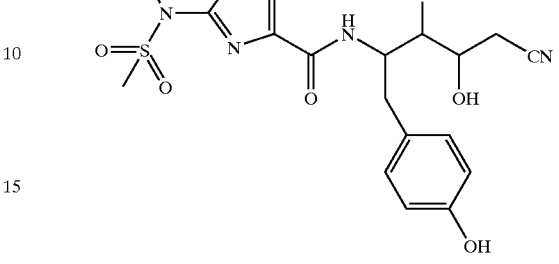
252

N-[4-cyano-2,3-dihydroxy-1-(4-hydroxybenzyl)butyl]-2-[methyl(methylsulfonyl)amino]-1,3-thiazole-4-carboxamide, or

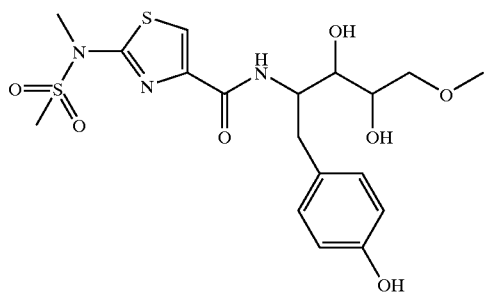
253

1,2-dideoxy-1-(4-hydroxyphenyl)-5-O-methyl-2-[({2-[methyl(methylsulfonyl)amino]-1,3-thiazol-4-yl}carbonyl)amino]pentitol.

BIOLOGY EXAMPLES

Example A

Enzyme Inhibition Assay

The compounds of the invention are analyzed for inhibitory activity by use of the MBP-C125 assay. This assay determines the relative inhibition of beta-secretase cleavage of a model APP substrate, MBP-C125SW, by the compounds assayed as compared with an untreated control. A detailed description of the assay parameters can be found, for example, in U.S. Pat. No. 5,942,400. Briefly, the substrate is a fusion peptide formed of maltose binding protein (MBP) and the carboxy terminal 125 amino acids of APP-SW, the Swedish mutation. The beta-secretase enzyme is derived from human brain tissue as described in Sinha et al, 1999, *Nature* 40:537–540) or recombinantly produced as the full-length enzyme (amino acids 1–501), and can be prepared, for example, from 293 cells expressing the recombinant cDNA, as described in WO00/47618.

Inhibition of the enzyme is analyzed, for example, by immunoassay of the enzyme's cleavage products. One exemplary ELISA uses an anti-MBP capture antibody that is deposited on precoated and blocked 96-well high binding plates, followed by incubation with diluted enzyme reaction supernatant, incubation with a specific reporter antibody, for example, biotinylated anti-SW192 reporter antibody, and further incubation with streptavidin/alkaline phosphatase. In the assay, cleavage of the intact MBP-C125SW fusion protein results in the generation of a truncated amino-terminal fragment, exposing a new SW-192 antibody-positive epitope at the carboxy terminus. Detection is effected by a fluorescent substrate signal on cleavage by the phosphatase. ELISA only detects cleavage following Leu 596 at the substrate's APP-SW 751 mutation site.

Specific Assay Procedure

Compounds are diluted in a 1:1 dilution series to a six-point concentration curve (two wells per concentration) in one 96-plate row per compound tested. Each of the test compounds is prepared in DMSO to make up a 10 millimolar stock solution. The stock solution is serially diluted in DMSO to obtain a final compound concentration of 200 micromolar at the high point of a 6-point dilution curve. Ten (10) microliters of each dilution is added to each of two wells on row C of a corresponding V-bottom plate to which 190 microliters of 52 millimolar NaOAc, 7.9% DMSO, pH 4.5 are pre-added. The NaOAc diluted compound plate is spun down to pellet precipitant and 20 microliters/well is transferred to a corresponding flat-bottom plate to which 30 microliters of ice-cold enzyme-substrate mixture (2.5 microliters MBP-C125SW substrate, 0.03 microliters enzyme and 24.5 microliters ice cold 0.09% TX100 per 30 microliters) is added. The final reaction mixture of 200 micromolar compound at the highest curve point is in 5% DMSO, 20 millimolar NaOAc, 0.06% TX100, at pH 4.5.

Warming the plates to 37 degrees C. starts the enzyme reaction. After 90 minutes at 37 degrees C., 200 microliters/well cold specimen diluent is added to stop the reaction and 20 microliters/well was transferred to a corresponding anti-MBP antibody coated ELISA plate for capture, containing 80 microliters/well specimen diluent. This reaction is incubated overnight at 4 degrees C. and the ELISA is developed the next day after a 2 hour incubation with anti-192SW antibody, followed by Streptavidin-AP conjugate and fluorescent substrate. The signal is read on a fluorescent plate reader.

Relative compound inhibition potency is determined by calculating the concentration of compound that showed a fifty percent reduction in detected signal ($IC_{50}$) compared to the enzyme reaction signal in the control wells with no added compound. In this assay, preferred compounds of the invention exhibit an $IC_{50}$ of less than 50 micromolar.

Example B

Cell Free Inhibition Assay Utilizing a Synthetic APP Substrate

A synthetic APP substrate that can be cleaved by beta-secretase and having N-terminal biotin and made fluorescent by the covalent attachment of Oregon green at the Cys residue is used to assay beta-secretase activity in the presence or absence of the inhibitory compounds of the invention. Useful substrates include the following:

Biotin-SEVNL-DAEFRC[oregon green]KK [SEQ ID NO: 1]

Biotin-SEVKM-DAEFRC[oregon green]KK [SEQ ID NO: 2]

Biotin-GLNIKTEEISEISY-EVEFRC[oregon green]KK [SEQ ID NO: 3]

Biotin-ADRGLTTRPGSGLTNIKTEEISEVNL-DAEFRC[oregon green]KK [SEQ ID NO:4]

Biotin-FVNQHLCoxGSHLVEALY-LVCoxGERGFFYTPKAC[oregon green]KK [SEQ ID NO: 5]

The enzyme (0.1 nanomolar) and test compounds (0.001–100 micromolar) are incubated in pre-blocked, low affinity, black plates (384 well) at 37 degrees for 30 minutes. The reaction is initiated by addition of 150 millimolar substrate to a final volume of 30 microliter per well. The final assay conditions are: 0.001–100 micromolar compound inhibitor; 0.1 molar sodium acetate (pH 4.5); 150 nanomolar substrate; 0.1 nanomolar soluble beta-secretase; 0.001% Tween 20, and 2% DMSO. The assay mixture is incubated for 3 hours at 37 degrees C., and the reaction is terminated by the addition of a saturating concentration of immunopure streptavidin. After incubation with streptavidin at room temperature for 15 minutes, fluorescence polarization is measured, for example, using a LJL Acqurest (Ex485 nm/Em530 nm). The activity of the beta-secretase enzyme is detected by changes in the fluorescence polarization that occur when the substrate is cleaved by the enzyme. Incubation in the presence or absence of compound inhibitor demonstrates specific inhibition of beta-secretase enzymatic cleavage of its synthetic APP substrate. In this assay, preferred compounds of the invention exhibit an $IC_{50}$ of less than 50 micromolar.

Example C

Beta-Secretase Inhibition: P26-P4'SW Assay

Synthetic substrates containing the beta-secretase cleavage site of APP are used to assay beta-secretase activity, using the methods described, for example, in published PCT application WO00/47618. The P26-P4'SW substrate is a peptide of the sequence:

(biotin) CGGADRGLTTRPGSGLTNIKTEEISEVNLDAEF [SEQ ID NO: 6]

The P26-P1 standard has the sequence:

(biotin)CGGADRGLTTRPGSGLTNIKTEEISEVNL [SEQ ID NO: 7].

Briefly, the biotin-coupled synthetic substrates are incubated at a concentration of from about 0 to about 200 micromolar in this assay. When testing inhibitory compounds, a substrate concentration of about 1.0 micromolar is preferred. Test compounds diluted in DMSO are added to the reaction mixture, with a final DMSO concentration of 5%. Controls also contain a final DMSO concentration of 5%. The concentration of beta secretase enzyme in the reaction is varied, to give product concentrations with the linear range of the ELISA assay, about 125 to 2000 picomolar, after dilution.

The reaction mixture also includes 20 millimolar sodium acetate, pH 4.5, 0.06% Triton X100, and is incubated at 37 degrees C. for about 1 to 3 hours. Samples are then diluted in assay buffer (for example, 145.4 nanomolar sodium chloride, 9.51 millimolar sodium phosphate, 7.7 millimolar sodium azide, 0.05% Triton X405, 6 g/liter bovine serum albumin, pH 7.4) to quench the reaction, then diluted further for immunoassay of the cleavage products.

Cleavage products can be assayed by ELISA. Diluted samples and standards are incubated in assay plates coated with capture antibody, for example, SW192, for about 24 hours at 4 degrees C. After washing in TTBS buffer (150 millimolar sodium chloride, 25 millimolar Tris, 0.05%

Tween 20, pH 7.5), the samples are incubated with streptavidin-AP according to the manufacturer's instructions. After a one hour incubation at room temperature, the samples are washed in TTBS and incubated with fluorescent substrate solution A (31.2 g/liter 2-amino-2-methyl-1-propanol, 30 mg/liter, pH 9.5). Reaction with streptavidin-alkaline phosphate permits detection by fluorescence. Compounds that are effective inhibitors of beta-secretase activity demonstrate reduced cleavage of the substrate as compared to a control.

Example D

Assays using Synthetic Oligopeptide-Substrates

Synthetic oligopeptides are prepared that incorporate the known cleavage site of beta-secretase, and optionally detectable tags, such as fluorescent or chromogenic moieties. Examples of such peptides, as well as their production and detection methods are described in U.S. Pat. No. 5,942,400, herein incorporated by reference. Cleavage products can be detected using high performance liquid chromatography, or fluorescent or chromogenic detection methods appropriate to the peptide to be detected, according to methods well known in the art.

By way of example, one such peptide has the sequence SEVNL-DAEF [SEQ ID NO: 8], and the cleavage site is between residues 5 and 6. Another preferred substrate has the sequence ADRGLTTRPGSGLTNIKTEEISEVNL-DAEF [SEQ ID NO: 9], and the cleavage site is between residues 26 and 27.

These synthetic APP substrates are incubated in the presence of beta-secretase under conditions sufficient to result in beta-secretase mediated cleavage of the substrate. Comparison of the cleavage results in the presence of the compound inhibitor to control results provides a measure of the compound's inhibitory activity.

Example E

Inhibition of Beta-Secretase Activity—Cellular Assay

An exemplary assay for the analysis of inhibition of beta-secretase activity utilizes the human embryonic kidney cell line HEKp293 (ATCC Accession No. CRL-1573) transfected with APP751 containing the naturally occurring double mutation Lys651Met52 to Asn651Leu652 (numbered for APP751), commonly called the Swedish mutation and shown to overproduce A beta (Citron et al., 1992, Nature 360:672–674), as described in U.S. Pat. No. 5,604,102.

The cells are incubated in the presence/absence of the inhibitory compound (diluted in DMSO) at the desired concentration, generally up to 10 micrograms/ml. At the end of the treatment period, conditioned media is analyzed for beta-secretase activity, for example, by analysis of cleavage fragments. A beta can be analyzed by immunoassay, using specific detection antibodies. The enzymatic activity is measured in the presence and absence of the compound inhibitors to demonstrate specific inhibition of beta-secretase mediated cleavage of APP substrate.

Example F

Inhibition of Beta-Secretase in Animal Models of AD

Various animal models can be used to screen for inhibition of beta-secretase activity. Examples of animal models useful in the invention include, but are not limited to, mouse, guinea pig, dog, and the like. The animals used can be wild type, transgenic, or knockout models. In addition, mammalian models can express mutations in APP, such as APP695-SW and the like described herein. Examples of transgenic non-human mammalian models are described in U.S. Pat. Nos. 5,604,102, 5,912,410 and 5,811,633.

PDAPP mice, prepared as described in Games et al., 1995, Nature 373:523–527 are useful to analyze in vivo suppression of A beta release in the presence of putative inhibitory compounds. As described in U.S. Pat. No. 6,191,166, 4 month old PDAPP mice are administered compound formulated in vehicle, such as corn oil. The mice are dosed with compound (1–30 mg/ml; preferably 1–10 mg/ml). After time, e.g., 3–10 hours, the animals are sacrificed, and brains removed for analysis.

Transgenic animals are administered an amount of the compound inhibitor formulated in a carrier suitable for the chosen mode of administration. Control animals are untreated, treated with vehicle, or treated with an inactive compound. Administration can be acute, i.e., single dose or multiple doses in one day, or can be chronic, i.e., dosing is repeated daily for a period of days. Beginning at time 0, brain tissue or cerebral fluid is obtained from selected animals and analyzed for the presence of APP cleavage peptides, including A beta, for example, by immunoassay using specific antibodies for A beta detection. At the end of the test period, animals are sacrificed and brain tissue or cerebral fluid is analyzed for the presence of A beta and/or beta-amyloid plaques. The tissue is also analyzed for necrosis.

Animals administered the compound inhibitors of the invention are expected to demonstrate reduced A beta in brain tissues or cerebral fluids and reduced beta amyloid plaques in brain tissue, as compared with non-treated controls.

Example G

Inhibition of A Beta Production in Human Patients

Patients suffering from Alzheimer's Disease (AD) demonstrate an increased amount of A beta in the brain. AD patients are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; A beta deposits in the brain; amyloid plaque in the brain; and scores for cognitive and memory function, as compared with control, non-treated patients.

Example H

Prevention of A Beta Production in Patients at Risk for AD

Patients predisposed or at risk for developing AD are identified either by recognition of a familial inheritance pattern, for example, presence of the Swedish Mutation, and/or by monitoring diagnostic parameters. Patients identified as predisposed or at risk for developing AD are administered an amount of the compound inhibitor formulated in a carrier suitable for the chosen mode of adminis tration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; amyloid plaque in the brain; and scores for cognitive and memory function, as compared with control, non-treated patients.

The invention has been described with reference to various specific and preferred embodiments and techniques. However, it should be understood that many variations and modifications may be made while remaining within the spirit and scope of the invention.

What is claimed is:

1. A compound of the formula I:

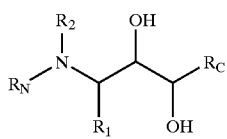

(I)

or a pharmaceutical salt thereof, wherein $R_1$ is aryl, or aryl ($C_1$–$C_6$)alkyl-, where the ring portions of each are optionally substituted with 1, 2, 3, or 4 groups independently selected from halogen, —OH, —SH, —C≡N, —NO$_2$, —NR$_{105}$R'$_{105}$, —CO$_2$R, —N(R)COR', —N(R)SO$_2$R', —C(=O)—($C_1$–$C_4$) alkyl, —SO$_2$-amino, —SO$_2$-monoalkylamino, —SO$_2$-dialkylamino, —C(=O)-amino, —C(=O)-monoalkylamino, —C(=O)-dialkylamino, —SO$_2$—($C_1$–$C_4$)alkyl, $C_1$–$C_6$ alkoxy optionally substituted with 1, 2, or 3 groups which are independently selected from halogen, $C_3$–$C_7$ cycloalkyl optionally substituted with 1, 2, or 3 groups independently selected from halogen, —OH, —SH, —C≡N, —CF$_3$, $C_1$–$C_3$ alkoxy, amino, —$C_1$–$C_6$ alkyl and mono- or dialkylamino, $C_1$–$C_{10}$ alkyl optionally substituted with 1, 2, or 3 groups independently selected from halogen, —OH, —SH, —C≡N, —CF$_3$, —$C_1$–$C_3$ alkoxy, amino, mono- or dialkylamino and —$C_1$–$C_3$ alkyl, and $C_2$–$C_{10}$ alkenyl or $C_2$–$C_{10}$ alkynyl each of which is optionally substituted with 1, 2, or 3 groups independently selected from halogen, —OH, —SH, —C≡N, —$CF_3$, $C_1$–$C_3$ alkoxy, amino, $C_1$–$C_6$ alkyl and mono- or dialkylamino;

R and R' independently are hydrogen, $C_1$–$C_{10}$ alkyl, or $C_1$–$C_{10}$ alkylaryl;

$R_2$ is H;

$R_c$ is hydrogen, —$(CR_{245}R_{250})_{0-4}$-aryl, —$(CR_{245}R_{250})_{0-4}$-aryl-aryl, —CH(aryl)$_2$, —$(CH_2)_{0-1}$—CH($(CH_2)_{0-6}$—OH)—$(CH_2)_{0-1}$-aryl, —CH(-aryl) —CO—O($C_1$–$C_4$ alkyl), —($C_1$–$C_6$ alkyl)-O—($C_1$–$C_6$ alkyl) —OH; —$CH_2$—NH—$CH_2$—CH (—O—$CH_2$—$CH_3$)$_2$, —$(CH_2)_{0-6}$—
C(=$NR_{235}$)($NR_{235}R_{240}$), $C_1$–$C_{10}$ alkyl optionally substituted with 1, 2, or 3 groups independently selected from the group consisting of $R_{110}$, $R_{120}$ and $R_{130}$,
$C_2$–$C_{10}$ alkyl optionally substituted with 1, 2, or 3 groups independently selected from the group consisting of $R_{205}$, $R_{110}$, $R_{120}$, $R_{130}$, —OC=ON$R_{235}R_{240}$, —S(=O)$_{0-2}$($C_1$–$C_6$ alkyl), —SH, and —S(=O)$_2$N$R_{235}R_{240}$,
$C_2$–$C_{10}$ alkenyl or $C_2$–$C_{10}$ alkynyl, each of which is optionally substituted with 1, 2, or 3 independently selected $R_{205}$ groups, wherein
each aryl is optionally substituted with 1, 2, or 3 $R_{200}$;

$R_{200}$ at each occurrence is independently selected from —OH, —$NO_2$, halogen, —$CO_2$H, C≡N, —$(CH_2)_{0-4}$—CO—N$R_{220}R_{225}$, —$(CH_2)_{0-4}$—CO—($C_1$–$C_{12}$ alkyl), —$(CH_2)_{0-4}$—CO—($C_2$–$C_{12}$ alkenyl), —$(CH_2)_{0-4}$—CO—($C_2$–$C_{12}$ alkynyl), —$(CH_2)_{0-4}$—CO—($C_3$–$C_7$ cycloalkyl), —$(CH_2)_{0-4}$—CO-aryl, —$(CH_2)_{0-4}$—CO—O—$R_{215}$, —$(CH_2)_{0-4}$—$SO_2$—N$R_{220}R_{225}$, —$(CH_2)_{0-4}$—SO—($C_1$–$C_8$ alkyl), —$(CH_2)_{0-4}$—$SO_2$—($C_1$–$C_{12}$ alkyl), —$(CH_2)_{0-4}$—$SO_2$—($C_3$–$C_7$ cycloalkyl), —$(CH_2)_{0-4}$—N(H or $R_{215}$)—CO—O—$R_{215}$, —$(CH_2)_{0-4}$—N(H or $R_{215}$)—CO—N($R_{215}$)$_2$, —$(CH_2)_{0-4}$—N—CS—N($R_{215}$)$_2$, —$(CH_2)_{0-4}$—N(—H or $R_{215}$)—CO—$R_{220}$, —$(CH_2)_{0-4}$—N$R_{220}R_{225}$, —$(CH_2)_{0-4}$—O—CO—($C_1$–$C_6$ alkyl), —$(CH_2)_{0-4}$—O—P(O)—(O$R_{240}$)$_2$, —$(CH_2)_{0-4}$—O—CO—N($R_{215}$)$_2$, —$(CH_2)_{0-4}$—O—CS—N($R_{215}$)$_2$, —$(CH_2)_{0-4}$—O—($R_{215}$), —$(CH_2)_{0-4}$—O—($R_{215}$)—COOH, —$(CH_2)_{0-4}$—S—($R_{215}$), —$(CH_2)_{0-4}$—O—($C_1$–$C_6$ alkyl optionally substituted with 1, 2, 3, or 5 —F), $C_3$–$C_7$ cycloalkyl, —$(CH_2)_{0-4}$—N(H or $R_{215}$)—$SO_2$—$R_{220}$, —$(CH_2)_{0-4}$—$C_3$–$C_7$ cycloalkyl,
$C_1$–$C_{10}$ alkyl optionally substituted with 1, 2, or 3 independently selected $R_{205}$ groups,
$C_2$–$C_{10}$ alkenyl and $C_2$–$C_{10}$ alkynyl, each of which is optionally substituted with 1 or 2 independently selected $R_{205}$ groups, wherein
the aryl groups at each occurrence are optionally substituted with 1, 2, or 3 groups that are independently $R_{205}$, $R_{210}$, or
$C_1$–$C_6$ alkyl substituted with 1, 2, or 3 groups that are independently $R_{205}$ or $R_{210}$;

$R_{205}$ at each occurrence is independently selected from $C_1$–$C_6$ alkyl, halogen, —OH, —O-phenyl, —SH, —S—$C_1$–$C_6$ alkyl, —C≡N, —$CF_3$, $C_1$–$C_6$ alkoxy, $NH_2$, NH($C_1$–$C_6$ alkyl) or N—($C_1$–$C_6$ alkyl)($C_1$–$C_6$ alkyl);

$R_{210}$ at each occurrence is independently selected from halogen, $C_1$–$C_6$ alkoxy, $C_1$–$C_6$ haloalkoxy, —N$R_{220}R_{225}$, OH, C≡N, —CO—($C_1$–$C_4$ alkyl), —$SO_2$—N$R_{235}R_{240}$, —CO—N$R_{235}R_{240}$, —$SO_2$—($C_1$–$C_4$ alkyl), =O, or
$C_1$–$C_6$ alkyl, $C_2$–$C_6$ alkenyl, $C_2$–$C_6$ alkynyl or $C_3$–$C_7$ cycloalkyl, each of which is optionally substituted with 1, 2, or 3 $R_{205}$ groups;

$R_{215}$ at each occurrence is independently selected from $C_1$–$C_6$ alkyl, —$(CH_2)_{0-2}$-(aryl), $C_2$–$C_6$ alkenyl, $C_2$–$C_6$ alkynyl, and $C_3$–$C_7$ cycloalkyl, wherein
the aryl group at each occurrence is optionally substituted with 1, 2, or 3 groups that are independently $R_{205}$ or $R_{210}$;

$R_{220}$ and $R_{225}$ at each occurrence are independently selected from —H, —$C_3$–$C_7$ cycloalkyl, —($C_1$–$C_2$ alkyl)-($C_3$–$C_7$ cycloalkyl), —($C_1$–$C_6$ alkyl)-O—($C_1$–$C_3$ alkyl), —$C_2$–$C_6$ alkenyl, —$C_2$–$C_6$ alkynyl, —$C_1$–$C_6$ alkyl chain with one double bond and one triple bond, -aryl, and
—$C_1$–$C_{10}$ alkyl optionally substituted with —OH, —$NH_2$ or halogen, wherein
the aryl, group at each occurrence is optionally substituted with 1, 2, or 3 independently selected $R_{270}$ groups $R_{235}$ and $R_{240}$ at each occurrence are independently H, or $C_1$–$C_6$ alkyl;

$R_{245}$ and $R_{250}$ at each occurrence are independently selected from —H, $C_1$–$C_4$ alkyl, $C_1$–$C_4$ alkylaryl, $C_1$–$C_4$ hydroxyalkyl, $C_1$–$C_4$ alkoxy, $C_1$–$C_4$ haloalkoxy, —$(CH_2)_{0-4}$—$C_3$–$C_7$ cycloalkyl, $C_2$–$C_6$ alkenyl, $C_2$–$C_6$ alkynyl, and phenyl; or $R_{245}$ and $R_{250}$ are taken together with the carbon to which they are attached to form a carbocycle of 3, 4, 5, 6, or 7 carbon atoms $R_{270}$ at each occurrence is independently $R_{205}$, halogen $C_1$–$C_6$ alkoxy, $C_1$–$C_6$ haloalkoxy, N$R_{235}R_{240}$, —OH, —C≡N, —CO—($C_1$–$C_4$ alkyl), —$SO_2$—N$R_{235}R_{240}$, —CO—N$R_{235}R_{240}$, —$SO_2$—($C_1$–$C_4$ alkyl), =O, or
$C_1$–$C_6$ alkyl, $C_2$–$C_6$ alkenyl, $C_2$–$C_6$ alkynyl or —$(CH_2)_{0-4}$—$C_3$–$C_7$ cycloalkyl, each of which is optionally substituted with 1, 2, or 3 $R_{205}$ groups;

$R_N$ is R'$_{100}$, —$SO_2$R'$_{100}$, —(CRR')$_{1-6}$R'$_{100}$, —C(=O)—(CRR')$_{0-6}$R$_{100}$, —C(=O)—(CRR')$_{1-6}$—O—R'$_{100}$, —C(=O)—(CRR')$_{1-6}$—S—R'$_{100}$, —C(=O)—(CRR')$_{1-6}$—C(=O)—R$_{100}$, —C(=O)—(CRR')$_{1-6}$—$SO_2$—R$_{100}$ or —C(=O)—(CRR')$_{1-6}$—N$R_{100}$—R'$_{100}$;

$R_{100}$ and R'$_{100}$ independently represent aryl, -aryl-W-aryl, -aryl-W-heteroaryl, -aryl-W-heterocyclyl, -heteroaryl-W-aryl, -heterocyclyl-W-aryl, —CH[$(CH_2)_{0-2}$—O—$R_{150}$]—$(CH_2)_{0-2}$-aryl, where the ring portions of each are optionally substituted with 1, 2, or 3 groups independently selected from
—OR, —$NO_2$, $C_1$–$C_6$ alkyl, halogen, —C≡N, —$OCF_3$, —$CF_3$, —$(CH_2)_{0-4}$—O—P(=O)(OR)(OR'), —$(CH_2)_{0-4}$—CO—N$R_{105}$R'$_{105}$, —$(CH_2)_{0-4}$—O—$(CH_2)_{0-4}$—CONR$_{102}$R$_{102}$', —$(CH_2)_{0-4}$—CO—($C_1$–$C_{12}$ alkyl), —$(CH_2)_{0-4}$—CO—($C_2$–$C_{12}$ alkenyl), —$(CH_2)_{0-4}$—CO—($C_2$–$C_{12}$ alkynyl), —$(CH_2)_{0-4}$—CO—$(CH_2)_{0-4}$($C_3$–$C_7$ cycloalkyl), —$(CH_2)_{0-4}$—$R_{110}$, —$(CH_2)_{0-4}$—$R_{120}$, —$(CH_2)_{0-4}$—$R_{130}$, —$(CH_2)_{0-4}$—CO—$R_{110}$, —$(CH_2)_{0-4}$—CO—$R_{120}$, —$(CH_2)_{0-4}$—CO—$R_{130}$, —$(CH_2)_{0-4}$—CO—$R_{140}$, —$(CH_2)_{0-4}$—CO—O—$R_{150}$, —$(CH_2)_{0-4}$—$SO_2$—N$R_{105}$R'$_{105}$, —$(CH_2)_{0-4}$—SO—($C_1$–$C_8$ alkyl), —$(CH_2)_{0-4}$—$SO_2$—($C_1$–$C_{12}$ alkyl), —$(CH_2)_{0-4}$—$SO_2$—$(CH_2)_{0-4}$—($C_3$–$C_7$ cycloalkyl), —$(CH_2)_{0-4}$—N($R_{150}$)—CO—O—$R_{150}$, —$(CH_2)_{0-4}$—N($R_{150}$)—CO—N($R_{150}$)$_2$, —$(CH_2)_{0-4}$—N($R_{150}$)—CS—N($R_{150}$)$_2$, —$(CH_2)_{0-4}$—N($R_{150}$)—CO—$R_{105}$, —$(CH_2)_{0-4}$—N$R_{105}$R'$_{105}$, —$(CH_2)_{0-4}$—$R_{140}$, —$(CH_2)_{0-4}$—O—CO—($C_1$–$C_6$ alkyl), —$(CH_2)_{0-4}$—O—P(O)—(O—$R_{110})_2$, —$(CH_2)_{0-4}$—O—CO—N$(R_{150})_2$, —$(CH_2)_{0-4}$—O—CS—N$(R_{150})_2$, —$(CR_2)_{0-4}$—O—$(R_{150})$, —$(CH_2)_{0-4}$—O—$R_{150}$'—COCH, —$(CH_2)_{0-4}$—S—$(R_{150})$, —$(CR_2)_{0-4}$—N$(R_{150})$—SO$_2$—$R_{105}$, —$(CH_2)_{0-4}$—$C_3$–$C_7$ cycloalkyl, ($C_2$–$C_{10}$alkenyl, and ($C_2$–$C_{10}$)alkynyl, or $R_{100}$ is $C_1$–$C_{10}$ alkyl optionally substituted with 1, 2, or 3 $R_{115}$ groups, or $R_{100}$ is —($C_1$–$C_6$ alkyl)—O-$C_1$–$C_6$ alkyl) or —($C_1$–$C_6$ alkyl)—S—($C_1$–$C_6$ alkyl), each of which is optionally substituted with 1, 2, or 3 $R_{115}$ groups, or $R_{100}$ is $C_3$–$C_8$ cycloalkyl optionally substituted with 1, 2, or 3 $R_{115}$ groups;

W is —$(CH_2)_{0-4}$—, —O—, —S(O)$_{0-2}$—, —N($R_{135}$)—, —CR(OH)— or —C(O)—;

$R_{102}$ and $R_{102}$' independently are hydrogen, or
$C_1$–$C_{10}$ alkyl optionally substituted with 1, 2, or 3 groups that are independently halogen, aryl or —$R_{110}$;

$R_{105}$ and $R'_{105}$ independently represent —H, —$R_{110}$, —$R_{120}$, $C_3$–$C_7$ cycloalkyl, —($C_1$–$C_2$ alkyl)-($C_3$–$C_7$ cycloalkyl), —($C_1$–$C_6$ alkyl)-O—($C_1$–$C_3$ alkyl), $C_2$–$C_6$ alkenyl, $C_2$–$C_6$ alkynyl, or $C_1$–$C_6$ alkyl chain with one double bond and one triple bond, or $C_1$–$C_6$ alkyl optionally substituted with —OH or —NH$_2$; or, $C_1$–$C_6$ alkyl optionally substituted with 1, 2, or 3 groups independently selected from halogen, or $R_{105}$ and $R'_{105}$ together with the atom to which they are attached form a 3 to 7 membered carbocyclic ring, where one member is optionally a heteratom selected from —O—, —S(O)$_{0-2}$—, —N($R_{135}$)—, the ring being optionally substituted with 1, 2 or 3 independently selected $R_{140}$ groups;

$R_{115}$ at each occurrence is independently halogen, —OH, —CO$_2R_{102}$, —$C_1$–$C_6$ thioalkoxy, —CO$_2$-phenyl, —NR$_{105}R'_{135}$, —SO$_2$—($C_1$–$C_8$ alkyl), —C(=O)$R_{150}$, $R_{180}$, —CONR$_{105}R'_{105}$, —SO$_2$NR$_{105}R'_{105}$, —NH—CO—($C_1$–$C_6$ alkyl), —NH—C(=O)—OH, —NH—C(=O)—OR, —NH—C(=O)—O-phenyl, —O—C(=O)—($C_1$–$C_6$ alkyl), —O—C(=O)-amino, —O—C(=O)-mono- or dialkylamino, —O—C(=O)-phenyl, —O—($C_1$–$C_6$ alkyl)-CO$_2$H, —NH—SO$_2$—($C_1$–$C_6$ alkyl), $C_1$–$C_6$ alkoxy or $C_1$–$C_6$ haloalkoxy;

$R_{135}$ is $C_1$–$C_6$ alkyl, $C_2$–$C_6$ alkenyl, $C_2$–$C_6$ alkynyl, $C_3$–$C_7$ cycloalkyl, —$(CH_2)_{0-2}$-(aryl), —$(CH_2)_{0-2}$-(heteroaryl), or —$(CH_2)_{0-2}$-(heterocyclyl);

$R_{140}$ is heterocyclyl optionally substituted with 1, 2, 3, or 4 groups independently selected from $C_1$–$C_6$ alkyl, $C_1$–$C_6$ alkoxy, halogen, hydroxy, cyano, nitro, amino, mono($C_1$–$C_6$ alkylamino, di($C_1$–$C_6$)alkylamino, $C_2$–$C_6$ alkenyl, $C_2$–$C_6$ alkynyl, $C_1$–$C_6$ haloalkyl, $C_1$–$C_6$ haloalkoxy, amino($C_1$–$C_6$alkyl, mono($C_1$–$C_6$) alkylamino($C_1$–$C_6$)alkyl, di($C_1$–$C_6$)alkylamino ($C_1$–$C_6$)alkyl, and =O;

$R_{145}$ is $C_1$–$C_6$ alkyl or CF$_3$;

$R_{150}$ is hydrogen, $C_3$–$C_7$ cycloalkyl, —($C_1$–$C_2$ alkyl)-($C_3$–$C_7$ cycloalkyl), $C_2$–$C_6$ alkenyl, $C_2$–$C_6$ alkynyl, $C_1$–$C_6$ alkyl with one double bond and one triple bond, —$R_{110}$, —$R_{120}$, or
$C_1$–$C_6$ alkyl optionally substituted with 1, 2, 3, or 4 groups independently selected from —OH, —NH$_2$, $C_1$–$C_3$ alkoxy, $R_{110}$, and halogen;

$R_{150}$' is $C_3$–$C_7$ cycloalkyl, —($C_1$–$C_3$ alkyl)-($C_3$–$C_7$ cycloalkyl), $C_2$–$C_6$ alkenyl, $C_2$–$C_6$ alkynyl, $C_1$–$C_6$ alkyl with one double bond and one triple bond, —$R_{110}$, —$R_{120}$, or
$C_1$–$C_6$ alkyl optionally substituted with 1, 2, 3, or 4 groups independently selected from —OH, —NH$_2$, $C_1$–$C_3$ alkoxy, $R_{110}$, and halogen;

$R_{155}$ is $C_3$–$C_7$ cycloalkyl, —($C_1$–$C_2$ alkyl)-($C_3$–$C_7$ cycloalkyl), $C_2$–$C_6$ alkenyl, $C_2$–$C_6$ alkynyl, $C_1$–$C_6$ alkyl with one double bond and one triple bond, —$R_{110}$, —$R_{120}$, or
$C_1$–$C_6$ alkyl optionally substituted with 1, 2, 3, or 4 groups independently selected from —OH, —NH$_2$, $C_1$–$C_3$ alkoxy, and halogen;

$R_{180}$ is selected from morpholinyl, thiomorpholinyl, piperazinyl, piperidinyl, homomorpholinyl, homothiomorpholinyl, homothiomorpholinyl S-oxide, homothiomorpholinyl S,S-dioxide-dioxide, pyrrolinyl and pyrrolidinyl, each of which is optionally substituted with 1, 2, 3, or 4 groups independently selected from $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$ alkenyl, $C_2$–$C_6$ alkynyl, $C_1$–$C_6$ haloalkyl, $C_1$–$C_6$ haloalkoxy, amino($C_1$–$C_6$) alkyl, mono ($C_1$–$C_6$)alkylamino($C_1$–$C_6$)alkyl, di($C_1$–$C_6$) alkylamino($C_1$–$C_6$)alkyl, and =O;

$R_{110}$ is aryl optionally substituted with 1 or 2 $R_{125}$ groups;

$R_{125}$ at each occurrence is independently halogen, amino, mono- or dialkylamino, —OH, —C≡N, —SO$_2$—NH$_2$, —SO$_2$—NH—$C_1$–$C_6$ alkyl, —SO$_2$—N($C_1$–$C_6$ alkyl)$_2$, —SO$_2$—($C_1$–$C_4$ alkyl), —CO—NH$_2$, —CO—NH—$C_1$–$C_6$ alkyl, or —CO—N($C_1$–$C_6$ alkyl)$_2$, or
$C_1$–$C_6$ alkyl, $C_2$–$C_6$ alkenyl or $C_2$–$C_6$ alkynyl, each of which is optionally substituted with 1, 2, or 3 groups that are independently selected from $C_1$–$C_3$ alkyl, halogen, —OH, —SH, —C≡N, —CF$_3$, $C_1$–$C_3$ alkoxy, amino, and mono- and dialkylamino, or
$C_1$–$C_6$ alkoxy optionally substituted with one, two or three of halogen;

$R_{120}$ is heteroaryl, which is optionally substituted with 1 or 2 $R_{125}$ groups; and $R_{130}$ is heterocyclyl optionally substituted with 1 or 2 $R_{125}$ groups.

2. A compound according to claim 1 wherein $R_1$ is aryl, or —$C_1$–$C_6$ alkyl-aryl, where the ring portions of each are optionally substituted with 1, 2, 3, or 4 groups independently selected from halogen, —OH, —SH, —C≡N, —NR$_{105}R'_{105}$, —CO$_2$R, —N(R)COR', or —N(R)SO$_2$R', —C(=O)—($C_1$–$C_4$)alkyl, —SO$_2$-amino, —SO$_2$-mono or dialkylamino, —C(=O)-amino, —C(=O)-mono or dialkylamino, —SO$_2$—($C_1$–$C_4$)alkyl, or
$C_1$–$C_6$ alkoxy optionally substituted with 1, 2, or 3 groups which are independently selected from halogen, or
$C_3$–$C_7$ cycloalkyl optionally substituted with 1, 2, or 3 groups independently selected from halogen, —OH, —SH, —C≡N, —CF$_3$, $C_1$–$C_3$ alkoxy, amino, —$C_1$–$C_6$ alkyl and mono- or dialkylamino, or
$C_1$–$C_{10}$ alkyl optionally substituted with 1, 2, or 3 groups independently selected from halogen, —OH, —SH, —C≡N, —CF$_3$, —$C_1$–$C_3$ alkoxy, amino, mono- or dialkylamino and —$C_1$–$C_3$ alkyl, or
$C_2$–$C_{10}$ alkenyl or $C_2$–$C_{10}$ alkynyl each of which is optionally substituted with 1, 2, or 3 groups independently selected from halogen, —OH, —SH, —C≡N, —CF$_3$, $C_1$–$C_3$ alkoxy, amino, $C_1$–$C_6$ alkyl and mono- or dialkylamino; and the heterocyclyl group is optionally further substituted with oxo.

3. A compound according to claim 2 wherein $R_C$ is $C_1$–$C_{10}$ alkyl optionally substituted with 1, 2, or 3 groups independently selected from the group consisting of $R_{110}$, $R_{120}$ and $R_{130}$, or $C_2$–$C_{10}$ alkyl optionally substituted with 1, 2, or 3 groups independently selected from the group consisting of $R_{205}$, $R_{110}$, $R_{120}$, $R_{130}$, —OC=ONR$_{235}$R$_{240}$, —S(=O)$_{0-2}$($C_1$–$C_6$ alkyl), —SH, and —S(=O)$_2$NR$_{235}$R$_{240}$, or $C_2$–$C_{10}$ alkenyl or $C_2$–$C_{10}$ alkynyl, each of which is optionally substituted with 1, 2, or 3 $R_{205}$ groups.

4. compound according to claim 3 wherein $R_N$ is —C(=O)—(CRR')$_{0-6}$R$_{100}$; and $R_{100}$ represents aryl, which is optionally substituted with 1, 2, or 3 groups independently selected from —OR, —NO$_2$, $C_1$–$C_6$ alkyl, halogen, —C≡N, —OCF$_3$, —CF$_3$, —(CH$_2$)$_{0-4}$—O—P(=O)(OR)(OR'), —(CH$_2$)$_{0-4}$—CO—NR$_{105}$R'$_{105}$, —(CH$_2$)$_{0-4}$—O—(CH$_2$)$_{0-4}$—CONR$_{102}$R$_{102}$', —(CH$_2$)$_{0-4}$—CO—($C_1$–$C_{12}$ alkyl), —(CH$_2$)$_{0-4}$—CO—($C_2$–$C_{12}$ alkenyl), —(CH$_2$)$_{0-4}$—CO—($C_2$–$C_{12}$ alkynyl), —(CH$_2$)$_{0-4}$—CO—(CH$_2$)$_{0-4}$($C_3$–$C_7$ cycloalkyl), —(CH$_2$)$_{0-4}$—R$_{110}$, —(CH$_2$)$_{0-4}$—R$_{120}$, —(CH$_2$)$_{0-4}$—R$_{130}$, —(CH$_2$)$_{0-4}$—CO—R$_{110}$, —(CH$_2$)$_{0-4}$—CO—R$_{120}$, —(CH$_2$)$_{0-4}$—CO—R$_{130}$, —(CH$_2$)$_{0-4}$—CO—R$_{140}$, —(CH$_2$)$_{0-4}$—CO—O—R$_{150}$, —(CH$_2$)$_{0-4}$—SO$_2$—NR$_{105}$R'$_{105}$, —(CH$_2$)$_{0-4}$—SO—($C_1$–$C_8$ alkyl), —(CH$_2$)$_{0-4}$—SO$_2$—($C_1$–$C_{12}$ alkyl), —(CH$_2$)$_{0-4}$—SO$_2$—(CH$_2$)$_{0-4}$—($C_3$–$C_7$ cycloalkyl), —(CH$_2$)$_{0-4}$—N(R$_{150}$)—CO—O—R$_{150}$, —(CH$_2$)$_{0-4}$—N(R$_{150}$)—CO—N(R$_{150}$)$_2$, —(CH$_2$)$_{0-4}$—N(R$_{150}$)—CS—N(R$_{150}$)$_2$, —(CH$_2$)$_{0-4}$—N(R$_{150}$)—CO—R$_{105}$, —(CH$_2$)$_{0-4}$—NR$_{105}$R'$_{105}$, —(CH$_2$)$_{0-4}$—R$_{140}$, —(CH$_2$)$_{0-4}$—O—CO—($C_1$–$C_6$ alkyl), —(CH$_2$)$_{0-4}$—O—P(O)—(O—R$_{110}$)$_2$, —(CH$_2$)$_{0-4}$—O—CO—N(R$_{150}$)$_2$, —(CH$_2$)$_{0-4}$—O—CS—N(R$_{150}$)$_2$, —(CH$_2$)$_{0-4}$—O—(R$_{150}$), —(CH$_2$)$_{0-4}$—O—R$_{150}$'—COOH, —(CH$_2$)$_{0-4}$—S—(R$_{150}$), —(CH$_2$)$_{0-4}$—N(R$_{150}$)—SO$_2$—R$_{105}$, —(CH$_2$)$_{0-4}$—$C_3$–$C_7$ cycloalkyl, ($C_2$–$C_{10}$)alkenyl, or ($C_2$–$C_{10}$)alkynyl.

5. A compound according to claim 4 wherein $R_N$ is —C(=O)—R$_{100}$; and $R_{100}$ represents aryl, which is optionally substituted with 1, 2, or 3 groups independently selected from —OR, —NO$_2$, $C_1$–$C_6$ alkyl, halogen, —C≡N, —OCF$_3$, —CF$_3$, —(CH$_2$)$_{0-4}$—O—P(=O)(OR)(OR'), —(CH$_2$)$_{0-4}$—CO—NR$_{105}$R'$_{105}$, —(CH$_2$)$_{0-4}$—O—(CH$_2$)$_{0-4}$—CONR$_{102}$R$_{102}$', —(CH$_2$)$_{0-4}$—CO—($C_1$–$C_{12}$ alkyl), —(CH$_2$)$_{0-4}$—CO—($C_2$–$C_{12}$ alkenyl), —(CH$_2$)$_{0-4}$—CO—($C_2$–$C_{12}$ alkynyl), —(CH$_2$)$_{0-4}$—CO—(CH$_2$)$_{0-4}$($C_3$–$C_7$ cycloalkyl), —(CH$_2$)$_{0-4}$—R$_{110}$, —(CH$_2$)$_{0-4}$—R$_{120}$, —(CH$_2$)$_{0-4}$—R$_{130}$, —(CH$_2$)$_{0-4}$—CO—R$_{110}$, —(CH$_2$)$_{0-4}$—CO—R$_{120}$, —(CH$_2$)$_{0-4}$—CO—R$_{130}$, —(CH$_2$)$_{0-4}$—R$_{140}$, —(CH$_2$)$_{0-4}$—CO—O—R$_{150}$, —(CH$_2$)$_{0-4}$—SO$_2$—NR$_{105}$R'$_{105}$, —(CH$_2$)$_{0-4}$—SO—($C_1$–$C_8$ alkyl), —(CH$_2$)$_{0-4}$—SO$_2$—($C_1$–$C_{12}$ alkyl), —(CH$_2$)$_{0-4}$—SO$_2$—(CH$_2$)$_{0-4}$—($C_3$–$C_7$ cycloalkyl), —(CH$_2$)$_{0-4}$—N(R$_{150}$)—CO—O—R$_{150}$, —(CH$_2$)$_{0-4}$—N(R$_{150}$)—CO—N(R$_{150}$)$_2$, —(CH$_2$)$_{0-4}$—N(R$_{150}$)—CS—N(R$_{150}$)$_2$, —(CH$_2$)$_{0-4}$—N(R$_{150}$)—CO—R$_{105}$, —(CH$_2$)$_{0-4}$—NR$_{105}$R'$_{105}$, —(CH$_2$)$_{0-4}$—R$_{140}$, —(CH$_2$)$_{0-4}$—O—(R$_{150}$), —(CH$_2$)$_{0-4}$—O—R$_{150}$'—COOH, —(CH$_2$)$_{0-4}$—S—(R$_{150}$), —(CH$_2$)$_{0-4}$—N(R$_{150}$)—SO$_2$—R$_{105}$, —(CH$_2$)$_{0-4}$—$C_3$–$C_7$ cycloalkyl, ($C_2$–$C_{10}$)alkenyl, and ($C_2$–$C_{10}$)alkynyl.

6. A compound according to claim 5 wherein $R_1$ is —CH$_2$-phenyl where the ring portion is optionally substituted with 1, 2, 3, or 4 groups independently selected from halogen, $C_1$–$C_4$ alkoxy, hydroxy, and $C_1$–$C_4$ alkyl optionally substituted with 1, 2, or 3 substituents halogen, OH, SH, NH$_2$, NH($C_1$–$C_6$ alkyl), N—($C_1$–$C_6$ alkyl)($C_1$–$C_6$ alkyl), C≡N, CF$_3$; and $R_C$ is $C_2$–$C_{10}$ alkyl, $C_2$–$C_{10}$ alkenyl or $C_2$–$C_{10}$ alkynyl, each of which is optionally substituted with with 1, 2, or 3 groups independently selected from the group consisting of halogen, —OH, phenyl, —O-phenyl, —SH, —S—$C_1$–$C_6$ alkyl, —C≡N, —CF$_3$, $C_1$–$C_6$ alkoxy, NH$_2$, NH($C_1$–$C_6$ alkyl) or N—($C_1$–$C_6$ alkyl)($C_1$–$C_6$ alkyl).

7. A compound according to claim 5 of the formula I-7:

I-7 wherein X is CH; and $A_3$ and $A_4$ are independently hydrogen, halogen, $C_1$–$C_4$ alkoxy, hydroxy, and $C_1$–$C_4$ alkyl optionally substituted with 1, 2, or 3 substituents halogen, OH, SH, NH$_2$, NH($C_1$–$C_6$ alkyl), N—($C_1$–$C_6$ alkyl)($C_1$–$C_6$ alkyl), C≡N, CF$_3$.

8. A compound according to claim 7 of the formula I-7-a:

I-7-a wherein $A_1$ and $A_2$ are independently —OR, —NO$_2$, $C_1$–$C_6$ alkyl, halogen, —C≡N, —OCF$_3$, —CF$_3$, —(CH$_2$)$_{0-4}$—O—P(=O)(OR)(OR'), —(CH$_2$)$_{0-4}$—CO—NR$_{105}$, R'$_{105}$, —(CH$_2$)$_{0-4}$—O—(CH$_2$)$_{0-4}$—CONR$_{102}$R$_{102}$', —(CH$_2$)$_{0-4}$—CO—($C_1$–$C_{12}$ alkyl), —(CH$_2$)$_{0-4}$—CO—($C_2$–$C_{12}$ alkenyl), —(CH$_2$)$_{0-4}$—CO—($C_2$–$C_{12}$ alkynyl), —(CH$_2$)$_{0-4}$—CO—(CH$_2$)$_{0-4}$($C_3$–$C_7$ cycloalkyl), —(CH$_2$)$_{0-4}$—R$_{110}$, —(CH$_2$)$_{0-4}$—R$_{120}$, —(CH$_2$)$_{0-4}$—R$_{130}$, —(CH$_2$)$_{0-4}$—CO—R$_{110}$, —(CH$_2$)$_{0-4}$—CO—R$_{120}$, —(CH$_2$)$_{0-4}$—CO—R$_{130}$, —(CH$_2$)$_{0-4}$—CO—R$_{140}$, —(CH$_2$)$_{0-4}$—CO—O—R$_{150}$, —(CH$_2$)$_{0-4}$—SO$_2$—NR$_{105}$R'$_{105}$, —(CH$_2$)$_{0-4}$—SO—($C_1$–$C_8$ alkyl), —(CH$_2$)$_{0-4}$—SO$_2$—($C_1$–$C_{12}$ alkyl), —(CH$_2$)$_{0-4}$—SO$_2$—(CH$_2$)$_{0-4}$—($C_3$–$C_7$ cycloalkyl), —(CH$_2$)$_{0-4}$—N(R$_{150}$)—CO—O—R$_{150}$, —(CH$_2$)$_{0-4}$—N(R$_{150}$)—CO—N(R$_{150}$)$_2$, —(CH$_2$)$_{0-4}$—N(R$_{150}$)—CS—N(R$_{150}$)$_2$, —(CH$_2$)$_{0-4}$—N(R$_{150}$)—CO—R$_{105}$, —(CH$_2$)$_{0-4}$—

$NR_{105}R'_{105}$, $—(CH_2)_{0-4}—R_{140}$, $—(CH_2)_{0-4}—O—CO—(C_1–C_6 \text{ alkyl})$, $—(CH_2)_{0-4}—O—P(O)—(O—R_{110})_2$, $—(CH_2)_{0-4}—O—CO—N(R_{150})_2$, $—(CH_2)_{0-4}—O—CS—N(R_{150})_2$, $—(CH_2)_{0-4}—O—(R_{150})$, $—(CH_2)_{0-4}—O—R_{150}'—COOH$, $—(CH_2)_{0-4}—S—(R_{150})$, $—(CH_2)_{0-4}—N(R_{150})—SO_2—R_{105}$, $—(CH_2)_{0-4}—C_3–C_7$ cycloalkyl, $(C_2–C_{10})$alkenyl, or $(C_2–C_{10})$alkynyl.

9. A compound according to claim 7 selected from the group consisting of

5-Bromo-N-[(1S,2R,3R)-1-(3,5-difluoro-benzyl)-2,3-dihydroxy-heptyl]-N',N'-dipropyl-isophthalamide, N-[(1S,2R,3R)-1-(3,5-Difluoro-benzyl)-2,3-dihydroxy-heptyl]-5-methyl-N',N'-dipropyl-isophthalamide, 5-Carboxamido-N-[(1S,2R,3R)-1-(3,5-difluoro-benzyl)-2,3-dihydroxy-heptyl]-N',N'-dipropyl-isophthalamide, N-[(1S,2R,3S)-1-benzyl-2,3-dihydroxy-heptyl]-5-methyl-N',N'-dipropyl-isophthalamide, N-[(1S,2R,3S)-1-(3,5-difluorobenzyl)-2,3-dihydroxy-heptyl]-5-methyl-N',N'-dipropyl-isophthalamide, 5-Carboxamido-N-[(1S,2R,3S)-1-(3,5-difluoro-benzyl)-2,3-dihydroxy-heptyl]-N',N'-dipropyl-isophthalamide, 2-({3-bromo-5-[(dipropylamino)carbonyl]benzoyl}amino)-1,2,5-trideoxy-6-S-methyl-1-phenyl-6-thio-D-xylo-hexitol, $N^1$-[(1S,2R,3R)-1-benzyl-2,3-dihydroxy-6-phenylhexyl]-$N^3,N^3$-dipropylbenzene-1,3,5-tricarboxamide, N'-[1-(3,5-difluorobenzyl)-2,3-dihydroxyheptyl]-5-methyl-N,N-dipropylisophthalamide, N'-[1-(3,5-difluorobenzyl)-2,3-dihydroxyoctyl]-5-methyl-N,N-dipropylisophthalamide, 1,2,5-trideoxy-1-(3,5-difluorophenyl)-2-({3-[(dipropylamino)carbonyl]-5-methylbenzoyl}amino)-6-O-methylhexitol, 1,2,5-trideoxy-1-(3,5-difluorophenyl)-2-({3-[(dipropylamino)carbonyl]-5-methylbenzoyl}amino)-6-S-methyl-6-thiohexitol, N'-[1-(3,5-difluorobenzyl)-2,3-dihydroxyoct-7-ynyl]-5-methyl-N,N-dipropylisophthalamide, 1,2,5,6-tetradeoxy-1-(3,5-difluorophenyl)-2-({3-[(dipropylamino)carbonyl]-5-methylbenzoyl}amino)-7-S-methyl-7-thioheptitol, N'-[6-cyano-1-(3,5-difluorobenzyl)-2,3-dihydroxyhexyl]-5-methyl-N,N-dipropylisophthalamide, N'-[5-cyano-1-(3,5-difluorobenzyl)-2,3-dihydroxypentyl]-5-methyl-N,N-dipropylisophthalamide, N'-[4-cyano-1-(3,5-difluorobenzyl)-2,3-dihydroxybutyl]-5-methyl-N,N-dipropylisophthalamide, 1,2-dideoxy-1-(3,5-difluorophenyl)-2-({3-[(dipropylamino)carbonyl]-5-methylbenzoyl}amino)-5-O-methylpentitol, $N^3$-[1-(3,5-difluorobenzyl)-2,3-dihydroxyheptyl]-$N^1,N^1$-dipropylbenzene-1,3,5-tricarboxamide, $N^3$-[1-(3,5-difluorobenzyl)-2,3-dihydroxyoctyl]-$N^1,N^1$-dipropylbenzene-1,3,5-tricarboxamide, 2-({3-(aminocarbonyl)-5-[(dipropylamino)carbonyl]benzoyl}amino)-1,2,5-trideoxy-1-(3,5-difluorophenyl)-6-O-methylhexitol, 2-({3-(aminocarbonyl)-5-[(dipropylamino)carbonyl]benzoyl}amino)-1,2,5-trideoxy-1-(3,5-difluorophenyl)-6-S-methyl-6-thiohexitol, $N^3$-[1-(3,5-difluorobenzyl)-2,3-dihydroxyoct-7-ynyl]-$N^1,N^1$-dipropylbenzene-1,3,5-tricarboxamide, 2-({3-(aminocarbonyl)-5-[(dipropylamino)carbonyl]benzoyl}amino)-1,2,5,6-tetradeoxy-1-(3,5-difluorophenyl)-7-S-methyl-7-thioheptitol, $N^3$-[6-cyano-1-(3,5-difluorobenzyl)-2,3-dihydroxyhexyl]-$N^1,N^1$-dipropylbenzene-1,3,5-tricarboxamide, $N^3$-[5-cyano-1-(3,5-difluorobenzyl)-2,3-dihydroxypentyl]-$N^1,N^1$-dipropylbenzene-1,3,5-tricarboxamide, $N^3$-[4-cyano-1-(3,5-difluorobenzyl)-2,3-dihydroxybutyl]-$N^1,N^1$-dipropylbenzene-1,3,5-tricarboxamide, 2-({3-(aminocarbonyl)-5-[(dipropylamino)carbonyl]benzoyl}amino)-1,2-dideoxy-1-(3,5-difluorophenyl)-5-O-methylpentitol, N'-(1-benzyl-2,3-dihydroxyheptyl)-5-methyl-N,N-dipropylisophthalamide, N'-(1-benzyl-2,3-dihydroxyoctyl)-5-methyl-N,N-dipropylisophthalamide, 1,2,5-trideoxy-2-({3-[(dipropylamino)carbonyl]-5-methylbenzoyl}amino)-6-O-methyl-1-phenylhexitol, 1,2,5-trideoxy-2-({3-[(dipropylamino)carbonyl]-5-methylbenzoyl}amino)-6-S-methyl-1-phenyl-6-thiohexitol, N'-(1-benzyl-2,3-dihydroxyoct-7-ynyl)-5-methyl-N,N-dipropylisophthalamide, 1,2,5,6-tetradeoxy-2-({3-[(dipropylamino)carbonyl]-5-methylbenzoyl}amino)-7-S-methyl-1-phenyl-7-thioheptitol, N'-(1-benzyl-6-cyano-2,3-dihydroxyhexyl)-5-methyl-N,N-dipropylisophthalamide, N'-(1-benzyl-5-cyano-2,3-dihydroxypentyl)-5-methyl-N,N-dipropylisophthalamide, N'-(1-benzyl-4-cyano-2,3-dihydroxybutyl)-5-methyl-N,N-dipropylisophthalamide, 1,2-dideoxy-2-({3-[(dipropylamino)carbonyl]-5-methylbenzoyl}amino)-5-O-methyl-1-phenylpentitol, $N^3$-(1-benzyl-2,3-dihydroxyheptyl)-$N^1,N^1$-dipropylbenzene-1,3,5-tricarboxamide, $N^3$-(1-benzyl-2,3-dihydroxyoctyl)-$N^1,N^1$-dipropylbenzene-1,3,5-tricarboxamide, 2-({3-(aminocarbonyl)-5-[(dipropylamino)carbonyl]benzoyl}amino)-1,2,5-trideoxy-6-O-methyl-1-phenylhexitol, 2-({3-(aminocarbonyl)-5-[(dipropylamino)carbonyl]benzoyl}amino)-1,2,5-trideoxy-6-S-methyl-1-phenyl-6-thiohexitol, $N^3$-(1-benzyl-2,3-dihydroxyoct-7-ynyl)-$N^1,N^1$-dipropylbenzene-1,3,5-tricarboxamide, 2-({3-(aminocarbonyl)-5-[(dipropylamino)carbonyl]benzoyl}amino)-1,2,5,6-tetradeoxy-7-S-methyl-1-phenyl-7-thioheptitol, $N^3$-(1-benzyl-6-cyano-2,3-dihydroxyhexyl)-$N^1,N^1$-dipropylbenzene-1,3,5-tricarboxamide, $N^3$-(1-benzyl-5-cyano-2,3-dihydroxypentyl)-$N^1,N^1$-dipropylbenzene-1,3,5-tricarboxamide, $N^3$-(1-benzyl-4-cyano-2,3-dihydroxybutyl)-$N^1$,$N^1$dipropylbenzene-1,3,5-tricarboxamide, 2-({3-(aminocarbonyl)-5-[(dipropylamino)carbonyl]benzoyl}amino)-1,2-dideoxy-5-O-methyl-1-phenylpentitol, N'-[2,3-dihydroxy-1-(4-hydroxybenzyl)heptyl]-5-methyl-N,N-dipropylisophthalamide, N'-[2,3-dihydroxy-1-(4-hydroxybenzyl)octyl]-5-methyl-N,N-dipropylisophthalamide, 1,2,5-trideoxy-2-({3-[(dipropylamino)carbonyl]-5-methylbenzoyl}amino)-1-(4-hydroxyphenyl)-6-O-methylhexitol, 1,2,5-trideoxy-2-({3-[(dipropylamino)carbonyl]-5-methylbenzoyl}amino)-1-(4-hydroxyphenyl)-6-S-methyl-6-thiohexitol, N'-[2,3-dihydroxy-1-(4-hydroxybenzyl)oct-7-ynyl]-5-methyl-N,N-dipropylisophthalamide, 1,2,5,6-tetradeoxy-2-({3-[(dipropylamino)carbonyl]-5-methylbenzoyl}amino)-1-(4-hydroxyphenyl)-7-S-methyl-7-thioheptitol, N'-[6-cyano-2,3-dihydroxy-1-(4-hydroxybenzyl)hexyl]-5-methyl-N,N-dipropylisophthalamide, N'-[5-cyano-2,3-dihydroxy-1-(4-hydroxybenzyl)pentyl]-5-methyl-N,N-dipropylisophthalamide, N'-[4-cyano-2,3-dihydroxy-1-(4-hydroxybenzyl)butyl]-5-methyl-N,N-dipropylisophthalamide, 1,2-dideoxy-2-({3-[(dipropylamino)carbonyl]-5-methylbenzoyl}amino)-1-(4-hydroxyphenyl)-5-O-methylpentitol, $N^3$-[2,3-dihydroxy-1-(4-hydroxybenzyl)heptyl]-$N^1$,$N^1$-dipropylbenzene-1,3,5-tricarboxamide, $N^3$-[2,3-dihydroxy-1-(4-hydroxybenzyl)octyl]-$N^1$,$N^1$-dipropylbenzene-1,3,5-tricarboxamide, 2-({3-(aminocarbonyl)-5-[(dipropylamino)carbonyl]benzoyl}amino)-1,2,5-trideoxy-1-(4-hydroxyphenyl)-6-O-methylhexitol, 2-({3-(aminocarbonyl)-5-[(dipropylamino)carbonyl]benzoyl}amino)-1,2,5-trideoxy-1-(4-hydroxyphenyl)-6-S-methyl-6-thiohexitol, $N^3$-[2,3-dihydroxy-1-(4-hydroxybenzyl)oct-7-ynyl]-$N^1$,$N^1$-dipropylbenzene-1,3,5-tricarboxamide, 2-({3-(aminocarbonyl)-5-[(dipropylamino)carbonyl]benzoyl}amino)-1,2,5,6-tetradeoxy-1-(4-hydroxyphenyl)-7-S-methyl-7-thioheptitol, $N^3$-[6-cyano-2,3-dihydroxy-1-(4-hydroxybenzyl)hexyl]-$N^1$,$N^1$-dipropylbenzene-1,3,5-tricarboxamide, $N^3$-[5-cyano-2,3-dihydroxy-1-(4-hydroxybenzyl)pentyl]-$N^1$,$N^1$-dipropylbenzene-1,3,5-tricarboxamide, $N^3$-[4-cyano-2,3-dihydroxy-1-(4-hydroxybenzyl)butyl]-$N^1$,$N^1$-dipropylbenzene-1,3,5-tricarboxamide, and 2-({3-(aminocarbonyl)-5-[(dipropylamino)carbonyl]benzoyl}amino)-1,2-dideoxy-1-(4-hydroxyphenyl)-5-O-methylpentitol.

\* \* \* \* \*

SEQUENCE LISTING

```
<160> NUMBER OF SEQ ID NOS: 9

<210> SEQ ID NO 1
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
<223> OTHER INFORMATION: covalent attachment of oregon green

<400> SEQUENCE: 1

Ser Glu Val Asn Leu Asp Ala Glu Phe Arg Cys Lys Lys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
<223> OTHER INFORMATION: covalent attachment of oregon green

<400> SEQUENCE: 2

Ser Glu Val Lys Met Asp Ala Glu Phe Arg Cys Lys Lys
1               5                   10

<210> SEQ ID NO 3
<211> LENGTH: 22
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (20)..(20)
<223> OTHER INFORMATION: covalent attachment of oregon green

<400> SEQUENCE: 3

Gly Leu Asn Ile Lys Thr Glu Glu Ile Ser Glu Ile Ser Tyr Glu Val
1               5                   10                  15

Glu Phe Arg Cys Lys Lys
```

-continued

```
<210> SEQ ID NO 4
<211> LENGTH: 34
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (32)..(32)
<223> OTHER INFORMATION: covalent attachment of oregon green

<400> SEQUENCE: 4

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe Arg Cys
            20                  25                  30

Lys Lys

<210> SEQ ID NO 5
<211> LENGTH: 33
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (7)..(7)
<223> OTHER INFORMATION: oxidized cysteine
<220> FEATURE:
<221> NAME/KEY: MISC_FEATURE
<222> LOCATION: (19)..(19)
<223> OTHER INFORMATION: oxidized cysteine
<220> FEATURE:
<221> NAME/KEY: MISC_FEATURE
<222> LOCATION: (31)..(31)
<223> OTHER INFORMATION: covalent attachment of oregon green

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Cys Lys
            20                  25                  30

Lys

<210> SEQ ID NO 6
<211> LENGTH: 33
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin

<400> SEQUENCE: 6

Cys Gly Gly Ala Asp Arg Gly Leu Thr Thr Arg Pro Gly Ser Gly Leu
1               5                   10                  15
```

-continued

```
Thr Asn Ile Lys Thr Glu Glu Ile Ser Glu Val Asn Leu Asp Ala Glu
            20                  25                  30
Phe

<210> SEQ ID NO 7
<211> LENGTH: 29
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin

<400> SEQUENCE: 7

Cys Gly Gly Ala Asp Arg Gly Leu Thr Thr Arg Pro Gly Ser Gly Leu
1               5                   10                  15
Thr Asn Ile Lys Thr Glu Glu Ile Ser Glu Val Asn Leu
            20                  25

<210> SEQ ID NO 8
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin

<400> SEQUENCE: 8

Ser Glu Val Asn Leu Asp Ala Glu Phe
1               5

<210> SEQ ID NO 9
<211> LENGTH: 30
<212> TYPE: PRT
<213> ORGANISM: Artificial Sequence
<220> FEATURE:
<223> OTHER INFORMATION: synthetic peptide

<400> SEQUENCE: 9

Ala Asp Arg Gly Leu Thr Thr Arg Pro Gly Ser Gly Leu Thr Asn Ile
1               5                   10                  15
Lys Thr Glu Glu Ile Ser Glu Val Asn Leu Asp Ala Glu Phe
            20                  25                  30
```